United States Patent
Okamoto et al.

(10) Patent No.: US 9,465,031 B2
(45) Date of Patent: Oct. 11, 2016

(54) METHOD OF EVALUATING PROSTATIC DISEASE

(75) Inventors: Naoyuki Okamoto, Kanagawa (JP); Takeshi Miura, Kanagawa (JP); Yohei Miyagi, Kanagawa (JP); Akira Imaizumi, Kanagawa (JP); Hiroshi Yamamoto, Tokyo (JP); Takayuki Tanaka, Kanagawa (JP); Takahiko Muramatsu, Tokyo (JP); Toshihiko Ando, Kanagawa (JP); Noriko Takahashi, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 53 days.

(21) Appl. No.: 12/971,419

(22) Filed: Dec. 17, 2010

(65) Prior Publication Data

US 2011/0138889 A1    Jun. 16, 2011

Related U.S. Application Data

(63) Continuation of application No. PCT/JP2009/061349, filed on Jun. 22, 2009.

(30) Foreign Application Priority Data

Jun. 20, 2008    (JP) .................................. 2008-162613

(51) Int. Cl.
  *G01N 33/48*    (2006.01)
  *G01N 33/574*    (2006.01)
  *G01N 33/68*    (2006.01)

(52) U.S. Cl.
  CPC .... *G01N 33/57434* (2013.01); *G01N 33/6812* (2013.01); *G01N 2800/342* (2013.01)

(58) Field of Classification Search
  CPC .............................................. G01N 33/57434
  USPC .......................................................... 702/19
  See application file for complete search history.

(56) References Cited

U.S. PATENT DOCUMENTS

| | | | |
|---|---|---|---|
| 6,059,724 A | 5/2000 | Campell et al. | |
| 6,300,136 B1 | 10/2001 | Koch et al. | |
| 6,631,330 B1 | 10/2003 | Poynard | |
| 6,964,850 B2 | 11/2005 | Bevilacqua et al. | |
| 8,244,476 B2 | 8/2012 | Zhang et al. | |
| 2004/0039553 A1 | 2/2004 | Poynard | |
| 2005/0283347 A1 | 12/2005 | Kimura et al. | |
| 2006/0170928 A1 | 8/2006 | Masilamani et al. | |
| 2007/0281895 A1 | 12/2007 | Crockard et al. | |
| 2008/0147368 A1 | 6/2008 | Sugimoto et al. | |
| 2008/0154515 A1 | 6/2008 | Zhang et al. | |
| 2008/0305962 A1 | 12/2008 | Wirtz | |
| 2009/0046286 A1 | 2/2009 | Masilamani et al. | |
| 2009/0047269 A1 | 2/2009 | Chinnaiyan et al. | |
| 2009/0075284 A1 | 3/2009 | Chinnaiyan et al. | |
| 2009/0127454 A1 | 5/2009 | Ritchie et al. | |
| 2010/0004871 A1 | 1/2010 | Goldknopf | |
| 2010/0009401 A1 | 1/2010 | Imaizumi et al. | |
| 2010/0009402 A1 | 1/2010 | Imaizumi et al. | |
| 2010/0017144 A1 | 1/2010 | Imaizumi et al. | |
| 2010/0017145 A1 | 1/2010 | Imaizumi et al. | |
| 2010/0173350 A1 | 7/2010 | Masilamani et al. | |
| 2010/0292331 A1 | 11/2010 | Mitchell et al. | |
| 2011/0035156 A1 | 2/2011 | Imaizumi et al. | |
| 2011/0091924 A1 | 4/2011 | Imaizumi et al. | |
| 2011/0143444 A1 | 6/2011 | Muramatsu et al. | |
| 2011/0282585 A9 | 11/2011 | Zhang et al. | |

FOREIGN PATENT DOCUMENTS

| | | |
|---|---|---|
| CN | 1315998 A | 10/2001 |
| CN | 1367830 A | 9/2002 |
| CN | 1878876 A | 12/2006 |
| EP | 1 570 779 A1 | 9/2005 |
| EP | 1 862 797 A1 | 12/2007 |
| IN | 209084 B | 9/2007 |
| JP | 61-126472 A | 6/1986 |
| JP | 2005-508505 A | 3/2005 |
| JP | 5746811 B2 | 7/2015 |
| WO | WO 97/48982 A1 | 12/1997 |
| WO | WO 00/04149 A2 | 1/2000 |
| WO | WO 00/20587 A | 4/2000 |
| WO | WO 00 65472 A1 | 11/2000 |
| WO | WO 02/16949 A1 | 2/2002 |
| WO | WO 2004/052191 A1 | 6/2004 |
| WO | WO 2006/098192 A1 | 9/2006 |
| WO | WO 2006/129513 A1 | 12/2006 |
| WO | WO 2007/107334 A1 | 9/2007 |
| WO | WO 2008/016111 A1 | 2/2008 |
| WO | WO 2008/075662 A1 | 6/2008 |
| WO | WO 2008/075663 A1 | 6/2008 |
| WO | WO 2008/075664 A1 | 6/2008 |
| WO | WO 2008/145385 A2 | 12/2008 |
| WO | WO 2009/099005 A1 | 8/2009 |
| WO | WO 2009/110517 A1 | 9/2009 |
| WO | WO 2009/154296 A1 | 12/2009 |
| WO | WO 2010/139711 A1 | 12/2010 |

OTHER PUBLICATIONS

International Search Report for PCT/JP2009/061349 dated Jul. 21, 2009, 4 pages.
Cascino et al., "Plasma Amino Acid Imbalance in Patients with Lung and Breast Cancer," Anticancer Research, 1995, 15:507-510.
Cynober, Luc A., Ed., Metabolic and Therapeutic Aspects of Amino Acids in Clinical Nutrition, 2nd Ed., 2004, 339-354.

(Continued)

*Primary Examiner* — Jerry Lin
(74) *Attorney, Agent, or Firm* — Foley & Lardner LLP

(57) ABSTRACT

According to the method of evaluating prostatic disease of the present invention, amino acid concentration data on concentration values of amino acids in blood collected from a subject to be evaluated is measured, and the state of prostatic disease including at least one of prostatic cancer and prostatic hypertrophy in the subject is evaluated based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the measured amino acid concentration data of the subject.

26 Claims, 117 Drawing Sheets

(56) References Cited

OTHER PUBLICATIONS

Kubota et al., "Amino Acid Profiles Correlate Diagnostically with Organ Site in Three Kinds of Malignant Tumors," Cancer, May 1, 1992, 69(9):2343-2348.

Park et al., "Arginine Metabolism in Benign and Malignant Disease of Breast and Colon: Evidence for Possible Inhibition of Tumor-Inflitrating Macrophages," Nutrition, May/Jun. 1991, 7(3):185-188.

Proenza et al., "Breast and lung cancer are associated with a decrease in blood cell amino acid content," Journal of Nutritional Biochemistry, 2003, 14:133-138.

Shimazaki et al., "Free amino acids in normal and tumorous tissues of human kidney, bladder, and prostate," GANN, Oct. 1974, 65:455-457.

Vissers et al., "Plasma arginine concentrations are reduced in cancer patients: evidence for arginine deficiency," Am. J. Clin. Nutr., 2005, 81:1142-1146.

Ando, Toshihiko, "Amino Index-Development of Health Check Method Based on Blood Amino Acid Concentration," Chemistry & Chemical Industry, Jan. 1, 2007, vol. 60(1), pp. 40-41, with English translation, 5 pages.

Elling et al., Freie aminosäuren im normalen und karzinomatösen Ovarialgewebe in Korrelation zum Seramspiegel-tumordiagnostische Möglichkeiten, Zent bl. Gynäkol., 1987 vol. 109, pp. 1013-1022, English abstract on first page.

Elling et al., "Therapiemonitoring bei Patientinnen mit Korpuskarzinom mit und ohne Progression durch freie Serumaminosauren," Zent bl. Gynäkol., 1989, vol. 111, pp. 1224-1230, English abstract of first page.

Evans et al., "Perturbations in Plasma Amino Acid Profiles in Small Cell Lung Cancer (SCLC) and Their Response to Treatment," Proc. Am. Association Cancer Res. Ann. Meet., Mar. 1988, vol. 29, p. 18, Section 69.

Fukasawa et al., "Serum Free Amino Acid Content in Hamsters with Cheek Pouch Carcinoma," Japanese Association for Oral Biology, 1992, vol. 34, pp. 555-559, with English translation, 10 pages.

Fukui et al., "Study on Branched Chain Amino Acid Metabolism in Last-Stage Hepatic Cancer," Journal of Clinical and Experimental Medicine, Apr. 1989, vol. 66, 4$^{th}$ Edition, pp. 1183-1187, with English translation, 16 pages.

Hirayama et al., "Plasma Amino Acid Patterns in Hepatocellular Carcinoma," Biochemical Medicine and Metabolic Biology, 1987, vol. 38(2), pp. 127-133.

Inoue, Yoshihiro, "Changes of Plasma Free Amino Acids in Hepatocellular Carcinoma: Clinical and Experimental Studies on Evaluation of Tyr/Phe Molar Ratio," Journal of the Iwate Medical Association, Jun. 1988, vol. 40, No. 3, pp. 351-361, with English translation, 20 pages.

Iwagaki et al., "Observation on the Plasma Amino Acids of Patients With Colorectal Cancer," Journal of Japan Society of Coloproctology, 1991, vol. 44(6), pp. 917-922, with English translation, 11 pages.

Kimura, Takeshi, "The Application of Amino Acid Informatics," Reports of the Research Committee of Essential Amino Acids (Japan), 2006, vol. 177, pp. 28-31, with English abstract, 1 page.

Kwon et al., "Plasma Free Amino Acids and Biochemical Parameters for Nutrition Assessment in Gastric Cancer Patients," Journal of Surgery and Metabolism/Nutrition, 2$^{nd}$ Ed, Apr. 1995, vol. 29(2), pp. 129-134, with English translation, 11 pages.

Lee et al., "Identification of Optimal Classification Functions for Biological Sample and State Discrimination from Metabolic Profiling Data," Bioinformatics, 2004, vol. 20(6), pp. 959-969.

Lee et al., "Plasma Amino Acid Levels in Patients With Colorectal Cancers and Liver Cirrhosis With Hepatocellular Carcinoma," Hepato-Gastroenterology, Sep.-Oct. 2003, vol. 50(53), pp. 1269-1273.

Murakami et al., "Changes of Amino Acids in Tumor-Bearing Rats with Total Parenteral Nutrition," JJPEN, 1987, vol. 9, No. 4, pp. 615-621, with English translation, 12 pages.

Nefyodov, et al., "Amino Acids and Their Derivatives in Blood Plasma of Patients With Breast Cancer Treated With Ukrain. Part V," Drugs Exptl. Clin. Res., 1996, vol. 22(3/4/5), pp. 155-157.

Noguchi et al., "Network Analysis of Plasma and Tissue Amino Acids and the Generation of an Amino Index for Potential Diagnostic Use," Am. J. Clin. Nutr., 2006, vol. 83(suppl), pp. 513S-519S.

Okamoto et al., "Development of New Lung Cancer Screening Method by Plasma Free Amino Acid Profile," 65$^{th}$ Annual Meeting of the Japan Cancer Association, Aug. 28, 2006, p. 287, Section 0-565, with English translation, 2 pages.

Okamoto et al., "Early Detection of Breast Cancer Using Plasma Free Amino Acid Profiles," 66$^{th}$ Annual Meeting of the Japan Cancer Association, Aug. 25, 2007, vol. 66, p. 517, Section P1210.

Okuyama, et al., "Study on Plasma Amino Acids Pattern in Liver Diseases by Using Multivariate Analysis," Journal of Liver, Gall-Bladder and Pancreas, 1987, vol. 15(1), pp. 111-117, with English translation, 1 page.

Rivera et al., "Blood Amino Acid Compartmentation in Mice Bearing Lewis Lung Carcinoma," Cancer Research, Nov. 1, 1987, vol. 47, pp. 5644-5646.

Wilson et al., "Free Serum Amino Acids in Patients With Advanced Cervical Carcinoma," Gynecologic Oncology, 1976, vol. 4, pp. 311-313.

Caballero et al., "Plasma amino acid concentrations in healthy elderly men and women," Am. J. Clin. Nutr., 1991, 53(5):1249-1252.

Vecer et al., "Tissue amino acids in patients with colorectal carcinoma," Vnitr. Lek., Apr. 1998, 44(4):192-194, Abstract.

Shangyi et al., "Preliminary Observations on Free Amino Acid Values of Plasma of Patients with Ovarian Cancer and Uterine cervix cancer," Chinese Journal of Clinical Oncology, Dec. 31, 1994, 21:94, with English abstract.

Fortunato et al., "Multivariate Discriminant Function Based on Six Biochemical Markers in Blood Can Predict the Cirrhotic Evolution of Chronic Hepatitis," Clinical Chemistry, 2001, 47(9):1696-1700.

Cascino et al., "Increased Plasma Free Tryptophan Levels in Human Cancer: A Tumor Related Effect?" Anticancer Research, 1991, 11:1313-1316.

Heber et al., "Metabolic Abnormalities in the Cancer Patient," Cancer, 1985, 55:225-229.

Lai et al., "Plasma free amino acid profile in cancer patients," Seminars in Cancer Biology, 2005, 15:267-276.

Landuyt et al., "Differential protein expression profile in gastrointestinal stromal tumors," Amino Acids, 2004 27:335-337.

Laviano et al., "Tumor-Induced Changes in Host Metabolism: A Possible Role for Free Tryptophan as a Marker of Neoplastic Disease," Developments in Tryptophan and Serotonin Metabolism, Allegri et al. Eds., 2003, 363-366.

Mellor et al., "IDO Expression by Dendritic Cells: Tolerance and Tryptophan Catabolism," Nature Reviews, Oct. 2004, 4:762-774.

Naini et al. "Preoperative and Postoperative Levels of Plasma Protein and Amino Acid in Esophageal and Lung Cancer Patients," Cancer, 1988, 62:355-360.

Norton et al., "Fasting Plasma Amino Acid Levels in Cancer Patients," Cancer, 1985, 56:1181-1186.

Rodriguez et al., "Arginase I in myeloid suppressor cells is induced by COX-2 in lung carcinoma," J. Exp. Med., Oct. 3, 2005, 202(7):931-939.

Muscaritoli et al., "Plasma Amino Acid Profile in Cancer Patients: Moving Toward a New Set of Tumor Markers?", Nutritional Support in Cancer and Transplant Patients, 2001, 107-118.

Miyake, Makoto, "Clinical Studies on the Metabolism of Plasma Amino Acids in Various Deseases," Journal of the Nagoya City University Medical Association, 1977, 28(2):308-351, with English translation.

Elling et al., "Therapy monitoring in endometrial carcinomas with and without progression by free serum amino acids," Zentralblatt fur Gynakologie, 1989, 111(18):1224-1230.

(56) References Cited

OTHER PUBLICATIONS

Elling et al., "Free amino acids in normal and ovarian cancer tissue in correlation to serum levels—tumour diagnostic possibilities," Zentralblatt fur Gynakologie, 1987, 109(16):1013-1022.

Hirai, Yoshinori, "A Study of Amino Acid Metabolism in Patients with Gastric Cancer," Journal of Japan Surgical Society, Jul. 1, 1965, 66:983-1013, with English translation.

Kwon et al., "Plasma Free Amino Acids and Various Nutritional Indices Analyzed in Relation to Growth of Gastric Cancer," Japanese Journal of Surgical Metabolism and Nutrition, Apr. 1995, 29(2):129-134, with English translation.

Hirayama et al., "Quantitative Metabolome Profiling of Colon and Stomach Cancer Microenvironment by Capillary Electophoresis Time-of-Flight Mass Spectrometry," Cancer Res., 2009, 69(11):4918-4925.

Leichtle et al., "Serum amino acid profiles and their alterations in colorectal cancer," Metabolomics, 2012, 8(4):643-653.

Qiu et al., "Serum Metabolite Profiling of Human Colorectal Cancer Using GC-TOFMS and UPLC-QTOFMS," Journal of Proteome Research, 2009, 8(10):4844-4850.

Selamnia et al., "De novo synthesis of arginine and ornithine from citrulline in human colon carcinoma cells: metabolic fate of L-ornithine," Biochimica et Biophysica Acta, 1998, 1425(1):93-102.

Tan et al., "Metabonomics Identifies Serum Metabolite Markers of Colorectal Cancer," Journal of Proteome Research, 2013, 12(6):3000-3009.

Heintzelman et al., "Characterization of the Autofluorescence of Polymorphonuclear Leukocytes, Mononuclear Leukocytes and Cervical Epithelial Cancer Cells for Improved Spectroscopic Discrimination of Inflammation from Dysplasia," Photochemistry and Photobiology, 2000, 71(3):327-332.

(BASIC PRINCIPLE OF THE INVENTION)

FIG.7

| USER ID | USER PASSWORD | NAME | ORGANIZATION ID | DEPARTMENT ID | DEPARTMENT NAME | E-MAIL ADDRESS | ... |
|---|---|---|---|---|---|---|---|
| : | : | : | : | : | : | : | : |

| INDIVIDUAL (SAMPLE) NO. | AMINO ACID CONCENTRATION DATA | | | | | |
|---|---|---|---|---|---|---|
| | Gly | Leu | Val | Ile | Phe | ... |
| U-1 | 9.5 | 11.2 | 2.7 | 8.5 | 4.9 | ... |
| U-2 | 8.5 | 10.5 | 3.9 | 9.8 | 6.1 | ... |
| : | : | : | : | : | : | : |

FIG.9

| INDIVIDUAL (SAMPLE) NO. | PROSTATIC DISEASE STATE INDEX DATA (T) | | | | AMINO ACID CONCENTRATION DATA | | | | | |
|---|---|---|---|---|---|---|---|---|---|---|
| | $T_1$ | $T_2$ | $T_3$ | ... | Gly | Leu | Val | Ile | Phe | ... |
| A-1 | 23.4 | 62.5 | 37.1 | ... | 9.5 | 11.2 | 2.7 | 8.5 | 4.9 | ... |
| A-2 | 27.5 | 66.1 | 39.5 | ... | 8.5 | 10.5 | 3.9 | 9.8 | 6.1 | ... |
| ... | | | | | | | | | | |

| INDIVIDUAL (SAMPLE) NO. | PROSTATIC DISEASE STATE INDEX DATA (T) | AMINO ACID CONCENTRATION DATA | | | |
|---|---|---|---|---|---|
| | $T_2$ | Gly | Leu | Phe | ... |
| A-1 | 62.5 | 9.5 | 11.2 | 4.9 | ... |
| A-2 | 66.1 | 8.5 | 10.5 | 6.1 | ... |
| ⋮ | ⋮ | ⋮ | ⋮ | ⋮ | ⋮ |

| RANK | CANDIDATE MULTIVARIATE DISCRIMINANT |
|---|---|
| 1 | $F_1$(Gly, Leu, Phe, ...) |
| 2 | $F_2$(Gly, Leu, Phe, ...) |
| 3 | $F_3$(Gly, Leu, Phe, ...) |
| ⋮ | ⋮ |

| RANK | CANDIDATE MULTIVARIATE DISCRIMINANT | VERIFICATION RESULT |
|---|---|---|
| 1 | $F_k$(Gly, Leu, Phe, ⋯) | 1.22 |
| 2 | $F_m$(Gly, Leu, Phe, ⋯) | 2.28 |
| 3 | $F_l$(Gly, Leu, Phe, ⋯) | 2.95 |
| ⋮ | ⋮ | ⋮ |

| INDIVIDUAL (SAMPLE) NO. | PROSTATIC DISEASE STATE INDEX DATA (T) | AMINO ACID CONCENTRATION DATA | |
|---|---|---|---|
| | $T_2$ | Leu | Phe ⋯ |
| A-1 | 62.5 | 11.2 | 4.9 ⋯ |
| A-2 | 66.1 | 10.5 | 6.1 ⋯ |
| ⋮ | ⋮ | ⋮ | ⋮ |

| RANK | MULTIVARIATE DISCRIMINANT | THRESHOLD VALUE | VERIFICATION RESULT |
|---|---|---|---|
| 1 | $F_p$(Phe, ⋯) | 0.23 | 0.62 |
| 2 | $F_p$(Gly, Leu, Phe) | -2.12 | 1.02 |
| 3 | $F_k$(Gly, Leu, Phe, ⋯) | 1.23 | 1.22 |
| ⋮ | ⋮ | ⋮ | ⋮ |

| INDIVIDUAL (SAMPLE) NO. | RANK | DISCRIMINANT VALUE |
|---|---|---|
| U-1 | 1 | 1.13 |
| ⋮ | ⋮ | ⋮ |

| INDIVIDUAL (SAMPLE) NO. | AMINO ACID CONCENTRATION DATA | | | | DISCRIMINANT VALUE | EVALUATION RESULT |
|---|---|---|---|---|---|---|
| | Gly | Leu | Phe | ... | | |
| U-1 | 9.5 | 11.2 | 4.9 | ... | | |
| U-2 | 8.5 | 10.5 | 6.1 | ... | | |
| ⋮ | ⋮ | ⋮ | ⋮ | ⋮ | | |

| No. | Formula | ROC_AUC |
|---|---|---|
| 1 | 0.2414(Tau)/(Trp)-0.02828(Thr)/(Ser)-0.002079(Glu)/(Asn)+2.126(Orn)/(Gln)+0.7159 | 0.9415 |
| 2 | 0.242(Tau)/(Trp)-0.02872(Thr)/(Ser)-0.004713(Asn)/(Glu)+2.099(Orn)/(Gln)+0.724 | 0.9414 |
| 3 | 0.2416(Tau)/(Trp)-0.01681(Thr)/(Asn)-0.005108(Glu)/(Ser)+2.143(Orn)/(Gln)+0.7275 | 0.9381 |
| 4 | 0.2418(Tau)/(Trp)+0.111(Asn)/(Thr)-0.005692(Glu)/(Ser)+2.136(Orn)/(Gln)+0.6399 | 0.9387 |
| 5 | 0.2422(Tau)/(Trp)+0.01399(Ser)/(Thr)-0.00188(Glu)/(Asn)+2.111(Orn)/(Gln)+0.6732 | 0.9406 |
| 6 | 0.2428(Tau)/(Trp)+0.01437(Ser)/(Thr)-0.004612(Asn)/(Glu)+2.085(Orn)/(Gln)+0.6804 | 0.9400 |
| 7 | 0.2438(Tau)/(Trp)+0.05608(Asn)/(Ser)+0.005348(Glu)/(Thr)+2.086(Orn)/(Gln)+0.6616 | 0.9376 |
| 8 | 0.2431(Tau)/(Trp)-0.00328(Ser)/(Glu)+0.1149(Asn)/(Thr)+2.09(Orn)/(Gln)+0.6519 | 0.9370 |
| 9 | 0.2429(Tau)/(Trp)-0.01761(Thr)/(Asn)-0.003299(Ser)/(Glu)+2.098(Orn)/(Gln)+0.7433 | 0.9365 |
| 10 | 0.2442(Tau)/(Trp)-0.003684(Thr)/(Glu)+0.05755(Asn)/(Ser)+2.062(Orn)/(Gln)+0.6788 | 0.9364 |
| 11 | 2.407(Tau)/(Gln)-0.03011(Thr)/(Ser)-0.001526(Glu)/(Asn)+0.2764(Orn)/(Trp)+0.6668 | 0.9331 |
| 12 | 0.2438(Tau)/(Trp)-0.008281(Ser)/(Asn)+0.00606(Glu)/(Thr)+2.087(Orn)/(Gln)+0.7051 | 0.9383 |
| 13 | 2.397(Tau)/(Gln)-0.03084(Thr)/(Ser)-0.004183(Asn)/(Glu)+0.2768(Orn)/(Trp)+0.6736 | 0.9324 |
| 14 | 0.2491(Tau)/(Trp)-0.02153(Thr)/(Ser)+0.003592(Glu)/(Asn)-0.01219(Gln)/(Orn)+1.032 | 0.9380 |
| 15 | 2.405(Tau)/(Gln)+0.01719(Ser)/(Thr)-0.001476(Glu)/(Asn)+0.2768(Orn)/(Trp)+0.6182 | 0.9322 |
| 16 | 2.394(Tau)/(Gln)+0.01787(Ser)/(Thr)-0.004047(Glu)/(Asn)+0.2772(Orn)/(Trp)+0.6233 | 0.9312 |
| 17 | 2.403(Tau)/(Gln)+0.1213(Asn)/(Thr)-0.002447(Glu)/(Ser)+0.2786(Orn)/(Trp)+0.5837 | 0.9314 |
| 18 | 2.401(Tau)/(Gln)-0.01879(Thr)/(Asn)-0.00149(Glu)/(Ser)+0.2791(Orn)/(Trp)+0.6806 | 0.9305 |
| 19 | -0.04406(Thr)/(Ser)+0.005207(Glu)/(Asn)-0.0178(Gln)/(Tau)+0.2986(Orn)/(Trp)+1.089 | 0.9306 |
| 20 | 0.2443(Tau)/(Trp)-0.003692(Thr)/(Glu)-0.008576(Ser)/(Asn)+2.063(Orn)/(Gln)+0.7239 | 0.9367 |
| 21 | -0.04516(Thr)/(Ser)-0.006092(Asn)/(Glu)-0.01775(Gln)/(Tau)+0.2987(Orn)/(Trp)+1.104 | 0.9306 |
| 22 | -0.0456(Thr)/(Ser)+0.006685(Glu)/(Asn)-0.019(Gln)/(Tau)-0.1499(Trp)/(Orn)+1.546 | 0.9353 |
| 23 | -0.04693(Thr)/(Ser)-0.007475(Asn)/(Glu)-0.01894(Gln)/(Tau)-0.1503(Trp)/(Orn)+1.565 | 0.9353 |
| 24 | 0.2493(Tau)/(Trp)-0.01296(Thr)/(Asn)+0.006516(Glu)/(Ser)-0.01229(Gln)/(Orn)+1.045 | 0.9367 |
| 25 | 0.2493(Tau)/(Trp)+0.09405(Asn)/(Thr)+0.006137(Glu)/(Ser)-0.01228(Gln)/(Orn)+0.973 | 0.9373 |
| 26 | 0.03023(Ser)/(Thr)-0.005939(Asn)/(Glu)-0.01765(Gln)/(Tau)+0.2993(Orn)/(Trp)+1.025 | 0.9296 |
| 27 | 0.02923(Ser)/(Thr)+0.005288(Glu)/(Asn)-0.0177(Gln)/(Tau)+0.2992(Orn)/(Trp)+1.013 | 0.9298 |
| 28 | 0.2497(Tau)/(Trp)+0.009025(Ser)/(Thr)+0.003741(Glu)/(Asn)-0.0121(Gln)/(Orn)+0.9993 | 0.9357 |
| 29 | 0.1159(Asn)/(Thr)+0.005943(Glu)/(Ser)-0.01759(Gln)/(Tau)+0.3011(Orn)/(Trp)+0.9935 | 0.9286 |
| 30 | -0.01908(Thr)/(Asn)+0.007023(Glu)/(Ser)-0.0176(Gln)/(Tau)+0.3017(Orn)/(Trp)+1.089 | 0.9285 |
| 31 | 0.2494(Tau)/(Trp)-0.02232(Thr)/(Ser)-0.005605(Asn)/(Glu)-0.01205(Gln)/(Orn)+1.043 | 0.9360 |
| 32 | 2.396(Tau)/(Gln)+0.06063(Asn)/(Ser)+0.009368(Glu)/(Thr)+0.2786(Orn)/(Trp)+0.6054 | 0.9291 |
| 33 | 2.382(Tau)/(Gln)-0.01981(Thr)/(Asn)-0.003165(Ser)/(Glu)+0.2802(Orn)/(Trp)+0.6955 | 0.9295 |
| 34 | 0.03259(Ser)/(Thr)+0.006776(Glu)/(Asn)-0.01891(Gln)/(Tau)-0.1504(Trp)/(Orn)+1.466 | 0.9346 |
| 35 | 2.384(Tau)/(Gln)-0.00312(Ser)/(Glu)+0.1262(Asn)/(Thr)+0.2797(Orn)/(Trp)+0.5936 | 0.9295 |
| 36 | 0.2508(Tau)/(Trp)+0.05058(Asn)/(Ser)+0.01606(Glu)/(Thr)-0.01199(Gln)/(Orn)+0.9829 | 0.9345 |
| 37 | 0.03383(Ser)/(Thr)-0.007344(Asn)/(Glu)-0.01885(Gln)/(Tau)-0.1509(Trp)/(Orn)+1.482 | 0.9345 |
| 38 | -0.02005(Thr)/(Asn)-0.003495(Ser)/(Glu)-0.01745(Gln)/(Tau)+0.3024(Orn)/(Trp)+1.104 | 0.9273 |
| 39 | 0.2407(Tau)/(Trp)+0.5125(Ser)/(Gln)+0.0007879(Glu)/(Asn)+0.2844(Orn)/(Thr)+0.6371 | 0.9335 |
| 40 | -0.01796(Thr)/(Asn)+0.00783(Glu)/(Ser)-0.01881(Gln)/(Tau)-0.152(Trp)/(Orn)+1.548 | 0.9329 |
| 41 | -0.003439(Ser)/(Glu)+0.1207(Asn)/(Thr)-0.01744(Gln)/(Tau)+0.3018(Orn)/(Trp)+1.004 | 0.9277 |
| 42 | 0.3442(Tau)/(Thr)+0.5069(Ser)/(Gln)+9.88e-05(Glu)/(Asn)+0.2844(Orn)/(Trp)+0.5738 | 0.9251 |
| 43 | 2.611(Tau)/(Gln)-0.03064(Thr)/(Ser)-0.0008109(Glu)/(Asn)-0.1395(Trp)/(Orn)+1.059 | 0.9325 |
| 44 | 0.1101(Asn)/(Thr)+0.006804(Glu)/(Ser)-0.01881(Gln)/(Tau)-0.1516(Trp)/(Orn)+1.457 | 0.9331 |
| 45 | 2.599(Tau)/(Gln)-0.03155(Thr)/(Ser)-0.005258(Asn)/(Glu)-0.1401(Trp)/(Orn)+1.07 | 0.9312 |
| 46 | -0.01909(Thr)/(Asn)-0.00396(Ser)/(Glu)-0.01865(Gln)/(Tau)-0.1531(Trp)/(Orn)+1.568 | 0.9317 |
| 47 | 0.25(Tau)/(Trp)+0.009724(Ser)/(Thr)-0.005517(Asn)/(Glu)-0.01197(Gln)/(Orn)+1.009 | 0.9343 |
| 48 | 2.379(Tau)/(Gln)-0.003606(Thr)/(Glu)+0.06196(Asn)/(Ser)+0.2796(Orn)/(Trp)+0.6225 | 0.9300 |
| 49 | -0.004247(Thr)/(Glu)+0.02223(Asn)/(Ser)-0.01743(Gln)/(Tau)+0.301(Orn)/(Trp)+1.049 | 0.9273 |
| 50 | 0.3422(Tau)/(Thr)+0.5159(Ser)/(Gln)-0.005021(Asn)/(Glu)+0.2846(Orn)/(Trp)+0.5809 | 0.9240 |

FIG.25

| No. | Formula | ROC_AUC |
|---|---|---|
| 51 | 'Ala/Trp-1.4591*Thr/Orn' | 0.8806 |
| 52 | 'Ala/Trp-6.3918*Met/Orn' | 0.8778 |
| 53 | 'Ala/Trp+7.8443*Orn/Arg' | 0.8749 |
| 54 | 'Ala/Trp-0.30491*Gln/Orn' | 0.8730 |
| 55 | 'Orn/Trp+0.10436*Ala/Ile' | 0.8724 |
| 56 | 'Ala/Trp-1.8107*Tyr/Orn' | 0.8721 |
| 57 | 'Ala/Trp-2.6565*Ile/Orn' | 0.8707 |
| 58 | 'Ala/Trp-1.5809*Leu/Orn' | 0.8696 |
| 59 | 'Orn/Trp+0.19353*Ala/Leu' | 0.8677 |
| 60 | 'Ala/Trp-2.6674*Phe/Orn' | 0.8670 |
| 61 | 'Ala/Trp-0.74343*Val/Orn' | 0.8668 |
| 62 | 'Ala/Trp-3.1395*Asn/Orn' | 0.8659 |
| 63 | 'Ala/Trp-1.9974*His/Orn' | 0.8659 |
| 64 | 'Ala/Trp+0.090345*Orn' | 0.8644 |
| 65 | 'Orn/Trp+0.030913*Ala/Met' | 0.8644 |
| 66 | 'Orn/Ile+0.15906*Ala/Trp' | 0.8641 |
| 67 | 'Ala/Trp-1.2549*Ser/Orn' | 0.8640 |
| 68 | 'Ala/Trp-0.8113*Pro/Orn' | 0.8640 |
| 69 | 'Orn/Trp+0.0014013*Ala' | 0.8622 |
| 70 | 'Ala/Trp-0.59737*Gly/Orn' | 0.8621 |
| 71 | 'Orn/Leu+0.076832*Ala/Trp' | 0.8619 |
| 72 | 'Ala/Trp+1.0933*Lys/Arg' | 0.8613 |
| 73 | 'Orn/Trp+0.36053*Ala/Val' | 0.8603 |
| 74 | 'Orn/Phe+0.16858*Ala/Trp' | 0.8598 |
| 75 | 'Orn/Trp-0.26803*Gln/Ala' | 0.8596 |
| 76 | 'Orn/Trp+0.11203*Ala/Arg' | 0.8587 |
| 77 | 'Ala/Trp-4.9121*Cit/Orn' | 0.8581 |
| 78 | 'Orn/Trp-1.3194*Thr/Ala' | 0.8575 |
| 79 | 'Orn/Trp+0.084673*Ala/Phe' | 0.8574 |
| 80 | 'Ala/Trp+5.1651*ABA/Ile' | 0.8553 |
| 81 | 'Ala/Trp+9.8826*Cit/Arg' | 0.8536 |
| 82 | 'Ala/Trp+1.5011*Ser/Arg' | 0.8532 |
| 83 | 'Ala/Trp+8.8269*ABA/Leu' | 0.8519 |
| 84 | 'Ala/Trp-1.3696*Glu/Orn' | 0.8513 |
| 85 | 'Orn/Trp+0.09274*Ala/His' | 0.8511 |
| 86 | 'Ala/Trp+17.5548*Orn/Lys' | 0.8495 |
| 87 | 'Ala/Trp-4.6874*His/Lys' | 0.8475 |
| 88 | 'Ala/Trp-0.64003*Gln/Lys' | 0.8449 |
| 89 | 'Orn/Trp-1.069*Ser/Ala' | 0.8447 |
| 90 | 'Orn/Trp-0.54403*Gly/Ala' | 0.8440 |
| 91 | 'Orn/Trp+0.21537*Ala/Lys' | 0.8439 |
| 92 | 'Orn/Trp+0.71529*ABA/Ile' | 0.8417 |
| 93 | 'Orn/Trp+1.31*ABA/Leu' | 0.8414 |
| 94 | 'Orn/Trp-0.70924*Pro/Ala' | 0.8409 |
| 95 | 'Orn/Trp-2.6882*Asn/Ala' | 0.8407 |
| 96 | 'Ala/Trp+1.0909*Ser/Ile' | 0.8403 |
| 97 | 'Ala/Trp-0.055984*Gln/Cit' | 0.8399 |
| 98 | 'Orn/Trp-0.0049721*Gln/ABA' | 0.8394 |
| 99 | 'Orn/Trp+0.058435*Ala/Tyr' | 0.8391 |
| 100 | 'Lys/Ile+0.32756*Pro/Met' | 0.7795 |

FIG.27

| No | Formula | ROC_AUC |
|---|---|---|
| 1 | [−8.9866]+[0.0522]Tau+[−0.0109]Thr+[0.0130]Ala+[0.0818]ABA+[−0.1097]Trp+[0.0788]Orn | 0.9481 |
| 2 | [−9.1310]+[0.0519]Tau+[0.0128]Ala+[0.0799]ABA+[−0.0077]Leu+[−0.1050]Trp+[0.0748]Orn | 0.9468 |
| 3 | [−7.7244]+[0.0525]Tau+[−0.0036]Gln+[0.0125]Ala+[0.0808]ABA+[−0.1078]Trp+[0.0759]Orn | 0.9468 |
| 4 | [−8.9978]+[0.0514]Tau+[0.0134]Ala+[0.0786]ABA+[−0.0231]Ile+[−0.1032]Trp+[0.0778]Orn | 0.9468 |
| 5 | [−3.8518]+[0.0584]Tau+[−0.0041]Gln+[0.0680]ABA+[−0.0024]Leu+[−0.0767]Trp+[0.0730]Orn | 0.9459 |
| 6 | [−3.7119]+[0.0589]Tau+[−0.0043]Thr+[−0.0041]Gln+[0.0672]ABA+[−0.0777]Trp+[0.0748]Orn | 0.9454 |
| 7 | [−9.1259]+[0.0510]Tau+[0.0132]Ala+[0.0834]ABA+[−0.0435]Met+[−0.1079]Trp+[0.0783]Orn | 0.9452 |
| 8 | [−3.8711]+[0.0586]Tau+[−0.0041]Gln+[0.0669]ABA+[−0.0005]Val+[−0.0785]Trp+[0.0730]Orn | 0.945 |
| 9 | [−4.0246]+[0.0588]Tau+[−0.0041]Gln+[0.0009]Pro+[0.0657]ABA+[−0.0794]Trp+[0.0724]Orn | 0.9449 |
| 10 | [−4.0165]+[0.0587]Tau+[−0.0042]Gln+[0.0006]Gly+[0.0659]ABA+[−0.0791]Trp+[0.0725]Orn | 0.9449 |
| 11 | [−9.5832]+[0.0531]Tau+[0.0003]Ser+[0.0127]Ala+[0.0750]ABA+[−0.1125]Trp+[0.0744]Orn | 0.9448 |
| 12 | [−4.0737]+[0.0594]Tau+[−0.0043]Gln+[0.0646]ABA+[0.0140]Met+[−0.0809]Trp+[0.0718]Orn | 0.9447 |
| 13 | [−9.5542]+[0.0531]Tau+[0.0127]Ala+[0.0752]ABA+[−0.1125]Trp+[0.0745]Orn | 0.9447 |
| 14 | [−9.0413]+[0.0517]Tau+[0.0128]Ala+[0.0809]ABA+[−0.0031]Val+[−0.1087]Trp+[0.0744]Orn | 0.9446 |
| 15 | [−3.6513]+[0.0578]Tau+[−0.0040]Gln+[0.0691]ABA+[−0.0110]Ile+[−0.0737]Trp+[0.0742]Orn | 0.9446 |
| 16 | [−3.9427]+[0.0588]Tau+[−0.0041]Gln+[0.0661]ABA+[−0.0792]Trp+[0.0729]Orn | 0.9445 |
| 17 | [−9.2446]+[0.0526]Tau+[0.0127]Ala+[0.0775]ABA+[−0.0046]His+[−0.1119]Trp+[0.0744]Orn | 0.9443 |
| 18 | [−9.5888]+[0.0530]Tau+[0.0026]Glu+[0.0126]Ala+[0.0764]ABA+[−0.1130]Trp+[0.0745]Orn | 0.9443 |
| 19 | [−4.5324]+[0.0593]Tau+[0.0081]Ser+[−0.0044]Gln+[0.0627]ABA+[−0.0799]Trp+[0.0718]Orn | 0.9443 |
| 20 | [−4.1478]+[0.0590]Tau+[−0.0042]Gln+[0.0654]ABA+[0.0032]His+[−0.0796]Trp+[0.0730]Orn | 0.944 |
| 21 | [−9.2565]+[0.0529]Tau+[−0.0015]Gly+[0.0127]Ala+[0.0758]ABA+[−0.1128]Trp+[0.0752]Orn | 0.944 |
| 22 | [−3.4408]+[0.0589]Tau+[−0.0039]Gln+[0.0661]ABA+[−0.0768]Trp+[0.0745]Orn+[−0.0085]Arg | 0.9437 |
| 23 | [−8.3070]+[0.0526]Tau+[0.0124]Ala+[−0.0874]Cit+[0.0903]ABA+[−0.1216]Trp+[0.0900]Orn | 0.9432 |
| 24 | [−8.9923]+[0.0520]Tau+[−0.0098]Pro+[0.0142]Ala+[0.0844]ABA+[−0.1153]Trp+[0.0811]Orn | 0.943 |
| 25 | [−9.8558]+[0.0536]Tau+[0.0126]Ala+[0.0743]ABA+[0.0078]Phe+[−0.1157]Trp+[0.0743]Orn | 0.9426 |
| 26 | [−9.9476]+[0.0532]Tau+[0.0126]Ala+[0.0732]ABA+[−0.1166]Trp+[0.0723]Orn+[0.0038]Lys | 0.9419 |
| 27 | [−5.7412]+[0.0585]Tau+[0.0081]Ser+[0.0563]ABA+[−0.0791]Trp+[0.0704]Orn+[−0.0125]Arg | 0.9419 |
| 28 | [−9.6876]+[0.0534]Tau+[0.0124]Ala+[0.0733]ABA+[0.0061]Tyr+[−0.1154]Trp+[0.0741]Orn | 0.9417 |
| 29 | [−9.8554]+[0.0531]Tau+[0.0142]Asn+[0.0123]Ala+[0.0716]ABA+[−0.1136]Trp+[0.0733]Orn | 0.9413 |
| 30 | [−5.8890]+[0.0514]Tau+[−0.0029]Gln+[0.0132]Ala+[−0.0968]Trp+[0.0784]Orn+[−0.0177]Arg | 0.9406 |
| 31 | [−7.5284]+[0.0516]Tau+[0.0134]Ala+[0.0025]His+[−0.1011]Trp+[0.0775]Orn+[−0.0191]Arg | 0.9403 |
| 32 | [−5.2980]+[0.0586]Tau+[0.0583]ABA+[0.0204]Met+[−0.0809]Trp+[0.0700]Orn+[−0.0126]Arg | 0.9403 |
| 33 | [−5.3047]+[0.0569]Tau+[−0.0060]Thr+[0.0662]ABA+[−0.0053]Leu+[−0.0739]Trp+[0.0721]Orn | 0.9403 |
| 34 | [−7.2974]+[0.0514]Tau+[−0.0011]Thr+[0.0134]Ala+[−0.1004]Trp+[0.0777]Orn+[−0.0186]Arg | 0.9402 |
| 35 | [−4.6397]+[0.0607]Tau+[−0.0046]Gln+[0.0662]ABA+[0.0228]Phe+[−0.0887]Trp+[0.0731]Orn | 0.94 |
| 36 | [−7.3401]+[0.0514]Tau+[0.0134]Ala+[−0.1006]Trp+[0.0774]Orn+[−0.0190]Arg | 0.94 |
| 37 | [−7.1795]+[0.0514]Tau+[−0.0088]Glu+[0.0138]Ala+[−0.0996]Trp+[0.0779]Orn+[−0.0203]Arg | 0.9399 |
| 38 | [−8.2375]+[0.0521]Tau+[0.0114]Ser+[0.0134]Ala+[−0.1011]Trp+[0.0773]Orn+[−0.0225]Arg | 0.9398 |
| 39 | [−7.3138]+[0.0513]Tau+[0.0134]Ala+[−0.0037]Met+[−0.1002]Trp+[0.0776]Orn+[−0.0187]Arg | 0.9397 |
| 40 | [−7.4717]+[0.0515]Tau+[0.0007]Gly+[0.0134]Ala+[−0.1005]Trp+[0.0771]Orn+[−0.0193]Arg | 0.9396 |
| 41 | [−7.1855]+[0.0510]Tau+[0.0134]Ala+[−0.0008]Val+[−0.0994]Trp+[0.0773]Orn+[−0.0190]Arg | 0.9394 |
| 42 | [−4.4325]+[0.0590]Tau+[0.0137]Glu+[−0.0038]Gln+[0.0699]ABA+[−0.0832]Trp+[0.0726]Orn | 0.9394 |
| 43 | [−5.2063]+[0.0579]Tau+[0.0007]Pro+[0.0600]ABA+[−0.0789]Trp+[0.0707]Orn+[−0.0106]Arg | 0.9394 |
| 44 | [−5.1094]+[0.0578]Tau+[−0.0010]Thr+[0.0606]ABA+[−0.0785]Trp+[0.0713]Orn+[−0.0101]Arg | 0.9393 |
| 45 | [−7.8341]+[0.0525]Tau+[0.0134]Ala+[0.0137]Phe+[−0.1061]Trp+[0.0770]Orn+[−0.0199]Arg | 0.9393 |
| 46 | [−8.0450]+[0.0516]Tau+[0.0134]Ala+[−0.1088]Trp+[0.0732]Orn+[0.0080]Lys+[−0.0218]Arg | 0.9392 |
| 47 | [−5.6617]+[0.0580]Tau+[−0.0058]Thr+[0.0605]ABA+[0.0066]Met+[−0.0804]Trp+[0.0710]Orn | 0.9392 |
| 48 | [−4.6036]+[0.0594]Tau+[−0.0045]Gln+[0.0626]ABA+[−0.0877]Trp+[0.0692]Orn+[0.0076]Lys | 0.9391 |
| 49 | [−6.0997]+[0.0584]Tau+[−0.0073]Thr+[0.0068]Ser+[0.0583]ABA+[−0.0797]Trp+[0.0710]Orn | 0.9391 |
| 50 | [−6.0733]+[0.0574]Tau+[0.0047]Ser+[0.0608]ABA+[−0.0051]Leu+[−0.0770]Trp+[0.0690]Orn | 0.939 |

FIG.28

| No | Formula | ROC_AUC |
|---|---|---|
| 51 | '-3.3455+0.012115*Ala-0.029973*Ile-0.10073*Trp+0.068742*Orn' | 0.8684 |
| 52 | '-4.5121+0.019528*Asn+0.010676*Ala-0.11463*Trp+0.063502*Orn' | 0.8613 |
| 53 | '-3.4022-0.0086175*Pro+0.012354*Ala-0.11251*Trp+0.068866*Orn' | 0.8663 |
| 54 | '-2.3565-0.0031756*Gln+0.011052*Ala-0.10737*Trp+0.064868*Orn' | 0.8685 |
| 55 | '-3.0918+0.011399*Ala-0.0061014*Val-0.10361*Trp+0.064991*Orn' | 0.8660 |
| 56 | '-3.2958+0.011171*Ala-0.01086*His-0.10992*Trp+0.064502*Orn' | 0.8643 |
| 57 | '-3.2432+0.010959*Ala-0.044651*Cit-0.1157*Trp+0.071532*Orn' | 0.8671 |
| 58 | '-3.5034+0.011676*Ala-0.053713*Met-0.10469*Trp+0.06924*Orn' | 0.8730 |
| 59 | '-3.4505+0.01138*Ala-0.01071*Leu-0.10153*Trp+0.064996*Orn' | 0.8694 |
| 60 | '-4.008+0.011052*Ala-0.11195*Trp+0.064645*Orn' | 0.8648 |
| 61 | '-4.3139+0.0034335*Ser+0.010985*Ala-0.11238*Trp+0.064368*Orn' | 0.8649 |
| 62 | '-3.711-0.0015035*Gly+0.011077*Ala-0.11193*Trp+0.06517*Orn' | 0.8657 |
| 63 | '-3.7458+0.011104*Ala-0.0074223*Phe-0.10903*Trp+0.064854*Orn' | 0.8651 |
| 64 | '-4.3209+0.010967*Ala-0.11506*Trp+0.062557*Orn+0.0030588*Lys' | 0.8675 |
| 65 | '-4.0122+0.011043*Ala+0.00019376*Tyr-0.11206*Trp+0.064629*Orn' | 0.8647 |
| 66 | '-4.0044-0.00070458*Glu+0.011083*Ala-0.11186*Trp+0.064689*Orn' | 0.8651 |
| 67 | '-3.5827-0.0080727*Thr+0.011292*Ala-0.10874*Trp+0.067538*Orn' | 0.8703 |
| 68 | '-1.296+0.041882*Asn-0.063846*Cit-0.10069*Trp+0.072123*Orn' | 0.8160 |
| 69 | '-3.2476+0.011919*Ala-0.10631*Trp+0.06859*Orn-0.016356*Arg' | 0.8801 |
| 70 | '-4.7742+0.01127*Ala+0.046186*ABA-0.11548*Trp+0.065743*Orn' | 0.8784 |
| 71 | '-0.4354+0.042546*Asn-0.0038585*Gln-0.089399*Trp+0.06345*Orn' | 0.8181 |
| 72 | '-1.5984+0.042792*Asn-0.02283*Ile-0.086312*Trp+0.065665*Orn' | 0.8133 |
| 73 | '-2.5416+0.039725*Asn+0.016563*Glu-0.098372*Trp+0.060782*Orn' | 0.8169 |
| 74 | '0.35434-0.048423*Cit-0.017012*Ile-0.084288*Trp+0.073523*Orn' | 0.8118 |
| 75 | '-1.8344+0.046951*Asn-0.051995*Met-0.087448*Trp+0.065831*Orn' | 0.8145 |
| 76 | '-1.71+0.03796*Asn-0.0025811*Gly-0.094318*Trp+0.063475*Orn' | 0.8093 |
| 77 | '-1.774-0.0090847*Thr+0.042012*Asn-0.091082*Trp+0.065193*Orn' | 0.8129 |
| 78 | '-1.4651+0.048419*Asn-0.089701*Trp+0.064911*Orn-0.016213*Arg' | 0.8220 |
| 79 | '-0.60051+0.016628*Glu-0.022049*Ile-0.081503*Trp+0.06609*Orn' | 0.8142 |
| 80 | '-2.7045+0.036313*Asn-0.10039*Trp+0.058966*Orn+0.0051786*Lys' | 0.8157 |
| 81 | '-1.6653+0.036655*Asn-0.0069469*His-0.093095*Trp+0.06205*Orn' | 0.8136 |
| 82 | '-0.59006-0.050381*Cit+0.013524*Tyr-0.10065*Trp+0.070104*Orn' | 0.8159 |
| 83 | '-1.5215+0.037197*Asn-0.0039976*Val-0.088638*Trp+0.062689*Orn' | 0.8126 |
| 84 | '-1.6581+0.038915*Asn-0.0091185*Leu-0.085737*Trp+0.062509*Orn' | 0.8113 |
| 85 | '-2.1155+0.035965*Asn-0.094516*Trp+0.062178*Orn' | 0.8131 |
| 86 | '-0.17965-0.050748*Cit-0.091986*Trp+0.071916*Orn' | 0.8131 |
| 87 | '-2.2334+0.03158*Asn+0.0076976*Tyr-0.0983*Trp+0.061458*Orn' | 0.8116 |
| 88 | '-0.44647+0.0088071*Glu-0.045795*Cit-0.092965*Trp+0.070588*Orn' | 0.8132 |
| 89 | '0.36575-0.050918*Cit-0.003443*Val-0.08655*Trp+0.072309*Orn' | 0.8125 |
| 90 | '-0.74206-0.048808*Cit-0.097143*Trp+0.068886*Orn+0.00472*Lys' | 0.8125 |
| 91 | '-1.9881+0.036622*Asn-0.0012888*Pro-0.094356*Trp+0.062752*Orn' | 0.8114 |
| 92 | '0.85091-0.0025706*Gln-0.03786*Cit-0.086359*Trp+0.070985*Orn' | 0.8149 |
| 93 | '-1.8696+0.038403*Asn-0.0084617*Phe-0.091463*Trp+0.06213*Orn' | 0.8122 |
| 94 | '-0.3621-0.052624*Cit+0.0058262*Phe-0.094716*Trp+0.072165*Orn' | 0.8113 |
| 95 | '-0.012445-0.049916*Cit-0.0026757*His-0.091296*Trp+0.071747*Orn' | 0.8128 |
| 96 | '1.0705-0.0030191*Gln-0.017506*Ile-0.075607*Trp+0.067675*Orn' | 0.8163 |
| 97 | '-0.84889+0.0086811*Ser-0.056635*Cit-0.094728*Trp+0.071886*Orn' | 0.8142 |
| 98 | '-1.9774-0.0023061*Ser+0.037939*Asn-0.094312*Trp+0.062406*Orn' | 0.8119 |
| 99 | '-0.072607-0.0022946*Thr-0.04977*Cit-0.090693*Trp+0.072712*Orn' | 0.8116 |
| 100 | '-0.80019-0.02093*Ile+0.016296*Tyr-0.089218*Trp+0.06478*Orn' | 0.8146 |

FIG.30

| No | Formula | ROC_AUC |
|---|---|---|
| 1 | −(5.585e−01)Tau+(8.805e−02)Thr−(5.689e−02)Ala−(2.983e−01)ABA+(5.404e−01)Trp−(5.441e−01)Orn+(3.718e+01) | 0.9529 |
| 2 | −(5.716e−01)Tau+(2.764e−02)Gln−(5.696e−02)Ala−(2.461e−01)ABA+(5.624e−01)Trp−(5.408e−01)Orn+(2.770e+01) | 0.9527 |
| 3 | (5.556e−01)Tau+(6.114e−02)Ala+(3.425e−01)ABA−(1.865e−01)Ile−(4.881e−01)Trp+(5.452e−01)Orn−(3.959e+01) | 0.9518 |
| 4 | (5.608e−01)Tau+(5.595e−02)Ala+(2.890e−01)ABA−(5.558e−01)Trp+(5.378e−01)Orn−(2.725e−02)Lys−(3.929e+01) | 0.9509 |
| 5 | (5.393e−01)Tau+(5.722e−02)Ala+(2.959e−01)ABA−(2.921e−01)Met−(5.177e−01)Trp+(5.147e−01)Orn−(3.778e+01) | 0.9507 |
| 6 | (5.675e−01)Tau+(5.739e−02)Ala+(2.767e−01)ABA−(2.226e−02)Tyr−(5.700e−01)Trp+(5.221e−01)Orn−(4.223e+01) | 0.9499 |
| 7 | (5.899e−01)Tau−(2.637e−02)Gln+(6.258e−02)Ala−(5.555e−01)Trp+(5.744e−01)Orn−(9.447e−02)Arg−(1.944e+01) | 0.9499 |
| 8 | −(5.636e−01)Tau+(3.335e−02)Ser−(5.515e−02)Ala−(2.878e−01)ABA+(5.707e−01)Trp−(5.193e−01)Orn+(3.929e+01) | 0.9493 |
| 9 | (5.696e−01)Tau+(5.652e−02)Ala+(2.749e−01)ABA−(3.427e−02)Phe−(5.673e−01)Trp+(5.232e−01)Orn−(4.167e+01) | 0.9493 |
| 10 | (5.880e−01)Tau−(5.794e−02)Thr+(6.306e−02)Ala−(5.522e−01)Trp+(5.769e−01)Orn−(9.621e−02)Arg−(2.978e+01) | 0.949 |
| 11 | (5.309e−01)Tau+(4.947e−02)Ala−(3.010e−01)Cit+(2.620e−01)ABA−(5.325e−01)Trp+(5.224e−01)Orn−(3.542e+01) | 0.9489 |
| 12 | −(5.678e−01)Tau+(4.212e−03)Glu−(5.607e−02)Ala−(2.706e−01)ABA+(5.762e−01)Trp−(5.188e−01)Orn+(4.262e+01) | 0.9488 |
| 13 | (5.678e−01)Tau+(5.584e−02)Ala+(2.707e−01)ABA−(5.769e−01)Trp+(5.181e−01)Orn−(4.259e+01) | 0.9487 |
| 14 | (5.660e−01)Tau+(5.690e−02)Ala+(2.857e−01)ABA+(5.731e−02)His−(5.660e−01)Trp+(5.206e−01)Orn−(3.931e+01) | 0.9486 |
| 15 | −(5.623e−01)Tau+(2.988e−02)Pro−(6.007e−02)Ala−(2.636e−01)ABA+(5.749e−01)Trp−(5.285e−01)Orn+(3.988e+01) | 0.9486 |
| 16 | −(5.893e−01)Tau+(3.103e−02)Glu−(6.440e−02)Ala+(5.615e−01)Trp−(5.647e−01)Orn+(1.160e−01)Arg+(3.230e+01) | 0.9486 |
| 17 | (5.631e−01)Tau+(5.899e−02)Ala+(3.686e−01)ABA−(1.128e−01)Leu−(4.819e−01)Trp+(5.465e−01)Orn−(3.841e+01) | 0.9484 |
| 18 | −(5.898e−01)Tau−(8.255e−03)Ser−(6.272e−02)Ala+(5.682e−01)Trp−(5.587e−01)Orn+(1.145e−01)Arg+(3.304e+01) | 0.9484 |
| 19 | (6.172e−01)Tau−(2.719e−02)Gln+(2.507e−01)ABA−(4.772e−01)Trp+(5.724e−01)Orn−(9.023e−03)Lys−(1.373e+01) | 0.9483 |
| 20 | (5.891e−01)Tau+(6.260e−02)Ala−(5.653e−01)Trp+(5.631e−01)Orn−(4.714e−03)Lys−(1.112e−01)Arg−(3.184e+01) | 0.9483 |
| 21 | (5.899e−01)Tau+(6.293e−02)Ala−(4.749e−03)Tyr−(5.668e−01)Trp+(5.605e−01)Orn−(1.127e−01)Arg−(3.224e+01) | 0.9483 |
| 22 | −(5.905e−01)Tau−(6.281e−02)Ala+(1.046e−02)Phe+(5.653e−01)Trp−(5.612e−01)Orn+(1.126e−01)Arg+(3.204e+01) | 0.9483 |
| 23 | −(5.679e−01)Tau+(1.152e−02)Gly−(5.596e−02)Ala−(2.599e−01)ABA+(5.781e−01)Trp−(5.220e−01)Orn+(4.000e+01) | 0.9481 |
| 24 | (5.897e−01)Tau+(6.258e−02)Ala−(5.680e−01)Trp+(5.595e−01)Orn−(1.128e−01)Arg−(3.232e+01) | 0.948 |
| 25 | (6.198e−01)Tau+(2.817e−02)Gln−(6.426e−03)Gly−(2.500e−01)ABA+(4.833e−01)Trp−(5.647e−01)Orn+(1.577e+01) | 0.948 |
| 26 | −(6.198e−01)Tau+(2.749e−02)Gln−(2.460e−01)ABA+(5.657e−03)His+(4.831e−01)Trp−(5.667e−01)Orn+(1.433e+01) | 0.9479 |
| 27 | −(5.905e−01)Tau−(6.342e−02)Ala+(3.728e−02)His+(5.631e−01)Trp−(5.625e−01)Orn+(1.115e−01)Arg+(3.023e+01) | 0.9479 |
| 28 | −(5.889e−01)Tau+(6.048e−03)Gly−(6.248e−02)Ala+(5.684e−01)Trp−(5.604e−01)Orn+(1.106e−01)Arg+(3.114e+01) | 0.9478 |
| 29 | (5.577e−01)Tau+(5.972e−02)Ala+(3.619e−01)ABA−(5.431e−02)Val−(5.091e−01)Trp+(5.406e−01)Orn−(3.642e+01) | 0.9476 |
| 30 | (6.232e−01)Tau−(2.585e−02)Gln+(2.268e−01)ABA−(4.685e−01)Trp+(5.800e−01)Orn−(5.958e−02)Arg−(1.104e+01) | 0.9476 |
| 31 | −(5.826e−01)Tau−(1.608e−01)Asn−(6.011e−02)Ala+(5.636e−01)Trp−(5.463e−01)Orn+(1.225e−01)Arg+(3.673e+01) | 0.9475 |
| 32 | (6.198e−01)Tau−(2.782e−02)Gln+(2.416e−01)ABA+(2.081e−02)Met−(4.868e−01)Trp+(5.651e−01)Orn−(1.477e+01) | 0.9473 |
| 33 | (6.140e−01)Tau−(5.338e−02)Thr−(2.563e−02)Gln+(2.627e−01)ABA−(4.620e−01)Trp+(5.805e−01)Orn−(1.225e+01) | 0.9473 |
| 34 | −(5.826e−01)Tau+(3.098e−02)Pro−(6.678e−02)Ala+(5.650e−01)Trp−(5.688e−01)Orn+(1.112e−01)Arg+(2.964e+01) | 0.9472 |
| 35 | (6.198e−01)Tau−(2.758e−02)Gln+(2.445e−01)ABA−(4.842e−01)Trp+(5.664e−01)Orn−(1.463e+01) | 0.9471 |
| 36 | (5.698e−01)Tau+(5.811e−02)Ala−(2.112e−01)Cit−(5.466e−01)Trp+(5.648e−01)Orn−(9.771e−02)Arg−(2.874e+01) | 0.947 |
| 37 | −(5.884e−01)Tau+(6.798e−02)Thr+(2.722e−02)Gln−(6.025e−02)Ala+(5.553e−01)Trp−(5.800e−01)Orn+(2.075e+01) | 0.947 |
| 38 | (6.206e−01)Tau−(2.797e−02)Gln+(1.201e−02)Pro+(2.470e−01)ABA−(4.871e−01)Trp+(5.618e−01)Orn−(1.590e+01) | 0.9469 |
| 39 | (5.678e−01)Tau+(7.544e−02)Asn+(5.483e−02)Ala+(2.632e−01)ABA−(5.792e−01)Trp+(5.139e−01)Orn−(4.503e+01) | 0.9469 |
| 40 | −(6.170e−01)Tau+(2.790e−02)Gln−(2.395e−01)ABA−(3.794e−02)Phe+(4.955e−01)Trp−(5.606e−01)Orn+(1.564e+01) | 0.9466 |
| 41 | (6.191e−01)Tau−(4.950e−03)Ser−(2.734e−02)Gln+(2.473e−01)ABA−(4.836e−01)Trp+(5.665e−01)Orn−(1.430e+01) | 0.9465 |
| 42 | (6.169e−01)Tau−(2.594e−02)Gln+(3.136e−01)ABA−(7.864e−02)Leu−(4.149e−01)Trp+(5.849e−01)Orn−(1.205e+01) | 0.9464 |
| 43 | −(5.839e−01)Tau−(6.395e−02)Ala+(1.611e−01)Met+(5.474e−01)Trp−(5.645e−01)Orn+(1.033e−01)Arg+(3.068e+01) | 0.9461 |
| 44 | −(5.934e−01)Tau+(2.976e−02)Gln−(6.557e−02)Ala+(1.796e−01)Ile+(5.053e−01)Trp−(5.960e−01)Orn+(2.049e+01) | 0.946 |
| 45 | (6.142e−01)Tau−(2.722e−02)Gln+(3.066e−01)ABA−(3.709e−02)Val−(4.337e−01)Trp+(5.819e−01)Orn−(9.955e+00) | 0.9459 |
| 46 | −(5.896e−01)Tau+(2.893e−02)Gln−(5.928e−02)Ala+(5.696e−01)Trp−(5.686e−01)Orn+(1.335e−02)Lys+(2.244e+01) | 0.9458 |
| 47 | (6.144e−01)Tau−(2.721e−02)Gln+(2.942e−01)ABA−(1.287e−01)Ile−(4.181e−01)Trp+(5.864e−01)Orn−(1.192e+01) | 0.9458 |
| 48 | −(5.915e−01)Tau+(2.712e−02)Glu+(2.981e−02)Gln−(6.059e−02)Ala+(5.732e−01)Trp−(5.624e−01)Orn+(2.381e+01) | 0.9457 |
| 49 | (5.917e−01)Tau−(2.947e−02)Gln+(8.641e−04)Gly+(5.909e−02)Ala−(5.782e−01)Trp+(5.578e−01)Orn−(2.401e+01) | 0.9456 |
| 50 | −(5.858e−01)Tau+(2.847e−02)Gln+(2.550e−02)Pro−(6.257e−02)Ala+(5.762e−01)Trp−(5.653e−01)Orn+(2.207e+01) | 0.9455 |

FIG.31

| No | Formula | ROC_AUC |
|---|---|---|
| 51 | 'Gln-2.4788*Ala+22.7878*Trp-20.9258*Orn' | 0.8685 |
| 52 | 'Gln+19.7079*Trp-22.3428*Orn' | 0.8148 |
| 53 | 'Asn-0.10593*Gln-1.9358*Trp+2.0921*Orn' | 0.8176 |
| 54 | 'Gln+4.714*Ile+17.3864*Trp-23.2158*Orn' | 0.8183 |
| 55 | 'Gln+2.9674*Leu+18.0961*Trp-24.2073*Orn' | 0.8185 |
| 56 | 'Gln+1.3163*Val+17.9707*Trp-22.9832*Orn' | 0.8148 |
| 57 | 'Gln-3.0368*Tyr+19.9365*Trp-20.6359*Orn' | 0.8204 |
| 58 | 'Gln+20.4749*Trp-24.394*Orn+2.2705*Arg' | 0.8184 |
| 59 | 'Trp-1.0605*Orn' | 0.8138 |
| 60 | 'Gln-1.9853*Ala+11.1361*Ile-20.5161*Orn' | 0.8275 |
| 61 | 'Glu-0.47041*Gln-9.8409*Trp+10.6722*Orn' | 0.8168 |
| 62 | 'Gln-6.1038*ABA+20.1674*Trp-22.7945*Orn' | 0.8219 |
| 63 | 'Gln+5.9146*Cit+20.6102*Trp-24.0887*Orn' | 0.8153 |
| 64 | 'Thr+0.80981*Gln+16.2211*Trp-19.1321*Orn' | 0.8158 |
| 65 | 'Ser-0.97721*Gln-18.5076*Trp+20.8386*Orn' | 0.8162 |
| 66 | 'Ile+3.8*Trp-4.7373*Orn' | 0.8145 |
| 67 | 'Gln+0.9761*His+19.7721*Trp-22.6864*Orn' | 0.8126 |
| 68 | 'Gln-2.1476*Ala+8.1849*Leu-23.2992*Orn' | 0.8223 |
| 69 | 'Gln-0.19713*Gly+19.308*Trp-21.8708*Orn' | 0.8150 |
| 70 | 'Gln+19.7038*Trp-22.6819*Orn+0.21941*Lys' | 0.8136 |
| 71 | 'Gln+0.65789*Phe+19.6217*Trp-22.5688*Orn' | 0.8143 |
| 72 | 'Gln+0.73978*Met+19.7776*Trp-22.576*Orn' | 0.8149 |
| 73 | 'Gln-0.091244*Pro+19.6693*Trp-22.2388*Orn' | 0.8152 |
| 74 | 'Asn-2.4536*Trp+2.4884*Orn' | 0.8140 |
| 75 | 'Asn-0.55853*Ile-2.0817*Trp+2.4892*Orn' | 0.8155 |
| 76 | 'Thr-3.5744*Asn+6.2326*Trp-6.965*Orn' | 0.8138 |
| 77 | 'Cit+2.367*Trp-2.6435*Orn' | 0.8138 |
| 78 | 'Glu-7.9025*Trp+7.9379*Orn' | 0.8163 |
| 79 | 'Glu-1.4664*Ile-4.7829*Trp+5.667*Orn' | 0.8176 |
| 80 | 'Thr+10.7348*Trp-12.1456*Orn' | 0.8142 |
| 81 | 'Asn-1.0829*Met-1.5906*Trp+1.8062*Orn' | 0.8132 |
| 82 | 'ABA-2.9543*Trp+3.1272*Orn' | 0.8230 |
| 83 | 'Met+3.4979*Trp-3.9247*Orn' | 0.8146 |
| 84 | 'Asn+0.36163*Glu-2.259*Trp+2.122*Orn' | 0.8163 |
| 85 | 'His+11.5641*Trp-12.5459*Orn' | 0.8127 |
| 86 | 'Phe+9.9741*Trp-11.0599*Orn' | 0.8129 |
| 87 | 'Asn-1.143*Cit-2.2411*Trp+2.4156*Orn' | 0.8160 |
| 88 | 'ABA-0.57755*Ile-1.9902*Trp+2.5134*Orn' | 0.8263 |
| 89 | 'Trp-1.1014*Orn+0.026148*Lys' | 0.8121 |
| 90 | 'Cit+0.53088*Ile+1.9944*Trp-2.624*Orn' | 0.8143 |
| 91 | 'Thr+2.4984*Ile+9.01*Trp-12.0839*Orn' | 0.8146 |
| 92 | 'Asn-0.38328*Phe-1.9931*Trp+2.185*Orn' | 0.8123 |
| 93 | 'Ile+0.40302*His+3.6234*Trp-4.6638*Orn' | 0.8126 |
| 94 | 'Asn-0.25704*His-2.2496*Trp+2.3446*Orn' | 0.8145 |
| 95 | 'Asn+0.75255*ABA-2.5573*Trp+2.594*Orn' | 0.8229 |
| 96 | 'Met+1.2287*Ile+4.7536*Trp-6.1256*Orn' | 0.8161 |
| 97 | 'Asn-2.317*Trp+2.4761*Orn-0.084686*Lys' | 0.8111 |
| 98 | 'Leu+5.3742*Trp-6.8957*Orn-0.0050643*Lys' | 0.8119 |
| 99 | 'Ile+3.8221*Trp-4.8685*Orn+0.0688*Lys' | 0.8143 |
| 100 | 'Ile+0.11892*Phe+3.835*Trp-4.8318*Orn' | 0.8153 |

FIG.34

| No. | Formula | ROC_AUC |
|---|---|---|
| 1 | 0.1869(Tau)/(Met)+0.1294(Ser)/(Cit)+0.2471(Asn)/(Thr)-0.7528(Glu)/(Pro)+0.4988 | 0.9689 |
| 2 | 0.186(Tau)/(Met)-0.03501(Thr)/(Asn)+0.1297(Ser)/(Cit)-0.7567(Glu)/(Pro)+0.6909 | 0.9689 |
| 3 | 0.2839(Tau)/(Asn)+0.03386(Thr)/(ABA)+0.1358(Ser)/(Cit)-0.7382(Glu)/(Pro)+0.391 | 0.9689 |
| 4 | 0.1212(Tau)/(ABA)+0.1287(Ser)/(Cit)-0.3711(Glu)/(Thr)+0.006222(Pro)/(Asn)+0.5422 | 0.9752 |
| 5 | 0.2734(Tau)/(Asn)+0.1383(Ser)/(Cit)-2.263(Glu)/(Gln)-0.9292(ABA)/(Thr)+0.7322 | 0.9711 |
| 6 | 0.1211(Tau)/(ABA)+0.1287(Ser)/(Cit)+0.07177(Asn)/(Pro)-0.3546(Glu)/(Thr)+0.5373 | 0.9745 |
| 7 | 0.2842(Tau)/(Asn)+0.03447(Thr)/(ABA)+0.1365(Ser)/(Cit)-2.266(Glu)/(Gln)+0.3495 | 0.9708 |
| 8 | 0.2732(Tau)/(Asn)+0.1375(Ser)/(Cit)-0.7435(Glu)/(Pro)-0.9272(ABA)/(Thr)+0.772 | 0.9689 |
| 9 | 0.1215(Tau)/(ABA)+0.1283(Ser)/(Cit)-0.3611(Glu)/(Thr)-0.001764(Gln)/(Asn)+0.5855 | 0.9752 |
| 10 | 0.2703(Tau)/(Asn)+0.1465(Ser)/(Cit)-0.3162(Glu)/(Orn)-0.005757(Gln)/(Thr)+0.6207 | 0.9752 |
| 11 | 0.2685(Tau)/(Asn)+0.1479(Ser)/(Cit)-0.3126(Glu)/(Orn)+0.008198(Pro)/(Thr)+0.5699 | 0.9739 |
| 12 | 0.118(Tau)/(ABA)-0.0315(Thr)/(Asn)+0.1351(Ser)/(Cit)-1.745(Glu)/(Gln)+0.6072 | 0.9686 |
| 13 | 0.2705(Tau)/(Asn)+0.05363(Thr)/(Pro)+0.1471(Ser)/(Cit)-0.3116(Glu)/(Orn)+0.544 | 0.9758 |
| 14 | 0.2837(Tau)/(Asn)+0.134(Ser)/(Cit)-0.4799(Glu)/(Thr)-1.273(ABA)/(Pro)+0.7512 | 0.9692 |
| 15 | 0.2704(Tau)/(Asn)+0.1532(Thr)/(Gln)+0.1469(Ser)/(Cit)-0.3154(Glu)/(Orn)+0.557 | 0.9748 |
| 16 | 0.2893(Tau)/(Asn)+0.1321(Ser)/(Cit)-0.4749(Glu)/(Thr)+0.02344(Pro)/(ABA)+0.3859 | 0.9698 |
| 17 | 0.1231(Tau)/(ABA)+0.1258(Ser)/(Cit)+1.461(Asn)/(Gln)-0.3566(Glu)/(Thr)+0.4538 | 0.9742 |
| 18 | 0.1606(Ser)/(Cit)-0.3098(Glu)/(Tau)+0.03468(Pro)/(Thr)+0.1687(Orn)/(Asn)+0.6238 | 0.9736 |
| 19 | -0.1048(Thr)/(Gln)+0.1607(Ser)/(Cit)-0.3039(Glu)/(Tau)+0.1746(Orn)/(Asn)+0.6814 | 0.9761 |
| 20 | 0.15(Ser)/(Cit)-0.2936(Glu)/(Tau)+0.01715(Pro)/(Asn)-0.9277(ABA)/(Thr)+1.057 | 0.9698 |
| 21 | 0.1437(Ser)/(Cit)-0.282(Glu)/(Thr)+0.00148(Pro)/(Asn)-0.8589(ABA)/(Tau)+1.183 | 0.9701 |
| 22 | -0.01994(Thr)/(Pro)+0.1603(Ser)/(Cit)-0.3063(Glu)/(Tau)+0.1728(Orn)/(Asn)+0.6825 | 0.9758 |
| 23 | 0.1604(Ser)/(Cit)-0.3051(Glu)/(Tau)+0.001153(Gln)/(Thr)+0.1745(Orn)/(Asn)+0.6574 | 0.9758 |
| 24 | 0.2746(Tau)/(Asn)+0.1381(Ser)/(Cit)-0.3998(Glu)/(Thr)-5.926(ABA)/(Gln)+0.7529 | 0.9686 |
| 25 | 0.1504(Ser)/(Cit)-0.08005(Asn)/(Pro)-0.2883(Glu)/(Tau)-0.9137(ABA)/(Thr)+1.133 | 0.9701 |
| 26 | 0.1183(Tau)/(ABA)+0.1349(Ser)/(Cit)+0.1986(Asn)/(Gln)-1.737(Glu)/(Gln)+0.4452 | 0.9670 |
| 27 | 0.1435(Ser)/(Cit)+0.135(Asn)/(Pro)-0.2667(Glu)/(Thr)-0.8603(ABA)/(Tau)+1.144 | 0.9708 |
| 28 | 0.05751(Asn)/(Pro)-0.4539(Glu)/(Ser)-0.6876(Cit)/(Tau)-1.086(ABA)/(Thr)+2.096 | 0.9758 |
| 29 | -0.3894(Glu)/(Thr)+0.008146(Pro)/(Asn)-0.6852(Cit)/(Tau)-1.775(ABA)/(Ser)+2.192 | 0.9742 |
| 30 | 0.1889(Tau)/(Met)+0.1234(Ser)/(Cit)-0.4542(Glu)/(Thr)+0.01188(Pro)/(Asn)+0.5526 | 0.9717 |
| 31 | 0.1204(Tau)/(ABA)-0.05057(Thr)/(Gln)+0.1315(Ser)/(Cit)-0.1476(Glu)/(Asn)+0.5632 | 0.9711 |
| 32 | 0.1609(Ser)/(Cit)-0.2864(Asn)/(Orn)-0.3109(Glu)/(Tau)+0.03694(Pro)/(Thr)+1.076 | 0.9720 |
| 33 | -0.02221(Thr)/(Pro)+0.1606(Ser)/(Cit)-0.295(Asn)/(Orn)-0.3073(Glu)/(Tau)+1.152 | 0.9730 |
| 34 | -0.02996(Thr)/(Gln)+0.1607(Ser)/(Cit)-0.2989(Asn)/(Orn)-0.3061(Glu)/(Tau)+1.143 | 0.9733 |
| 35 | 0.1221(Tau)/(ABA)+0.05157(Thr)/(Glu)+0.1311(Ser)/(Cit)-0.001221(Pro)/(Asn)+0.252 | 0.9714 |
| 36 | 0.1211(Tau)/(ABA)+0.1321(Ser)/(Cit)-0.1562(Glu)/(Asn)+0.05517(Pro)/(Thr)+0.4754 | 0.9689 |
| 37 | 0.1206(Tau)/(ABA)-0.0851(Thr)/(Pro)+0.1317(Ser)/(Cit)-0.1533(Glu)/(Asn)+0.6186 | 0.9692 |
| 38 | 0.1881(Tau)/(Met)+0.1238(Ser)/(Cit)-0.0184(Asn)/(Pro)-0.4373(Glu)/(Thr)+0.5944 | 0.9726 |
| 39 | 0.2669(Tau)/(Asn)-0.1033(Thr)/(Orn)+0.1502(Ser)/(Cit)-2.376(Glu)/(Gln)+0.7144 | 0.9682 |
| 40 | 0.1604(Ser)/(Cit)-0.2996(Asn)/(Orn)-0.3071(Glu)/(Tau)-0.0009884(Gln)/(Thr)+1.146 | 0.9733 |
| 41 | -0.2159(Thr)/(Tau)+0.1383(Ser)/(Cit)+0.1412(Asn)/(ABA)-0.4966(Glu)/(Pro)+1.024 | 0.9664 |
| 42 | 0.03065(Thr)/(ABA)+0.1496(Ser)/(Cit)-0.2998(Glu)/(Tau)+0.01882(Pro)/(Asn)+0.7027 | 0.9686 |
| 43 | -0.4734(Glu)/(Ser)+0.01248(Pro)/(Asn)-0.6877(Cit)/(Tau)-1.102(ABA)/(Thr)+2.079 | 0.9739 |
| 44 | 0.1207(Tau)/(ABA)+0.1309(Ser)/(Cit)-0.1489(Glu)/(Asn)-0.001185(Gln)/(Thr)+0.5631 | 0.9730 |
| 45 | 0.06083(Ser)/(ABA)-0.3785(Glu)/(Thr)+0.00712(Pro)/(Asn)-0.682(Cit)/(Tau)+1.501 | 0.9686 |
| 46 | 0.2944(Tau)/(Asn)+0.1351(Ser)/(Cit)-0.5452(Glu)/(Thr)-0.02066(Gln)/(Orn)+0.803 | 0.9736 |
| 47 | 0.1192(Tau)/(ABA)-0.03894(Thr)/(Asn)+0.1364(Ser)/(Cit)+0.01076(Gln)/(Glu)+0.3091 | 0.9667 |
| 48 | 0.3055(Tau)/(Asn)+0.1372(Ser)/(Cit)-2.686(Glu)/(Ala)-0.009989(Gln)/(Thr)+0.6899 | 0.9711 |
| 49 | 0.1868(Tau)/(Met)-0.09977(Thr)/(Pro)+0.1275(Ser)/(Cit)-0.1789(Glu)/(Asn)+0.6499 | 0.9698 |
| 50 | 0.1881(Tau)/(Met)+0.1237(Ser)/(Cit)-0.4355(Glu)/(Thr)-0.0002196(Gln)/(Asn)+0.5915 | 0.9723 |

FIG.35

| No. | Formula | ROC_AUC |
|---|---|---|
| 51 | 'Ala/ABA-0.27842*Glu' | 0.8173 |
| 52 | 'Ala/Glu+3.5354*Ser/ABA' | 0.8123 |
| 53 | 'Ala/Glu+7.212*Ser/Met' | 0.8082 |
| 54 | 'Ser/ABA-0.068446*Glu' | 0.8075 |
| 55 | 'Ala/Glu-0.91184*ABA' | 0.8072 |
| 56 | 'Orn/Ile+0.32626*Ser/Met' | 0.8063 |
| 57 | 'Ser/ABA-27.5269*Glu/Ala' | 0.8057 |
| 58 | 'Ala/ABA-68.4263*Glu/Val' | 0.8050 |
| 59 | 'Ser/ABA-11.1929*Glu/Lys' | 0.8044 |
| 60 | 'Ala/Glu-211.9273*ABA/Val' | 0.8044 |
| 61 | 'Ala/ABA+3.8492*Ser/Glu' | 0.8044 |
| 62 | 'Ala/Glu-0.90078*Met' | 0.8025 |
| 63 | 'Ser/ABA-17.0085*Glu/Val' | 0.8013 |
| 64 | 'Ser/ABA+1.9869*Val/Ile' | 0.8003 |
| 65 | 'Ala/Ile-54.8399*ABA/Val' | 0.7987 |
| 66 | 'Ser/ABA-4.3704*Glu/Tyr' | 0.7978 |
| 67 | 'Ser/ABA-46.7637*Met/Lys' | 0.7975 |
| 68 | 'Ala/ABA-40.2211*Glu/Gly' | 0.7959 |
| 69 | 'Ser/ABA-8.1411*Glu/Pro' | 0.7956 |
| 70 | 'Ala/ABA-31.4425*Glu/Pro' | 0.7953 |
| 71 | 'Ser/ABA-3.3116*Glu/Orn' | 0.7950 |
| 72 | 'Ala/Glu-37.8581*ABA/Orn' | 0.7937 |
| 73 | 'Ala/ABA-44.5114*Glu/Lys' | 0.7934 |
| 74 | 'Ser/ABA+1.0986*Ala/Ile' | 0.7931 |
| 75 | 'Ala/Ile+0.91027*Ser/ABA' | 0.7931 |
| 76 | 'Ala/Glu-39.7344*Met/Orn' | 0.7918 |
| 77 | 'Ala/ABA-97.1521*Glu/Gln' | 0.7909 |
| 78 | 'Ala/Ile+1.9055*Ser/Met' | 0.7909 |
| 79 | 'Ala/ABA-17.4737*Glu/Tyr' | 0.7906 |
| 80 | 'Ala/Glu-0.28868*Trp' | 0.7903 |
| 81 | 'Ser/ABA-13.3092*Ile/Lys' | 0.7903 |
| 82 | 'Ala/ABA-13.0514*Glu/Orn' | 0.7899 |
| 83 | 'Ala/ABA+7.5172*Val/Ile' | 0.7884 |
| 84 | 'Ser/ABA+2.2522*Asn/Glu' | 0.7877 |
| 85 | 'Ala/Ile-10.4428*Met/Orn' | 0.7868 |
| 86 | 'Ala/Glu+1.5688*Pro/ABA' | 0.7858 |
| 87 | 'Ala/Glu+1.1608*Gly/ABA' | 0.7858 |
| 88 | 'Ala/Ile+2.0401*Leu/Trp' | 0.7858 |
| 89 | 'Ala/ABA+8.9645*Asn/Glu' | 0.7855 |
| 90 | 'Ala/Glu-58.3437*ABA/Tyr' | 0.7849 |
| 91 | 'Ala/Glu+3.225*Val/Trp' | 0.7849 |
| 92 | 'Ala/Ile-20.0576*ABA/Leu' | 0.7846 |
| 93 | 'Ala/Ile-9.7007*ABA/Orn' | 0.7846 |
| 94 | 'Ala/Glu+2.0722*Val/Met' | 0.7843 |
| 95 | 'Ser/ABA-22.341*Glu/Gln' | 0.7827 |
| 96 | 'Ala/ABA+2.6567*Thr/Glu' | 0.7824 |
| 97 | 'Ser/ABA-8.9906*Glu/Gly' | 0.7818 |
| 98 | 'Ser/ABA-3.4618*Glu/His' | 0.7818 |
| 99 | 'Orn/Ile+0.15406*Ser/ABA' | 0.7811 |
| 100 | 'Orn/Ile+0.16997*Ala/Phe' | 0.8840 |

FIG.37

| No | Formula | ROC_AUC |
|---|---|---|
| 1 | [2.9877]+[0.0822]Tau+[-0.1512]Glu+[0.0191]Ala+[-0.4979]Cit+[-0.0741]Trp+[0.1054]Orn | 0.9887 |
| 2 | [2.7092]+[0.0708]Tau+[-0.1086]Glu+[0.0244]Gly+[-0.4666]Cit+[-0.1528]ABA+[0.1018]Orn | 0.9871 |
| 3 | [0.4381]+[0.0830]Tau+[0.0602]Ser+[-0.1069]Glu+[-0.4571]Cit+[-0.1384]ABA+[0.0970]Orn | 0.9868 |
| 4 | [4.0442]+[0.0727]Tau+[-0.1312]Glu+[0.0220]Gly+[-0.4973]Cit+[-0.1235]Met+[0.1235]Orn | 0.9862 |
| 5 | [7.1911]+[0.0713]Tau+[0.0843]Asn+[-0.1371]Glu+[-0.4442]Cit+[-0.2007]Met+[0.1077]Orn | 0.9858 |
| 6 | [-0.7947]+[0.0933]Tau+[0.0610]Ser+[-0.1161]Glu+[-0.4778]Cit+[-0.0376]Trp+[0.1099]Orn | 0.9858 |
| 7 | [2.3945]+[0.0753]Tau+[-0.1240]Glu+[-0.0047]Gln+[0.0233]Gly+[-0.4743]Cit+[0.1137]Orn | 0.9858 |
| 8 | [5.7293]+[0.0710]Tau+[-0.1135]Glu+[-0.4732]Cit+[-0.2159]Met+[0.1150]Orn+[0.0513]Arg | 0.9852 |
| 9 | [-5.0696]+[0.0709]Tau+[-0.1213]Glu+[0.0218]Gly+[-0.5120]Cit+[0.0212]Val+[0.1229]Orn | 0.9852 |
| 10 | [2.7559]+[0.0709]Tau+[-0.1293]Glu+[-0.4621]Cit+[0.0264]Val+[-0.1796]Met+[0.1215]Orn | 0.9849 |
| 11 | [0.4888]+[0.0666]Tau+[-0.1186]Glu+[0.0010]Pro+[0.0204]Gly+[-0.4839]Cit+[0.1163]Orn | 0.9849 |
| 12 | [2.2877]+[0.0702]Tau+[-0.1199]Glu+[0.0206]Gly+[-0.4749]Cit+[-0.0304]Trp+[0.1126]Orn | 0.9846 |
| 13 | [0.9688]+[0.0659]Tau+[-0.1189]Glu+[0.0205]Gly+[-0.4872]Cit+[-0.0036]Phe+[0.1166]Orn | 0.9846 |
| 14 | [-1.1749]+[0.0661]Tau+[-0.1036]Glu+[0.0188]Gly+[-0.4962]Cit+[0.1156]Orn+[0.0195]Arg | 0.9846 |
| 15 | [0.6244]+[0.0662]Tau+[-0.1183]Glu+[0.0206]Gly+[-0.4861]Cit+[0.1167]Orn | 0.9846 |
| 16 | [0.6356]+[0.0663]Tau+[-0.1183]Glu+[0.0206]Gly+[-0.4859]Cit+[0.1167]Orn+[-0.0001]Lys | 0.9843 |
| 17 | [0.8386]+[0.0656]Tau+[-0.1173]Glu+[0.0203]Gly+[-0.4852]Cit+[0.0024]Ile+[0.1166]Orn | 0.9843 |
| 18 | [-0.4580]+[0.0676]Tau+[-0.1199]Glu+[0.0222]Gly+[-0.4882]Cit+[0.0061]Leu+[0.1169]Orn | 0.9843 |
| 19 | [3.8565]+[0.0714]Tau+[0.0333]Thr+[-0.1031]Glu+[-0.4364]Cit+[-0.1671]ABA+[0.0988]Orn | 0.984 |
| 20 | [1.2276]+[0.0799]Tau+[-0.1283]Glu+[-0.4622]Cit+[0.0321]Val+[-0.0807]Trp+[0.1070]Orn | 0.984 |
| 21 | [-1.0436]+[0.0721]Tau+[0.0172]Thr+[-0.1166]Glu+[0.0178]Gly+[-0.4905]Cit+[0.1181]Orn | 0.984 |
| 22 | [6.6216]+[0.0879]Tau+[-0.1445]Glu+[0.0261]Pro+[-0.4151]Cit+[-0.2456]Met+[0.1114]Orn | 0.9836 |
| 23 | [7.8249]+[0.0668]Tau+[-0.1302]Glu+[-0.4224]Cit+[-0.1433]Met+[0.0110]Ile+[0.1100]Orn | 0.9836 |
| 24 | [0.5028]+[0.0605]Tau+[-0.1104]Glu+[-0.4654]Cit+[0.0236]Val+[-0.0263]Ile+[0.1136]Orn | 0.9833 |
| 25 | [4.1172]+[0.0779]Tau+[0.0313]Thr+[-0.1241]Glu+[-0.4429]Cit+[-0.1377]Met+[0.1194]Orn | 0.9833 |
| 26 | [0.0724]+[0.0632]Tau+[-0.1188]Glu+[0.0207]Gly+[-0.4945]Cit+[0.0095]His+[0.1191]Orn | 0.9833 |
| 27 | [12.7680]+[-0.1193]Glu+[-0.0033]Gln+[-0.5338]Cit+[-0.2963]ABA+[0.0269]Val+[0.0924]Orn | 0.983 |
| 28 | [-3.6624]+[0.0684]Tau+[-0.1047]Glu+[-0.4865]Cit+[0.0215]Val+[0.1133]Orn+[0.0279]Arg | 0.983 |
| 29 | [7.1588]+[0.0599]Tau+[-0.1034]Glu+[-0.4087]Cit+[-0.1398]ABA+[0.0007]Trp+[0.0939]Orn | 0.983 |
| 30 | [7.1793]+[0.0599]Tau+[-0.1034]Glu+[-0.4084]Cit+[-0.1387]ABA+[0.0939]Orn | 0.983 |
| 31 | [7.5885]+[0.0598]Tau+[-0.1046]Glu+[-0.4109]Cit+[-0.1368]ABA+[-0.0052]Phe+[0.0940]Orn | 0.983 |
| 32 | [7.1814]+[0.0599]Tau+[-0.1034]Glu+[-0.4084]Cit+[-0.1387]ABA+[-0.0000]Ile+[0.0939]Orn | 0.983 |
| 33 | [2.5358]+[0.0745]Tau+[-0.1126]Glu+[-0.4817]Cit+[0.0651]Tyr+[-0.0473]Trp+[0.1091]Orn | 0.983 |
| 34 | [10.4833]+[0.0678]Tau+[-0.1064]Glu+[-0.0049]Gln+[-0.3992]Cit+[-0.1640]ABA+[0.0882]Orn | 0.983 |
| 35 | [12.9844]+[0.0487]Ser+[-0.1338]Glu+[-0.4953]Cit+[-0.1296]ABA+[-0.1725]Met+[0.1020]Orn | 0.9827 |
| 36 | [11.4477]+[-0.1163]Glu+[-0.5259]Cit+[-0.2180]Met+[-0.0227]Trp+[0.1162]Orn+[0.0606]Arg | 0.9827 |
| 37 | [6.8150]+[0.0566]Tau+[-0.1027]Glu+[-0.4144]Cit+[-0.1441]ABA+[0.0953]Orn+[0.0032]Lys | 0.9827 |
| 38 | [4.5781]+[0.0609]Tau+[-0.0897]Glu+[-0.4308]Cit+[-0.1542]ABA+[0.0940]Orn+[0.0289]Arg | 0.9827 |
| 39 | [10.6733]+[-0.1127]Glu+[-0.5254]Cit+[-0.2512]ABA+[0.0294]Val+[-0.0287]Trp+[0.0902]Orn | 0.9827 |
| 40 | [9.5045]+[0.0639]Tau+[-0.1156]Glu+[-0.4031]Cit+[-0.1141]ABA+[-0.0953]Met+[0.0966]Orn | 0.9827 |
| 41 | [3.8426]+[0.0661]Tau+[-0.0971]Glu+[-0.4454]Cit+[-0.0429]Trp+[0.1028]Orn+[0.0291]Arg | 0.9824 |
| 42 | [4.5266]+[0.0702]Tau+[0.0650]Asn+[-0.1153]Glu+[-0.4274]Cit+[-0.0481]Trp+[0.0965]Orn | 0.9824 |
| 43 | [6.5986]+[0.0611]Tau+[-0.1053]Glu+[-0.4041]Cit+[-0.1553]ABA+[0.0072]Leu+[0.0920]Orn | 0.9824 |
| 44 | [-0.6473]+[0.0675]Tau+[0.0435]Asn+[-0.1159]Glu+[0.0174]Gly+[-0.4808]Cit+[0.1119]Orn | 0.9824 |
| 45 | [3.2598]+[0.0735]Tau+[0.0244]Thr+[-0.1144]Glu+[-0.4453]Cit+[-0.0324]Trp+[0.1094]Orn | 0.9824 |
| 46 | [6.6800]+[0.0693]Tau+[-0.1252]Glu+[-0.4100]Cit+[-0.1823]Met+[0.0355]Phe+[0.1125]Orn | 0.9824 |
| 47 | [7.3051]+[0.0552]Tau+[-0.1238]Glu+[-0.4378]Cit+[-0.1511]Met+[0.1145]Orn+[0.0095]Lys | 0.9824 |
| 48 | [12.2091]+[-0.1147]Glu+[-0.5197]Cit+[-0.1191]ABA+[-0.1920]Met+[0.1117]Orn+[0.0562]Arg | 0.9824 |
| 49 | [4.9246]+[0.0629]Tau+[0.0694]Asn+[-0.1059]Glu+[-0.4261]Cit+[-0.1553]ABA+[0.0907]Orn | 0.9824 |
| 50 | [7.0618]+[0.0579]Tau+[-0.1260]Glu+[-0.4364]Cit+[-0.1282]Met+[0.0192]His+[0.1136]Orn | 0.9821 |

FIG.38

| No | Formula | ROC_AUC |
|---|---|---|
| 51 | '6.047-0.075843*Glu+0.01222 1*Ala-0.22054*Met-0.051477*Trp' | 0.8340 |
| 52 | '2.9973-0.08583*Glu+0.0090941*Ala-0.25788*Met+0.045669*Orn' | 0.8349 |
| 53 | '4.9269+0.043177*Ser-0.068292*Glu-0.13225*ABA-0.19363*Met' | 0.8374 |
| 54 | '2.6576+0.03391*Ser-0.079902*Glu-0.24535*Met+0.042776*Orn' | 0.8292 |
| 55 | '5.0624-0.071355*Glu+0.010655*Ala-0.13093*ABA-0.18595*Met' | 0.8475 |
| 56 | '3.6529+0.061275*Asn-0.076673*Glu-0.25253*Met+0.04236*Orn' | 0.8302 |
| 57 | '2.8784+0.030668*Ser-0.07919*Glu+0.0081867*Ala-0.26945*Met' | 0.8371 |
| 58 | '3.8596+0.051842*Asn-0.076184*Glu+0.0077848*Ala-0.26884*Met' | 0.8321 |
| 59 | '5.9046+0.067894*Asn-0.060756*Glu-0.11264*ABA-0.19621*Met' | 0.8358 |
| 60 | '5.0982-0.075747*Glu+0.0094178*Ala-0.22598*Met-0.012871*Phe' | 0.8230 |
| 61 | '4.744-0.069384*Glu+0.0091485*Ala-0.21377*Met-0.013607*Ile' | 0.8252 |
| 62 | '3.8263+0.026799*Ser+0.04913*Asn-0.07147*Glu-0.2587*Met' | 0.8201 |
| 63 | '4.6153-0.075979*Glu+0.0090494*Ala-0.23166*Met' | 0.8230 |
| 64 | '3.2943-0.081633*Glu-0.24502*Met+0.039884*Tyr+0.043924*Orn' | 0.8189 |
| 65 | '5.1676-0.075649*Glu+0.0094071*Ala-0.22019*Met-0.01277*His' | 0.8179 |
| 66 | '4.2528+0.0074102*Thr-0.075612*Glu+0.0085509*Ala-0.24022*Met' | 0.8217 |
| 67 | '4.0827-0.080165*Glu+0.0077314*Ala-0.2518*Met+0.023934*Tyr' | 0.8239 |
| 68 | '6.1604-0.081599*Glu-0.0031208*Gln+0.0096343*Ala-0.22119*Met' | 0.8280 |
| 69 | '0.70289+0.032255*Ser+0.0074583*Ala-0.17245*ABA-0.18051*Met' | 0.7918 |
| 70 | '5.5246-0.067939*Glu-0.097935*ABA-0.16362*Met+0.041956*Orn' | 0.8160 |
| 71 | '1.9963+0.026461*Ser+0.051342*Asn-0.15607*ABA-0.18819*Met' | 0.7940 |
| 72 | '4.8325-0.07676*Glu+0.0092042*Ala-0.22791*Met-0.0035373*Arg' | 0.8220 |
| 73 | '0.78861+0.0333*Ser-0.16015*Met-0.049437*Ile+0.038276*Orn' | 0.8088 |
| 74 | '4.7704-0.064781*Glu-0.178*Met-0.017863*Ile+0.047955*Orn' | 0.8123 |
| 75 | '4.6491-0.075706*Glu+0.0090664*Ala-0.23075*Met-0.00062835*Leu' | 0.8236 |
| 76 | '5.5076-0.079747*Glu-0.0040222*Gly+0.0094333*Ala-0.23162*Met' | 0.8230 |
| 77 | '2.8152+0.038391*Ser-0.12733*ABA-0.1267*Met-0.030374*Ile' | 0.8019 |
| 78 | '3.8522-0.078949*Glu+0.0087933*Ala+0.0049586*Val-0.2411*Met' | 0.8233 |
| 79 | '4.349-0.079482*Glu+0.0077032*Pro+0.0082911*Ala-0.24902*Met' | 0.8239 |
| 80 | '3.5631-0.075635*Glu+0.0088547*Ala-0.24209*Met+0.006668*Lys' | 0.8245 |
| 81 | '3.8377+0.015294*Thr-0.075819*Glu-0.22726*Met+0.0455*Orn' | 0.8129 |
| 82 | '1.1241+0.034287*Ser-0.1512*ABA-0.16756*Met+0.027424*Orn' | 0.7811 |
| 83 | '1.2557+0.0067599*Ala-0.15647*Met-0.046253*Ile+0.038356*Orn' | 0.7972 |
| 84 | '3.1831+0.031497*Ser-0.076965*Glu-0.25715*Met+0.033346*Tyr' | 0.8220 |
| 85 | '3.6793+0.070166*Asn-0.12118*ABA-0.13863*Met-0.025564*Ile' | 0.8047 |
| 86 | '4.0493-0.081808*Glu+0.014012*Pro-0.24297*Met+0.043997*Orn' | 0.8082 |
| 87 | '4.1311+0.036457*Ser-0.062816*Glu-0.20033*Met-0.016034*Ile' | 0.8170 |
| 88 | '4.2525+0.05363*Asn-0.072577*Glu-0.25169*Met+0.027755*Tyr' | 0.8154 |
| 89 | '1.5059+0.06481*Asn-0.17313*Met-0.045194*Ile+0.038945*Orn' | 0.8072 |
| 90 | '4.9884+0.069478*Asn-0.05964*Glu-0.21376*Met-0.013408*Ile' | 0.8129 |
| 91 | '5.4818-0.068929*Glu-0.1157*ABA-0.1797*Met+0.044978*Tyr' | 0.8236 |
| 92 | '5.8709+0.07254*Asn-0.063145*Glu-0.21921*Met-0.02759*Trp' | 0.8170 |
| 93 | '4.9114+0.067506*Asn-0.066287*Glu-0.23149*Met' | 0.8123 |
| 94 | '4.6339-0.073157*Glu-0.19722*Met+0.043934*Orn' | 0.8028 |
| 95 | '4.3914+0.064348*Asn-0.073047*Glu+0.012103*Pro-0.2658*Met' | 0.8236 |
| 96 | '4.8287+0.036776*Ser-0.068079*Glu-0.20826*Met-0.023472*Trp' | 0.8179 |
| 97 | '4.0241+0.034966*Ser-0.070406*Glu-0.21954*Met' | 0.8104 |
| 98 | '0.72827+0.031651*Ser+0.006301*Ala-0.17036*Met-0.046278*Ile' | 0.7931 |
| 99 | '1.7137+0.054593*Asn+0.0064894*Ala-0.15956*ABA-0.17525*Met' | 0.7972 |
| 100 | '5.333+0.074869*Asn-0.067668*Glu-0.2237*Met-0.0090745*Arg' | 0.8097 |

FIG.40

| No | Formula | ROC_AUC |
|---|---|---|
| 1 | −(4.097e−01)Tau−(1.075e−01)Ser+(2.661e−01)Glu+(5.515e−01)Cit+(6.323e−01)Met−(2.142e−01)Orn−(2.535e+00) | 0.9783 |
| 2 | −(2.104e−01)Glu+(1.901e−02)Ala−(5.927e−01)Cit−(7.443e−01)Met+(2.017e−01)Orn+(9.727e−02)Arg+(1.985e+01) | 0.977 |
| 3 | −(2.290e−01)Glu+(2.202e−02)Ala−(6.570e−01)Cit−(7.004e−01)ABA+(1.724e−02)Val+(1.566e−01)Orn+(2.268e+01) | 0.977 |
| 4 | (3.469e−01)Glu+(2.557e−02)Gln−(3.792e−02)Gly−(1.823e−02)Ala+(9.075e−01)Cit−(2.319e−01)Orn−(2.911e+01) | 0.9767 |
| 5 | −(2.541e−01)Glu+(2.531e−02)Ala−(5.963e−01)Cit−(7.328e−01)Met+(2.051e−01)Orn+(1.435e−02)Lys+(2.559e+01) | 0.9767 |
| 6 | −(2.353e−01)Glu+(3.079e−02)Ala−(6.160e−01)Cit−(5.313e−01)ABA−(4.954e−01)Met+(1.913e−01)Orn+(3.133e+01) | 0.9758 |
| 7 | (5.350e−01)Tau+(9.278e−02)Ser−(3.618e−01)Glu−(2.414e−02)Gln−(7.255e−01)Cit+(2.176e−01)Orn+(3.097e+00) | 0.9752 |
| 8 | (2.652e−01)Glu−(2.466e−02)Ala+(5.914e−01)Cit−(1.445e−02)Val+(7.338e−01)Met−(2.015e−01)Orn−(2.577e+01) | 0.9752 |
| 9 | (3.016e−01)Glu+(3.158e−02)Pro−(3.179e−02)Gly−(1.906e−02)Ala+(9.193e−01)Cit−(2.482e−01)Orn−(1.733e+01) | 0.9752 |
| 10 | (2.069e−01)Glu+(6.177e−01)Cit−(2.034e−02)Val+(7.208e−01)Met−(2.057e−01)Orn−(1.156e−01)Arg−(2.030e+01) | 0.9752 |
| 11 | −(4.446e−01)Tau+(3.170e−01)Glu−(3.579e−02)Ala+(7.519e−01)Cit+(3.049e−01)Trp−(2.057e−01)Orn−(6.820e+00) | 0.9752 |
| 12 | −(5.350e−01)Ser+(3.376e−01)Glu−(1.824e−02)Ala+(7.425e−01)Cit−(2.124e−01)Orn+(1.500e+01) | 0.9752 |
| 13 | (2.536e−01)Glu+(1.426e−02)Gln−(2.664e−02)Ala+(6.716e−01)Cit+(6.749e−01)ABA−(1.679e−01)Orn−(3.402e+01) | 0.9748 |
| 14 | −(2.938e−01)Glu+(2.459e−02)Gly−(9.137e−01)Cit+(3.047e−02)Val−(1.042e−01)Leu+(2.579e−01)Orn+(2.603e+01) | 0.9748 |
| 15 | (6.101e−02)Ser+(2.927e−01)Glu−(4.212e−02)Gly−(1.519e−02)Ala+(9.223e−01)Cit−(2.408e−01)Orn−(1.825e+01) | 0.9748 |
| 16 | −(5.263e−02)Thr−(3.008e−01)Glu+(3.605e−02)Gly+(1.618e−02)Ala−(9.196e−01)Cit+(2.439e−01)Orn+(1.851e+01) | 0.9748 |
| 17 | −(2.115e−01)Glu+(1.703e−02)Gly+(2.251e−02)Ala−(6.828e−01)Cit−(6.779e−01)ABA+(1.691e−01)Orn+(2.192e+01) | 0.9745 |
| 18 | (3.023e−01)Glu−(2.537e−02)Gly−(2.044e−02)Ala+(9.184e−01)Cit+(8.811e−02)Tyr−(2.374e−01)Orn−(2.057e+01) | 0.9742 |
| 19 | −(3.761e−01)Tau+(2.462e−01)Glu+(5.996e−01)Cit+(6.410e−01)ABA−(4.259e−02)Val−(1.605e−01)Orn−(3.703e+00) | 0.9742 |
| 20 | (2.698e−02)Ser+(3.383e−01)Glu−(1.879e−02)Ala+(9.080e−01)Cit−(2.443e−01)Orn+(1.692e−02)Lys−(2.747e+01) | 0.9742 |
| 21 | −(5.002e−01)Tau+(3.086e−01)Glu+(2.354e−02)Gln−(5.938e−02)Gly+(7.737e−01)Cit−(2.276e−01)Orn+(2.872e−01) | 0.9742 |
| 22 | −(3.911e−01)Tau+(2.580e−01)Glu+(1.175e−02)Gln+(6.434e−01)Cit+(5.727e−01)ABA−(1.960e−01)Orn−(1.919e+01) | 0.9742 |
| 23 | −(5.186e−01)Tau+(3.446e−01)Glu−(2.271e−02)Ala+(7.476e−01)Cit−(2.273e−01)Orn−(3.555e−02)Lys+(3.009e+00) | 0.9739 |
| 24 | −(3.968e−01)Tau+(2.107e−01)Glu−(4.114e−02)Gly+(5.954e−01)Cit+(6.625e−01)ABA−(5.525e−02)Val+(1.431e+00) | 0.9739 |
| 25 | −(2.927e−01)Glu+(3.327e−02)Gly−(9.234e−01)Cit−(5.081e−04)Val+(2.462e−01)Orn+(1.981e+01) | 0.9739 |
| 26 | (3.803e−02)Thr+(3.385e−01)Glu−(1.970e−02)Ala+(9.067e−01)Cit−(2.474e−01)Orn+(1.650e−02)Lys−(2.807e+01) | 0.9739 |
| 27 | (5.729e−03)Ser+(3.764e−01)Glu+(2.307e−02)Gln−(2.117e−02)Ala+(8.959e−01)Cit−(2.341e−01)Orn−(3.628e+01) | 0.9739 |
| 28 | −(3.968e−02)Thr−(3.758e−01)Glu−(2.348e−02)Gln+(2.301e−02)Ala−(8.939e−01)Cit+(2.390e−01)Orn+(3.910e+01) | 0.9739 |
| 29 | (2.410e−02)Ser+(3.303e−01)Glu−(1.832e−02)Ala+(9.114e−01)Cit+(7.218e−03)Val−(2.434e−01)Orn−(2.543e+01) | 0.9739 |
| 30 | (2.246e−01)Glu+(5.669e−03)Pro−(2.489e−02)Ala+(6.736e−01)Cit+(6.826e−01)ABA−(1.709e−01)Orn−(2.593e+01) | 0.9739 |
| 31 | −(2.443e−01)Glu+(3.729e−02)Ala−(6.773e−01)Cit−(6.368e−01)ABA+(4.328e−02)Val−(2.699e−01)Trp+(3.567e+01) | 0.9736 |
| 32 | −(3.260e−01)Glu+(2.144e−02)Ala−(9.014e−01)Cit−(2.759e−02)Val−(1.261e−01)Leu+(2.532e−01)Orn+(2.751e+01) | 0.9736 |
| 33 | −(2.930e−01)Glu+(3.329e−02)Gly−(9.233e−01)Cit+(2.459e−01)Orn+(1.971e+01) | 0.9736 |
| 34 | −(2.946e−01)Glu+(3.299e−02)Gly−(9.222e−01)Cit+(2.481e−01)Orn−(7.567e−03)Lys+(2.129e+01) | 0.9736 |
| 35 | −(3.871e−01)Tau+(2.036e−01)Glu−(4.026e−02)Gly+(6.596e−01)Cit+(5.790e−01)ABA−(1.919e−01)Orn−(1.907e+00) | 0.9736 |
| 36 | −(2.611e−01)Glu+(2.500e−02)Ala−(5.984e−01)Cit−(7.273e−01)Met+(1.897e−02)Tyr+(2.092e−01)Orn+(2.728e+01) | 0.9736 |
| 37 | −(2.999e−01)Glu+(1.567e−02)Ala−(9.102e−01)Cit−(1.665e−01)Phe+(2.192e−01)Orn+(7.449e−02)Arg+(2.520e+01) | 0.9736 |
| 38 | (2.836e−01)Glu+(9.157e−01)Cit−(3.841e−03)Val+(1.447e−01)Phe−(2.279e−01)Orn−(9.023e−02)Arg−(2.662e+01) | 0.9736 |
| 39 | −(3.945e−01)Tau+(2.801e−01)Glu+(5.757e−01)Cit+(6.114e−01)Met−(1.019e−01)Tyr−(2.244e−01)Orn−(7.107e+00) | 0.9736 |
| 40 | −(2.955e−01)Glu+(3.302e−02)Gly−(9.221e−01)Cit+(1.151e−03)Val−(2.476e−01)Orn−(7.948e−03)Lys+(2.113e+01) | 0.9736 |
| 41 | −(3.331e−01)Glu+(2.105e−02)Ala−(9.021e−01)Cit−(1.579e−01)Phe+(2.234e−01)Orn+(3.097e+01) | 0.9736 |
| 42 | −(5.360e−01)Tau−(6.878e−02)Ser+(3.268e−01)Glu+(7.399e−01)Cit−(2.303e−01)Orn−(2.652e−02)Lys+(4.981e+00) | 0.9736 |
| 43 | −(3.776e−02)Ser+(2.547e−01)Glu−(2.499e−02)Ala+(5.774e−01)Cit+(7.475e−01)Met−(2.023e−01)Orn−(2.478e+01) | 0.9736 |
| 44 | (3.102e−01)Glu−(3.424e−02)Ala+(8.414e−01)Cit−(2.206e−02)Val+(3.938e−01)Trp−(1.977e−01)Orn−(3.274e+01) | 0.9736 |
| 45 | −(8.279e−02)Asn+(3.234e−01)Glu+(2.899e−02)Pro−(1.845e−02)Ala+(9.107e−01)Cit−(2.411e−01)Orn−(2.168e+01) | 0.9736 |
| 46 | −(3.325e−01)Glu+(2.116e−02)Ala−(9.023e−01)Cit−(1.204e−03)Val−(1.570e−01)Phe+(2.240e−01)Orn+(3.111e+01) | 0.9733 |
| 47 | (1.962e−02)Thr+(3.009e−01)Glu−(3.670e−02)Ala+(8.508e−01)Cit+(3.718e−01)Trp−(2.135e−01)Orn−(3.711e+01) | 0.9733 |
| 48 | (3.965e−01)Tau+(1.064e−01)Ser−(2.238e−01)Glu−(5.132e−01)Cit−(7.182e−01)ABA+(4.740e−02)Val−(2.384e+00) | 0.9733 |
| 49 | (5.104e−01)Tau−(3.779e−01)Glu−(2.356e−02)Gln+(2.457e−02)Ala−(7.412e−01)Cit+(2.147e−01)Orn+(5.139e+00) | 0.9733 |
| 50 | −(2.411e−01)Glu−(6.539e−01)Cit−(5.370e−01)ABA+(3.480e−02)Val−(4.310e−01)Met+(1.974e−01)Orn+(3.439e+01) | 0.9733 |

FIG.41

| No | Formula | ROC_AUC |
|---|---|---|
| 51 | 'Glu-0.21095*Ala+2.511*ABA+3.2268*Met' | 0.8459 |
| 52 | 'Glu-0.15156*Ala+3.9679*Met-0.71876*Orn' | 0.8336 |
| 53 | 'Ser-1.9215*Glu+0.30189*Ala-8.3618*Met' | 0.8327 |
| 54 | 'Glu-0.21155*Ala+3.3643*Met+0.86139*Trp' | 0.8333 |
| 55 | 'Asn-0.95086*Glu+0.14886*Ala-4.4309*Met' | 0.8248 |
| 56 | 'Glu-0.2223*Ala+3.1879*ABA+0.9822*Trp' | 0.8258 |
| 57 | 'Glu-0.16975*Ala+3.756*Met' | 0.8198 |
| 58 | 'Ser-1.8083*Glu+0.29712*Ala-7.7811*ABA' | 0.8176 |
| 59 | 'Glu-0.19526*Ala+3.6498*Met+0.41298*Ile' | 0.8236 |
| 60 | 'Glu-0.17274*Ala+3.3453*Met+0.43566*His' | 0.8047 |
| 61 | 'Glu-0.14056*Ala+3.9332*Met-0.4051*Tyr' | 0.8248 |
| 62 | 'Glu-0.2221*Ala+3.7529*ABA+0.66394*Ile' | 0.8201 |
| 63 | 'Glu-0.18503*Ala+3.2795*ABA+0.69635*His' | 0.8239 |
| 64 | 'Glu+0.053497*Gln-0.15959*Ala+3.2098*Met' | 0.8138 |
| 65 | 'Glu+0.087173*Gln-0.16333*Ala+3.0533*ABA' | 0.8167 |
| 66 | 'Glu-0.1572*Ala+3.5877*ABA-0.57099*Orn' | 0.8182 |
| 67 | 'Glu-0.14907*Ala-0.10897*Val+3.7401*Met' | 0.8173 |
| 68 | 'Ser+0.21581*Ala-4.7076*ABA-4.7455*Met' | 0.7903 |
| 69 | 'Thr-5.2554*Glu+0.85467*Ala-20.8619*Met' | 0.8167 |
| 70 | 'Glu-0.16958*Ala+4.0996*Met-0.12306*Lys' | 0.8195 |
| 71 | 'Glu-0.17842*Ala+3.7732*ABA' | 0.8176 |
| 72 | 'Glu-0.18073*Ala+3.3378*ABA+0.36914*Arg' | 0.8302 |
| 73 | 'Glu-0.097878*Pro-0.15334*Ala+3.8779*Met' | 0.8236 |
| 74 | 'Glu+0.054246*Gly-0.1657*Ala+3.5638*Met' | 0.8179 |
| 75 | 'Glu-0.17223*Ala+3.6768*Met+0.14883*Phe' | 0.8186 |
| 76 | 'Glu-0.16904*Ala+3.5935*Met+0.073547*Arg' | 0.8148 |
| 77 | 'Glu-0.17403*Ala+3.7246*Met+0.053862*Leu' | 0.8179 |
| 78 | 'Ser-3.9455*ABA-4.1563*Met+0.41186*Lys' | 0.8013 |
| 79 | 'Asn+0.092797*Ala-2.0708*ABA-2.4358*Met' | 0.7887 |
| 80 | 'Glu-0.17539*Pro+3.9015*Met-0.7852*Orn' | 0.8079 |
| 81 | 'Asn-1.5625*Glu+0.26224*Ala-6.4628*ABA' | 0.8179 |
| 82 | 'Glu+0.12718*Gly-0.17004*Ala+3.4262*ABA' | 0.8239 |
| 83 | 'Glu-0.15666*Ala+3.7383*ABA-0.11257*Val' | 0.8192 |
| 84 | 'Ser-1.4452*Glu-0.14682*Gln-5.001*ABA' | 0.8006 |
| 85 | 'Glu+4.0476*Met-0.88714*Orn-0.1439*Lys' | 0.8019 |
| 86 | 'Glu-0.18729*Ala+3.6267*ABA+0.45004*Phe' | 0.8204 |
| 87 | 'Ser-1.338*Glu-6.5249*Met+0.3103*Lys' | 0.8157 |
| 88 | 'Glu-0.27488*Pro+2.3456*ABA+3.1942*Met' | 0.8208 |
| 89 | 'Glu-0.194*Ala+3.735*ABA+0.18172*Leu' | 0.8189 |
| 90 | 'Asn-0.69981*Glu+0.15779*Pro-3.4828*Met' | 0.8142 |
| 91 | 'Glu-0.17821*Ala+4.0053*ABA-0.095029*Lys' | 0.8220 |
| 92 | 'Glu+0.035687*Gln+3.2752*Met-0.82355*Orn' | 0.8057 |
| 93 | 'Glu-0.16553*Ala+3.7791*ABA-0.16276*Tyr' | 0.8223 |
| 94 | 'Asn-1.7404*ABA-2.1638*Met+0.16447*Lys' | 0.7969 |
| 95 | 'Glu+2.9567*ABA+3.4019*Met-0.29349*Lys' | 0.8195 |
| 96 | 'Glu+0.046994*Pro-0.18744*Ala+3.7779*ABA' | 0.8179 |
| 97 | 'Thr-31.6989*Glu+5.6062*Ala-120.0056*ABA' | 0.8170 |
| 98 | 'Asn-1.6365*ABA-2.1871*Met+0.37757*Orn' | 0.7928 |
| 99 | 'Ser-1.7052*Glu+0.30927*Pro-7.3954*Met' | 0.8101 |
| 100 | 'Ser-1.2959*Glu-5.0112*ABA-0.53996*Arg' | 0.8138 |

FIG.44

| No. | Formula | ROC_AUC |
|---|---|---|
| 1 | −0.3433(Thr)/(Orn)+0.2477(Ser)/(Ile)−0.02636(Asn)/(Glu)−0.07731(Gln)/(Tau)+2.622 | 0.9577 |
| 2 | 0.2488(Ser)/(Ile)−0.03783(Asn)/(Glu)−0.07621(Gln)/(Tau)+1.116(Orn)/(Thr)+1.332 | 0.9577 |
| 3 | −0.3444(Thr)/(Orn)+0.4494(Ser)/(Leu)+0.03878(Glu)/(Asn)−0.07985(Gln)/(Tau)+2.591 | 0.9571 |
| 4 | 0.2492(Ser)/(Ile)+0.09131(Glu)/(Asn)−0.07588(Gln)/(Tau)+1.114(Orn)/(Thr)+1.197 | 0.9577 |
| 5 | 0.4289(Ser)/(Leu)+0.05359(Glu)/(Asn)−0.07931(Gln)/(Tau)+1.102(Orn)/(Thr)+1.302 | 0.9603 |
| 6 | 0.5947(Tau)/(Ile)−0.347(Thr)/(Ser)−0.046(Asn)/(Glu)+5.75(Orn)/(Gln)+0.7472 | 0.9583 |
| 7 | −0.3414(Thr)/(Orn)+0.4548(Ser)/(Leu)−0.02142(Asn)/(Glu)−0.07969(Gln)/(Tau)+2.643 | 0.9571 |
| 8 | −0.3425(Thr)/(Orn)+0.2503(Ser)/(Ile)+0.07624(Glu)/(Asn)−0.07663(Gln)/(Tau)+2.507 | 0.9558 |
| 9 | −0.04084(Asn)/(Glu)−0.07437(Gln)/(Tau)−0.6815(Ile)/(Ser)+1.109(Orn)/(Thr)+2.175 | 0.9545 |
| 10 | −0.3444(Thr)/(Orn)+0.04217(Glu)/(Asn)−0.07815(Gln)/(Tau)−0.3775(Leu)/(Ser)+3.424 | 0.9577 |
| 11 | 0.4389(Ser)/(Leu)−0.03252(Asn)/(Glu)−0.07884(Gln)/(Tau)+1.091(Orn)/(Thr)+1.388 | 0.9551 |
| 12 | −0.3432(Thr)/(Orn)−0.02952(Asn)/(Glu)−0.07535(Gln)/(Tau)−0.6867(Ile)/(Ser)+3.462 | 0.9538 |
| 13 | 0.08307(Glu)/(Asn)−0.07456(Gln)/(Tau)−0.6689(Ile)/(Ser)+1.114(Orn)/(Thr)+2.036 | 0.9558 |
| 14 | 0.6047(Tau)/(Ile)+0.3545(Ser)/(Thr)−0.04393(Asn)/(Glu)−0.06647(Gln)/(Orn)+1.32 | 0.9603 |
| 15 | −0.3499(Thr)/(Orn)+1.615(Asn)/(Leu)+0.3688(Glu)/(Ser)−0.07078(Gln)/(Tau)+2.245 | 0.9679 |
| 16 | 0.603(Tau)/(Ile)−0.3956(Thr)/(Ser)−0.04364(Asn)/(Glu)−0.06676(Gln)/(Orn)+2.09 | 0.9603 |
| 17 | −0.02975(Ser)/(Glu)+0.8023(Ile)/(Asn)−0.0668(Gln)/(Tau)+1.106(Orn)/(Thr)+1.17 | 0.9686 |
| 18 | −0.3399(Thr)/(Orn)−0.02655(Asn)/(Glu)−0.07773(Gln)/(Tau)−0.3863(Leu)/(Ser)+3.496 | 0.9577 |
| 19 | −0.3448(Thr)/(Orn)+0.06833(Glu)/(Asn)−0.07516(Gln)/(Tau)−0.6816(Ile)/(Ser)+3.36 | 0.9551 |
| 20 | −0.4218(Thr)/(Ser)−0.0483(Asn)/(Glu)−0.0757(Gln)/(Tau)+0.5859(Orn)/(Ile)+2.266 | 0.9532 |
| 21 | −0.4043(Thr)/(Ser)+0.102(Glu)/(Asn)−0.07664(Gln)/(Tau)−0.2169(Leu)/(Orn)+3.137 | 0.9500 |
| 22 | 0.5954(Tau)/(Ile)+0.2962(Ser)/(Thr)−0.04616(Asn)/(Glu)+5.716(Orn)/(Gln)+0.09355 | 0.9558 |
| 23 | 0.05696(Glu)/(Asn)−0.07774(Gln)/(Tau)−0.3582(Leu)/(Ser)+1.097(Orn)/(Thr)+2.097 | 0.9609 |
| 24 | −0.03744(Asn)/(Glu)−0.077(Gln)/(Tau)−0.3715(Leu)/(Ser)+1.083(Orn)/(Thr)+2.217 | 0.9545 |
| 25 | −0.3482(Thr)/(Orn)−0.02679(Ser)/(Glu)+0.8326(Asn)/(Ile)−0.06713(Gln)/(Tau)+2.442 | 0.9686 |
| 26 | 1.14(Asn)/(Thr)+0.3726(Glu)/(Ser)−0.07412(Gln)/(Tau)+1.25(Orn)/(Leu)+1.092 | 0.9641 |
| 27 | 0.5804(Tau)/(Ile)−0.02991(Ser)/(Glu)+1.042(Asn)/(Thr)+5.748(Orn)/(Gln)+0.02736 | 0.9679 |
| 28 | −0.3508(Thr)/(Tau)+0.4679(Ser)/(Leu)−0.02898(Asn)/(Glu)+6.543(Orn)/(Gln)+1.148 | 0.9519 |
| 29 | −0.02665(Ser)/(Glu)+1.128(Asn)/(Thr)−0.07323(Gln)/(Tau)+1.248(Orn)/(Leu)+1.31 | 0.9603 |
| 30 | 0.5995(Tau)/(Ile)−0.3552(Thr)/(Orn)−0.02827(Asn)/(Glu)−0.08413(Gln)/(Ser)+2.119 | 0.9571 |
| 31 | −0.3392(Thr)/(Tau)−0.03788(Asn)/(Glu)−0.7069(Ile)/(Ser)+6.309(Orn)/(Gln)+2.036 | 0.9468 |
| 32 | −0.417(Thr)/(Ser)−0.05074(Asn)/(Glu)−0.0764(Gln)/(Tau)−0.2184(Leu)/(Orn)+3.312 | 0.9506 |
| 33 | −0.3008(Thr)/(Tau)−0.02824(Ser)/(Glu)+0.7796(Asn)/(Ile)+6.172(Orn)/(Gln)+1.043 | 0.9635 |
| 34 | −0.4311(Thr)/(Ser)−0.05427(Asn)/(Glu)−0.07502(Gln)/(Tau)−0.374(Ile)/(Orn)+3.275 | 0.9462 |
| 35 | 0.5933(Tau)/(Ile)−0.3348(Thr)/(Ser)+0.1109(Glu)/(Asn)+5.716(Orn)/(Gln)+0.5794 | 0.9583 |
| 36 | 0.5943(Tau)/(Ile)−0.03792(Asn)/(Glu)−0.0731(Gln)/(Ser)+1.121(Orn)/(Thr)+0.7557 | 0.9603 |
| 37 | 1.028(Tau)/(Leu)+0.9895(Asn)/(Thr)+0.3114(Glu)/(Ser)+5.865(Orn)/(Gln)−0.1545 | 0.9724 |
| 38 | −0.3708(Thr)/(Ser)+0.09743(Glu)/(Asn)−0.07646(Gln)/(Tau)+1.219(Orn)/(Leu)+2.016 | 0.9506 |
| 39 | −0.3492(Thr)/(Orn)+0.8462(Asn)/(Ile)+0.4321(Glu)/(Ser)−0.06704(Gln)/(Tau)+2.194 | 0.9712 |
| 40 | 1.005(Tau)/(Leu)−0.03065(Ser)/(Glu)+0.9893(Asn)/(Thr)+5.893(Orn)/(Gln)+0.07513 | 0.9705 |
| 41 | −0.4162(Thr)/(Ser)+0.1279(Glu)/(Asn)−0.07453(Gln)/(Tau)−0.3729(Ile)/(Orn)+3.067 | 0.9487 |
| 42 | −0.3469(Thr)/(Orn)−0.02555(Ser)/(Glu)+1.613(Asn)/(Leu)−0.07021(Gln)/(Tau)+2.449 | 0.9647 |
| 43 | 0.3666(Ser)/(Thr)−0.0487(Asn)/(Glu)−0.07554(Gln)/(Tau)+0.5827(Orn)/(Ile)+1.463 | 0.9487 |
| 44 | −0.3498(Thr)/(Tau)+0.4665(Ser)/(Leu)+0.0783(Glu)/(Asn)+6.512(Orn)/(Gln)+1.044 | 0.9532 |
| 45 | 0.806(Asn)/(Ile)+0.4294(Glu)/(Ser)−0.06758(Gln)/(Tau)+1.103(Orn)/(Thr)+0.9264 | 0.9686 |
| 46 | 0.5603(Tau)/(Ile)+0.5892(Asn)/(Ser)+0.5782(Glu)/(Thr)−0.0622(Gln)/(Orn)+1.189 | 0.9609 |
| 47 | 1.501(Asn)/(Leu)+0.3662(Glu)/(Ser)−0.07152(Gln)/(Tau)+1.085(Orn)/(Thr)+1.001 | 0.9647 |
| 48 | −0.346(Thr)/(Tau)+0.2558(Ser)/(Ile)−0.03431(Asn)/(Glu)+6.394(Orn)/(Gln)+1.153 | 0.9526 |
| 49 | −0.355(Thr)/(Tau)+0.5013(Ser)/(Leu)−0.02773(Asn)/(Glu)−0.07442(Gln)/(Orn)+2.592 | 0.9513 |
| 50 | 0.605(Tau)/(Ile)−0.385(Thr)/(Ser)+0.08611(Glu)/(Asn)−0.06645(Gln)/(Orn)+1.936 | 0.9603 |

FIG.45

| No. | Formula | ROC_AUC |
|---|---|---|
| 51 | 'Orn/Ile−2.5762*Thr/Ala' | 0.9276 |
| 52 | 'Orn/Leu−1.2462*Thr/Ala' | 0.9237 |
| 53 | 'Orn/Trp−2.7875*Thr/Ala' | 0.9218 |
| 54 | 'Orn/Phe−2.4289*Thr/Ala' | 0.9212 |
| 55 | 'Ala/Trp−2.2748*Thr/Orn' | 0.9192 |
| 56 | 'Orn/Phe−0.89908*Gly/Ala' | 0.9141 |
| 57 | 'Ala/Trp+6.9092*Orn/Arg' | 0.9141 |
| 58 | 'Orn/Trp+0.18596*Ala/Phe' | 0.9103 |
| 59 | 'Orn/Phe+0.25801*Ala/Trp' | 0.9096 |
| 60 | 'Ala/Trp−3.0431*Phe/Orn' | 0.9096 |
| 61 | 'Ala/Trp−6.6291*Met/Orn' | 0.9090 |
| 62 | 'Orn/Phe−1.5383*Ser/Ala' | 0.9077 |
| 63 | 'Ala/Trp−1.4486*Leu/Orn' | 0.9077 |
| 64 | 'Orn/Ile−0.079797*Thr/Glu' | 0.9051 |
| 65 | 'Ala/Trp−2.4933*Ile/Orn' | 0.9045 |
| 66 | 'Orn/Trp+0.076017*Ala/Met' | 0.9038 |
| 67 | 'Orn/Leu+0.12414*Ala/Trp' | 0.9026 |
| 68 | 'Orn/Phe+0.065057*Ala/Met' | 0.9019 |
| 69 | 'Orn/Trp−1.0704*Gly/Ala' | 0.9019 |
| 70 | 'Orn/Trp+0.18557*Ala/Ile' | 0.9013 |
| 71 | 'Orn/Ile+0.26182*Ala/Trp' | 0.8994 |
| 72 | 'Orn/Leu−0.46878*Gly/Ala' | 0.8981 |
| 73 | 'Orn/Phe−1.1776*Pro/Ala' | 0.8974 |
| 74 | 'Orn/Ile−0.92532*Gly/Ala' | 0.8968 |
| 75 | 'Orn/Trp−1.9728*Ser/Ala' | 0.8962 |
| 76 | 'Orn/Trp+0.20535*Ala/Arg' | 0.8955 |
| 77 | 'Ala/Trp−1.3719*Ser/Orn' | 0.8942 |
| 78 | 'Ala/Trp−0.92682*Gly/Orn' | 0.8942 |
| 79 | 'Orn/Phe+0.1695*Ala/Arg' | 0.8929 |
| 80 | 'Orn/Phe−0.36777*Gln/Ala' | 0.8929 |
| 81 | 'Orn/Trp+0.35474*Ala/Leu' | 0.8929 |
| 82 | 'Orn/Ile+1.4196*Glu/Phe' | 0.8923 |
| 83 | 'Orn/Trp−0.46026*Gln/Ala' | 0.8917 |
| 84 | 'Ala/Trp+0.062088*Orn' | 0.8910 |
| 85 | 'Orn/Phe+0.16916*Ala/Ile' | 0.8904 |
| 86 | 'Ala/Trp−1.9074*His/Orn' | 0.8891 |
| 87 | 'Orn/Leu−0.20483*Gln/Ala' | 0.8885 |
| 88 | 'Orn/Ile+0.18085*Ala/Arg' | 0.8878 |
| 89 | 'Orn/Trp+0.21937*Ala/His' | 0.8872 |
| 90 | 'Ala/Trp−0.79737*Pro/Orn' | 0.8872 |
| 91 | 'Orn/Leu−3.5211*Cit/Val' | 0.8865 |
| 92 | 'Orn/Phe+1.848*Glu/Ile' | 0.8859 |
| 93 | 'Orn/Phe+0.0016596*Ala' | 0.8859 |
| 94 | 'Orn/Ile+3.7328*Glu/Lys' | 0.8859 |
| 95 | 'Orn/Trp+0.0022086*Ala' | 0.8859 |
| 96 | 'Orn/Phe+0.32164*Ala/Leu' | 0.8853 |
| 97 | 'Orn/Leu−0.79524*Ser/Ala' | 0.8853 |
| 98 | 'Orn/Ile+9.4048*Glu/Gln' | 0.8846 |
| 99 | 'Orn/Leu+0.08927*Ala/Arg' | 0.8846 |
| 100 | 'Orn/Ile+0.16997*Ala/Phe' | 0.8840 |

FIG.47

| No | Formula | ROC_AUC |
|---|---|---|
| 1 | [-30.7069]+[0.3015]Tau+[-0.1160]Thr+[0.0859]Ser+[0.0344]Ala+[0.3505]Orn+[-0.1562]Arg | 0.9878 |
| 2 | [-23.0868]+[0.1888]Tau+[0.0235]Ala+[0.0386]Val+[-0.1647]Trp+[0.2281]Orn+[-0.0996]Arg | 0.9859 |
| 3 | [-21.4692]+[0.2449]Tau+[0.1626]Asn+[0.0258]Ala+[-0.1429]Trp+[0.2544]Orn+[-0.1478]Arg | 0.9859 |
| 4 | [-14.7274]+[0.3130]Tau+[-0.1957]Thr+[0.0449]Ala+[-0.2252]Trp+[0.4245]Orn+[-0.0433]Lys | 0.9846 |
| 5 | [-9.2789]+[0.2677]Tau+[-0.1364]Thr+[-0.0141]Gln+[0.0313]Ala+[-0.1794]Trp+[0.2917]Orn | 0.9846 |
| 6 | [-11.0403]+[0.2725]Tau+[-0.1983]Thr+[0.0484]Ala+[-0.1747]Phe+[-0.2151]Trp+[0.4100]Orn | 0.984 |
| 7 | [-16.9566]+[0.1900]Tau+[-0.1127]Thr+[0.0341]Ala+[-0.0985]Ile+[0.3938]Orn+[-0.0994]Arg | 0.9833 |
| 8 | [-24.0329]+[0.2616]Tau+[0.0552]Ser+[0.0297]Ala+[-0.1367]Trp+[0.2275]Orn+[-0.1292]Arg | 0.9827 |
| 9 | [-11.1644]+[0.2232]Tau+[-0.0122]Gln+[0.0204]Ala+[-0.1175]Trp+[0.2422]Orn+[-0.0835]Arg | 0.9814 |
| 10 | [-17.5272]+[0.2257]Tau+[-0.1506]Thr+[0.0379]Ala+[0.0214]Val+[-0.2445]Trp+[0.2757]Orn | 0.9814 |
| 11 | [-24.7692]+[0.2265]Tau+[-0.1401]Thr+[0.1460]Glu+[0.0373]Ala+[-0.1513]Ile+[0.3218]Orn | 0.9814 |
| 12 | [-18.9213]+[0.3294]Tau+[-0.0354]Gln+[0.0811]Val+[-0.1072]Leu+[0.3851]Orn+[-0.0777]Arg | 0.9814 |
| 13 | [-23.7425]+[0.2382]Tau+[-0.0761]Thr+[0.1673]Asn+[0.0246]Ala+[0.3218]Orn+[-0.1594]Arg | 0.9808 |
| 14 | [-27.4081]+[0.2191]Tau+[0.0518]Ser+[0.0741]Glu+[0.0206]Ala+[0.1836]Orn+[-0.1148]Arg | 0.9808 |
| 15 | [-13.5877]+[0.2293]Tau+[-0.1267]Thr+[0.0351]Ala+[-0.0867]Cit+[-0.2072]Trp+[0.2702]Orn | 0.9801 |
| 16 | [-7.8413]+[0.2232]Tau+[-0.1150]Thr+[-0.0193]Gln+[0.0228]Ala+[-0.0900]Ile+[0.2971]Orn | 0.9801 |
| 17 | [-14.5481]+[0.2054]Tau+[-0.1072]Thr+[0.0289]Ala+[-0.1264]Phe+[0.3720]Orn+[-0.0891]Arg | 0.9801 |
| 18 | [-22.8535]+[0.2099]Tau+[0.1446]Asn+[0.0213]Ala+[-0.0556]Ile+[0.2571]Orn+[-0.1403]Arg | 0.9801 |
| 19 | [-21.1329]+[0.1477]Tau+[-0.0886]Thr+[0.0187]Ala+[0.0468]Val+[-0.1597]Ile+[0.2454]Orn | 0.9801 |
| 20 | [-22.1239]+[0.2176]Tau+[0.1621]Asn+[0.0210]Ala+[-0.0331]Leu+[0.2363]Orn+[-0.1419]Arg | 0.9801 |
| 21 | [-20.4509]+[0.1972]Tau+[0.1272]Asn+[0.0181]Ala+[-0.0552]Phe+[0.2266]Orn+[-0.1225]Arg | 0.9801 |
| 22 | [-25.8181]+[0.1741]Tau+[0.0193]Ala+[0.0537]Val+[-0.0718]Leu+[0.2252]Orn+[-0.0919]Arg | 0.9795 |
| 23 | [-14.7181]+[0.1955]Tau+[0.0232]Ala+[-0.0896]Cit+[-0.1368]Trp+[0.2286]Orn+[-0.0800]Arg | 0.9795 |
| 24 | [-19.5293]+[0.2194]Tau+[0.0266]Ala+[0.1609]ABA+[-0.1843]Trp+[0.2352]Orn+[-0.0852]Arg | 0.9788 |
| 25 | [-22.6024]+[0.2098]Tau+[0.1523]Asn+[0.0202]Ala+[-0.1329]Met+[0.2440]Orn+[-0.1371]Arg | 0.9788 |
| 26 | [-14.7196]+[0.1849]Tau+[0.0225]Ala+[-0.1276]Trp+[0.2079]Orn+[-0.0010]Lys+[-0.0817]Arg | 0.9788 |
| 27 | [-14.7141]+[0.2309]Tau+[-0.1381]Thr+[0.0155]Glu+[0.0367]Ala+[-0.2150]Trp+[0.2657]Orn | 0.9782 |
| 28 | [-16.7494]+[0.1871]Tau+[0.0528]Glu+[0.0224]Ala+[-0.1227]Trp+[0.2023]Orn+[-0.0810]Arg | 0.9782 |
| 29 | [-14.8437]+[0.1870]Tau+[0.0225]Ala+[0.0591]Met+[-0.1433]Trp+[0.2041]Orn+[-0.0882]Arg | 0.9782 |
| 30 | [-14.7565]+[0.1822]Tau+[0.0223]Ala+[0.0212]Tyr+[-0.1356]Trp+[0.2008]Orn+[-0.0877]Arg | 0.9782 |
| 31 | [-6.6355]+[0.2153]Tau+[-0.1001]Thr+[-0.0170]Gln+[0.0186]Ala+[-0.1029]Phe+[0.2700]Orn | 0.9782 |
| 32 | [-14.7401]+[0.1840]Tau+[0.0225]Ala+[-0.1292]Trp+[0.2074]Orn+[-0.0821]Arg | 0.9782 |
| 33 | [-17.4744]+[0.2504]Tau+[-0.1802]Thr+[0.0445]Ser+[0.0407]Ala+[-0.2313]Trp+[0.2902]Orn | 0.9782 |
| 34 | [-20.7877]+[0.1718]Tau+[0.0827]Glu+[0.0198]Ala+[-0.0520]Ile+[0.2043]Orn+[-0.0722]Arg | 0.9782 |
| 35 | [-14.5851]+[0.1835]Tau+[-0.0005]Gly+[0.0224]Ala+[-0.1289]Trp+[0.2073]Orn+[-0.0819]Arg | 0.9782 |
| 36 | [-14.7949]+[0.1827]Tau+[0.0226]Ala+[-0.0041]Ile+[-0.1250]Trp+[0.2095]Orn+[-0.0818]Arg | 0.9782 |
| 37 | [-16.9257]+[0.1589]Tau+[-0.0507]Thr+[0.0545]Val+[-0.1137]Ile+[-0.0882]Trp+[0.2258]Orn | 0.9782 |
| 38 | [-14.2956]+[0.2502]Tau+[-0.1395]Thr+[0.0392]Ala+[-0.0390]Tyr+[-0.2208]Trp+[0.2898]Orn | 0.9776 |
| 39 | [-5.4665]+[0.2256]Tau+[-0.1115]Thr+[-0.0210]Gln+[0.0218]Ala+[-0.0498]Leu+[0.2743]Orn | 0.9776 |
| 40 | [-14.9230]+[0.1838]Tau+[0.0045]Pro+[0.0219]Ala+[-0.1303]Trp+[0.2059]Orn+[-0.0830]Arg | 0.9776 |
| 41 | [-14.8241]+[0.1833]Tau+[0.0226]Ala+[0.0023]His+[-0.1308]Trp+[0.2083]Orn+[-0.0826]Arg | 0.9776 |
| 42 | [-16.1801]+[0.2017]Tau+[-0.0865]Thr+[0.0259]Ala+[0.3164]Orn+[-0.0254]Lys+[-0.0809]Arg | 0.9776 |
| 43 | [-18.8483]+[0.1684]Tau+[0.0665]Glu+[0.0184]Ala+[-0.0225]Leu+[0.1858]Orn+[-0.0756]Arg | 0.9776 |
| 44 | [-13.8351]+[0.2460]Tau+[-0.1403]Thr+[0.0367]Ala+[-0.0249]His+[-0.1989]Trp+[0.2685]Orn | 0.9776 |
| 45 | [-13.5482]+[0.2273]Tau+[-0.1346]Thr+[-0.0000]Gly+[0.0357]Ala+[-0.2173]Trp+[0.2607]Orn | 0.9776 |
| 46 | [-11.3649]+[0.2350]Tau+[-0.0293]Gln+[-0.2391]Cit+[0.0638]Val+[-0.1060]Leu+[0.3080]Orn | 0.9769 |
| 47 | [-28.3046]+[0.1666]Tau+[0.0196]Ala+[0.0455]Val+[-0.0980]Ile+[0.2692]Orn+[-0.0940]Arg | 0.9769 |
| 48 | [-14.9224]+[0.1858]Tau+[0.0225]Ala+[0.0057]Leu+[-0.1372]Trp+[0.2063]Orn+[-0.0830]Arg | 0.9769 |
| 49 | [-14.5197]+[0.1845]Tau+[0.0224]Ala+[-0.0229]Phe+[-0.1187]Trp+[0.2141]Orn+[-0.0791]Arg | 0.9769 |
| 50 | [-20.6818]+[0.1957]Tau+[-0.0617]Thr+[0.0604]Glu+[0.0238]Ala+[0.2393]Orn+[-0.0826]Arg | 0.9769 |

FIG.48

| No | Formula | ROC_AUC |
|---|---|---|
| 51 | '-2.9976-0.087926*Thr+0.019668*Ala-0.11044*Ile+0.21889*Orn' | 0.9218 |
| 52 | '-9.1522+0.098139*Glu+0.010955*Ala-0.09401*Ile+0.13631*Orn' | 0.9103 |
| 53 | '-1.4381-0.075453*Thr+0.018192*Ala-0.061447*Leu+0.18071*Orn' | 0.9064 |
| 54 | '-0.36711-0.05637*Thr+0.01993*Ala-0.15437*Trp+0.13911*Orn' | 0.9141 |
| 55 | '-2.2519+0.016793*Ala-0.12313*Trp+0.13323*Orn-0.045379*Arg' | 0.9077 |
| 56 | '-4.6321+0.014167*Ala-0.074885*Ile+0.17564*Orn-0.057588*Arg' | 0.9019 |
| 57 | '-2.5257+0.011407*Ala-0.15486*Met-0.085127*Phe+0.13408*Orn' | 0.9000 |
| 58 | '-2.1392+0.015957*Ala-0.14393*Met-0.11408*Trp+0.11451*Orn' | 0.9026 |
| 59 | '-2.8071+0.015323*Ala-0.043741*Ile-0.11498*Trp+0.11528*Orn' | 0.8923 |
| 60 | '-1.7694+0.014021*Ala-0.065007*Phe-0.099905*Trp+0.11228*Orn' | 0.8981 |
| 61 | '-1.3907+0.013423*Ala-0.12987*Cit-0.136*Trp+0.11943*Orn' | 0.8955 |
| 62 | '-1.0943-0.060877*Thr+0.014545*Ala-0.12287*Phe+0.17649*Orn' | 0.9064 |
| 63 | '-3.2424+0.010487*Ala-0.046405*Ile-0.081319*Phe+0.12983*Orn' | 0.8962 |
| 64 | '0.11745-0.016623*Gly+0.0090916*Ala-0.11666*Phe+0.13281*Orn' | 0.8923 |
| 65 | '-3.0116+0.01201*Ala-0.088363*Phe+0.14799*Orn-0.043898*Arg' | 0.8942 |
| 66 | '-3.5898+0.013951*Ala-0.042307*Leu+0.15986*Orn-0.056089*Arg' | 0.8968 |
| 67 | '-0.76097-0.025846*Ser+0.015703*Ala-0.15186*Trp+0.11432*Orn' | 0.9000 |
| 68 | '-7.9106+0.09747*Glu+0.018189*Val-0.10716*Ile+0.12555*Orn' | 0.8917 |
| 69 | '-2.2122+0.015397*Ala-0.024204*Leu-0.11772*Trp+0.10878*Orn' | 0.8962 |
| 70 | '-4.5301+0.011807*Ala-0.15684*Met-0.055168*Ile+0.13555*Orn' | 0.8929 |
| 71 | '-4.4205+0.041726*Glu+0.014043*Ala-0.13629*Trp+0.097832*Orn' | 0.8923 |
| 72 | '-5.194+0.052518*Glu+0.0091112*Ala-0.10659*Phe+0.11649*Orn' | 0.8891 |
| 73 | '-3.5695+0.012086*Ala-0.16645*Met-0.032257*Leu+0.12668*Orn' | 0.8821 |
| 74 | '-1.6986+0.014748*Ala-0.016371*His-0.13836*Trp+0.09468*Orn' | 0.8885 |
| 75 | '-2.3918+0.014737*Ala-0.14815*Trp+0.093866*Orn' | 0.8878 |
| 76 | '-6.0718+0.044368*Asn+0.10172*Glu-0.086697*Ile+0.11259*Orn' | 0.8885 |
| 77 | '-2.6477+0.010466*Ala-0.025287*Leu-0.083098*Phe+0.12223*Orn' | 0.8917 |
| 78 | '-0.16779-0.011194*Gly+0.014507*Ala-0.15034*Trp+0.10484*Orn' | 0.8904 |
| 79 | '-2.8809+0.079399*Glu-0.05531*Ile-0.043255*Phe+0.11721*Orn' | 0.8891 |
| 80 | '-7.4349+0.075363*Glu+0.010303*Ala-0.048889*Leu+0.12048*Orn' | 0.8872 |
| 81 | '-3.8115+0.085532*Glu-0.10233*Cit-0.069364*Ile+0.13469*Orn' | 0.8846 |
| 82 | '-2.1331+0.014867*Ala-0.14229*Trp+0.098821*Orn-0.0043005*Lys' | 0.8929 |
| 83 | '-2.9972+0.01472*Ala+0.0051445*Val-0.15708*Trp+0.091077*Orn' | 0.8853 |
| 84 | '1.5079-0.062522*Thr+0.073523*Tyr-0.13882*Phe+0.15843*Orn' | 0.8853 |
| 85 | '2.694-0.018969*Gly+0.034883*Tyr-0.1262*Phe+0.12536*Orn' | 0.8641 |
| 86 | '-3.6351+0.010674*Ala-0.070858*Ile-0.035992*His+0.12215*Orn' | 0.8744 |
| 87 | '-2.4913+0.014771*Ala+0.011531*ABA-0.15048*Trp+0.093969*Orn' | 0.8865 |
| 88 | '-1.7842-0.023494*Ser+0.0096814*Ala-0.11262*Phe+0.13651*Orn' | 0.8904 |
| 89 | '-2.156-0.006993*Pro+0.015597*Ala-0.1442*Trp+0.098818*Orn' | 0.8878 |
| 90 | '-2.2218-0.00041966*Gln+0.014636*Ala-0.14689*Trp+0.094749*Orn' | 0.8878 |
| 91 | '-2.4878+0.014481*Ala+0.0070525*Tyr-0.15234*Trp+0.092557*Orn' | 0.8885 |
| 92 | '-2.3225-0.0092394*Asn+0.015027*Ala-0.14625*Trp+0.095871*Orn' | 0.8878 |
| 93 | '-0.82054-0.18973*Met+0.06988*Tyr-0.096114*Phe+0.12257*Orn' | 0.8962 |
| 94 | '-2.1269+0.0096308*Ala-0.10154*Phe-0.021765*His+0.11472*Orn' | 0.8801 |
| 95 | '-4.4957+0.0093809*Ala-0.14696*Cit-0.076008*Ile+0.154*Orn' | 0.8795 |
| 96 | '3.3075+0.034224*Asn-0.019015*Gly-0.11278*Phe+0.11831*Orn' | 0.8609 |
| 97 | '-3.6352+0.085672*Glu-0.066316*Ile+0.1296*Orn-0.021108*Arg' | 0.8827 |
| 98 | '-2.3038+0.0082037*Ala-0.09766*Cit-0.10043*Phe+0.13053*Orn' | 0.8782 |
| 99 | '-6.493+0.10759*Glu+0.081008*ABA-0.085898*Ile+0.12433*Orn' | 0.8846 |
| 100 | '-3.1041+0.0091097*Ala-0.11219*Phe+0.11633*Orn' | 0.8763 |

FIG.50

| No. | Formula | ROC_AUC |
|---|---|---|
| 1 | (6.270e−01)Tau+(7.477e−02)Ala+(1.920e−01)Val−(3.664e−01)Leu+(6.145e−01)Orn−(2.293e−01)Arg−(7.605e+01) | 0.9814 |
| 2 | −(5.479e−01)Tau+(1.009e−01)Thr+(9.382e−02)Ala+(5.729e−01)Trp−(5.697e−01)Orn+(1.675e−01)Arg+(3.402e+01) | 0.9801 |
| 3 | −(5.237e−01)Tau−(2.911e−01)Asn+(7.693e−02)Ala+(5.782e−01)Trp−(4.866e−01)Orn+(2.530e−01)Arg+(3.657e+01) | 0.9795 |
| 4 | (5.910e−01)Tau+(3.101e−01)Asn+(6.691e−02)Ala−(2.577e−01)Ile+(6.194e−01)Orn−(3.162e−01)Arg−(5.616e+01) | 0.9788 |
| 5 | (4.796e−01)Tau−(1.683e−01)Thr+(8.070e−02)Ala+(3.452e−01)ABA−(6.153e−01)Trp+(4.873e−01)Orn−(3.468e+01) | 0.9776 |
| 6 | −(6.085e−01)Tau−(6.889e−02)Ala−(1.419e−01)Val+(4.386e−01)Ile−(6.009e−01)Orn+(2.270e−01)Arg+(7.616e+01) | 0.9776 |
| 7 | −(6.076e−01)Tau+(1.560e−01)Thr−(3.162e−01)Asn−(6.246e−02)Ala−(6.522e−01)Orn+(2.780e−01)Arg+(6.226e+01) | 0.9769 |
| 8 | (6.251e−01)Tau+(2.179e−01)Glu+(7.471e−02)Ala−(2.666e−01)Phe+(6.544e−01)Orn−(2.384e−01)Arg−(6.399e+01) | 0.9769 |
| 9 | −(5.691e−01)Tau+(2.089e−01)Thr−(2.838e−01)Glu−(7.435e−02)Ala+(3.463e−01)Ile−(6.530e−01)Orn+(5.815e+01) | 0.9763 |
| 10 | −(5.866e−01)Tau−(2.988e−01)Glu−(7.604e−02)Ala+(2.833e−01)Ile−(6.512e−01)Orn+(2.377e−01)Arg+(6.289e+01) | 0.9763 |
| 11 | (5.982e−01)Tau+(2.960e−01)Asn+(6.227e−02)Ala−(2.832e−01)Met+(6.155e−01)Orn−(3.026e−01)Arg−(6.547e+01) | 0.9763 |
| 12 | −(6.207e−01)Tau+(1.411e−01)Thr−(8.132e−02)Ala−(2.753e−01)Phe−(6.901e−01)Orn+(1.901e−01)Arg+(5.031e+01) | 0.9763 |
| 13 | (6.454e−01)Tau+(1.084e−01)Ser+(2.630e−01)Glu+(6.892e−02)Ala+(6.372e−01)Orn−(3.030e−01)Arg−(8.693e+01) | 0.9756 |
| 14 | (6.454e−01)Tau+(2.481e−01)Asn+(6.121e−02)Ala+(2.322e−02)Val+(6.346e−01)Orn−(3.389e−01)Arg−(7.689e+01) | 0.975 |
| 15 | (5.219e−01)Tau+(8.703e−02)Ala+(2.410e−01)ABA−(5.976e−01)Trp+(5.165e−01)Orn−(1.951e−01)Arg−(3.848e+01) | 0.975 |
| 16 | (5.204e−01)Tau+(7.884e−02)Ala+(1.076e−01)Val−(7.029e−01)Trp+(4.360e−01)Orn−(1.651e−01)Arg−(5.040e+01) | 0.975 |
| 17 | (6.416e−01)Tau+(6.990e−02)Ala+(8.310e−02)Val−(3.812e−01)Phe+(6.168e−01)Orn−(2.252e−01)Arg−(6.928e+01) | 0.975 |
| 18 | −(5.996e−01)Tau+(1.569e−01)Thr−(8.515e−02)Ala+(2.664e−01)Ile−(7.063e−01)Orn+(1.971e−01)Arg+(4.895e+01) | 0.975 |
| 19 | (6.317e−01)Tau+(2.627e−01)Asn−(1.418e−02)Gly+(6.168e−02)Ala+(6.437e−01)Orn−(3.370e−01)Arg−(6.839e+01) | 0.9744 |
| 20 | (6.136e−01)Tau−(1.504e−01)Thr+(8.848e−02)Ala−(1.661e−01)Leu+(7.217e−01)Orn−(2.112e−01)Arg−(4.826e+01) | 0.9744 |
| 21 | (6.183e−01)Tau+(5.696e−02)Pro+(7.483e−02)Ala−(2.974e−01)Ile+(6.667e−01)Orn−(2.755e−01)Arg−(5.977e+01) | 0.9744 |
| 22 | −(5.248e−01)Tau−(8.318e−02)Ala−(2.908e−01)Met+(5.827e−01)Trp−(4.929e−01)Orn+(2.252e−01)Arg+(3.724e+01) | 0.9744 |
| 23 | −(5.499e−01)Tau+(1.718e−01)Thr−(9.147e−02)Ala+(1.096e−01)Phe+(5.896e−01)Trp−(5.478e−01)Orn+(3.323e+01) | 0.9744 |
| 24 | −(6.349e−01)Tau+(1.166e−01)Thr−(1.808e−01)Glu−(7.442e−02)Ala−(6.998e−01)Orn+(2.353e−01)Arg+(7.131e+01) | 0.9744 |
| 25 | (6.366e−01)Tau+(2.579e−01)Asn+(3.560e−04)Pro+(6.298e−02)Ala+(6.387e−01)Orn−(3.412e−01)Arg−(7.157e+01) | 0.9744 |
| 26 | (6.272e−01)Tau+(2.819e−01)Asn+(6.206e−02)Ala−(1.385e−01)ABA+(6.230e−01)Orn−(3.256e−01)Arg−(6.821e+01) | 0.9744 |
| 27 | (6.039e−01)Tau+(3.036e−01)Asn+(7.073e−02)Ala−(1.635e−01)Leu+(6.367e−01)Orn−(2.256e−01)Arg−(5.489e+01) | 0.9744 |
| 28 | (6.593e−01)Tau+(1.033e−01)Ser−(2.916e−02)Gly+(7.229e−02)Ala+(6.703e−01)Orn−(3.151e−01)Arg−(7.419e+01) | 0.9744 |
| 29 | (6.377e−01)Tau+(2.698e−01)Asn−(9.884e−03)Gln+(6.101e−02)Ala+(6.390e−01)Orn−(3.294e−01)Arg−(6.669e+01) | 0.9737 |
| 30 | −(6.374e−01)Tau+(1.355e−01)Thr−(8.375e−02)Ala+(1.328e−01)His−(7.067e−01)Orn+(2.265e−01)Arg+(5.771e+01) | 0.9737 |
| 31 | (6.767e−01)Tau+(8.883e−02)Ser+(7.138e−02)Ala+(3.206e−02)Val−(6.524e−01)Orn−(3.201e−01)Arg−(8.669e+01) | 0.9737 |
| 32 | (6.306e−01)Tau+(2.928e−01)Asn+(6.527e−02)Ala−(7.638e−02)Tyr+(6.292e−01)Orn−(3.324e−01)Arg−(6.819e+01) | 0.9737 |
| 33 | −(6.368e−01)Tau−(2.573e−01)Asn−(6.313e−02)Ala−(6.393e−01)Orn+(1.575e−03)Lys+(3.400e−01)Arg+(7.137e+01) | 0.9737 |
| 34 | (6.365e−01)Tau+(2.581e−01)Asn+(6.302e−02)Ala+(6.387e−01)Orn−(3.411e−01)Arg−(7.154e+01) | 0.9737 |
| 35 | −(5.482e−01)Tau+(1.864e−01)Thr−(9.399e−02)Ala+(1.467e−01)Ile+(5.565e−01)Trp−(5.697e−01)Orn+(3.288e+01) | 0.9737 |
| 36 | (6.344e−01)Tau+(9.170e−02)Ser+(8.167e−02)Ala−(2.500e−01)Ile+(6.587e−01)Orn−(2.933e−01)Arg−(6.583e+01) | 0.9737 |
| 37 | (6.483e−01)Tau+(4.023e−02)Ser+(2.101e−01)Asn+(6.544e−02)Ala+(6.409e−01)Orn−(3.449e−01)Arg−(7.525e+01) | 0.9737 |
| 38 | −(5.644e−01)Tau−(5.030e−02)Ser−(9.167e−02)Ala+(5.759e−01)Trp−(5.372e−01)Orn+(2.243e−01)Arg+(4.310e+01) | 0.9731 |
| 39 | (6.428e−01)Tau+(2.282e−01)Glu−(2.748e−03)Gln+(7.060e−02)Ala+(6.725e−01)Orn−(2.784e−01)Arg−(7.706e+01) | 0.9731 |
| 40 | (5.528e−01)Tau+(1.171e−01)Glu+(9.010e−02)Ala−(5.781e−01)Trp+(5.450e−01)Orn−(2.035e−01)Arg−(4.225e+01) | 0.9731 |
| 41 | −(6.678e−01)Tau−(8.969e−02)Ser−(7.654e−02)Ala+(3.157e−02)Tyr−(6.624e−01)Orn+(3.168e−01)Arg+(7.849e+01) | 0.9731 |
| 42 | (6.222e−01)Tau+(2.564e−01)Asn+(6.016e−02)Ala−(1.269e−01)Cit+(6.499e−01)Orn−(3.240e−01)Arg−(6.926e+01) | 0.9731 |
| 43 | (5.422e−01)Tau+(8.959e−02)Ala−(1.020e−01)Cit−(5.869e−01)Trp+(5.522e−01)Orn+(1.953e−01)Arg−(3.638e+01) | 0.9731 |
| 44 | −(6.425e−01)Tau−(2.305e−01)Glu−(7.141e−02)Ala−(6.737e−01)Orn+(1.259e−02)Lys+(2.736e−01)Arg+(7.692e+01) | 0.9731 |
| 45 | −(4.264e−01)Tau−(6.393e−02)Ala+(4.399e−01)Cit−(2.354e−01)ABA+(5.910e−01)Trp−(4.647e−01)Orn+(3.273e+01) | 0.9731 |
| 46 | −(6.530e−01)Tau+(1.392e−01)Thr−(7.439e−02)Ala−(3.503e−02)Val−(7.010e−01)Orn+(2.367e−01)Arg+(7.318e+01) | 0.9731 |
| 47 | −(6.210e−01)Tau−(8.149e−02)Ala+(4.526e−02)Cit+(2.515e−01)Ile−(6.869e−01)Orn+(2.657e−01)Arg+(5.807e+01) | 0.9731 |
| 48 | (6.249e−01)Tau+(8.248e−02)Ala−(2.534e−01)Ile+(6.819e−01)Orn−(2.710e−01)Arg−(5.867e+01) | 0.9731 |
| 49 | (6.688e−01)Tau+(8.734e−02)Ser−(6.161e−03)Gln+(7.389e−02)Ala+(6.645e−01)Orn−(3.131e−01)Arg−(7.650e+01) | 0.9724 |
| 50 | −(5.005e−01)Tau+(1.412e−01)Thr−(7.560e−02)Ala−(1.123e−01)Val+(7.317e−01)Trp−(4.194e−01)Orn+(4.813e+01) | 0.9724 |

FIG.51

| No. | Formula | ROC_AUC |
|---|---|---|
| 51 | 'Ala-8.4224*Trp+5.3481*Orn-2.1032*Arg' | 0.9026 |
| 52 | 'Thr-0.51638*Ala+4.6091*Trp-2.7952*Orn' | 0.9096 |
| 53 | 'Ala-9.9634*Cit-10.8793*Trp+7.4492*Orn' | 0.8962 |
| 54 | 'Ala-7.6348*Met-8.0569*Trp+5.0335*Orn' | 0.8955 |
| 55 | 'Ala-10.4276*Trp+4.8373*Orn' | 0.8865 |
| 56 | 'Ala-2.4059*Ile-8.5994*Trp+5.0743*Orn' | 0.8910 |
| 57 | 'Glu+0.28824*Ala-3.0186*Trp+1.5152*Orn' | 0.8904 |
| 58 | 'Ala-1.5949*Leu-8.3063*Trp+5.0345*Orn' | 0.8936 |
| 59 | 'Ser-0.7761*Ala+7.9675*Trp-3.8984*Orn' | 0.8904 |
| 60 | 'Ala-3.0287*Phe-8.6881*Trp+5.0832*Orn' | 0.8910 |
| 61 | 'Gly-1.4315*Ala+15.3015*Trp-7.8431*Orn' | 0.8923 |
| 62 | 'Ala-1.446*His-9.3867*Trp+4.6731*Orn' | 0.8846 |
| 63 | 'Ala+0.51178*Val-11.3649*Trp+4.7025*Orn' | 0.8853 |
| 64 | 'Pro-3.1128*Ala+30.651*Trp-14.6198*Orn' | 0.8827 |
| 65 | 'Ala+0.71096*Tyr-11.0921*Trp+4.913*Orn' | 0.8833 |
| 66 | 'Ala-10.1616*Trp+4.9088*Orn-0.20261*Lys' | 0.8833 |
| 67 | 'Ala+0.72384*ABA-10.5342*Trp+4.8526*Orn' | 0.8865 |
| 68 | 'Gln-40.3749*Ala+420.719*Trp-196.9439*Orn' | 0.8897 |
| 69 | 'Asn-9.5444*Ala+98.9165*Trp-46.1359*Orn' | 0.8885 |
| 70 | 'Ala-3.4368*Leu+7.8691*Orn-3.1424*Arg' | 0.8872 |
| 71 | 'Thr-0.31374*Ala+1.2076*Leu-2.5378*Orn' | 0.9045 |
| 72 | 'Glu+0.10029*Ala-0.87768*Ile+0.94499*Orn' | 0.9051 |
| 73 | 'Glu+0.11835*Ala-0.636*Leu+1.0305*Orn' | 0.8756 |
| 74 | 'Thr-0.28661*Ala+1.691*Ile-2.4486*Orn' | 0.9103 |
| 75 | 'Ala-5.1033*Ile+8.326*Orn-3.325*Arg' | 0.8987 |
| 76 | 'Thr-0.31341*Ala+2.4563*Phe-2.7101*Orn' | 0.9000 |
| 77 | 'Ala-16.2562*Cit-5.1355*Leu+12.5273*Orn' | 0.8737 |
| 78 | 'Cit-0.1432*Val+0.33762*Leu-0.5791*Orn' | 0.8750 |
| 79 | 'Ala-6.7779*Phe+8.4677*Orn-3.0454*Arg' | 0.8955 |
| 80 | 'Ala-11.3195*Met-2.9361*Leu+7.4296*Orn' | 0.8821 |
| 81 | 'Ala+1.8404*Val-3.1575*Leu-9.9293*Trp' | 0.8545 |
| 82 | 'Glu+0.13309*Ala-1.4056*Phe+1.2612*Orn' | 0.8821 |
| 83 | 'Gly-0.63034*Ala+3.3452*Leu-5.9914*Orn' | 0.8679 |
| 84 | 'Ala-11.5889*Met-5.8386*Phe+7.8493*Orn' | 0.8981 |
| 85 | 'Ala-2.9653*Leu-5.5413*Phe+7.7813*Orn' | 0.8801 |
| 86 | 'Ala-12.0002*Met-4.0844*Ile+7.8669*Orn' | 0.8891 |
| 87 | 'Ala+1.9828*Val-7.1675*Leu+8.1183*Orn' | 0.8494 |
| 88 | 'Gly-0.60462*Ala+6.8278*Phe-6.175*Orn' | 0.8878 |
| 89 | 'Ala-14.2417*Cit-10.2674*Phe+12.7406*Orn' | 0.8750 |
| 90 | 'Ala+1.4605*Val-3.6871*Ile-10.6364*Trp' | 0.8583 |
| 91 | 'Glu+0.23532*Val-0.75881*Leu+0.93764*Orn' | 0.8622 |
| 92 | 'Ala-4.7627*Leu+8.0641*Orn' | 0.8397 |
| 93 | 'Ala-15.6012*Cit-7.5195*Ile+13.162*Orn' | 0.8801 |
| 94 | 'Ala-4.0461*Ile-6.2843*Phe+8.159*Orn' | 0.8917 |
| 95 | 'Ala-10.2269*Phe+8.6026*Orn' | 0.8737 |
| 96 | 'Glu+0.17734*Ala-3.2574*Met+1.6107*Orn' | 0.8763 |
| 97 | 'Glu+0.14*Val-0.91729*Ile+0.86284*Orn' | 0.8859 |
| 98 | 'Glu+0.231*Ala-0.64428*Ile-2.0228*Trp' | 0.8526 |
| 99 | 'Ala-10.7647*Trp' | 0.8417 |
| 100 | 'Glu+0.30307*Ala-3.2838*Trp' | 0.8500 |

FIG. 54

| No. | Formula | ROC_AUC |
|---|---|---|
| 1 | 3.767(Ser)/(Gln)−0.3057(Glu)/(Tau)+0.0655(Ala)/(Asn)+0.2621(Val)/(Thr)−0.1627 | 0.7797 |
| 2 | −0.982(Thr)/(Ser)−0.3145(Glu)/(Tau)+0.07489(Ala)/(Asn)+8.907(Met)/(Gln)+1.677 | 0.7652 |
| 3 | −0.9496(Thr)/(Ser)−0.3105(Glu)/(Tau)−0.357(Gln)/(Ala)+0.08543(Val)/(Asn)+2.789 | 0.7899 |
| 4 | −0.9485(Thr)/(Ser)−0.3052(Glu)/(Tau)+0.8031(Ala)/(Gln)+0.0868(Val)/(Asn)+1.677 | 0.7841 |
| 5 | −0.8666(Thr)/(Ser)−0.2694(Glu)/(Tau)−0.07861(Gln)/(Tyr)+0.08966(Val)/(Asn)+2.777 | 0.8000 |
| 6 | 3.846(Ser)/(Gln)−4.396(Asn)/(Ala)−0.304(Glu)/(Tau)+0.2642(Val)/(Thr)+0.9224 | 0.7739 |
| 7 | −0.9424(Thr)/(Ser)−0.2657(Glu)/(Tau)+0.7498(Ala)/(Gln)+0.9658(Cit)/(Asn)+1.737 | 0.7667 |
| 8 | −0.9632(Thr)/(Ser)−0.2587(Glu)/(Tau)−0.3487(Gln)/(Ala)+0.4935(ABA)/(Asn)+3.039 | 0.7580 |
| 9 | 3.627(Ser)/(Gln)−0.2545(Glu)/(Tau)+0.1895(Ala)/(Thr)+0.9933(Cit)/(Asn)−0.1282 | 0.7551 |
| 10 | −0.9527(Thr)/(Ser)−0.2744(Glu)/(Tau)−0.3519(Gln)/(Ala)+0.9953(Cit)/(Asn)+2.793 | 0.7826 |
| 11 | −0.09866(Thr)/(Cit)+3.853(Ser)/(Gln)−0.2801(Glu)/(Tau)+0.06603(Ala)/(Asn)+0.9686 | 0.7594 |
| 12 | −1.03(Thr)/(Ser)−0.2936(Glu)/(Tau)+0.08351(Ala)/(Asn)+5.533(Tyr)/(Gln)+1.336 | 0.7884 |
| 13 | −0.9961(Thr)/(Ser)−0.3183(Glu)/(Tau)−0.3738(Gln)/(Ala)+0.8543(Met)/(Asn)+2.838 | 0.7565 |
| 14 | 4.305(Ser)/(Gln)−0.3008(Glu)/(Tau)+0.335(Ile)/(Thr)+0.6236(Tyr)/(Asn)−0.2741 | 0.7623 |
| 15 | −2.567(Thr)/(Ala)+3.918(Ser)/(Gln)−0.3047(Glu)/(Tau)+0.378(Phe)/(Asn)+1.197 | 0.7667 |
| 16 | −1.02(Thr)/(Ser)−0.2687(Glu)/(Tau)+0.8473(Ala)/(Gln)+0.1983(His)/(Asn)+1.831 | 0.7536 |
| 17 | −2.885(Thr)/(Ala)+3.783(Ser)/(Gln)−0.3097(Glu)/(Tau)+0.09093(Val)/(Asn)+1.317 | 0.7841 |
| 18 | −2.81(Asn)/(Ser)−0.2986(Glu)/(Tau)+0.133(Pro)/(Thr)−0.251(Gly)/(Tyr)+3.571 | 0.7754 |
| 19 | −0.9616(Thr)/(Ser)−0.3016(Glu)/(Tau)−0.01554(Gln)/(Met)+0.07365(Ala)/(Asn)+2.421 | 0.7536 |
| 20 | −0.9006(Thr)/(Ser)−0.2892(Glu)/(Tau)+0.7823(Ala)/(Gln)+0.334(Phe)/(Asn)+1.663 | 0.7667 |
| 21 | 3.927(Ser)/(Gln)−0.2948(Glu)/(Tau)+0.1706(Ala)/(Thr)+0.3794(Phe)/(Asn)−0.1571 | 0.7638 |
| 22 | −0.9355(Thr)/(Ser)−0.3009(Glu)/(Tau)+0.06855(Ala)/(Asn)+0.8508(Val)/(Gln)+1.722 | 0.7623 |
| 23 | 3.824(Ser)/(Gln)−0.3006(Glu)/(Tau)+0.1986(Ala)/(Thr)+0.09366(Val)/(Asn)−0.2487 | 0.7725 |
| 24 | −0.07283(Thr)/(Cit)+4.403(Ser)/(Gln)−0.2714(Glu)/(Tau)+0.5721(Tyr)/(Asn)+0.3881 | 0.7638 |
| 25 | 3.955(Ser)/(Gln)−0.3028(Glu)/(Tau)+0.07044(Ala)/(Asn)+0.8107(Phe)/(Thr)−0.1015 | 0.7522 |
| 26 | −0.1072(Thr)/(Ile)+4.315(Ser)/(Gln)−0.3104(Glu)/(Tau)+0.6233(Tyr)/(Asn)+0.1298 | 0.7536 |
| 27 | −0.09912(Thr)/(Met)+4.836(Ser)/(Gln)−0.3078(Glu)/(Tau)+0.6256(Tyr)/(Asn)+0.2442 | 0.7681 |
| 28 | −0.1039(Thr)/(Cit)+4.009(Ser)/(Gln)−4.724(Asn)/(Ala)−0.2823(Glu)/(Tau)+2.118 | 0.7681 |
| 29 | 4.33(Ser)/(Gln)−0.2889(Glu)/(Tau)+0.1612(Val)/(Thr)+0.5724(Tyr)/(Asn)−0.3762 | 0.7652 |
| 30 | −1.025(Thr)/(Ser)−0.2877(Glu)/(Tau)−0.08457(Gln)/(Tyr)+0.08186(Ala)/(Asn)+2.741 | 0.7942 |
| 31 | −1.03(Thr)/(Ser)−5.341(Asn)/(Ala)−0.3178(Glu)/(Tau)+9.11(Met)/(Gln)+3.019 | 0.7565 |
| 32 | 3.554(Ser)/(Gln)−0.266(Glu)/(Tau)+0.06477(Ala)/(Asn)+2.609(Cit)/(Thr)−0.02202 | 0.7522 |
| 33 | −0.1935(Thr)/(Orn)+4.151(Ser)/(Gln)−0.2421(Glu)/(Tau)+0.6314(Tyr)/(Asn)+0.2809 | 0.7855 |
| 34 | 0.8277(Ser)/(Thr)−0.2946(Glu)/(Tau)+0.7734(Ala)/(Gln)+0.08886(Val)/(Asn)−0.1343 | 0.7812 |
| 35 | 4.742(Ser)/(Gln)−0.3016(Glu)/(Tau)+1.324(Met)/(Thr)+0.6337(Tyr)/(Asn)−0.5015 | 0.7594 |
| 36 | 4.348(Ser)/(Gln)−0.2875(Glu)/(Tau)+0.1894(Leu)/(Thr)+0.6376(Tyr)/(Asn)−0.327 | 0.7594 |
| 37 | 0.8303(Ser)/(Thr)−0.2999(Glu)/(Tau)−0.3446(Gln)/(Ala)+0.08756(Val)/(Asn)+0.9335 | 0.7855 |
| 38 | 4.508(Ser)/(Gln)−0.2878(Glu)/(Tau)+0.6077(Tyr)/(Asn)+0.5336(Phe)/(Thr)−0.3993 | 0.7609 |
| 39 | −0.5852(Thr)/(Tyr)+4.33(Ser)/(Gln)−0.273(Glu)/(Tau)+0.08285(Ala)/(Asn)+1.046 | 0.7725 |
| 40 | −0.8962(Thr)/(Ser)−0.2895(Glu)/(Tau)+0.06948(Ala)/(Asn)+2.628(Phe)/(Gln)+1.756 | 0.7565 |
| 41 | −0.9647(Thr)/(Ser)−0.03565(Asn)/(ABA)−0.2533(Glu)/(Tau)−0.3352(Gln)/(Ala)+3.314 | 0.7551 |
| 42 | −1.021(Thr)/(Ser)−0.2751(Glu)/(Tau)−0.3781(Gln)/(Ala)+0.1946(His)/(Asn)+3.005 | 0.7667 |
| 43 | −0.1997(Thr)/(Orn)+3.358(Ser)/(Gln)−0.2444(Glu)/(Tau)+0.0645(Ala)/(Asn)+0.878 | 0.7522 |
| 44 | −0.8873(Thr)/(Ser)−0.246(Glu)/(Tau)−0.3033(Gln)/(Ala)+0.2069(Orn)/(Asn)+2.804 | 0.7652 |
| 45 | −0.9042(Thr)/(Ser)−0.2824(Glu)/(Tau)−0.08028(Gln)/(Val)+0.06569(Ala)/(Asn)+2.268 | 0.7551 |
| 46 | 0.2779(Ser)/(Asn)−0.2986(Glu)/(Tau)+0.7143(Ala)/(Gln)+0.2452(Val)/(Thr)−0.001185 | 0.7768 |
| 47 | −1.01(Thr)/(Ser)−0.2788(Glu)/(Tau)+0.8668(Ala)/(Gln)+0.5739(Tyr)/(Asn)+1.222 | 0.7971 |
| 48 | −0.4772(Thr)/(Pro)+4.907(Ser)/(Gln)−0.3136(Glu)/(Tau)+0.6462(Tyr)/(Asn)+0.1369 | 0.7594 |
| 49 | −0.8255(Thr)/(Ser)−0.2247(Glu)/(Tau)−0.02891(Gln)/(His)+0.88(Cit)/(Asn)+2.394 | 0.7522 |
| 50 | 0.8004(Ser)/(Thr)−0.2583(Glu)/(Tau)−0.3307(Gln)/(Ala)+0.9568(Cit)/(Asn)+0.9771 | 0.7580 |

FIG.55

| No. | Formula | ROC_AUC |
|---|---|---|
| 51 | 'Tyr/Asn+2.3048*Orn/Lys' | 0.746377 |
| 52 | 'Tyr/Asn−0.47943*Thr/Orn' | 0.742029 |
| 53 | 'Orn/Arg−2.1895*Asn/Tyr' | 0.737681 |
| 54 | 'Tyr/Asn+1.8544*Ser/Lys' | 0.736232 |
| 55 | 'Tyr/Thr+0.18064*Ser/Asn' | 0.734783 |
| 56 | 'Tyr/Asn−0.77871*Trp/Orn' | 0.734783 |
| 57 | 'Tyr/Asn−1.8459*Met/Orn' | 0.734783 |
| 58 | 'Tyr/Thr+0.50265*Ser/Arg' | 0.733333 |
| 59 | 'Tyr/Asn−0.46984*His/Orn' | 0.733333 |
| 60 | 'Cit/Arg−0.19691*Thr/Tyr' | 0.733333 |
| 61 | 'Tyr/Asn−1.404*Thr/Ser' | 0.731884 |
| 62 | 'Tyr/Thr−0.0026605*Lys' | 0.730435 |
| 63 | 'Tyr/Asn−0.24499*Gly/Orn' | 0.730435 |
| 64 | 'Tyr/Asn+8.7332*Met/Lys' | 0.730435 |
| 65 | 'Tyr/Asn+7.9558*Cit/Lys' | 0.728986 |
| 66 | 'Tyr/Arg−0.12927*Thr/Cit' | 0.728986 |
| 67 | 'Tyr/Thr+0.07135*Ala/Trp' | 0.727536 |
| 68 | 'Tyr/Asn−0.15166*Val/Orn' | 0.727536 |
| 69 | 'Tyr/Asn−0.29636*Leu/Orn' | 0.727536 |
| 70 | 'Tyr/Thr+0.2297*Ala/Lys' | 0.724638 |
| 71 | 'Tyr/Asn−0.075268*Gln/Orn' | 0.723188 |
| 72 | 'Tyr/Thr−0.009247*Trp' | 0.721739 |
| 73 | 'Tyr/Asn+0.52851*Ala/Lys' | 0.72029 |
| 74 | 'Tyr/Thr+2.3485*Cit/Arg' | 0.718841 |
| 75 | 'Tyr/Asn+2.6164*Ile/Lys' | 0.718841 |
| 76 | 'Tyr/Arg−0.85419*Thr/Ser' | 0.718841 |
| 77 | 'Cit/Arg−0.40507*Asn/Tyr' | 0.718841 |
| 78 | 'Tyr/Asn−0.0058145*Lys' | 0.717391 |
| 79 | 'Tyr/Asn+1.1218*Ser/Arg' | 0.717391 |
| 80 | 'Tyr/Asn+5.1838*Cit/Arg' | 0.717391 |
| 81 | 'Tyr/Arg−0.4832*Trp/Orn' | 0.717391 |
| 82 | 'Tyr/Thr+0.20416*Ser/Trp' | 0.715942 |
| 83 | 'Cit/Arg−0.25077*Thr/Ser' | 0.715942 |
| 84 | 'Tyr/Thr+0.7453*Ser/Lys' | 0.714493 |
| 85 | 'Tyr/Asn−0.60377*Glu/Orn' | 0.714493 |
| 86 | 'Tyr/Asn+0.48732*Ser/Trp' | 0.714493 |
| 87 | 'Tyr/Asn+0.99845*Orn/Arg' | 0.713043 |
| 88 | 'Tyr/Asn+0.14095*Ala/His' | 0.713043 |
| 89 | 'Tyr/Arg−0.30011*Thr/Orn' | 0.713043 |
| 90 | 'Tyr/Arg−0.21752*Asn/Cit' | 0.713043 |
| 91 | 'Orn/Arg+1.8557*Ser/Gly' | 0.711594 |
| 92 | 'Cit/Arg−0.98043*Thr/Ala' | 0.711594 |
| 93 | 'Tyr/Asn−0.077779*Ala/Orn' | 0.710145 |
| 94 | 'Orn/Arg+3.5578*Tyr/Lys' | 0.710145 |
| 95 | 'Tyr/Arg−0.66405*Asn/Orn' | 0.710145 |
| 96 | 'Tyr/Thr+0.44239*Val/Lys' | 0.708696 |
| 97 | 'Tyr/Asn+3.6555*Phe/Lys' | 0.708696 |
| 98 | 'Tyr/Asn+1.412*Leu/Lys' | 0.708696 |
| 99 | 'Tyr/Thr−0.46142*Asn/Orn' | 0.707246 |
| 100 | 'Tyr/Asn+2.244*Ser/Gly' | 0.707246 |

FIG.57

| No | Formula | ROC_AUC |
|---|---|---|
| 1 | [10.5275]+[-0.0504]Thr+[0.0420]Ser+[-0.0542]Glu+[-0.0218]Gly+[0.0271]Tyr+[-0.0665]Trp | 0.8319 |
| 2 | [10.8412]+[-0.0582]Thr+[0.0907]Ser+[-0.1038]Asn+[-0.1020]Glu+[-0.0456]Gly+[0.0132]Ala | 0.8203 |
| 3 | [12.8395]+[-0.0373]Thr+[0.0708]Ser+[-0.0540]Asn+[-0.0781]Glu+[-0.0314]Gly+[-0.0532]Trp | 0.8188 |
| 4 | [5.9822]+[-0.0520]Thr+[-0.0081]Pro+[0.0143]Ala+[0.0196]Val+[-0.0836]Trp+[-0.0199]Lys | 0.8159 |
| 5 | [6.1401]+[-0.0527]Thr+[0.0118]Ala+[0.0179]Val+[-0.0820]Trp+[-0.0044]Orn+[-0.0187]Lys | 0.8159 |
| 6 | [5.8416]+[-0.0525]Thr+[0.0115]Ala+[0.0179]Val+[-0.0015]Ile+[-0.0795]Trp+[-0.0183]Lys | 0.813 |
| 7 | [12.0799]+[-0.0632]Glu+[-0.0079]Gln+[-0.0122]Pro+[0.0954]Ile+[-0.0465]Leu+[-0.0500]Trp | 0.813 |
| 8 | [7.0725]+[-0.0390]Thr+[-0.0126]Pro+[0.0136]Ala+[0.0334]Ile+[-0.0714]Trp+[-0.0176]Lys | 0.8116 |
| 9 | [11.8853]+[-0.0419]Thr+[0.0468]Ser+[-0.0600]Glu+[-0.0031]Pro+[-0.0242]Gly+[-0.0588]Trp | 0.8116 |
| 10 | [5.5523]+[-0.0540]Thr+[0.0066]Ser+[0.0113]Ala+[0.0166]Val+[-0.0800]Trp+[-0.0180]Lys | 0.8116 |
| 11 | [5.8523]+[-0.0514]Thr+[-0.0037]Asn+[0.0116]Ala+[0.0176]Val+[-0.0791]Trp+[-0.0185]Lys | 0.8116 |
| 12 | [8.4147]+[-0.0528]Thr+[-0.0330]Glu+[0.0160]Val+[0.0589]Tyr+[-0.0796]Trp+[-0.0202]Lys | 0.8116 |
| 13 | [9.3947]+[-0.0463]Thr+[-0.0367]Glu+[0.0276]Ile+[0.0592]Tyr+[-0.0703]Trp+[-0.0198]Lys | 0.8116 |
| 14 | [8.3924]+[-0.0132]Tau+[-0.0556]Thr+[0.0122]Ala+[0.0395]His+[-0.0691]Trp+[-0.0226]Lys | 0.8116 |
| 15 | [13.1762]+[-0.0340]Thr+[0.0665]Ser+[-0.0675]Asn+[-0.0790]Glu+[-0.0305]Gly+[-0.0133]Lys | 0.8101 |
| 16 | [11.8921]+[-0.0349]Thr+[0.0794]Ser+[-0.0661]Asn+[-0.0805]Glu+[-0.0337]Gly+[-0.0185]Leu | 0.8101 |
| 17 | [12.4057]+[-0.0365]Thr+[0.0767]Ser+[-0.0633]Asn+[-0.0821]Glu+[-0.0334]Gly+[-0.0389]Phe | 0.8101 |
| 18 | [5.8569]+[-0.0521]Thr+[0.0114]Ala+[0.0174]Val+[-0.0796]Trp+[-0.0184]Lys | 0.8101 |
| 19 | [6.1612]+[-0.0029]Tau+[-0.0523]Thr+[0.0115]Ala+[0.0168]Val+[-0.0791]Trp+[-0.0182]Lys | 0.8101 |
| 20 | [6.0471]+[-0.0512]Thr+[-0.0385]Asn+[0.0098]Ala+[0.0729]Tyr+[-0.0603]Trp+[-0.0184]Lys | 0.8087 |
| 21 | [5.7182]+[-0.0529]Thr+[0.0116]Ala+[0.0203]Val+[-0.0064]Leu+[-0.0773]Trp+[-0.0181]Lys | 0.8087 |
| 22 | [12.1320]+[-0.0402]Thr+[0.0579]Ser+[-0.0618]Glu+[-0.0235]Gly+[-0.0601]Trp+[-0.0207]Arg | 0.8087 |
| 23 | [11.7691]+[-0.0635]Thr+[0.0508]Ser+[-0.0637]Glu+[-0.0304]Gly+[0.0109]Ala+[-0.0831]Trp | 0.8087 |
| 24 | [7.9456]+[-0.0541]Thr+[-0.0090]Gly+[0.0101]Ala+[0.0505]Tyr+[-0.0630]Trp+[-0.0165]Lys | 0.8087 |
| 25 | [6.2491]+[-0.0549]Thr+[0.0084]Ala+[0.0163]Ile+[0.0582]Tyr+[-0.0737]Trp+[-0.0190]Lys | 0.8072 |
| 26 | [5.5110]+[-0.0532]Thr+[0.0009]Gln+[0.0117]Ala+[0.0182]Val+[-0.0814]Trp+[-0.0196]Lys | 0.8072 |
| 27 | [7.1852]+[-0.0506]Thr+[-0.0060]Pro+[0.0136]Ala+[0.0327]His+[-0.0627]Trp+[-0.0215]Lys | 0.8072 |
| 28 | [8.2245]+[-0.0115]Tau+[-0.0452]Thr+[-0.0076]Pro+[0.0135]Ala+[-0.0562]Trp+[-0.0139]Lys | 0.8072 |
| 29 | [6.3459]+[-0.0489]Thr+[0.0376]Ser+[-0.0339]Glu+[0.0530]Tyr+[-0.0686]Trp+[-0.0306]Arg | 0.8072 |
| 30 | [7.8497]+[-0.0502]Thr+[-0.0102]Gly+[0.0124]Ala+[0.0156]Val+[-0.0777]Trp+[-0.0179]Lys | 0.8058 |
| 31 | [5.6745]+[-0.0510]Thr+[0.0113]Ala+[0.0151]Val+[0.0239]Phe+[-0.0871]Trp+[-0.0199]Lys | 0.8058 |
| 32 | [5.8721]+[-0.0506]Thr+[0.0120]Ala+[0.0181]Val+[-0.0809]Trp+[-0.0174]Lys+[-0.0070]Arg | 0.8058 |
| 33 | [11.9432]+[-0.0428]Thr+[0.0500]Ser+[-0.0602]Glu+[-0.0254]Gly+[-0.0083]Leu+[-0.0507]Trp | 0.8058 |
| 34 | [5.4435]+[-0.0532]Thr+[0.0108]Ala+[0.0398]Cit+[0.0160]Val+[-0.0757]Trp+[-0.0179]Lys | 0.8058 |
| 35 | [6.0839]+[-0.0565]Thr+[0.0089]Ala+[0.0536]Tyr+[0.0283]Phe+[-0.0766]Trp+[-0.0194]Lys | 0.8058 |
| 36 | [8.4128]+[-0.0456]Thr+[0.0706]Ser+[-0.0940]Asn+[-0.0777]Glu+[-0.0306]Gly+[0.0514]Tyr | 0.8058 |
| 37 | [9.8209]+[-0.0230]Tau+[-0.0450]Thr+[-0.0547]Asn+[-0.0408]Glu+[0.0821]Tyr+[-0.0215]Lys | 0.8058 |
| 38 | [6.1032]+[-0.0493]Thr+[0.0434]Ser+[-0.0699]Asn+[-0.0551]Glu+[-0.0075]Gln+[0.0658]Tyr | 0.8058 |
| 39 | [6.3578]+[-0.0552]Thr+[-0.0043]Pro+[0.0104]Ala+[0.0529]Tyr+[-0.0630]Trp+[-0.0165]Lys | 0.8058 |
| 40 | [6.4925]+[-0.0631]Thr+[0.0100]Ala+[0.0532]Tyr+[0.0297]His+[-0.0731]Trp+[-0.0235]Lys | 0.8058 |
| 41 | [6.0744]+[-0.0568]Thr+[0.0121]Ala+[0.0150]Val+[-0.0248]His+[-0.0837]Trp+[-0.0234]Lys | 0.8043 |
| 42 | [7.8258]+[-0.0179]Tau+[-0.0618]Thr+[0.0096]Ala+[0.0668]Tyr+[-0.0701]Trp+[-0.0183]Lys | 0.8043 |
| 43 | [7.8179]+[-0.0538]Thr+[-0.0357]Glu+[0.0110]Ala+[0.0186]Val+[-0.0827]Trp+[-0.0201]Lys | 0.8029 |
| 44 | [6.5031]+[-0.0729]Asn+[-0.0415]Glu+[0.0390]Ile+[0.0699]Tyr+[-0.0620]Trp+[-0.0232]Lys | 0.8029 |
| 45 | [9.9998]+[-0.0398]Thr+[0.0392]Ser+[-0.0496]Glu+[-0.0050]Gln+[-0.0478]Trp+[-0.0158]Arg | 0.8029 |
| 46 | [7.9863]+[-0.0567]Thr+[-0.0264]Glu+[0.0085]Ala+[0.0529]Tyr+[-0.0653]Trp+[-0.0175]Lys | 0.8014 |
| 47 | [6.6186]+[-0.0598]Thr+[0.0088]Ala+[0.0532]Met+[0.0526]Tyr+[-0.0689]Trp+[-0.0201]Lys | 0.8014 |
| 48 | [5.8186]+[-0.0491]Thr+[0.0214]Cit+[0.0140]Val+[0.0595]Tyr+[-0.0709]Trp+[-0.0182]Lys | 0.8014 |
| 49 | [12.5026]+[-0.0441]Thr+[0.0502]Ser+[-0.0624]Glu+[-0.0258]Gly+[-0.0192]Phe+[-0.0517]Trp | 0.8014 |
| 50 | [5.9628]+[-0.0455]Thr+[0.0318]Ser+[-0.0762]Asn+[-0.0434]Glu+[0.0736]Tyr+[-0.0191]Lys | 0.8014 |

FIG.58

| No | Formula | ROC_AUC |
|---|---|---|
| 51 | '6.7824-0.044039*Thr+0.062614*Tyr-0.050286*Trp-0.014027*Lys' | 0.7580 |
| 52 | '6.8825-0.046787*Thr-0.027375*Glu+0.045651*Tyr-0.016518*Lys' | 0.7507 |
| 53 | '6.1867-0.043631*Thr-0.022829*Glu+0.043882*Tyr-0.0555*Trp' | 0.7478 |
| 54 | '5.1109-0.045392*Thr+0.050761*Tyr-0.015595*Lys' | 0.7319 |
| 55 | '4.8762-0.043153*Thr+0.048046*Tyr-0.054226*Trp' | 0.7333 |
| 56 | '6.9859-0.043137*Thr-0.0044166*Gln+0.054921*Tyr-0.05311*Trp' | 0.7449 |
| 57 | '6.7465-0.040329*Thr+0.022552*Ser-0.03451*Glu-0.049918*Trp' | 0.7580 |
| 58 | '6.8643-0.045308*Thr+0.010851*Ala-0.052541*Trp-0.012829*Lys' | 0.7768 |
| 59 | '8.2642-0.042825*Thr+0.036114*Ser-0.050595*Glu-0.022054*Gly' | 0.7609 |
| 60 | '5.0446-0.038841*Thr-0.03873*Asn+0.069987*Tyr-0.016917*Lys' | 0.7464 |
| 61 | '5.3239-0.038455*Thr+0.055803*Tyr-0.053815*Trp-0.015143*Arg' | 0.7435 |
| 62 | '8.3575-0.034734*Thr-0.034044*Glu-0.012631*Lys' | 0.7348 |
| 63 | '6.7503-0.041309*Thr-0.0080541*Gly+0.047123*Tyr-0.015338*Lys' | 0.7116 |
| 64 | '9.702-0.031054*Thr-0.034784*Glu-0.034717*Trp-0.010868*Lys' | 0.7435 |
| 65 | '4.7031-0.053803*Thr+0.0052144*Ala+0.045337*Tyr-0.017602*Lys' | 0.7551 |
| 66 | '7.826-0.042709*Thr+0.024382*Ser-0.044754*Glu-0.0060432*Gln' | 0.7551 |
| 67 | '7.3499-0.04127*Thr+0.016353*Ser-0.036189*Glu-0.012463*Lys' | 0.7580 |
| 68 | '7.4055-0.046963*Thr-0.032598*Glu+0.0069746*Ala-0.015808*Lys' | 0.7522 |
| 69 | '7.4796-0.031438*Thr-0.02877*Glu-0.041115*Trp' | 0.7304 |
| 70 | '4.5451-0.047897*Thr+0.061341*Cit+0.044495*Tyr-0.015255*Lys' | 0.7449 |
| 71 | '4.4116-0.051452*Thr+0.0057888*Ala+0.041333*Tyr-0.063855*Trp' | 0.7333 |
| 72 | '5.9092-0.044736*Thr-0.0024433*Gln+0.052913*Tyr-0.013591*Lys' | 0.7348 |
| 73 | '4.4276-0.045574*Thr+0.051102*Tyr+0.011587*Orn-0.015766*Lys' | 0.7406 |
| 74 | '4.3796-0.04685*Thr+0.011301*Ser+0.046283*Tyr-0.0576*Trp' | 0.7348 |
| 75 | '7.0954-0.039057*Thr-0.029336*Glu+0.077177*Cit-0.012627*Lys' | 0.7449 |
| 76 | '10.3723-0.03091*Thr-0.037859*Glu-0.0046119*Gln-0.037823*Trp' | 0.7333 |
| 77 | '7.5056+0.059007*Ser-0.086445*Asn-0.068694*Glu-0.029987*Gly' | 0.7594 |
| 78 | '6.3876-0.043638*Thr-0.026778*Glu+0.0076643*Ala-0.056084*Trp' | 0.7377 |
| 79 | '5.0915-0.041853*Thr+0.051301*Tyr-0.0092957*His-0.051922*Trp' | 0.7290 |
| 80 | '11.5117-0.031111*Thr-0.043519*Glu-0.013461*Gly-0.012953*Lys' | 0.7174 |
| 81 | '6.2306-0.039592*Thr-0.0071671*Gly+0.044436*Tyr-0.051011*Trp' | 0.7304 |
| 82 | '4.968-0.047004*Thr+0.048547*Tyr+0.014929*His-0.018716*Lys' | 0.7420 |
| 83 | '5.1387-0.037722*Thr+0.09483*Cit-0.011066*Lys' | 0.7116 |
| 84 | '4.6306-0.040826*Thr-0.017646*Asn+0.056377*Tyr-0.051041*Trp' | 0.7362 |
| 85 | '5.1181-0.043705*Thr+0.052246*Tyr-0.014731*Lys-0.0048562*Arg' | 0.7420 |
| 86 | '5.2144-0.044337*Thr-0.001615*Pro+0.05039*Tyr-0.015312*Lys' | 0.7333 |
| 87 | '5.4796-0.045031*Thr+0.0072809*Ala-0.014182*Lys' | 0.7232 |
| 88 | '4.3704-0.045025*Thr+0.045355*Cit+0.043178*Tyr-0.051555*Trp' | 0.7290 |
| 89 | '6.2944-0.031448*Thr-0.010762*Lys' | 0.7058 |
| 90 | '5.0138-0.041619*Thr-0.031536*Met+0.053114*Tyr-0.051433*Trp' | 0.7406 |
| 91 | '4.3213-0.045703*Thr+0.0059509*Val+0.04625*Tyr-0.062977*Trp' | 0.7319 |
| 92 | '8.6055-0.034212*Thr-0.037426*Glu-0.0049309*Gln' | 0.7188 |
| 93 | '5.2793-0.034745*Thr-0.027022*Glu' | 0.7000 |
| 94 | '4.6044-0.046756*Thr+0.0044361*Val+0.048887*Tyr-0.017032*Lys' | 0.7406 |
| 95 | '4.793-0.047026*Thr+0.0051336*Ser+0.04958*Tyr-0.015466*Lys' | 0.7435 |
| 96 | '5.2087-0.047272*Thr+0.029068*Met+0.047828*Tyr-0.01763*Lys' | 0.7391 |
| 97 | '5.0149-0.042343*Thr-0.0016964*Pro+0.047609*Tyr-0.053007*Trp' | 0.7391 |
| 98 | '5.3994-0.044714*Thr-0.026672*ABA+0.05188*Tyr-0.015418*Lys' | 0.7232 |
| 99 | '4.4743-0.043351*Thr+0.047599*Tyr-0.053093*Trp+0.0062793*Orn' | 0.7290 |
| 100 | '5.0364-0.045503*Thr+0.049865*Tyr+0.004225*Phe-0.016088*Lys' | 0.7377 |

FIG.60

| No | Formula | ROC_AUC |
|---|---|---|
| 1 | (4.304e-01)Thr+(3.478e-01)Asn−(8.812e-02)Ala−(6.361e-01)Tyr+(5.022e-01)Trp+(1.712e-01)Lys−(4.808e+01) | 0.8203 |
| 2 | −(2.544e-01)Thr+(5.190e-01)Ser−(5.165e-01)Asn−(5.833e-01)Glu−(2.214e-01)Gly−(9.954e-02)Lys+(9.212e+01) | 0.8159 |
| 3 | (5.475e-01)Thr−(1.268e-01)Ala−(1.399e-01)Val−(1.971e-01)His+(7.556e-01)Trp+(2.340e-01)Lys−(5.435e+01) | 0.8145 |
| 4 | −(4.818e-01)Thr+(3.830e-01)Ser−(5.066e-01)Glu−(2.052e-01)Gly+(2.553e-01)Tyr−(5.072e-01)Trp+(9.073e+01) | 0.8145 |
| 5 | −(5.073e-01)Thr+(1.128e-01)Ala+(1.361e-01)Val+(4.041e-01)Met−(7.125e-01)Trp−(2.012e-01)Lys+(5.165e+01) | 0.813 |
| 6 | −(2.648e-01)Thr+(5.425e-01)Ser−(4.396e-01)Asn−(5.670e-01)Glu−(2.304e-01)Gly−(2.602e-01)Phe+(8.252e+01) | 0.813 |
| 7 | −(5.301e-01)Thr−(9.117e-02)Pro+(1.546e-01)Ala+(1.708e-01)Val−(7.847e-01)Trp−(2.045e-01)Lys+(5.835e+01) | 0.813 |
| 8 | −(2.646e-01)Thr+(5.692e-01)Ser−(4.705e-01)Asn−(5.586e-01)Glu−(2.357e-01)Gly−(1.307e-01)Leu+(8.170e+01) | 0.813 |
| 9 | −(3.363e-01)Thr+(4.875e-01)Ser−(5.766e-01)Asn−(5.141e-01)Glu−(2.210e-01)Gly+(6.027e-02)Ala+(5.691e+01) | 0.8116 |
| 10 | (5.218e-01)Thr+(4.866e-01)Glu+(1.812e-01)Gly−(1.575e-01)Ala+(6.314e-01)Trp+(1.860e-01)Lys−(1.321e+02) | 0.8116 |
| 11 | (4.453e-01)Thr+(1.444e-01)Pro−(1.618e-01)Ala−(3.422e-01)Ile+(7.709e-01)Trp+(2.080e-01)Lys−(7.571e+01) | 0.8101 |
| 12 | −(2.769e-01)Thr+(5.253e-01)Ser−(4.469e-01)Asn−(5.689e-01)Glu−(2.222e-01)Gly−(2.731e-01)Trp+(8.453e+01) | 0.8101 |
| 13 | −(4.192e-01)Thr+(3.208e-01)Ser−(3.221e-01)Glu+(5.059e-01)Tyr−(5.282e-01)Trp−(2.876e-01)Arg+(4.781e+01) | 0.8101 |
| 14 | (5.446e-01)Thr−(1.295e-01)Ala−(9.886e-02)ABA−(1.640e-01)Val+(7.807e-01)Trp+(2.011e-01)Lys−(5.499e+01) | 0.8087 |
| 15 | −(5.439e-01)Thr+(9.321e-02)Ala+(4.780e-01)Tyr+(2.144e-01)His−(6.120e-01)Trp−(2.155e-01)Lys+(5.346e+01) | 0.8087 |
| 16 | (5.177e-01)Thr+(3.412e-01)Glu−(1.203e-01)Ala−(1.572e-01)Val+(7.332e-01)Trp+(1.971e-01)Lys−(6.843e+01) | 0.8087 |
| 17 | −(4.270e-01)Ser+(6.283e-01)Asn+(4.929e-01)Glu+(2.203e-01)Gly−(4.668e-02)Ala+(3.595e-01)Trp−(5.427e+01) | 0.8087 |
| 18 | (1.439e-01)Tau+(6.104e-01)Thr+(1.133e-01)Pro−(1.876e-01)Ala+(7.209e-01)Trp+(1.975e-01)Lys−(1.054e+02) | 0.8087 |
| 19 | (5.433e-01)Thr+(6.716e-02)Pro−(1.173e-01)Ala−(5.108e-01)Tyr+(6.268e-01)Trp+(1.807e-01)Lys−(6.183e+01) | 0.8087 |
| 20 | (5.462e-01)Thr−(6.426e-03)Gln−(1.297e-01)Ala−(1.714e-01)Val+(7.823e-01)Trp+(2.084e-01)Lys−(5.286e+01) | 0.8087 |
| 21 | −(5.549e-01)Thr−(1.319e-01)Ala+(1.758e-01)Val−(3.099e-02)Ile−(7.761e-01)Trp−(2.013e-01)Lys+(5.572e+01) | 0.8072 |
| 22 | (5.483e-01)Thr−(1.308e-01)Ala−(1.690e-01)Val+(7.825e-01)Trp+(2.033e-01)Lys−(5.603e+01) | 0.8072 |
| 23 | −(5.065e-01)Thr+(8.654e-02)Ala+(1.168e-01)Ile+(5.240e-01)Tyr−(6.431e-01)Trp−(1.850e-01)Lys+(5.350e+01) | 0.8072 |
| 24 | (5.457e-01)Thr−(1.315e-01)Ala−(1.686e-01)Val+(7.843e-01)Trp+(2.191e-02)Orn+(2.022e-01)Lys−(5.677e+01) | 0.8058 |
| 25 | (1.290e-01)Tau+(5.349e-01)Thr−(8.594e-02)Ala−(5.607e-01)Tyr+(5.876e-01)Trp+(1.739e-01)Lys−(6.518e+01) | 0.8058 |
| 26 | −(5.407e-01)Thr−(1.206e-01)Ala+(3.334e-01)Cit+(1.547e-01)Val−(7.216e-01)Trp−(1.935e-01)Lys+(5.046e+01) | 0.8058 |
| 27 | −(4.920e-01)Thr+(8.698e-02)Ala+(4.550e-01)Tyr+(2.597e-01)Phe−(6.654e-01)Trp−(1.817e-01)Lys+(4.876e+01) | 0.8058 |
| 28 | −(2.923e-01)Thr+(4.593e-01)Ser−(6.109e-01)Asn−(4.733e-01)Glu−(1.882e-01)Gly+(2.664e-01)Tyr+(5.314e+01) | 0.8058 |
| 29 | −(5.421e-01)Thr−(1.109e-01)Gly+(1.478e-01)Ala+(1.503e-01)Val−(7.787e-01)Trp−(2.075e-01)Lys+(7.943e+01) | 0.8058 |
| 30 | (5.408e-01)Thr+(1.041e-01)Gly−(1.123e-01)Ala−(5.076e-01)Tyr+(6.265e-01)Trp+(1.843e-01)Lys−(7.824e+01) | 0.8043 |
| 31 | −(3.680e-01)Ser+(7.324e-01)Asn+(4.311e-01)Glu+(1.710e-01)Gly−(3.158e-01)Tyr+(1.154e-01)Lys−(5.212e+01) | 0.8043 |
| 32 | (2.599e-02)Tau+(5.525e-01)Thr−(1.314e-01)Ala−(1.634e-01)Val+(7.802e-01)Trp+(2.035e-01)Lys−(5.945e+01) | 0.8043 |
| 33 | (5.392e-01)Thr+(2.836e-01)Glu−(9.573e-02)Ala−(4.713e-01)Tyr+(6.046e-01)Trp+(1.787e-01)Lys−(7.162e+01) | 0.8043 |
| 34 | −(5.620e-01)Thr−(1.333e-01)Ala+(2.071e-01)Val−(8.368e-02)Leu−(7.594e-01)Trp−(1.995e-01)Lys+(5.484e+01) | 0.8043 |
| 35 | −(3.794e-01)Thr+(3.435e-01)Ser−(5.541e-01)Asn−(4.352e-01)Glu−(6.117e-02)Gln+(4.877e-01)Tyr+(4.800e+01) | 0.8043 |
| 36 | −(5.088e-01)Thr+(3.648e-01)Ser−(4.850e-01)Glu−(2.168e-01)Gly+(9.137e-02)Ala−(5.634e-01)Trp+(8.123e+01) | 0.8043 |
| 37 | (4.479e-01)Thr+(2.725e-01)Glu−(1.358e-01)Val−(5.530e-01)Tyr+(6.051e-01)Trp+(1.864e-01)Lys−(6.292e+01) | 0.8043 |
| 38 | (1.073e-01)Tau+(5.838e-01)Thr−(1.365e-01)Ala−(3.539e-01)His+(6.654e-01)Trp+(2.470e-01)Lys−(8.248e+01) | 0.8043 |
| 39 | (4.926e-01)Thr−(1.179e-01)Ala−(1.314e-01)Val−(2.455e-01)Phe+(7.710e-01)Trp+(2.000e-01)Lys−(4.921e+01) | 0.8029 |
| 40 | −(4.314e-01)Thr+(4.657e-01)Ser−(5.861e-01)Glu−(3.585e-02)Pro−(2.336e-01)Gly−(4.445e-01)Trp+(1.069e+02) | 0.8029 |
| 41 | (5.572e-01)Asn+(3.064e-01)Glu−(2.988e-01)Ile−(5.346e-01)Tyr+(4.381e-01)Trp+(1.693e-01)Lys−(4.257e+01) | 0.8029 |
| 42 | −(2.927e-01)Thr+(5.331e-01)Ser−(4.915e-01)Asn−(5.912e-01)Glu−(2.778e-02)Gln−(1.954e-01)Gly+(8.252e+01) | 0.8029 |
| 43 | −(5.522e-01)Thr−(1.316e-01)Ala+(8.842e-02)Leu+(3.137e-01)His−(7.149e-01)Trp−(2.461e-01)Lys+(6.842e+01) | 0.8029 |
| 44 | (5.334e-01)Thr−(1.351e-01)Ala−(1.711e-01)Val+(7.919e-01)Trp+(1.948e-01)Lys+(5.429e-02)Arg−(5.625e+01) | 0.8014 |
| 45 | (5.443e-01)Thr+(4.079e-02)Asn−(1.334e-01)Ala−(1.710e-01)Val+(7.827e-01)Trp+(2.058e-01)Lys−(5.649e+01) | 0.8014 |
| 46 | (5.740e-01)Thr+(8.627e-02)Pro−(1.651e-01)Ala−(3.275e-01)His+(6.844e-01)Trp+(2.452e-01)Lys−(7.812e+01) | 0.8014 |
| 47 | −(3.388e-01)Thr+(2.378e-01)Ser−(5.956e-01)Asn−(3.313e-01)Glu+(5.858e-01)Tyr−(1.448e-01)Lys+(4.103e+01) | 0.8014 |
| 48 | (3.941e-01)Thr+(3.317e-01)Glu−(2.291e-01)Ile−(5.669e-01)Tyr+(5.720e-01)Trp+(1.833e-01)Lys−(7.513e+01) | 0.8014 |
| 49 | (4.102e-01)Thr+(1.059e-01)Pro−(1.368e-01)Ala−(5.044e-01)Phe+(7.180e-01)Trp+(1.787e-01)Lys−(5.689e+01) | 0.8014 |
| 50 | −(2.552e-01)Thr+(4.235e-01)Ser−(4.574e-01)Asn−(4.391e-01)Glu−(1.892e-01)Gly+(5.635e-01)Cit+(5.319e+01) | 0.8014 |

FIG.61

| No | Formula | ROC_AUC |
|---|---|---|
| 51 | 'Thr-0.25646*Ala+1.1585*Trp+0.31049*Lys' | 0.7725 |
| 52 | 'Thr-0.83955*Ser+1.1082*Glu+0.48047*Gly' | 0.7623 |
| 53 | 'Thr-1.1937*Tyr+1.1657*Trp' | 0.7275 |
| 54 | 'Thr+0.10718*Gln-1.4121*Tyr+1.1391*Trp' | 0.7435 |
| 55 | 'Thr-0.093678*Ala-0.87488*Tyr+0.32161*Lys' | 0.7536 |
| 56 | 'Thr+0.055489*Gln-1.2472*Tyr+0.29193*Lys' | 0.7348 |
| 57 | 'Ser-1.4544*Asn-1.1312*Glu-0.49547*Gly' | 0.7609 |
| 58 | 'Thr+0.59173*Glu-1.0604*Tyr+1.1654*Trp' | 0.7406 |
| 59 | 'Thr+0.686*Glu-0.15863*Ala+0.3205*Lys' | 0.7449 |
| 60 | 'Thr-0.12326*Ala-0.82421*Tyr+1.1897*Trp' | 0.7348 |
| 61 | 'Thr+0.29296*Gly-0.20701*Ala+0.33496*Lys' | 0.7391 |
| 62 | 'Thr-1.622*Tyr+1.3445*Trp+0.44842*Arg' | 0.7464 |
| 63 | 'Thr+0.67326*Glu-0.18614*Ala+1.2126*Trp' | 0.7362 |
| 64 | 'Thr+0.72491*Glu+0.1275*Gln-0.92253*Tyr' | 0.7261 |
| 65 | 'Thr+0.2911*Gly-0.23587*Ala+1.2738*Trp' | 0.7159 |
| 66 | 'Thr+0.20201*Gly-1.2224*Tyr+1.2005*Trp' | 0.7290 |
| 67 | 'Thr-0.19505*Ala+1.2175*Trp' | 0.7101 |
| 68 | 'Thr-0.62985*Ser+1.0574*Glu+0.13949*Gln' | 0.7551 |
| 69 | 'Thr-0.16492*Ala+0.30922*Lys' | 0.7246 |
| 70 | 'Thr+0.10513*Gln-1.0384*Tyr' | 0.7130 |
| 71 | 'Thr+1.3503*Glu+0.45179*Gly+1.2645*Trp' | 0.7319 |
| 72 | 'Thr+1.1*Glu+0.40673*Gly' | 0.7116 |
| 73 | 'Thr-0.99942*Cit-1.0257*Tyr+1.0511*Trp' | 0.7232 |
| 74 | 'Thr-1.3487*Tyr+0.31061*His+1.1497*Trp' | 0.7333 |
| 75 | 'Thr+0.87079*Glu+0.37899*Gly-2.3198*Cit' | 0.7348 |
| 76 | 'Thr+0.5065*Asn-1.5078*Tyr+1.2007*Trp' | 0.7406 |
| 77 | 'Thr+0.94718*Met-1.4084*Tyr+1.1351*Trp' | 0.7362 |
| 78 | 'Thr-0.21134*Ser-1.0642*Tyr+1.1163*Trp' | 0.7304 |
| 79 | 'Thr+0.98924*Glu+1.1872*Trp' | 0.7246 |
| 80 | 'Thr-0.13639*Ala-1.5965*Cit+0.2869*Lys' | 0.7551 |
| 81 | 'Thr+1.0851*Glu+0.13547*Gln' | 0.7174 |
| 82 | 'Thr-1.1695*Tyr+1.1316*Trp-0.15101*Orn' | 0.7304 |
| 83 | 'Thr+1.2986*Glu+0.14289*Gln+1.1566*Trp' | 0.7348 |
| 84 | 'Thr-0.10158*Ile-1.1885*Tyr+1.2351*Trp' | 0.7261 |
| 85 | 'Thr-0.81574*Tyr' | 0.6841 |
| 86 | 'Thr-1.1621*Tyr-0.15492*Phe+1.2362*Trp' | 0.7261 |
| 87 | 'Thr+0.82617*Glu+0.34578*Gly-0.13188*Ala' | 0.7174 |
| 88 | 'Thr-0.042076*ABA-1.1911*Tyr+1.1687*Trp' | 0.7319 |
| 89 | 'Thr+0.076956*Gln-0.21237*Ala+1.2042*Trp' | 0.7348 |
| 90 | 'Thr+0.14959*Pro-0.20899*Ala+0.31977*Lys' | 0.7449 |
| 91 | 'Thr+0.32403*Gly-2.7245*Cit' | 0.7145 |
| 92 | 'Thr+0.15626*Pro-0.24183*Ala+1.2568*Trp' | 0.7188 |
| 93 | 'Thr-0.54552*Ser+0.93464*Glu+1.0523*Trp' | 0.7623 |
| 94 | 'Thr+0.76597*Glu+0.29534*Gly-0.66863*Tyr' | 0.7217 |
| 95 | 'Thr+1.1323*Glu+0.088624*Gln+0.27996*Lys' | 0.7406 |
| 96 | 'Thr-0.25555*Ala+1.3767*Trp+0.36025*Arg' | 0.7188 |
| 97 | 'Thr-0.15197*Ala-0.46797*His+0.39618*Lys' | 0.7478 |
| 98 | 'Thr+0.87074*Glu+0.11869*Gln-1.9792*Cit' | 0.7348 |
| 99 | 'Thr-0.79297*Ser+0.43497*Gly+1.0726*Trp' | 0.7116 |
| 100 | 'Thr+0.78685*Glu' | 0.7014 |

FIG. 64

| No. | Formula | ROC_AUC |
|---|---|---|
| 1 | 0.1222(Tau)/(ABA)+0.1432(Thr)/(Cit)-0.3773(Glu)/(Ser)+0.01159(Pro)/(Asn)+0.4989 | 0.9765 |
| 2 | 0.1931(Asn)/(Pro)-0.3956(Glu)/(Thr)-0.8459(Cit)/(Tau)-1.995(ABA)/(Ser)+2.376 | 0.9760 |
| 3 | -0.4232(Glu)/(Thr)+0.00388(Pro)/(Asn)-0.8497(Cit)/(Tau)-1.99(ABA)/(Ser)+2.431 | 0.9772 |
| 4 | 0.2271(Tau)/(Cit)+0.05399(Ser)/(ABA)+0.09306(Asn)/(Pro)-0.3449(Glu)/(Thr)+0.6568 | 0.9763 |
| 5 | 0.1223(Tau)/(ABA)+0.1422(Thr)/(Cit)+0.09694(Asn)/(Pro)-0.3538(Glu)/(Ser)+0.5066 | 0.9754 |
| 6 | 0.2268(Tau)/(Cit)+0.05536(Ser)/(ABA)-0.1387(Glu)/(Asn)-0.01406(Gln)/(Thr)+0.7557 | 0.9754 |
| 7 | 0.2266(Tau)/(Cit)+0.1296(Asn)/(ABA)-0.2995(Glu)/(Thr)-0.01952(Gln)/(Ser)+0.7752 | 0.9735 |
| 8 | 0.2263(Tau)/(Cit)+0.05383(Ser)/(ABA)+2.031(Asn)/(Gln)-0.3419(Glu)/(Thr)+0.5295 | 0.9758 |
| 9 | 0.04808(Thr)/(ABA)-0.4673(Glu)/(Ser)+0.006854(Pro)/(Asn)-0.8681(Cit)/(Tau)+1.785 | 0.9763 |
| 10 | 0.04805(Thr)/(ABA)+0.1526(Asn)/(Pro)-0.4434(Glu)/(Ser)-0.8642(Cit)/(Tau)+1.753 | 0.9763 |
| 11 | 0.2262(Tau)/(Cit)+0.1298(Asn)/(ABA)-0.3119(Glu)/(Ser)-0.01118(Gln)/(Thr)+0.7352 | 0.9728 |
| 12 | 0.227(Tau)/(Cit)+0.05432(Ser)/(ABA)-0.3507(Glu)/(Thr)-0.004935(Gln)/(Asn)+0.7522 | 0.9767 |
| 13 | 0.2279(Tau)/(Cit)+0.05375(Ser)/(ABA)-0.3675(Glu)/(Thr)+0.008231(Pro)/(Asn)+0.6633 | 0.9761 |
| 14 | 0.1215(Tau)/(ABA)+0.1558(Ser)/(Cit)-0.4082(Glu)/(Thr)+0.008442(Pro)/(Asn)+0.4867 | 0.9779 |
| 15 | 1.57(Asn)/(Gln)-0.4746(Glu)/(Ser)-0.838(Cit)/(Tau)-1.412(ABA)/(Thr)+2.223 | 0.9749 |
| 16 | 0.2904(Tau)/(Asn)+0.1719(Ser)/(Cit)-0.005171(Gln)/(Thr)+0.1587(Orn)/(Glu)+0.04318 | 0.9756 |
| 17 | -0.4745(Glu)/(Ser)-0.003381(Gln)/(Asn)-0.8418(Cit)/(Tau)-1.446(ABA)/(Thr)+2.398 | 0.9753 |
| 18 | 0.1595(Asn)/(Pro)-0.4573(Glu)/(Ser)-0.8403(Cit)/(Tau)-1.459(ABA)/(Thr)+2.3 | 0.9751 |
| 19 | -0.4821(Glu)/(Ser)+0.00701(Pro)/(Asn)-0.8443(Cit)/(Tau)-1.459(ABA)/(Thr)+2.334 | 0.9760 |
| 20 | 0.2269(Tau)/(Cit)+0.7036(Ser)/(Gln)+0.1283(Asn)/(ABA)-0.3062(Glu)/(Thr)+0.5401 | 0.9724 |
| 21 | 0.1216(Tau)/(ABA)+0.1552(Ser)/(Cit)+0.06113(Asn)/(Pro)-0.389(Glu)/(Thr)+0.4938 | 0.9770 |
| 22 | 0.225(Tau)/(Cit)+0.07522(Asn)/(Pro)-0.3476(Glu)/(Thr)-1.552(ABA)/(Ser)+1.274 | 0.9753 |
| 23 | 0.06044(Ser)/(ABA)+0.2137(Asn)/(Pro)-0.4054(Glu)/(Thr)-0.8521(Cit)/(Tau)+1.647 | 0.9758 |
| 24 | 0.2283(Tau)/(Cit)+0.04087(Thr)/(ABA)+1.794(Asn)/(Gln)-0.3617(Glu)/(Ser)+0.6195 | 0.9735 |
| 25 | 0.1181(Tau)/(ABA)+0.1499(Thr)/(Cit)+0.01346(Ser)/(Asn)-2.053(Glu)/(Gln)+0.4901 | 0.9742 |
| 26 | 0.1237(Tau)/(ABA)+0.0534(Thr)/(Glu)+0.1544(Ser)/(Cit)+0.08611(Asn)/(Pro)+0.1621 | 0.9733 |
| 27 | 1.824(Asn)/(Gln)-0.405(Glu)/(Thr)-0.8412(Cit)/(Tau)-2.007(ABA)/(Ser)+2.295 | 0.9776 |
| 28 | 0.2297(Tau)/(Cit)+0.04293(Thr)/(ABA)-0.3736(Glu)/(Ser)+0.01144(Pro)/(Asn)+0.7062 | 0.9738 |
| 29 | 0.229(Tau)/(Cit)+0.04283(Thr)/(ABA)+0.05634(Asn)/(Pro)-0.354(Glu)/(Ser)+0.725 | 0.9744 |
| 30 | 0.2239(Tau)/(Cit)+0.05616(Ser)/(ABA)+0.1533(Asn)/(Glu)-0.01028(Gln)/(Thr)+0.4045 | 0.9742 |
| 31 | 0.2895(Tau)/(Asn)+0.1725(Ser)/(Cit)-0.009288(Pro)/(Thr)+0.1581(Orn)/(Glu)+0.02785 | 0.9754 |
| 32 | 0.2278(Tau)/(Cit)+0.2393(Thr)/(Gln)+0.05515(Ser)/(ABA)-0.1356(Glu)/(Asn)+0.6272 | 0.9747 |
| 33 | 0.1213(Tau)/(ABA)+0.1445(Thr)/(Cit)+0.03735(Ser)/(Pro)-0.137(Glu)/(Asn)+0.492 | 0.9726 |
| 34 | 0.2256(Tau)/(Cit)-0.3883(Glu)/(Ser)+0.01156(Pro)/(Asn)-1.293(ABA)/(Thr)+1.218 | 0.9747 |
| 35 | 0.1181(Tau)/(ABA)+0.15(Thr)/(Cit)-0.03523(Asn)/(Ser)-2.035(Glu)/(Gln)+0.5363 | 0.9742 |
| 36 | 0.2275(Tau)/(Cit)-0.01922(Thr)/(Pro)+0.1308(Asn)/(ABA)-0.3026(Glu)/(Ser)+0.6771 | 0.9728 |
| 37 | 0.04773(Thr)/(ABA)-0.4596(Glu)/(Ser)-0.002256(Gln)/(Asn)-0.866(Cit)/(Tau)+1.839 | 0.9758 |
| 38 | 0.2271(Tau)/(Cit)+0.04913(Ser)/(Pro)+0.13(Asn)/(ABA)-0.2811(Glu)/(Thr)+0.6192 | 0.9719 |
| 39 | 0.2247(Tau)/(Cit)-0.3511(Glu)/(Thr)-0.005043(Gln)/(Asn)-1.569(ABA)/(Ser)+1.371 | 0.9756 |
| 40 | 0.2271(Tau)/(Cit)+0.1485(Thr)/(Gln)+0.1299(Asn)/(ABA)-0.3051(Glu)/(Ser)+0.6393 | 0.9726 |
| 41 | 0.2915(Tau)/(Asn)+0.08113(Thr)/(Pro)+0.1712(Ser)/(Cit)+0.1577(Orn)/(Glu)-0.04112 | 0.9745 |
| 42 | 0.2258(Tau)/(Cit)-0.3709(Glu)/(Thr)+0.0101(Pro)/(Asn)-1.548(ABA)/(Ser)+1.267 | 0.9758 |
| 43 | 0.1209(Tau)/(ABA)+0.1456(Thr)/(Cit)-0.1407(Glu)/(Asn)+0.01603(Pro)/(Ser)+0.494 | 0.9724 |
| 44 | 0.2902(Tau)/(Asn)+0.08489(Thr)/(Gln)+0.1724(Ser)/(Cit)+0.1583(Orn)/(Glu)-0.002951 | 0.9753 |
| 45 | -0.4121(Glu)/(Thr)-0.005404(Gln)/(Asn)-0.8459(Cit)/(Tau)-2.011(ABA)/(Ser)+2.516 | 0.9770 |
| 46 | 0.2214(Tau)/(Cit)+0.1535(Asn)/(Glu)-0.009053(Gln)/(Thr)-1.639(ABA)/(Ser)+1.039 | 0.9740 |
| 47 | 0.2221(Tau)/(Cit)+0.1357(Thr)/(Gln)+0.1527(Asn)/(Glu)-1.639(ABA)/(Ser)+0.9616 | 0.9742 |
| 48 | 0.2246(Tau)/(Cit)-0.1382(Glu)/(Asn)-0.01281(Gln)/(Thr)-1.602(ABA)/(Ser)+1.377 | 0.9738 |
| 49 | 0.1212(Tau)/(ABA)+0.1451(Thr)/(Cit)-0.3598(Glu)/(Ser)+0.004888(Gln)/(Asn)+0.4622 | 0.9751 |
| 50 | 0.04654(Thr)/(ABA)+1.386(Asn)/(Gln)-0.4604(Glu)/(Ser)-0.8619(Cit)/(Tau)+1.706 | 0.9751 |

FIG.65

| No. | Formula | ROC_AUC |
|---|---|---|
| 51 | 'Asn/ABA−25.5194*Met/Lys' | 0.8225 |
| 52 | 'Lys/ABA+20.2676*Asn/Ile' | 0.8216 |
| 53 | 'Lys/Ile+0.37995*Ser/ABA' | 0.8181 |
| 54 | 'Lys/ABA+11.435*Asn/Met' | 0.8142 |
| 55 | 'Lys/ABA+9.6271*Ser/Ile' | 0.8138 |
| 56 | 'Lys/Ile−27.4842*ABA/Val' | 0.8129 |
| 57 | 'Lys/Ile+0.95491*Asn/ABA' | 0.8120 |
| 58 | 'Asn/ABA−8.295*Ile/Lys' | 0.8079 |
| 59 | 'Ala/Ile−54.4608*ABA/Val' | 0.8062 |
| 60 | 'Lys/ABA+2.4636*Ala/Ile' | 0.8056 |
| 61 | 'Lys/Ile−10.6372*ABA/Leu' | 0.8049 |
| 62 | 'Lys/Ile+0.18476*Pro/ABA' | 0.8046 |
| 63 | 'Lys/Ile+0.10213*Ala/ABA' | 0.8033 |
| 64 | 'Lys/ABA+4.7094*Val/Ile' | 0.8003 |
| 65 | 'Ala/Ile+0.75114*Ser/ABA' | 0.8001 |
| 66 | 'Ala/Ile−21.2079*ABA/Leu' | 0.7994 |
| 67 | 'Ala/Ile−47.4504*ABA/Lys' | 0.7989 |
| 68 | 'Asn/ABA+0.98421*Val/Ile' | 0.7980 |
| 69 | 'Lys/ABA+7.3425*Thr/Ile' | 0.7971 |
| 70 | 'Thr/ABA−74.2*Met/Lys' | 0.7948 |
| 71 | 'Lys/Ile−0.10228*ABA' | 0.7942 |
| 72 | 'Lys/Ile+0.81069*Ser/Met' | 0.7942 |
| 73 | 'Lys/ABA+3.6046*Thr/Met' | 0.7937 |
| 74 | 'Lys/ABA+3.3373*Gly/Ile' | 0.7935 |
| 75 | 'Ala/Ile+1.9021*Asn/ABA' | 0.7921 |
| 76 | 'Asn/ABA+0.52573*Ala/Ile' | 0.7921 |
| 77 | 'Lys/ABA+4.1553*Ser/Met' | 0.7916 |
| 78 | 'Ala/Ile−0.21237*ABA' | 0.7884 |
| 79 | 'Lys/Ile+2.2016*Asn/Met' | 0.7882 |
| 80 | 'Lys/ABA−35.2286*Ile/Leu' | 0.7875 |
| 81 | 'Asn/ABA+0.69081*Gly/Ile' | 0.7873 |
| 82 | 'Lys/Ile−4.2456*ABA/Orn' | 0.7873 |
| 83 | 'Lys/ABA+4.8812*Asn/Glu' | 0.7868 |
| 84 | 'Lys/ABA+2.0565*Ser/Glu' | 0.7866 |
| 85 | 'Lys/ABA+1.6564*Thr/Glu' | 0.7862 |
| 86 | 'Lys/Ile+0.13124*Gly/ABA' | 0.7860 |
| 87 | 'Lys/Ile+0.30509*Thr/ABA' | 0.7860 |
| 88 | 'Asn/ABA−7.3476*Ile/Leu' | 0.7860 |
| 89 | 'Lys/Ile−4.9749*ABA/Phe' | 0.7841 |
| 90 | 'Lys/Ile−6.5727*ABA/Tyr' | 0.7837 |
| 91 | 'Thr/ABA−26.2807*Ile/Lys' | 0.7836 |
| 92 | 'Lys/ABA−56.4271*Glu/Ala' | 0.7830 |
| 93 | 'Asn/ABA+0.24362*Gln/Ile' | 0.7827 |
| 94 | 'Lys/ABA+0.98711*Ala/Met' | 0.7825 |
| 95 | 'Lys/ABA+4.1882*Pro/Ile' | 0.7821 |
| 96 | 'Asn/ABA+2.0947*Ser/Ile' | 0.7811 |
| 97 | 'Lys/Ile−4.5805*ABA/Trp' | 0.7811 |
| 98 | 'Ala/Ile+0.25962*Gly/ABA' | 0.7809 |
| 99 | 'Lys/ABA+1.1929*Gln/Ile' | 0.7809 |
| 100 | 'Lys/Ile+0.32756*Pro/Met' | 0.7795 |

FIG.67

| No | Formula | ROC_AUC |
|---|---|---|
| 1 | [4.5786]+[0.0817]Tau+[-0.0684]Glu+[0.0150]Ala+[-0.4888]Cit+[-0.3668]ABA+[0.0265]Val | 0.981666 |
| 2 | [8.0538]+[0.0792]Tau+[-0.0646]Glu+[0.0180]Ala+[-0.4632]Cit+[-0.2967]ABA | 0.980242 |
| 3 | [2.2087]+[0.1184]Tau+[0.0145]Ala+[-0.4394]Cit+[-0.3550]ABA+[0.0277]Val+[-0.1422]Met | 0.979886 |
| 4 | [4.8703]+[0.0842]Tau+[0.0347]Ser+[-0.0670]Glu+[0.0151]Ala+[-0.4619]Cit+[-0.2751]ABA | 0.981488 |
| 5 | [5.3406]+[0.0445]Tau+[-0.0523]Glu+[-0.5365]Cit+[-0.1870]Met+[0.0974]Orn+[0.0679]Arg | 0.983624 |
| 6 | [6.0848]+[0.0639]Tau+[0.0445]Thr+[-0.0535]Glu+[-0.5084]Cit+[-0.2524]ABA+[0.0840]Orn | 0.984336 |
| 7 | [7.8120]+[0.0793]Tau+[-0.0639]Glu+[0.0177]Ala+[-0.4607]Cit+[-0.2983]ABA+[0.0023]Leu | 0.980242 |
| 8 | [6.3933]+[0.0816]Tau+[0.0164]Thr+[-0.0645]Glu+[0.0168]Ala+[-0.4517]Cit+[-0.3000]ABA | 0.980954 |
| 9 | [6.4840]+[0.0798]Tau+[-0.0623]Glu+[0.0168]Ala+[-0.4604]Cit+[-0.2834]ABA+[0.0162]Arg | 0.980598 |
| 10 | [8.4796]+[0.0892]Tau+[-0.0610]Glu+[-0.4355]Cit+[-0.3337]ABA+[0.0376]Val+[-0.1084]Met | 0.981488 |
| 11 | [7.7063]+[0.0766]Tau+[-0.0651]Glu+[0.0176]Ala+[-0.4609]Cit+[-0.2949]ABA+[0.0027]Lys | 0.980598 |
| 12 | [8.4215]+[0.0787]Tau+[-0.0654]Glu+[0.0185]Ala+[-0.4646]Cit+[-0.2923]ABA+[-0.0081]Ile | 0.98131 |
| 13 | [11.9413]+[0.0848]Tau+[-0.0731]Glu+[-0.0052]Gln+[0.0191]Ala+[-0.4748]Cit+[-0.3378]ABA | 0.981844 |
| 14 | [6.1419]+[0.0806]Tau+[-0.0595]Glu+[0.0088]Gly+[0.0165]Ala+[-0.4613]Cit+[-0.2848]ABA | 0.9822 |
| 15 | [1.3053]+[0.1005]Tau+[0.0125]Ala+[-0.4296]Cit+[-0.3317]ABA+[0.0193]Val | 0.976504 |
| 16 | [9.1498]+[0.0785]Tau+[-0.0666]Glu+[0.0187]Ala+[-0.4677]Cit+[-0.2841]ABA+[-0.0228]Trp | 0.981666 |
| 17 | [7.2830]+[0.0797]Tau+[-0.0656]Glu+[0.0173]Ala+[-0.4719]Cit+[-0.3033]ABA+[0.0184]Tyr | 0.98131 |
| 18 | [1.3681]+[0.0918]Tau+[-0.5074]Cit+[-0.3166]ABA+[0.0288]Val+[0.0756]Orn | 0.980776 |
| 19 | [1.3434]+[0.0984]Tau+[0.0126]Ala+[-0.4173]Cit+[-0.3214]ABA+[0.0253]Val+[-0.0292]Ile | 0.980242 |
| 20 | [5.8634]+[0.0536]Tau+[-0.0424]Glu+[-0.4975]Cit+[-0.1976]ABA+[0.0810]Orn+[0.0403]Arg | 0.983268 |
| 21 | [10.9801]+[0.0875]Tau+[-0.0780]Glu+[0.0214]Ala+[-0.4724]Cit+[-0.2969]ABA+[-0.1325]Met | 0.982912 |
| 22 | [7.9734]+[0.0970]Tau+[0.0674]Ser+[-0.0638]Glu+[-0.4027]Cit+[-0.2029]ABA+[-0.1396]Met | 0.97953 |
| 23 | [8.0863]+[0.0793]Tau+[-0.0646]Glu+[0.0180]Ala+[-0.4631]Cit+[-0.2968]ABA+[-0.0006]His | 0.980242 |
| 24 | [-1.2778]+[0.0977]Tau+[0.0170]Gly+[0.0099]Ala+[-0.4348]Cit+[-0.3363]ABA+[0.0204]Val | 0.980064 |
| 25 | [2.0832]+[0.1160]Tau+[0.0459]Ser+[0.0142]Ala+[-0.4233]Cit+[-0.2631]ABA+[-0.1221]Met | 0.97864 |
| 26 | [9.8153]+[0.0841]Tau+[-0.0610]Glu+[-0.4780]Cit+[-0.3542]ABA+[0.0406]Val+[-0.0558]Phe | 0.982734 |
| 27 | [7.4717]+[0.0821]Tau+[-0.0580]Glu+[-0.4346]Cit+[-0.3139]ABA+[0.0365]Val+[-0.0333]Trp | 0.981488 |
| 28 | [1.6272]+[0.0879]Tau+[-0.0495]Glu+[0.0207]Gly+[-0.4384]Cit+[-0.3331]ABA+[0.0323]Val | 0.9822 |
| 29 | [6.1500]+[0.0825]Tau+[-0.0557]Glu+[-0.4260]Cit+[-0.3213]ABA+[0.0329]Val | 0.97953 |
| 30 | [1.9838]+[0.0929]Tau+[-0.5119]Cit+[-0.3114]ABA+[0.0307]Val+[-0.0182]Trp+[0.0748]Orn | 0.981132 |
| 31 | [3.7207]+[0.0901]Tau+[0.0443]Ser+[-0.0487]Glu+[0.0122]Gly+[-0.4101]Cit+[-0.2116]ABA | 0.978284 |
| 32 | [9.9583]+[0.0791]Tau+[-0.0678]Glu+[0.0187]Ala+[-0.4781]Cit+[-0.2941]ABA+[-0.0268]Phe | 0.98131 |
| 33 | [2.5538]+[0.0899]Tau+[0.0363]Thr+[-0.4619]Cit+[-0.2589]ABA+[0.0771]Orn | 0.978284 |
| 34 | [3.6416]+[0.1015]Tau+[0.0147]Ala+[-0.4179]Cit+[-0.2530]ABA+[-0.0915]Met+[0.0248]Arg | 0.977394 |
| 35 | [0.0786]+[0.0817]Tau+[0.0159]Gly+[0.0129]Ala+[-0.5156]Cit+[-0.2739]ABA+[0.0739]Orn | 0.98309 |
| 36 | [4.5300]+[0.0809]Tau+[-0.0554]Glu+[-0.4215]Cit+[-0.2983]ABA+[0.0299]Val+[0.0191]Arg | 0.979352 |
| 37 | [1.6244]+[0.0960]Tau+[0.0152]Gly+[0.0128]Ala+[-0.4189]Cit+[-0.2734]ABA | 0.977928 |
| 38 | [4.0630]+[0.0817]Tau+[0.0250]Thr+[-0.0588]Glu+[-0.4086]Cit+[-0.3259]ABA+[0.0295]Val | 0.979708 |
| 39 | [0.7038]+[0.0812]Tau+[-0.5069]Cit+[-0.3107]ABA+[0.0263]Val+[0.0774]Orn+[0.0077]Lys | 0.980954 |
| 40 | [1.4006]+[0.1002]Tau+[0.0126]Ala+[-0.4298]Cit+[-0.3301]ABA+[0.0202]Val+[-0.0029]Leu | 0.976326 |
| 41 | [6.4974]+[0.0830]Tau+[-0.0556]Glu+[-0.4306]Cit+[-0.3301]ABA+[0.0396]Val+[-0.0261]Ile | 0.981132 |
| 42 | [2.1879]+[0.1069]Tau+[0.0130]Ala+[-0.4319]Cit+[-0.3438]ABA+[0.0223]Val+[-0.0237]His | 0.97864 |
| 43 | [3.5495]+[0.0757]Tau+[-0.5158]Cit+[-0.1749]ABA+[-0.1097]Met+[0.0909]Orn+[0.0588]Arg | 0.981666 |
| 44 | [2.6729]+[0.1024]Tau+[0.0151]Gly+[0.0142]Ala+[-0.4141]Cit+[-0.2708]ABA+[-0.0720]Met | 0.97775 |
| 45 | [4.6806]+[0.0840]Tau+[-0.0596]Glu+[-0.4362]Cit+[-0.3260]ABA+[0.0322]Val+[0.0274]Tyr | 0.98042 |
| 46 | [1.3749]+[0.1004]Tau+[0.0126]Ala+[-0.4293]Cit+[-0.3319]ABA+[0.0194]Val+[-0.0015]Tyr | 0.976326 |
| 47 | [1.3819]+[0.1017]Tau+[0.0126]Ala+[-0.4302]Cit+[-0.3322]ABA+[0.0196]Val+[-0.0011]Lys | 0.976682 |
| 48 | [-0.3272]+[0.0547]Tau+[-0.5272]Cit+[-0.0631]Ile+[0.0159]Leu+[0.0986]Orn+[0.0625]Arg | 0.979174 |
| 49 | [0.7728]+[0.0771]Tau+[0.0246]Thr+[-0.5171]Cit+[-0.2276]ABA+[0.0888]Orn+[0.0384]Arg | 0.980776 |
| 50 | [6.6874]+[0.0813]Tau+[-0.0569]Glu+[-0.4312]Cit+[-0.3195]ABA+[0.0360]Val+[-0.0090]Leu | 0.98042 |

FIG.68

| No | Formula | ROC_AUC |
|---|---|---|
| 51 | '-0.44771+0.09198*Asn-0.17307*ABA-0.20712*Met+0.022773*Lys' | 0.8329 |
| 52 | '-1.0188+0.064638*Asn-0.16067*ABA-0.045461*Ile+0.017241*Lys' | 0.8177 |
| 53 | '-1.7825+0.032787*Ser-0.16144*ABA-0.050387*Ile+0.019708*Lys' | 0.8131 |
| 54 | '2.1407+0.06032*Asn-0.051896*Glu+0.0072128*Ala-0.22523*Met' | 0.7994 |
| 55 | '-1.1567+0.036748*Ser-0.17446*ABA-0.18005*Met+0.023784*Lys' | 0.8133 |
| 56 | '3.9337+0.086749*Asn-0.037908*Glu-0.12245*ABA-0.15852*Met' | 0.8103 |
| 57 | '2.158-0.13815*ABA-0.099236*Met-0.032283*Ile+0.023059*Lys' | 0.8087 |
| 58 | '4.1343-0.050029*Glu+0.010494*Ala-0.13199*ABA-0.15585*Met' | 0.8138 |
| 59 | '3.7476-0.040876*Glu-0.1426*ABA-0.16248*Met+0.021965*Lys' | 0.8152 |
| 60 | '0.60226+0.07683*Asn-0.04417*Glu-0.24172*Met+0.018046*Lys' | 0.8070 |
| 61 | '2.6689+0.090246*Asn-0.12363*ABA-0.10521*Met-0.028466*Ile' | 0.8006 |
| 62 | '1.273-0.054875*Glu+0.0082229*Ala-0.23473*Met+0.016578*Lys' | 0.8104 |
| 63 | '0.53464+0.082813*Asn+0.0069399*Ala-0.15668*ABA-0.16583*Met' | 0.7998 |
| 64 | '2.4366+0.018221*Thr-0.055083*Glu+0.0075036*Ala-0.20942*Met' | 0.7946 |
| 65 | '-0.48738+0.0063291*Ala-0.15699*ABA-0.044728*Ile+0.015721*Lys' | 0.7998 |
| 66 | '-0.093059+0.0096159*Pro-0.14793*ABA-0.04988*Ile+0.019736*Lys' | 0.8051 |
| 67 | '1.3815+0.032174*Ser-0.058707*Glu+0.0084101*Ala-0.23072*Met' | 0.8017 |
| 68 | '2.2148+0.071566*Asn-0.047485*Glu-0.1998*Met+0.02524*Orn' | 0.7894 |
| 69 | '-0.075823+0.0079329*Ala-0.17259*ABA-0.17312*Met+0.020612*Lys' | 0.7989 |
| 70 | '2.2997-0.058344*Glu+0.0085254*Ala-0.20243*Met+0.027994*Orn' | 0.7928 |
| 71 | '0.17898+0.055008*Asn+0.0058862*Ala-0.14422*ABA-0.042401*Ile' | 0.8012 |
| 72 | '3.3209+0.075227*Asn-0.035762*Glu-0.15391*Met-0.022462*Ile' | 0.7907 |
| 73 | '-0.10515-0.1405*ABA-0.046398*Ile+0.02437*Orn+0.018415*Lys' | 0.7925 |
| 74 | '0.066267+0.067498*Asn-0.14533*ABA+0.011142*Val-0.054474*Ile' | 0.8015 |
| 75 | '-0.060178+0.024828*Thr-0.1615*ABA-0.17213*Met+0.02192*Lys' | 0.8019 |
| 76 | '3.5186-0.045225*Glu+0.0087548*Ala-0.15189*Met-0.023538*Ile' | 0.7942 |
| 77 | '0.66627+0.066709*Asn+0.005989*Ala-0.14668*Met-0.039151*Ile' | 0.7812 |
| 78 | '-0.047724+0.037119*Ser-0.051666*Glu-0.23192*Met+0.019008*Lys' | 0.8051 |
| 79 | '-0.17825+0.013657*Thr-0.14912*ABA-0.04109*Ile+0.017548*Lys' | 0.7957 |
| 80 | '1.792-0.024601*Glu-0.14262*ABA-0.033872*Ile+0.017337*Lys' | 0.8030 |
| 81 | '-1.1213+0.081207*Asn-0.17229*Met-0.03722*Ile+0.019477*Lys' | 0.7944 |
| 82 | '0.96759-0.14167*ABA-0.041465*Ile+0.018727*Lys' | 0.7926 |
| 83 | '1.2313+0.023062*Thr-0.048125*Glu-0.21909*Met+0.017336*Lys' | 0.7949 |
| 84 | '-0.51411+0.0063378*Gly-0.14106*ABA-0.040101*Ile+0.018389*Lys' | 0.7923 |
| 85 | '2.6154+0.014973*Thr+0.061204*Asn-0.046853*Glu-0.20369*Met' | 0.7875 |
| 86 | '0.78533+0.021118*Ser+0.083378*Asn-0.15004*ABA-0.15807*Met' | 0.7912 |
| 87 | '0.13232-0.14865*ABA+0.0085262*Val-0.052649*Ile+0.016716*Lys' | 0.7985 |
| 88 | '0.89223+0.073827*Asn-0.13018*Met-0.041974*Ile+0.028069*Orn' | 0.7775 |
| 89 | '-0.26949+0.026662*Ser+0.0070141*Ala-0.14649*ABA-0.047303*Ile' | 0.7983 |
| 90 | '3.936+0.040387*Ser-0.049499*Glu-0.12854*ABA-0.15159*Met' | 0.7965 |
| 91 | '2.6368+0.072283*Asn-0.048912*Glu+0.0091329*Pro-0.21155*Met' | 0.7905 |
| 92 | '0.56289+0.065268*Asn-0.14047*ABA-0.063164*Ile+0.023638*Leu' | 0.7971 |
| 93 | '0.5531+0.077618*Asn+0.010278*Val-0.14114*Met-0.048945*Ile' | 0.7830 |
| 94 | '0.6469+0.066087*Asn-0.12609*ABA-0.043671*Ile+0.020257*Orn' | 0.7932 |
| 95 | '1.3621+0.012951*Thr+0.082136*Asn-0.14419*ABA-0.15156*Met' | 0.7969 |
| 96 | '2.1793-0.031631*Glu+0.0083247*Ala-0.13952*ABA-0.031825*Ile' | 0.8008 |
| 97 | '-1.4294+0.027603*Ser-0.038933*Glu-0.18166*ABA+0.014011*Lys' | 0.8026 |
| 98 | '2.1679+0.074521*Asn-0.048298*Glu+0.0066723*Val-0.20853*Met' | 0.7889 |
| 99 | '0.46617-0.14486*ABA-0.059718*Ile+0.018482*Leu+0.016464*Lys' | 0.7946 |
| 100 | '1.1055+0.093005*Asn-0.1374*ABA-0.14769*Met+0.016114*Orn' | 0.7869 |

FIG.70

| No | Formula | ROC_AUC |
|---|---|---|
| 1 | −(3.158e−01)Tau+(1.439e−01)Glu−(5.537e−02)Gly+(6.746e−01)Cit+(6.473e−01)ABA−(4.858e−02)Val+(2.269e+00) | 0.9783 |
| 2 | (3.216e−01)Tau+(1.049e−01)Ser−(1.743e−01)Glu−(5.907e−01)Cit+(7.103e−01)ABA+(4.135e−02)Val+(6.923e−01) | 0.9783 |
| 3 | (3.786e−02)Thr−(1.870e−01)Glu+(2.076e−02)Ala−(7.169e−01)Cit−(6.590e−01)ABA+(1.222e−01)Orn+(2.301e+01) | 0.9763 |
| 4 | −(2.050e−01)Glu+(2.209e−02)Ala−(6.564e−01)Cit−(7.069e−01)Met+(1.570e−01)Orn+(4.721e−02)Lys+(2.016e+01) | 0.9761 |
| 5 | −(2.009e−01)Glu+(3.020e−02)Ala−(6.849e−01)Cit−(5.383e−01)ABA−(4.224e−01)Met+(1.468e−01)Orn+(3.124e+01) | 0.9758 |
| 6 | (1.925e−01)Glu−(2.157e−02)Ala+(7.167e−01)Cit+(6.589e−01)ABA−(1.241e−02)Val−(1.207e−01)Orn−(2.401e+01) | 0.9758 |
| 7 | (3.207e−01)Tau+(2.311e−02)Ala−(6.402e−01)Cit−(6.744e−01)ABA−(1.451e−01)Met+(1.047e−01)Orn+(3.956e+00) | 0.9758 |
| 8 | (3.187e−01)Tau+(7.625e−02)Gly−(6.839e−01)Cit−(6.435e−01)ABA+(3.010e−02)Val+(9.938e−02)Orn−(1.450e+01) | 0.9758 |
| 9 | (3.161e−01)Tau+(3.482e−02)Thr+(1.808e−02)Ala−(6.285e−01)Cit−(7.037e−01)ABA+(9.103e−02)Orn−(6.940e−01) | 0.9753 |
| 10 | −(3.085e−01)Tau+(1.447e−01)Glu−(4.409e−02)Gly−(2.450e−02)Ala+(6.800e−01)Cit+(6.472e−01)ABA−(3.168e+00) | 0.9753 |
| 11 | −(1.576e−01)Glu+(4.737e−02)Gly−(7.664e−01)Cit−(6.054e−01)ABA+(2.319e−02)Val+(1.360e−01)Orn+(1.742e+01) | 0.9753 |
| 12 | −(3.052e−01)Tau+(1.344e−01)Glu−(5.515e−02)Gly+(7.370e−01)Cit+(5.703e−01)ABA−(1.321e−01)Orn−(2.761e+00) | 0.9751 |
| 13 | −(4.851e−02)Thr+(1.664e−01)Glu−(7.245e−01)Cit+(6.537e−01)ABA−(1.264e−01)Orn−(4.229e−02)Lys+(2.030e+01) | 0.9751 |
| 14 | (3.403e−01)Tau+(7.738e−02)Gly−(6.752e−01)Cit−(6.376e−01)ABA+(5.807e−02)Val−(1.114e−01)Ile−(9.571e+00) | 0.9751 |
| 15 | −(1.712e−01)Glu−(6.998e−01)Cit−(5.208e−01)ABA−(4.262e−01)Met+(1.557e−01)Orn+(6.220e−02)Lys+(2.874e+01) | 0.9751 |
| 16 | −(3.334e−01)Tau−(8.183e−02)Gly+(6.684e−01)Cit+(6.378e−01)ABA−(4.347e−02)Val+(1.634e−01)Met+(9.875e+00) | 0.9749 |
| 17 | (3.207e−01)Tau+(1.825e−02)Ala−(6.232e−01)Cit−(7.076e−01)ABA+(1.459e−02)Val+(8.717e−02)Orn−(7.586e−01) | 0.9749 |
| 18 | −(1.620e−01)Glu+(3.796e−02)Gly+(1.973e−02)Ala−(7.505e−01)Cit−(6.259e−01)ABA+(1.300e−01)Orn+(1.781e+01) | 0.9747 |
| 19 | −(3.365e−01)Tau−(1.348e−01)Ser+(1.713e−01)Glu+(6.287e−01)Cit+(6.445e−01)ABA+(1.689e−01)Met−(1.185e+01) | 0.9747 |
| 20 | (1.897e−01)Glu+(2.311e−03)Pro−(2.369e−02)Ala+(7.280e−01)Cit+(6.457e−01)ABA−(1.287e−01)Orn−(2.614e+01) | 0.9745 |
| 21 | −(1.898e−01)Glu+(2.327e−02)Ala−(7.277e−01)Cit−(6.462e−01)ABA+(1.272e−01)Orn+(2.604e+01) | 0.9745 |
| 22 | −(1.351e−01)Glu+(3.111e−02)Gly−(7.937e−01)Cit−(5.658e−01)ABA+(1.448e−01)Orn+(9.851e−02)Arg+(1.541e+01) | 0.9745 |
| 23 | (1.945e−01)Glu+(2.613e−03)Gln−(2.377e−02)Ala+(7.276e−01)Cit+(6.450e−01)ABA−(1.268e−01)Orn−(2.761e+01) | 0.9745 |
| 24 | −(1.750e−01)Glu+(1.962e−02)Ala−(7.099e−01)Cit−(6.709e−01)ABA+(1.170e−01)Orn+(3.555e−02)Lys+(1.985e+01) | 0.9745 |
| 25 | −(1.618e−01)Glu+(1.586e−02)Ala−(7.526e−01)Cit−(6.177e−01)ABA+(1.290e−01)Orn+(9.491e−02)Arg+(1.819e+01) | 0.9745 |
| 26 | −(3.221e−01)Tau−(7.702e−02)Gly+(7.017e−01)Cit+(6.206e−01)ABA−(3.272e−02)Leu−(1.081e−01)Orn+(1.174e+01) | 0.9744 |
| 27 | (2.959e−01)Tau+(5.585e−02)Gly−(7.307e−01)Cit−(5.927e−01)ABA+(1.169e−01)Orn+(1.020e−01)Arg−(1.211e+01) | 0.9744 |
| 28 | −(3.612e−02)Thr+(1.540e−01)Glu−(4.121e−02)Gly+(7.748e−01)Cit+(5.934e−01)ABA−(1.444e−01)Orn−(2.010e+01) | 0.9744 |
| 29 | (4.046e−02)Ser−(1.877e−01)Glu+(2.213e−02)Ala−(7.076e−01)Cit−(6.690e−01)ABA+(1.203e−01)Orn+(2.238e+01) | 0.9744 |
| 30 | −(3.260e−01)Tau−(4.768e−02)Thr−(2.332e−02)Ala+(6.114e−01)Cit+(7.047e−01)ABA+(1.432e−01)Met−(4.290e+00) | 0.9742 |
| 31 | −(3.011e−01)Tau+(1.839e−01)Glu−(2.288e−02)Ala+(6.217e−01)Cit+(6.980e−01)ABA−(3.502e−02)Val−(6.243e+00) | 0.9742 |
| 32 | −(1.928e−01)Glu+(2.409e−02)Ala−(7.287e−01)Cit−(6.443e−01)ABA−(1.580e−02)His+(1.261e−01)Orn+(2.718e+01) | 0.9740 |
| 33 | −(1.688e−01)Glu+(7.487e−01)Cit−(6.200e−01)ABA+(8.202e−02)Phe+(1.312e−01)Orn+(5.055e−02)Lys+(2.895e+01) | 0.9740 |
| 34 | (2.968e−01)Tau+(2.461e−01)Asn+(6.041e−02)Gly−(6.170e−01)Cit−(6.828e−01)ABA+(2.749e−02)Val−(1.543e+01) | 0.9740 |
| 35 | −(1.886e−01)Glu+(2.523e−02)Ala−(7.380e−01)Cit−(6.325e−01)ABA−(2.839e−02)Leu+(1.353e−01)Orn+(2.830e+01) | 0.9740 |
| 36 | (3.478e−01)Tau+(8.076e−02)Gly−(6.772e−01)Cit−(6.001e−01)ABA−(1.817e−01)Ile+(1.440e−01)Leu−(9.714e+00) | 0.9738 |
| 37 | −(1.886e−01)Glu+(2.706e−02)Ala−(7.391e−01)Cit−(6.304e−01)ABA−(5.758e−02)Tyr+(1.289e−01)Orn+(2.873e+01) | 0.9738 |
| 38 | −(3.113e−01)Tau−(1.017e−01)Ser+(1.691e−01)Glu−(2.466e−02)Ala+(5.944e−01)Cit+(7.143e−01)ABA−(1.934e+00) | 0.9738 |
| 39 | (3.109e−01)Tau+(4.258e−02)Thr−(1.794e−01)Glu−(6.409e−01)Cit−(6.759e−01)ABA+(4.234e−02)Val+(8.531e+00) | 0.9738 |
| 40 | (3.335e−01)Tau+(8.842e−02)Ser−(1.419e−01)Glu+(3.414e−02)Gly−(6.672e−01)Cit−(6.438e−01)ABA+(4.194e+00) | 0.9738 |
| 41 | (4.900e−02)Ser−(1.662e−01)Glu−(7.163e−01)Cit−(6.627e−01)ABA+(1.256e−01)Orn+(4.461e−02)Lys+(1.991e+01) | 0.9738 |
| 42 | −(3.035e−01)Tau+(1.873e−01)Glu−(3.286e−02)Ala+(6.514e−01)Cit+(6.372e−01)ABA+(2.035e−01)Met−(1.665e+01) | 0.9737 |
| 43 | (3.249e−01)Tau+(2.530e−02)Ala−(6.660e−01)Cit−(6.477e−01)ABA−(1.187e−01)Ile+(1.288e−01)Orn+(5.862e+00) | 0.9737 |
| 44 | −(3.134e−01)Tau−(6.930e−02)Gly−(1.514e−02)Ala+(6.874e−01)Cit+(6.430e−01)ABA−(1.036e−01)Orn+(1.137e+01) | 0.9737 |
| 45 | (3.442e−01)Tau+(2.460e−02)Ala−(6.124e−01)Cit−(6.780e−01)ABA−(1.883e−01)Ile+(1.036e−01)Leu+(3.749e+00) | 0.9737 |
| 46 | −(1.478e−01)Glu+(4.698e−02)Gly−(7.868e−01)Cit−(5.774e−01)ABA+(2.164e−02)His+(1.516e−01)Orn+(2.036e+01) | 0.9737 |
| 47 | −(3.262e−01)Tau+(1.764e−01)Glu+(6.583e−01)Cit+(6.469e−01)ABA−(6.194e−02)Val+(8.257e−02)Ile−(1.308e+01) | 0.9737 |
| 48 | −(3.366e−01)Tau+(6.637e−01)Cit+(6.344e−01)ABA−(4.926e−02)Val+(1.535e−01)Ile−(1.332e−01)Orn−(4.964e+00) | 0.9735 |
| 49 | −(3.314e−01)Tau−(2.254e−02)Ala+(6.024e−01)Cit+(7.142e−01)ABA−(2.307e−02)Val+(1.270e−01)Met−(3.132e+00) | 0.9735 |
| 50 | −(4.921e−02)Thr+(1.873e−01)Glu+(7.341e−01)Cit+(6.371e−01)ABA−(1.711e−02)Val−(1.317e−01)Orn−(2.549e+01) | 0.9735 |

FIG.71

| No | Formula | ROC_AUC |
|---|---|---|
| 51 | 'Asn-1.4832*ABA-1.979*Met+0.21288*Lys' | 0.8300 |
| 52 | 'Glu-0.24343*Ala+2.9751*ABA+3.3394*Met' | 0.8151 |
| 53 | 'Asn-2.1516*ABA-0.61193*Ile+0.23668*Lys' | 0.8174 |
| 54 | 'Ser-4.0213*ABA-4.5328*Met+0.6012*Lys' | 0.8099 |
| 55 | 'Asn+0.077168*Ala-1.6743*ABA-1.8877*Met' | 0.8015 |
| 56 | 'Ser-4.887*ABA-1.4435*Ile+0.59704*Lys' | 0.8119 |
| 57 | 'Asn-0.38295*Glu-2.8481*Met+0.21655*Lys' | 0.8067 |
| 58 | 'Asn-2.1228*Met-0.4244*Ile+0.23238*Lys' | 0.7941 |
| 59 | 'Ala-21.2676*ABA-6.6969*Ile+2.3144*Lys' | 0.8008 |
| 60 | 'Asn+0.099365*Ala-2.3531*ABA-0.66507*Ile' | 0.7964 |
| 61 | 'Asn-0.59781*Glu+0.10979*Ala-3.2158*Met' | 0.7958 |
| 62 | 'Glu-0.28953*Ala+4.4593*ABA+1.1089*Ile' | 0.7999 |
| 63 | 'Ser-1.6044*Glu+0.28992*Ala-7.173*Met' | 0.7990 |
| 64 | 'Ala-19.4176*ABA-21.1007*Met+2.5494*Lys' | 0.8006 |
| 65 | 'Ser+0.2672*Ala-5.4738*ABA-1.6009*Ile' | 0.7951 |
| 66 | 'Glu+3.7234*ABA+4.3365*Met-0.62489*Lys' | 0.8133 |
| 67 | 'Ser-1.1406*Glu-6.4892*Met+0.55875*Lys' | 0.8042 |
| 68 | 'Glu-0.19007*Ala+5.0474*Met-0.36082*Lys' | 0.8067 |
| 69 | 'Ser-1.4993*Glu+0.27884*Ala-6.992*ABA' | 0.7985 |
| 70 | 'Thr-5.4032*ABA-6.3114*Met+0.82502*Lys' | 0.8014 |
| 71 | 'Ser+0.2472*Ala-4.7211*ABA-4.4769*Met' | 0.7787 |
| 72 | 'Asn-1.349*ABA-1.4143*Met' | 0.7850 |
| 73 | 'Asn-0.67336*Glu+0.12779*Ala-3.5268*ABA' | 0.7889 |
| 74 | 'Asn-1.3595*ABA-1.5706*Met+0.18453*Orn' | 0.7875 |
| 75 | 'ABA+0.77812*Met+0.28419*Ile-0.19061*Lys' | 0.8081 |
| 76 | 'Thr+6.8904*Asn-10.7328*ABA-11.789*Met' | 0.7960 |
| 77 | 'Glu+6.0012*ABA+1.6361*Ile-0.79951*Lys' | 0.8014 |
| 78 | 'Ser-4.8274*Met-1.2788*Ile+0.6661*Lys' | 0.7892 |
| 79 | 'ABA+0.37478*Ile-0.2025*Orn-0.1438*Lys' | 0.7912 |
| 80 | 'Thr-2.292*Glu+0.40192*Ala-10.0522*Met' | 0.7958 |
| 81 | 'Ser-1.0925*Glu-6.1352*ABA+0.47965*Lys' | 0.8028 |
| 82 | 'Glu-0.1959*Ala+4.9401*ABA-0.3114*Lys' | 0.7957 |
| 83 | 'Thr-1.5127*Glu-8.4771*Met+0.71572*Lys' | 0.7907 |
| 84 | 'Asn-0.4312*Glu-2.8858*ABA+0.20769*Lys' | 0.7992 |
| 85 | 'Thr-1.3421*Glu-4.162*ABA-4.587*Met' | 0.7962 |
| 86 | 'Thr-9.2004*ABA-2.6394*Ile+1.164*Lys' | 0.7937 |
| 87 | 'Glu-0.24272*Ala+3.6357*Met+0.70736*Ile' | 0.7910 |
| 88 | 'Glu-0.18391*Ala+4.1187*Met-0.5713*Orn' | 0.7887 |
| 89 | 'Asn+0.05347*Ala-3.0354*Met+0.2159*Lys' | 0.7768 |
| 90 | 'Ala-16.899*ABA-6.1267*Ile+3.0804*Orn' | 0.7878 |
| 91 | 'Asn-1.2948*ABA-1.3616*Met-0.074079*Trp' | 0.7876 |
| 92 | 'Ser+4.1443*Asn-13.5458*Met+1.0731*Lys' | 0.7811 |
| 93 | 'Asn-1.3946*ABA-1.4864*Met+0.058785*Tyr' | 0.7827 |
| 94 | 'Ala-19.6764*ABA+1.2335*Val-7.0972*Ile' | 0.7944 |
| 95 | 'Ala-18.4565*ABA-8.3279*Ile+2.8719*Leu' | 0.7973 |
| 96 | 'Asn-1.3479*ABA-1.4098*Met-0.0060638*Phe' | 0.7853 |
| 97 | 'Ala-13.4063*ABA-8.2283*Met-3.7974*Ile' | 0.7921 |
| 98 | 'ABA+0.44225*Ile-0.13835*Leu-0.12657*Lys' | 0.7953 |
| 99 | 'ABA+0.32035*Ile-0.14438*Lys' | 0.7916 |
| 100 | 'Asn+0.082589*Ala-2.0038*Met-0.49879*Ile' | 0.7777 |

|  | CANCER PATIENT GROUP AND HEALTHY GROUP | PROSTATIC HYPERTROPHY GROUP AND CANCER PATIENT GROUP | PROSTATIC DISEASE GROUP AND HEALTHY GROUP |
|---|---|---|---|
| INDEX FORMULA 1 | 0.917 | 0.636 | 0.717 |
| INDEX FORMULA 10 | 0.672 | 0.394 | 0.608 |
| INDEX FORMULA 11 | 0.422 | 0.601 | 0.499 |
| INDEX FORMULA 13 | 0.356 | 0.617 | 0.420 |

| No | Formula | ROC_AUC |
|---|---|---|
| 1 | 3.18118+0.08585*Asn+0.01405*Ala-0.01816*Val-0.11079*Met-0.08095*Trp-0.02272*Arg | 0.8499 |
| 2 | 1.49710+0.07499*Asn+0.01262*Ala-0.01688*Val-0.15978*Met+0.02564*Tyr-0.08662*Trp | 0.8495 |
| 3 | 1.13199+0.08698*Asn+0.02143*Glu+0.01288*Ala-0.01845*Val-0.13310*Met-0.08247*Trp | 0.8494 |
| 4 | 1.25593+0.07783*Asn+0.00644*Pro+0.01225*Ala-0.01701*Val-0.13327*Met-0.07926*Trp | 0.8475 |
| 5 | 0.04345+0.06634*Asn+0.01286*Ala-0.01787*Val-0.13892*Met+0.03972*His-0.08602*Trp | 0.8468 |
| 6 | -0.29488+0.05771*Asn+0.00820*Ala-0.01114*Val-0.12988*Met+0.01559*Tyr-0.06411*Trp | 0.8455 |
| 7 | 1.45959+0.07999*Asn+0.01264*Ala-0.01927*Val-0.14133*Met+0.02341*Ile-0.08507*Trp | 0.8448 |
| 8 | -1.88989+0.05520*Asn+0.01225*Ala-0.12414*Met-0.02573*Leu+0.04274*His-0.07162*Trp | 0.8442 |
| 9 | 2.76154+0.07801*Asn+0.01364*Ala-0.02762*Cit-0.01692*Val-0.12788*Met-0.08402*Trp | 0.8438 |
| 10 | 1.24016+0.07814*Asn+0.01317*Ala-0.01659*Val-0.14046*Met+0.02072*Phe-0.08904*Trp | 0.8422 |
| 11 | 0.89278+0.06529*Asn+0.01213*Ala-0.02174*Val+0.04396*His-0.09486*Trp-0.03306*Arg | 0.8422 |
| 12 | -0.61954+0.06922*Asn+0.01261*Ala-0.13341*Met-0.02380*Leu+0.03046*Phe-0.07946*Trp | 0.8415 |
| 13 | -0.66071+0.07631*Asn+0.01875*Glu+0.01193*Ala-0.12121*Met-0.02270*Leu-0.06906*Trp | 0.8411 |
| 14 | 2.60808+0.08560*Asn-0.00234*Gln+0.01323*Ala-0.01610*Val-0.12785*Met-0.08014*Trp | 0.8405 |
| 15 | 1.70068+0.07704*Asn+0.01339*Ala-0.01490*Val-0.12434*Met-0.00565*Leu-0.07761*Trp | 0.8403 |
| 16 | 1.52674+0.07186*Asn+0.01333*Ala+0.03958*ABA-0.01743*Val-0.13535*Met-0.08195*Trp | 0.8401 |
| 17 | 2.96742+0.07668*Asn+0.01277*Ala-0.01899*Val-0.08902*Trp-0.01383*Orn-0.02757*Arg | 0.84 |
| 18 | 1.45305+0.00712*Thr+0.07042*Asn+0.01280*Ala-0.01640*Val-0.13442*Met-0.07953*Trp | 0.8396 |
| 19 | -0.27821+0.05982*Asn+0.00841*Ala-0.01416*Val-0.12598*Met+0.02403*Ile-0.06621*Trp | 0.8394 |
| 20 | -0.89061+0.06070*Asn+0.00843*Ala-0.01182*Val-0.12506*Met+0.02887*Phe-0.06876*Trp | 0.8389 |
| 21 | 1.95886+0.07926*Asn+0.01668*Glu+0.01224*Ala-0.02100*Val-0.08954*Trp-0.02681*Arg | 0.8388 |
| 22 | 2.25927+0.07928*Asn-0.00286*Gly+0.01316*Ala-0.01641*Val-0.12812*Met-0.08019*Trp | 0.8388 |
| 23 | 1.88383+0.07877*Asn+0.01328*Ala-0.01612*Val-0.12810*Met-0.07963*Trp-0.00189*Lys | 0.8388 |
| 24 | -1.54154+0.01175*Ala-0.10547*Met+0.03185*Ile-0.03932*Leu+0.05498*His-0.06738*Trp | 0.8385 |
| 25 | 2.46208+0.07507*Asn+0.01196*Ala-0.02254*Val+0.02130*Ile-0.09108*Trp-0.03171*Arg | 0.8384 |
| 26 | 1.70502+0.07712*Asn+0.01326*Ala-0.01615*Val-0.13002*Met-0.08096*Trp | 0.8383 |
| 27 | 1.66599+0.00080*Ser+0.07647*Asn+0.01325*Ala-0.01617*Val-0.13008*Met-0.08090*Trp | 0.8383 |
| 28 | 2.86589+0.07407*Asn+0.01268*Ala-0.01169*Cit-0.01962*Val-0.08963*Trp-0.02674*Arg | 0.8379 |
| 29 | -0.95646+0.01112*Ala-0.01539*Val+0.03860*Ile-0.03492*Leu+0.05485*His-0.07699*Trp | 0.8377 |
| 30 | -1.17805+0.06524*Asn+0.01438*Glu+0.00776*Ala-0.10593*Met-0.02355*Leu-0.05257*Trp | 0.8372 |
| 31 | -0.30112+0.06710*Asn+0.01182*Ala-0.14564*Met-0.01987*Leu-0.02313*Tyr-0.07598*Trp | 0.8371 |
| 32 | -0.35898+0.07084*Asn+0.01177*Ala-0.12460*Met+0.02472*Ile-0.02832*Leu-0.07097*Trp | 0.8369 |
| 33 | -1.31735+0.05595*Asn+0.00799*Ala-0.11555*Met-0.02217*Leu-0.01374*His-0.05059*Trp | 0.836 |
| 34 | -0.49778+0.05736*Asn+0.00886*Ala-0.01129*Val-0.12158*Met-0.06128*Trp+0.01402*Orn | 0.8338 |
| 35 | 2.58586+0.07482*Asn+0.01259*Ala-0.01947*Val-0.08804*Trp-0.02923*Arg | 0.8332 |
| 36 | -1.53223+0.06011*Asn+0.00792*Ala-0.12025*Met-0.03031*Leu+0.04328*Phe-0.05826*Trp | 0.8324 |
| 37 | -0.83862+0.05833*Asn+0.00762*Ala-0.11784*Met+0.04086*Ile-0.03956*Leu-0.05137*Trp | 0.8324 |
| 38 | -0.89513+0.05733*Asn+0.00771*Ala-0.12424*Met-0.02228*Leu+0.01671*Tyr-0.05443*Trp | 0.8319 |
| 39 | 0.30950+0.06283*Asn+0.01129*Ala-0.01620*Val+0.03091*Ile-0.02501*Leu-0.07988*Trp | 0.8303 |
| 40 | -2.23452+0.05521*Asn+0.01128*Ala-0.14437*Met+0.03201*His-0.08695*Trp | 0.8303 |
| 41 | -0.04241+0.06911*Asn+0.01247*Ala-0.12221*Met-0.01854*Leu-0.07074*Trp | 0.8299 |
| 42 | 0.82176+0.01287*Ala-0.01557*Val-0.10948*Met+0.04835*His-0.08169*Trp | 0.8298 |
| 43 | -1.03135+0.01266*Ala-0.10097*Met-0.02581*Leu+0.05158*His-0.06818*Trp | 0.8294 |
| 44 | -0.52610+0.01207*Ala-0.01283*Val-0.02000*Leu+0.05071*His-0.07877*Trp | 0.8285 |
| 45 | -1.07369+0.06716*Asn+0.00451*Pro+0.01100*Ala-0.14095*Met-0.08299*Trp | 0.8274 |
| 46 | -1.23291+0.07191*Asn+0.01371*Glu+0.01118*Ala-0.13912*Met-0.08469*Trp | 0.8272 |
| 47 | 0.09885+0.07105*Asn+0.01208*Ala-0.12547*Met-0.08296*Trp-0.01518*Arg | 0.8263 |
| 48 | -0.97901+0.05351*Asn+0.00888*Ala-0.01192*Val-0.13395*Met-0.06595*Trp+0.01060*Lys | 0.8232 |
| 49 | -0.66209+0.06708*Asn+0.01170*Ala-0.13878*Met-0.08346*Trp | 0.8228 |
| 50 | -1.71170+0.05816*Asn+0.00783*Ala-0.12449*Met-0.06622*Trp | 0.8206 |

FIG.76

| No | Formula | ROC_AUC |
|---|---|---|
| 51 | 2.60950+0.01239*Ala-0.01806*Val-0.13517*Met+0.02191*Ile+0.03044*Tyr-0.08440*Trp | 0.8203 |
| 52 | -2.17929+0.01122*Ala-0.03103*Leu+0.05003*His-0.07384*Trp | 0.8195 |
| 53 | -0.68471+0.03804*Asn+0.00666*Ala-0.00950*Val+0.04307*Ile-0.03536*Leu-0.05963*Trp | 0.8194 |
| 54 | 2.57935+0.01284*Ala-0.01528*Val-0.13062*Met+0.02982*Tyr+0.01195*Phe-0.08582*Trp | 0.8192 |
| 55 | 2.56685+0.01296*Ala-0.01532*Val-0.13044*Met+0.03070*Tyr-0.08339*Trp+0.00259*Lys | 0.8179 |
| 56 | 2.89994+0.01325*Ala-0.01437*Val-0.08791*Met+0.03356*Ile-0.01973*Leu-0.06757*Trp | 0.8177 |
| 57 | 2.82796+0.01297*Ala-0.01519*Val-0.12665*Met+0.03080*Tyr-0.08134*Trp | 0.8177 |
| 58 | -0.34311+0.01122*Ala-0.01690*Val+0.04413*His-0.09097*Trp | 0.817 |
| 59 | -0.01587+0.06844*Asn+0.01054*Ala-0.01484*Val-0.14389*Met+0.03137*Ile-0.03109*Leu | 0.8166 |
| 60 | 1.44725+0.01161*Ala-0.01535*Val+0.03220*Ile-0.02617*Leu+0.01567*Tyr-0.07451*Trp | 0.8158 |
| 61 | 0.43949+0.06034*Asn+0.01145*Ala-0.01729*Val-0.09015*Trp | 0.8155 |
| 62 | 1.56074+0.01203*Ala-0.01435*Val+0.03149*Ile-0.02700*Leu+0.01272*Phe-0.07463*Trp | 0.8154 |
| 63 | 0.72772+0.01250*Ala-0.12498*Met-0.02369*Leu+0.02567*Tyr-0.02498*Phe-0.07758*Trp | 0.8154 |
| 64 | -1.64474+0.05308*Asn+0.00834*Ala-0.12873*Met-0.02398*Leu-0.05485*Trp+0.01118*Lys | 0.8152 |
| 65 | 0.76116+0.01252*Ala-0.10267*Met+0.02527*Ile-0.03270*Leu+0.02679*Phe-0.07050*Trp | 0.8145 |
| 66 | 2.82135+0.01290*Ala-0.01667*Val-0.10410*Met+0.02105*Ile+0.00838*Phe-0.08089*Trp | 0.8132 |
| 67 | 0.80985+0.01183*Ala-0.12095*Met+0.02533*Ile-0.02960*Leu+0.02698*Tyr-0.06959*Trp | 0.8131 |
| 68 | 1.61439+0.08721*Asn+0.01142*Pro-0.01572*Val-0.13240*Met+0.02913*Tyr-0.06367*Trp | 0.8125 |
| 69 | -0.96378+0.05879*Asn+0.00694*Ala-0.00820*Val-0.13356*Met+0.04330*Ile-0.04397*Leu | 0.8119 |
| 70 | -2.68987+0.04399*Asn+0.01844*Glu+0.00600*Ala-0.03621*Leu+0.03861*Phe-0.06767*Trp | 0.8109 |
| 71 | 2.85706+0.01338*Ala-0.01400*Val-0.09934*Met+0.01547*Phe-0.07990*Trp | 0.8105 |
| 72 | 1.16988+0.08930*Asn+0.01352*Pro-0.01594*Val-0.11329*Met+0.02937*Phe-0.06687*Trp | 0.8105 |
| 73 | 2.80665+0.01295*Ala-0.01683*Val-0.10312*Met+0.02220*Ile-0.07962*Trp+0.00189*Lys | 0.8103 |
| 74 | -1.14192+0.05596*Asn+0.01102*Ala-0.02530*Leu-0.07569*Trp | 0.8102 |
| 75 | 3.00407+0.01296*Ala-0.01678*Val-0.10077*Met+0.02247*Ile-0.07811*Trp | 0.8099 |
| 76 | -1.32055+0.01143*Ala-0.12061*Met+0.04171*His-0.08439*Trp | 0.8095 |
| 77 | -0.49205+0.08148*Asn+0.01338*Pro-0.10382*Met-0.02607*Leu+0.03965*Phe-0.05946*Trp | 0.8095 |
| 78 | 1.68133-0.09229*Asn+0.01117*Pro-0.01844*Val-0.11022*Met+0.02604*Ile-0.06209*Trp | 0.8093 |
| 79 | 1.89672+0.01213*Ala-0.01477*Val+0.03249*Ile-0.02444*Leu-0.07189*Trp | 0.8091 |
| 80 | -1.03885+0.00775*Ala-0.09534*Met-0.03166*Leu+0.04321*Phe+0.01968*His-0.05528*Trp | 0.8083 |
| 81 | 3.54894+0.01295*Ala-0.01606*Val-0.08091*Trp-0.01747*Arg | 0.8073 |
| 82 | -3.02583+0.06434*Asn+0.01593*Glu+0.00626*Ala-0.13622*Met-0.04411*Leu+0.03937*Phe | 0.8051 |
| 83 | 3.21371-0.01355*Ala-0.01383*Val-0.09252*Met-0.07417*Trp | 0.8049 |
| 84 | 1.96557+0.08980*Asn-0.01800*Val-0.14394*Met+0.03186*Ile+0.03514*Tyr-0.07229*Trp | 0.8046 |
| 85 | -0.91398+0.00860*Ser+0.00831*Ala-0.09480*Met-0.02984*Leu+0.04529*Phe-0.05591*Trp | 0.8044 |
| 86 | -2.21653+0.03263*Asn+0.00589*Ala+0.03851*Ile-0.05008*Leu+0.03575*Phe-0.06624*Trp | 0.8042 |
| 87 | 0.30663+0.08334*Asn-0.12647*Met-0.03681*Ile-0.03148*Leu+0.03355*Tyr-0.06034*Trp | 0.8028 |
| 88 | -1.42859+0.03953*Asn+0.00686*Ala-0.02516*Leu-0.05740*Trp | 0.8028 |
| 89 | 1.81509-0.01156*Ala-0.01767*Val-0.01767*Ile-0.08638*Trp | 0.8026 |
| 90 | -0.11981+0.00820*Ala-0.08596*Met-0.02960*Leu+0.04381*Phe-0.05551*Trp | 0.8019 |
| 91 | -0.32031+0.00756*Ala-0.09308*Met+0.04324*Ile-0.04996*Leu+0.04489*Phe-0.05635*Trp | 0.8018 |
| 92 | -0.98986+0.00697*Ala-0.02540*Leu+0.01480*His-0.05515*Trp | 0.8017 |
| 93 | 0.45845+0.00854*Ala-0.00568*Val-0.08358*Met-0.02322*Leu+0.04211*Phe-0.05664*Trp | 0.8007 |
| 94 | -1.69044+0.05898*Asn+0.00726*Ala-0.12672*Met-0.03139*Leu | 0.7997 |
| 95 | -0.46509+0.00678*Ala+0.00819*Val+0.04402*Ile-0.04304*Leu+0.03580*Phe-0.06421*Trp | 0.7996 |
| 96 | -0.43285+0.00490*Pro+0.00748*Ala-0.09197*Met-0.03085*Leu+0.04581*Phe-0.05572*Trp | 0.7995 |
| 97 | 2.37510+0.09551*Asn-0.01429*Val-0.08955*Met+0.04511*Ile-0.01971*Leu-0.05545*Trp | 0.7993 |
| 98 | -0.33267+0.00777*Ala-0.10201*Met-0.03059*Leu+0.01695*Tyr+0.04161*Phe-0.05867*Trp | 0.799 |
| 99 | -0.73085+0.06009*Asn+0.00824*Ala-0.11096*Met-0.02079*Leu-0.05105*Trp | 0.799 |
| 100 | 1.39459+0.00837*Ala-0.00895*Val-0.07971*Met+0.04604*Ile-0.03226*Leu-0.05170*Trp | 0.7987 |

FIG.77

| No | Formula | ROC_AUC |
|---|---|---|
| 101 | 0.34835+0.08444*Asn-0.09929*Met+0.03749*Ile-0.03447*Leu+0.02978*Phe-0.05934*Trp | 0.7969 |
| 102 | -0.46905+0.00814*Ala+0.03435*ABA-0.09244*Met-0.03181*Leu+0.04399*Phe-0.05573*Trp | 0.7968 |
| 103 | -1.29111+0.00631*Ala+0.04047*Ile-0.05064*Leu+0.03828*Phe-0.06347*Trp | 0.7967 |
| 104 | 0.13759+0.01120*Ala+0.02419*Ile-0.03278*Leu-0.06868*Trp | 0.7965 |
| 105 | 0.05363+0.00734*Ala-0.01440*Val+0.01994*Ile-0.07158*Trp | 0.7962 |
| 106 | -0.42367+0.01159*Glu+0.00780*Ala-0.07952*Met-0.03259*Leu+0.04604*Phe-0.05646*Trp | 0.7958 |
| 107 | 1.32413+0.00891*Ala-0.01026*Val-0.08055*Met-0.05863*Trp | 0.7957 |
| 108 | -2.42705+0.05766*Asn+0.00758*Ala-0.13157*Met+0.02305*Phe-0.07357*Trp | 0.7955 |
| 109 | -2.35359+0.05575*Asn+0.00618*Ala-0.14579*Met+0.03957*Ile-0.05912*Leu+0.03574*Phe | 0.7954 |
| 110 | -0.45098+0.00740*Ala-0.01228*Val+0.02367*Phe-0.07350*Trp | 0.7949 |
| 111 | 1.90141+0.08607*Asn-0.01423*Val-0.13694*Met+0.03508*Tyr+0.02368*Phe-0.07411*Trp | 0.7939 |
| 112 | 2.31776+0.08639*Asn-0.01349*Val-0.12629*Met+0.03636*Tyr-0.06482*Trp | 0.7938 |
| 113 | -2.13016+0.03643*Asn+0.00658*Ala-0.03207*Leu+0.03560*Phe-0.06551*Trp | 0.7938 |
| 114 | -1.99198+0.00694*Ala-0.03439*Leu+0.03595*Phe-0.06536*Trp+0.00798*Lys | 0.7935 |
| 115 | -0.17392+0.06065*Asn+0.00868*Ala-0.01064*Val-0.11651*Met-0.06030*Trp | 0.7934 |
| 116 | -1.30729+0.01422*Glu+0.00664*Ala-0.03472*Leu+0.04060*Phe-0.06302*Trp | 0.7929 |
| 117 | 0.77507+0.08669*Asn-0.08800*Met+0.03821*Ile-0.02954*Leu-0.05189*Trp | 0.7926 |
| 118 | 0.07999+0.00890*Ala-0.01204*Val-0.09861*Met+0.02817*Phe-0.06800*Trp+0.01742*Orn | 0.7919 |
| 119 | 0.26903+0.00771*Ala-0.01137*Val-0.06598*Trp | 0.7918 |
| 120 | -1.69920+0.00668*Ala-0.03257*Leu+0.03703*Phe+0.01223*His-0.06284*Trp | 0.7917 |
| 121 | -1.66480+0.05740*Asn+0.00663*Ala-0.13400*Met+0.03962*Ile-0.05072*Leu | 0.7909 |
| 122 | -0.28797+0.00081*Gly+0.00820*Ala-0.08765*Met-0.02938*Leu+0.04401*Phe-0.05564*Trp | 0.7906 |
| 123 | 2.31467+0.09283*Asn-0.01684*Val-0.10061*Met+0.03339*Ile-0.06276*Trp | 0.7889 |
| 124 | 0.75230+0.00849*Ala-0.07557*Met-0.02017*Leu-0.04918*Trp | 0.7888 |
| 125 | -1.55001+0.03678*Asn+0.00617*Ala+0.03861*Ile-0.04323*Leu-0.05816*Trp | 0.7887 |
| 126 | -0.84281+0.00717*Ala-0.01016*Val+0.04726*Ile-0.04028*Leu-0.06272*Trp+0.01128*Lys | 0.7886 |
| 127 | -1.54404+0.01401*Glu+0.00593*Ala+0.04046*Ile-0.05406*Leu+0.04105*Phe-0.06406*Trp | 0.7883 |
| 128 | -1.69102+0.00656*Ala+0.04280*Ile-0.04851*Leu-0.06033*Trp+0.01034*Lys | 0.7883 |
| 129 | -0.02148+0.00896*Ala-0.01540*Val-0.11645*Met+0.02320*Ile-0.07228*Trp+0.01321*Lys | 0.7876 |
| 130 | -2.62543+0.04982*Asn+0.00664*Ala-0.15079*Met+0.04194*Ile-0.05580*Leu+0.01078*Lys | 0.7874 |
| 131 | -1.30102+0.07469*Asn+0.01067*Pro-0.11857*Met+0.02537*Ile-0.04369*Leu+0.01977*Phe | 0.7872 |
| 132 | -0.59355+0.00813*Ala-0.09569*Met-0.03000*Leu+0.04129*Phe-0.05512*Trp+0.00773*Arg | 0.7866 |
| 133 | 0.56396+0.00863*Ala-0.01135*Val-0.08979*Met+0.02927*Phe-0.06657*Trp | 0.7865 |
| 134 | -1.19284+0.00633*Ala+0.04055*Ile-0.05062*Leu+0.03833*Phe-0.06343*Trp-0.00123*Arg | 0.786 |
| 135 | 0.57102+0.00790*Ala-0.08215*Met+0.04237*Ile-0.04001*Leu-0.04982*Trp | 0.7859 |
| 136 | -1.35645+0.00619*Ala+0.04036*Ile-0.05068*Leu+0.00316*Tyr+0.03734*Phe-0.06436*Trp | 0.7857 |
| 137 | -1.30826+0.00017*Ser+0.00631*Ala+0.04045*Ile-0.05064*Leu+0.03829*Phe-0.06348*Trp | 0.7853 |
| 138 | -0.90464+0.00801*Ala-0.11222*Met+0.04617*Ile-0.04682*Leu-0.05541*Trp+0.01533*Lys | 0.7819 |
| 139 | -0.58070+0.00845*Ala-0.09469*Met-0.03023*Leu+0.04251*Phe-0.05656*Trp+0.01528*Orn | 0.7844 |
| 140 | 0.36076+0.07913*Asn-0.12843*Met-0.01994*Leu+0.03300*Tyr+0.02909*Phe-0.06703*Trp | 0.7842 |
| 141 | -0.40390+0.00669*Ala+0.04034*Ile-0.04290*Leu-0.05543*Trp | 0.7838 |
| 142 | -1.35732+0.00633*Ala+0.04010*Ile-0.05051*Leu+0.03797*Phe-0.06355*Trp+0.00173*Orn | 0.7832 |
| 143 | -0.73921+0.00852*Ala+0.02215*Cit-0.09566*Met-0.03000*Leu+0.04130*Phe-0.05122*Trp | 0.7825 |
| 144 | -2.31871+0.00618*Ala+0.04252*Ile-0.05506*Leu+0.03588*Phe-0.06735*Trp+0.00896*Lys | 0.7819 |
| 145 | 0.08652+0.00921*Ala-0.01215*Val-0.10864*Met-0.06602*Trp+0.01357*Lys | 0.7816 |
| 146 | -0.44818+0.00892*Ala-0.01286*Val-0.11368*Met-0.02495*Phe-0.07211*Trp+0.01230*Lys | 0.7814 |
| 147 | 0.47013+0.00720*Ala-0.00929*Val+0.04456*Ile-0.03494*Leu-0.05699*Trp | 0.7811 |
| 148 | -1.05754+0.00703*Ala-0.03142*Leu+0.03790*Phe-0.06218*Trp | 0.7807 |
| 149 | -1.28964+0.00830*Ala-0.11047*Met-0.03309*Leu+0.04113*Phe-0.05928*Trp+0.01279*Lys | 0.7805 |
| 150 | -2.80334+0.03440*Asn+0.00610*Ala-0.07629*Trp | 0.7802 |

FIG.78

| No | Formula | ROC_AUC |
|---|---|---|
| 151 | -1.52117+0.00640*Ala+0.00741*Cit+0.03933*Ile-0.05008*Leu+0.03678*Phe-0.06240*Trp | 0.7798 |
| 152 | -1.68205+0.00697*Ala-0.12512*Met+0.04318*Ile-0.05716*Leu+0.01353*Lys | 0.7795 |
| 153 | -1.13655+0.00620*Ala-0.10846*Met+0.03933*Ile-0.05728*Leu+0.03669*Phe | 0.7794 |
| 154 | -0.64633+0.06001*Asn-0.09783*Met+0.04784*Ile-0.05101*Leu+0.04716*Phe-0.04837*Trp | 0.7788 |
| 155 | -0.17314+0.00738*Ala-0.02372*Leu-0.05438*Trp | 0.7775 |
| 156 | -0.62397+0.07634*Asn-0.13189*Met+0.03347*Ile-0.04127*Leu+0.02307*Tyr | 0.7751 |
| 157 | -0.84671-0.00488*Thr+0.00658*Ala+0.04124*Ile-0.05092*Leu+0.03774*Phe-0.06306*Trp | 0.7738 |
| 158 | -0.17539+0.00801*Ala-0.09041*Met-0.06435*Trp | 0.7736 |
| 159 | 0.25523+0.07609*Asn-0.13076*Met+0.03169*Tyr-0.06870*Trp | 0.7723 |
| 160 | -1.34636+0.00729*Ala-0.02755*Leu-0.05850*Trp+0.00930*Lys | 0.7697 |
| 161 | -0.07262+0.07301*Asn+0.03507*Ile-0.03355*Leu-0.05655*Trp | 0.7676 |
| 162 | 1.19303+0.08567*Asn-0.01313*Val-0.10775*Met+0.04160*Ile-0.02977*Leu | 0.7669 |
| 163 | -0.16116+0.07962*Asn-0.10583*Met+0.03443*Ile-0.03848*Leu | 0.7661 |
| 164 | -0.43475+0.07788*Asn-0.11076*Met+0.03404*Ile-0.04137*Leu+0.01335*Phe | 0.7654 |
| 165 | -0.18996+0.00752*Ala-0.09082*Met-0.03049*Leu | 0.7645 |
| 166 | -0.25621+0.00693*Ala-0.09760*Met+0.04076*Ile-0.05066*Leu | 0.7637 |
| 167 | -0.69697+0.05406*Asn-0.10413*Met+0.05067*Ile-0.04556*Leu-0.04507*Trp+0.01195*Lys | 0.7636 |
| 168 | -1.15444+0.04907*Ile-0.05590*Leu+0.04005*Phe-0.05661*Trp+0.00952*Lys | 0.7623 |
| 169 | -0.12610+0.05934*Asn-0.08645*Met-0.05222*Trp | 0.7604 |
| 170 | -1.816+0.015*Glu+0.009*Ala+0.0268ABA-0.040*Leu | 0.7601 |
| 171 | -0.97896+0.00736*Ala-0.00858*Val-0.12455*Met+0.04685*Ile-0.05036*Leu+0.01408*Lys | 0.7586 |
| 172 | -1.48020+0.05352*Asn-0.11907*Met+0.04789*Ile-0.05129*Leu+0.01052*Lys | 0.755 |
| 173 | -0.54652+0.05995*Asn-0.10042*Met+0.04542*Ile-0.04935*Leu | 0.7529 |
| 174 | -1.66934+0.01183*Glu+0.00577*Ala-0.03818*Leu | 0.7478 |
| 175 | -2.27862+0.00649*Ala-0.13472*Met+0.04290*Ile-0.06425*Leu+0.03413*Phe+0.01232*Lys | 0.7445 |
| 176 | -0.84091+0.05439*Asn-0.00688*Val-0.11653*Met+0.05119*Ile-0.04895*Leu+0.01068*Lys | 0.7436 |
| 177 | -1.65013+0.00543*Ala+0.03761*Ile-0.05490*Leu | 0.742 |
| 178 | -0.40623+0.06098*Asn-0.08933*Met-0.02645*Leu | 0.739 |
| 179 | 1.22345+0.03488*Ile-0.03201*Leu+0.02412*Tyr-0.05470*Trp | 0.7262 |
| 180 | 2.09282+0.01218*Ala-0.01537*Val-0.08313*Trp | 0.7206 |
| 181 | -1.65715+0.03964*Asn+0.04143*Ile-0.05354*Leu | 0.7201 |
| 182 | -2.30810+0.00566*Ala-0.04189*Leu+0.02646*Phe | 0.7185 |
| 183 | 1.52485+0.03687*Ile-0.03407*Leu+0.02408*Phe-0.05356*Trp | 0.7161 |
| 184 | -0.07931+0.04728*Ile-0.05096*Leu+0.04241*Phe-0.05205*Trp | 0.7161 |
| 185 | -0.46175-0.08743*Met+0.05304*Ile-0.05688*Leu+0.04656*Phe-0.05018*Trp+0.01339*Lys | 0.7146 |
| 186 | -2.16368+0.04893*Asn+0.00946*Ala-0.09388*Trp | 0.7135 |
| 187 | 0.77015+0.07956*Asn-0.09116*Met-0.05810*Trp | 0.7126 |
| 188 | 0.49262+0.01187*Ala-0.02286*Leu-0.06983*Trp | 0.7111 |
| 189 | -0.31347+0.04939*Ile-0.04807*Leu-0.04879*Trp+0.01093*Lys | 0.7106 |
| 190 | 1.03116+0.04694*Ile-0.04182*Leu-0.04327*Trp | 0.7059 |
| 191 | -3.91603+0.00903*Ala-0.04388*Leu+0.04725*His | 0.6954 |
| 192 | 0.63524+0.01079*Ala-0.08580*Trp-0.01530*Arg | 0.6932 |
| 193 | 3.28213-0.01394*Val+0.02947*Ile-0.06039*Trp | 0.6891 |
| 194 | -1.35911+0.00980*Thr+0.00953*Ala-0.08846*Trp | 0.6889 |
| 195 | 1.08615+0.01217*Ala-0.10740*Met-0.07788*Trp | 0.6859 |
| 196 | 0.40968+0.03558*Ile-0.04364*Leu+0.01086*Phe | 0.6828 |
| 197 | -1.45112+0.04466*Ile-0.05731*Leu+0.00894*Lys | 0.6817 |
| 198 | -1.25902+0.04259*Ile-0.05926*Leu+0.03168*Phe | 0.6815 |
| 199 | 0.38186-0.02776*Leu+0.04105*Phe-0.04834*Trp | 0.677 |
| 200 | 0.25989+0.07892*Asn-0.10069*Met-0.02222*Leu | 0.6626 |

FIG. 80

| No | Formula | ROC_AUC |
|---|---|---|
| 1 | 2.48506+0.07557*Asn+0.01311*Ala-0.01544*Val-0.16644*Met+0.02693*Tyr-0.08447*Trp | 0.8515 |
| 2 | 2.09620+0.08472*Asn+0.01899*Glu+0.01298*Ala-0.01536*Val-0.13906*Met-0.07803*Trp | 0.8497 |
| 3 | 2.22930+0.08103*Asn+0.01112*Pro+0.01232*Ala-0.01606*Val-0.15674*Met-0.07703*Trp | 0.8488 |
| 4 | 2.37381+0.05222*Asn+0.01030*Ala-0.01105*Val-0.14443*Met+0.02219*Tyr-0.06449*Trp | 0.8485 |
| 5 | 3.65348+0.08939*Asn+0.01403*Ala-0.01468*Val-0.11965*Met-0.07753*Trp-0.02062*Arg | 0.8482 |
| 6 | 1.30829+0.06509*Asn+0.01297*Ala-0.01496*Val-0.15024*Met+0.03694*His-0.08226*Trp | 0.8468 |
| 7 | -0.41039+0.05776*Asn+0.01311*Ala-0.14105*Met-0.02234*Leu+0.04021*His-0.07262*Trp | 0.8435 |
| 8 | 3.20681+0.08162*Asn+0.01359*Ala-0.01938*Cit-0.01366*Val-0.13298*Met-0.08218*Trp | 0.8433 |
| 9 | 2.61566+0.07753*Asn+0.01313*Ala-0.01629*Val-0.14632*Met+0.01848*Ile-0.08270*Trp | 0.8429 |
| 10 | 2.15399+0.08057*Asn+0.01339*Ala-0.01385*Val-0.15277*Met+0.02280*Phe-0.08818*Trp | 0.8424 |
| 11 | 3.48862+0.08129*Asn-0.00417*Gly+0.01361*Ala-0.01409*Val-0.13707*Met-0.07882*Trp | 0.8417 |
| 12 | 0.41580+0.07860*Asn+0.01920*Glu+0.01309*Ala-0.13024*Met-0.02142*Leu-0.06877*Trp | 0.8413 |
| 13 | 1.68702+0.05657*Asn+0.01069*Ala-0.01014*Val-0.14554*Met+0.03702*Phe-0.07382*Trp | 0.8413 |
| 14 | 2.31801+0.00866*Thr+0.07206*Asn+0.01318*Ala-0.01352*Val-0.14551*Met-0.07971*Trp | 0.8407 |
| 15 | 2.90166+0.08027*Asn+0.01350*Ala-0.01319*Val-0.13358*Met-0.08074*Trp-0.00779*Orn | 0.8407 |
| 16 | 2.49960+0.05441*Asn+0.01063*Ala-0.01259*Val-0.13065*Met+0.01845*Ile-0.06490*Trp | 0.8406 |
| 17 | 1.46679+0.01273*Ala-0.01654*Val-0.14220*Met+0.03004*Tyr+0.04830*His-0.08349*Trp | 0.8405 |
| 18 | 2.18075+0.05794*Asn+0.01193*Ala-0.01839*Val+0.03429*His-0.08446*Trp-0.03156*Arg | 0.8405 |
| 19 | 2.66634+0.07809*Asn+0.01381*Ala-0.01235*Val-0.13413*Met-0.00518*Leu-0.07719*Trp | 0.8402 |
| 20 | 3.07845+0.08035*Asn-0.00104*Gln+0.01364*Ala-0.01331*Val-0.13808*Met-0.07911*Trp | 0.8400 |
| 21 | 0.99781+0.06389*Asn+0.02004*Glu+0.01035*Ala-0.10869*Met-0.02376*Leu-0.05247*Trp | 0.8399 |
| 22 | 0.44122+0.07581*Asn+0.01355*Ala-0.14875*Met-0.02287*Leu+0.03580*Phe-0.08247*Trp | 0.8399 |
| 23 | -0.38166+0.01314*Ala-0.10710*Met+0.02563*Ile-0.03549*Leu+0.05299*His-0.06633*Trp | 0.8398 |
| 24 | 0.91249+0.01571*Thr+0.01243*Ala-0.01453*Val-0.12975*Met+0.04824*His-0.07866*Trp | 0.8394 |
| 25 | 0.54510+0.01190*Ala-0.01373*Val+0.02963*Ile-0.03103*Leu+0.04692*His-0.07374*Trp | 0.8392 |
| 26 | 2.82592+0.07954*Asn+0.01366*Ala-0.01345*Val-0.13743*Met-0.07922*Trp-0.00152*Lys | 0.8392 |
| 27 | 2.79890+0.07424*Asn+0.01530*Glu+0.01200*Ala-0.01819*Val-0.08102*Trp-0.02689*Arg | 0.8388 |
| 28 | 2.19674+0.07471*Asn+0.01351*Ala+0.03665*ABA-0.01530*Val-0.14151*Met-0.07915*Trp | 0.8388 |
| 29 | 1.45580+0.01378*Ala-0.01117*Val-0.09940*Met-0.01500*Leu+0.05339*His-0.07075*Trp | 0.8384 |
| 30 | 2.70790-0.00058*Ser+0.07933*Asn+0.01362*Ala-0.01352*Val-0.13895*Met-0.08004*Trp | 0.8376 |
| 31 | 0.77479+0.05550*Asn+0.01093*Ala-0.13701*Met-0.02751*Leu+0.05330*Phe-0.06628*Trp | 0.8375 |
| 32 | 0.80131+0.07031*Asn+0.01319*Ala-0.15511*Met-0.01842*Leu+0.02139*Tyr-0.07600*Trp | 0.8370 |
| 33 | 0.86543+0.07074*Asn+0.01331*Ala-0.13569*Met+0.01983*Ile-0.02444*Leu-0.07212*Trp | 0.8367 |
| 34 | 2.23564+0.05247*Asn+0.01101*Ala-0.01042*Val-0.12951*Met-0.06046*Trp+0.01301*Orn | 0.8339 |
| 35 | 1.42107+0.05173*Asn+0.01070*Ala-0.11723*Met+0.03185*Ile-0.03213*Leu-0.05389*Trp | 0.8331 |
| 36 | 1.77308+0.04811*Asn+0.01197*Ala-0.01405*Val+0.02519*Ile-0.02238*Leu-0.07819*Trp | 0.8287 |
| 37 | 1.77249+0.05135*Asn+0.01058*Ala-0.01093*Val-0.13484*Met-0.06544*Trp+0.00959*Lys | 0.8265 |
| 38 | 3.39438+0.01312*Ala-0.01772*Val-0.12621*Met+0.02128*Ile+0.03221*Tyr-0.08273*Trp | 0.8242 |
| 39 | 0.57018+0.07427*Asn+0.01269*Ala-0.15311*Met-0.08294*Trp | 0.8224 |
| 40 | 1.06470+0.01093*Ala-0.10503*Met-0.02988*Leu+0.05090*Phe+0.02066*His-0.06473*Trp | 0.8218 |
| 41 | -0.70322+0.01209*Ala-0.03040*Leu+0.04463*His-0.07147*Trp | 0.8215 |
| 42 | 0.95983+0.05570*Asn+0.01035*Ala-0.13153*Met-0.06675*Trp | 0.8211 |
| 43 | 3.56547+0.01421*Ala-0.01254*Val-0.07929*Met+0.03023*Ile-0.01836*Leu-0.06873*Trp | 0.8205 |
| 44 | 3.18683+0.01359*Ala-0.01457*Val-0.12237*Met+0.03021*Tyr+0.01446*Phe-0.08425*Trp | 0.8203 |
| 45 | 0.74800+0.04941*Asn+0.01063*Ala-0.12456*Met-0.02220*Leu-0.05725*Trp+0.01127*Lys | 0.8189 |
| 46 | 1.44005+0.01401*Ala-0.09317*Met+0.02416*Ile-0.03290*Leu+0.03162*Phe-0.07345*Trp | 0.8185 |
| 47 | 1.84556+0.05047*Asn+0.01161*Ala-0.01561*Val-0.08707*Trp | 0.8182 |
| 48 | 1.39953+0.01387*Ala-0.11567*Met-0.02513*Leu+0.02521*Tyr+0.02981*Phe-0.07766*Trp | 0.8177 |
| 49 | 1.46220+0.00772*Pro+0.01049*Ala-0.10563*Met-0.03072*Leu+0.05490*Phe-0.06320*Trp | 0.8176 |
| 50 | 1.03806+0.01153*Ala-0.01620*Val+0.03925*His-0.08555*Trp | 0.8176 |

FIG. 81

| No | Formula | ROC_AUC |
|---|---|---|
| 51 | 3.39804+0.01371*Ala−0.01515*Val−0.09660*Met+0.01861*Ile+0.01331*Phe−0.08137*Trp | 0.8175 |
| 52 | 0.73414+0.06543*Asn+0.01107*Ala−0.01227*Val−0.14216*Met+0.02847*Ile−0.02875*Leu | 0.8174 |
| 53 | 2.31149+0.01288*Ala−0.01221*Val+0.02798*Ile−0.02695*Leu+0.01782*Phe−0.07652*Trp | 0.8167 |
| 54 | 2.41765+0.01235*Ala−0.01416*Val+0.02923*Ile−0.02515*Leu+0.01802*Tyr−0.07550*Trp | 0.8164 |
| 55 | 1.49158+0.01119*Met−0.10079*Met+0.03652*Ile−0.04476*Leu+0.05498*Phe−0.06522*Trp | 0.8163 |
| 56 | −0.47532+0.03680*Asn+0.02582*Glu+0.00864*Ala−0.04090*Leu+0.04901*Phe−0.06863*Trp | 0.8139 |
| 57 | 2.66073+0.01063*Ala−0.01126*Val−0.12264*Met+0.02171*Tyr+0.03282*Phe−0.07522*Trp | 0.8134 |
| 58 | 1.65614+0.00964*Ala−0.00705*Val+0.03591*Ile−0.04123*Leu+0.04187*Phe−0.06825*Trp | 0.8127 |
| 59 | 3.21747+0.08557*Asn+0.01457*Pro−0.01597*Val−0.14851*Met+0.02538*Tyr−0.05810*Trp | 0.8126 |
| 60 | 2.52632+0.01150*Ala−0.00467*Val−0.09123*Met−0.02318*Leu+0.05046*Phe−0.06491*Trp | 0.8126 |
| 61 | 3.35382+0.08762*Asn+0.01464*Pro−0.01644*Val−0.12852*Met+0.01522*Ile−0.05594*Trp | 0.8121 |
| 62 | 1.42442+0.00537*Ser+0.01135*Ala−0.09843*Met−0.02801*Leu+0.05396*Phe−0.06496*Trp | 0.8115 |
| 63 | 1.60854+0.01087*Ala−0.11390*Met−0.02940*Leu+0.02087*Tyr+0.05033*Phe−0.06730*Trp | 0.8110 |
| 64 | 1.35333+0.01870*Glu+0.01100*Ala−0.08345*Met−0.03441*Leu+0.05743*Phe−0.06435*Trp | 0.8109 |
| 65 | −0.31651+0.01243*Ala−0.12411*Met+0.04289*His−0.08119*Trp | 0.8107 |
| 66 | 0.21178+0.02027*Asn+0.00904*Ala+0.03138*Ile−0.04671*Leu+0.04382*Phe−0.06978*Trp | 0.8107 |
| 67 | 2.50146+0.09170*Asn+0.01717*Pro−0.01526*Val−0.14779*Met+0.03372*Phe−0.06561*Trp | 0.8103 |
| 68 | 1.29468+0.02836*Asn+0.00943*Ala−0.02326*Leu−0.05943*Trp | 0.8092 |
| 69 | 2.67808+0.07875*Asn+0.01361*Ala−0.01354*Val−0.13891*Met−0.07998*Trp | 0.8090 |
| 70 | 0.33195+0.04659*Asn+0.01205*Ala−0.02428*Leu−0.07554*Trp | 0.8090 |
| 71 | 0.62968+0.08660*Asn+0.01732*Pro−0.14287*Met−0.02549*Leu+0.04837*Phe−0.05889*Trp | 0.8087 |
| 72 | 1.80035+0.00168*Thr+0.01131*Ala−0.09541*Met−0.02786*Leu+0.05337*Phe−0.06540*Trp | 0.8080 |
| 73 | 1.56334+0.01134*Ala+0.02213*ABA−0.09523*Met−0.02877*Leu+0.05203*Phe−0.06412*Trp | 0.8078 |
| 74 | 3.95797+0.01353*Ala−0.01423*Val−0.07623*Trp−0.01510*Arg | 0.8071 |
| 75 | 3.39041+0.07109*Asn+0.01259*Ala−0.01682*Val−0.08220*Trp−0.02920*Arg | 0.8069 |

FIG. 81 (Continued)

| No | Formula | ROC_AUC |
|---|---|---|
| 76 | 1.11371+0.07344*Asn+0.01357*Ala-0.13428*Met-0.01617*Leu-0.07342*Trp | 0.8062 |
| 77 | 3.76913+0.01432*Ala-0.01220*Val-0.08094*Met-0.07383*Trp | 0.8060 |
| 78 | 0.03507+0.01354*Ala-0.10219*Met-0.02472*Leu+0.05216*His-0.06769*Trp | 0.8059 |
| 79 | 1.89911+0.01139*Ala-0.09251*Met-0.02785*Leu+0.05291*Phe-0.06526*Trp | 0.8054 |
| 80 | 1.67752+0.00052*Gln+0.01136*Ala-0.09380*Met-0.02807*Leu+0.05304*Phe-0.06549*Trp | 0.8043 |
| 81 | 1.63501+0.00128*Gly+0.01140*Ala-0.09481*Met-0.02744*Leu+0.05312*Phe-0.06571*Trp | 0.8043 |
| 82 | 1.69418+0.01331*Ala-0.01440*Val-0.10940*Met+0.04917*His-0.07829*Trp | 0.8039 |
| 83 | 2.12133+0.00936*Ala-0.01143*Val+0.02442*Phe-0.07775*Trp | 0.8035 |
| 84 | 2.79067+0.01223*Ala-0.01644*Val+0.01558*Ile-0.08312*Trp | 0.8032 |
| 85 | 1.61059+0.01120*Ala-0.10155*Met-0.02762*Leu+0.05233*Phe-0.06597*Trp+0.00680*Arg | 0.8032 |
| 86 | 0.50062+0.05028*Asn+0.00881*Ala-0.15094*Met+0.03426*Ile-0.05215*Leu+0.04120*Phe | 0.8030 |
| 87 | -0.76161+0.06245*Asn+0.01208*Ala-0.16385*Met+0.03093*His-0.08511*Trp | 0.8029 |
| 88 | 0.79895+0.01238*Ala-0.01164*Val-0.02011*Leu+0.04612*His-0.07455*Trp | 0.8027 |
| 89 | 0.26788+0.07192*Asn+0.01230*Ala-0.17139*Met+0.01668*Tyr-0.08598*Trp | 0.8024 |
| 90 | 0.21126+0.02100*Glu+0.00922*Ala+0.03213*Ile-0.05355*Leu+0.05129*Phe 0.06744*Trp | 0.8024 |
| 91 | 1.18937+0.08223*Asn+0.01296*Ala-0.13910*Met-0.08123*Trp-0.01600*Arg | 0.8022 |
| 92 | 0.64682+0.05346*Asn+0.00919*Ala-0.12637*Met-0.02746*Leu | 0.8021 |
| 93 | -1.10727+0.01167*Ala+0.02290*Ile-0.04026*Leu+0.04504*His-0.07042*Trp | 0.8018 |
| 94 | 3.72852+0.08001*Asn-0.01731*Val-0.14408*Met+0.02748*Ile+0.03582*Tyr-0.06620*Trp | 0.8009 |
| 95 | 2.41914+0.01135*Ala-0.01078*Val-0.11076*Met+0.03427*Phe-0.07167*Trp+0.01542*Orn | 0.8007 |
| 96 | 0.73280+0.00948*Ala+0.03289*Ile-0.04692*Leu+0.04528*Phe-0.06883*Trp | 0.8004 |
| 97 | 0.06410+0.07579*Asn+0.01248*Ala-0.16567*Met+0.02018*Phe-0.09026*Trp | 0.8002 |
| 98 | 1.91768+0.07429*Asn-0.12962*Met+0.02611*Ile-0.02131*Leu+0.02999*Tyr-0.05580*Trp | 0.8002 |
| 99 | 0.74071+0.01109*Ala-0.10970*Met-0.03273*Leu+0.05221*Phe-0.06843*Trp+0.01262*Lys | 0.7995 |
| 100 | 1.48231+0.01154*Ala-0.10145*Met-0.02835*Leu+0.05137*Phe-0.06425*Trp+0.01305*Orn | 0.7992 |

FIG. 82

| No | Formula | ROC_AUC |
|---|---|---|
| 101 | 1.13139+0.01078*Ala−0.09605*Met+0.03653*Ile−0.04012*Leu−0.05660*Trp+0.01385*Lys | 0.7990 |
| 102 | 2.78769+0.01132*Ala−0.06949*Met−0.01809*Leu−0.05345*Trp | 0.7989 |
| 103 | 1.64170+0.00941*Ala−0.00930*Val+0.03709*Ile−0.03620*Leu−0.06171*Trp+0.01098*Lys | 0.7988 |
| 104 | 2.93003+0.01277*Ala−0.01395*Val−0.08020*Trp | 0.7984 |
| 105 | 2.83424+0.00973*Ala−0.01100*Val−0.06784*Trp | 0.7984 |
| 106 | 0.07744+0.05640*Asn+0.01021*Ala−0.15431*Met+0.03594*Phe−0.07941*Trp | 0.7984 |
| 107 | 1.68214+0.05490*Asn+0.01086*Ala−0.11333*Met−0.01769*Leu−0.05438*Trp | 0.7982 |
| 108 | 1.70517+0.00977*Ala+0.03168*Ile−0.03686*Leu−0.05755*Trp | 0.7977 |
| 109 | 0.61523+0.02150*Glu+0.00952*Ala−0.03855*Leu+0.05031*Phe−0.06717*Trp | 0.7971 |
| 110 | 3.59199+0.05584*Asn−0.01296*Val−0.12494*Met+0.02116*Ile+0.02985*Tyr−0.05311*Trp | 0.7971 |
| 111 | 0.35742+0.08314*Asn+0.01186*Pro−0.16701*Met+0.01360*Tyr+0.02710*Phe−0.07136*Trp | 0.7970 |
| 112 | 1.47515+0.01143*Ala+0.01848*Cit−0.10132*Met−0.02750*Leu+0.05131*Phe−0.06321*Trp | 0.7970 |
| 113 | 2.47825+0.05313*Asn−0.11140*Met+0.03453*Ile−0.03254*Leu+0.03006*Tyr−0.04194*Trp | 0.7967 |
| 114 | 1.98071+0.01087*Ala−0.01123*Val−0.11545*Met+0.03351*Phe−0.07670*Trp+0.01004*Lys | 0.7960 |
| 115 | 0.50794+0.02443*Asn+0.00925*Ala−0.03201*Leu+0.04243*Phe−0.06975*Trp | 0.7955 |
| 116 | 2.60556+0.01075*Ala−0.01382*Val−0.10569*Met+0.01862*Ile−0.06940*Trp+0.01076*Lys | 0.7955 |
| 117 | 0.21536+0.00935*Ala−0.03544*Leu+0.04242*Phe−0.07135*Trp+0.00920*Lys | 0.7954 |
| 118 | 1.76165+0.08160*Asn−0.11337*Met+0.02485*Ile−0.02400*Leu+0.03597*Phe−0.06054*Trp | 0.7951 |
| 119 | 1.44449+0.06402*Asn+0.01209*Pro−0.12615*Met−0.02829*Leu+0.05578*Phe−0.04813*Trp | 0.7947 |
| 120 | 2.54676+0.05584*Asn+0.01082*Ala−0.00983*Val−0.12236*Met−0.06096*Trp | 0.7947 |
| 121 | 4.05545+0.08350*Asn−0.01332*Val−0.09858*Met+0.03126*Ile−0.00795*Leu−0.05480*Trp | 0.7941 |
| 122 | 3.33798+0.08446*Asn−0.01322*Val−0.14312*Met+0.03282*Tyr+0.02459*Phe−0.06948*Trp | 0.7933 |
| 123 | 0.66311+0.00943*Ala−0.03274*Leu+0.04242*Phe+0.01097*His−0.06855*Trp | 0.7933 |
| 124 | 1.51089+0.01312*Ala−0.02229*Leu−0.07001*Trp | 0.7923 |
| 125 | 0.79846+0.00514*Pro+0.00903*Ala−0.03365*Leu+0.04462*Phe−0.06754*Trp | 0.7923 |

FIG. 82 (Continued)

| No | Formula | ROC_AUC |
|---|---|---|
| 126 | 1.15938+0.00979*Ala-0.03140*Leu+0.04412*Phe-0.06859*Trp | 0.7922 |
| 127 | -0.28274+0.00900*Ala+0.03399*Ile-0.05173*Leu+0.04352*Phe-0.07176*Trp+0.00975*Lys | 0.7910 |
| 128 | 2.09242+0.01007*Ala-0.02215*Leu-0.05760*Trp | 0.7906 |
| 129 | 2.81812+0.01116*Ala-0.01010*Val-0.10044*Met+0.03639*Phe-0.07296*Trp | 0.7906 |
| 130 | 3.49248+0.01370*Ala-0.01448*Val-0.11579*Met+0.03144*Tyr-0.07936*Trp | 0.7893 |
| 131 | 1.80259+0.01345*Ala-0.09679*Met-0.07683*Trp | 0.7885 |
| 132 | -0.56952+0.02392*Glu+0.00897*Ala-0.04416*Leu+0.04898*Phe-0.07030*Trp+0.01095*Lys | 0.7878 |
| 133 | 3.54221+0.08662*Asn-0.01440*Val-0.11776*Met+0.02366*Ile+0.02257*Phe-0.06672*Trp | 0.7877 |
| 134 | -1.36281+0.01025*Ala+0.03054*His-0.08998*Trp | 0.7868 |
| 135 | -0.61774+0.07561*Asn+0.01668*Pro-0.14627*Met+0.01391*Ile-0.03803*Leu+0.03191*Phe | 0.7866 |
| 136 | 2.78291+0.00995*Ala-0.00893*Val+0.03563*Ile-0.03061*Leu-0.05790*Trp | 0.7861 |
| 137 | 1.21156+0.01067*Ala-0.10931*Met+0.03533*Phe-0.07853*Trp | 0.7861 |
| 138 | 2.06510+0.01080*Ala-0.08746*Met-0.06609*Trp | 0.7857 |
| 139 | 3.68159+0.01378*Ala-0.01526*Val-0.09010*Met+0.02041*Ile-0.07693*Trp | 0.7848 |
| 140 | -0.72292+0.04184*Asn+0.01029*Ala-0.09138*Trp | 0.7838 |
| 141 | -2.41068+0.00956*Ala-0.04209*Leu+0.04302*His | 0.7835 |
| 142 | 1.02141+0.00958*Ala-0.02695*Leu-0.06108*Trp+0.01005*Lys | 0.7812 |
| 143 | 0.20791+0.02356*Asn+0.00840*Ala-0.07769*Trp | 0.7801 |
| 144 | 2.77926+0.01299*Ala-0.01289*Val+0.02847*Ile-0.02276*Leu-0.07203*Trp | 0.7793 |
| 145 | 1.32189+0.01206*Ala-0.08165*Trp-0.01386*Arg | 0.7765 |
| 146 | 2.02836+0.05918*Asn-0.10478*Met+0.03605*Ile-0.04004*Leu+0.05457*Phe-0.04922*Trp | 0.7765 |
| 147 | 1.94720+0.07887*Asn-0.13602*Met+0.02600*Tyr-0.06318*Trp | 0.7757 |
| 148 | -0.25086+0.00922*Thr+0.01059*Ala-0.08656*Trp | 0.7749 |
| 149 | 3.90881+0.08233*Asn-0.01301*Val-0.12989*Met+0.03516*Tyr-0.06065*Trp | 0.7706 |
| 150 | 2.78716+0.05257*Asn-0.01099*Val-0.12881*Met+0.02926*Tyr-0.05353*Trp+0.01064*Lys | 0.7686 |

FIG. 83

| No | Formula | ROC_AUC |
|---|---|---|
| 151 | 1.74093+0.00967*Ala-0.08345*Met-0.02769*Leu | 0.7685 |
| 152 | 1.79984+0.08478*Asn-0.12288*Met+0.02668*Phe-0.06746*Trp | 0.7673 |
| 153 | 2.51230+0.08296*Asn-0.10521*Met-0.05720*Trp | 0.7669 |
| 154 | 2.12827+0.05807*Asn-0.11984*Met+0.02488*Tyr-0.05362*Trp | 0.7664 |
| 155 | 0.21057+0.00862*Ala+0.02198*Phe-0.08461*Trp | 0.7658 |
| 156 | 4.06625+0.08469*Asn-0.01454*Val-0.10483*Met+0.02685*Ile-0.05880*Trp | 0.7654 |
| 157 | 1.26162+0.03766*Ile-0.04937*Leu+0.04613*Phe-0.05594*Trp+0.01225*Lys | 0.7635 |
| 158 | 2.96640+0.05875*Asn-0.08049*Met+0.03379*Ile-0.02898*Leu-0.03716*Trp | 0.7631 |
| 159 | 1.05599+0.05674*Asn-0.11700*Met+0.03588*Ile-0.04737*Leu+0.04373*Phe | 0.7629 |
| 160 | 1.08592+0.07157*Asn-0.10801*Met+0.02647*Ile-0.02747*Leu | 0.7624 |
| 161 | 2.64843+0.06258*Asn-0.09130*Met-0.04765*Trp | 0.7623 |
| 162 | 1.64193+0.03378*Asn+0.03370*Ile-0.04304*Leu+0.04588*Phe-0.05408*Trp | 0.7621 |
| 163 | 2.04677+0.05688*Asn-0.09401*Met+0.03401*Ile-0.03654*Leu | 0.7602 |
| 164 | 3.27337-0.05603*Met+0.03887*Ile-0.04151*Leu+0.05427*Phe-0.04736*Trp | 0.7594 |
| 165 | -1.00911+0.02155*Glu+0.01032*Ala+0.02181*ABA-0.03921*Leu | 0.7578 |
| 166 | 1.78729+0.05174*Asn-0.09520*Met+0.03629*Ile-0.03561*Leu-0.04100*Trp+0.01348*Lys | 0.7576 |
| 167 | 0.48417+0.01920*Glu+0.00788*Ala-0.03825*Leu | 0.7549 |
| 168 | 0.40670+0.00770*Ala+0.03174*Ile-0.04828*Leu | 0.7536 |
| 169 | 0.56780+0.06702*Asn-0.13381*Met+0.02746*Ile-0.03142*Leu+0.02447*Tyr | 0.7536 |
| 170 | 1.38262+0.08081*Asn-0.14851*Met+0.02367*Tyr+0.02304*Phe-0.07150*Trp | 0.7534 |
| 171 | 0.90049+0.05040*Asn-0.10850*Met+0.03628*Ile-0.04322*Leu+0.01213*Lys | 0.7523 |
| 172 | 3.03755+0.05707*Asn-0.00801*Val-0.09387*Met+0.03759*Ile-0.03088*Leu | 0.7488 |
| 173 | 3.21521-0.00849*Val+0.04049*Ile-0.03370*Leu-0.04445*Trp+0.01361*Lys | 0.7462 |
| 174 | 2.46829+0.07499*Asn-0.01204*Val-0.10836*Met+0.03220*Ile-0.01959*Leu | 0.7453 |
| 175 | 0.58982+0.07213*Asn-0.11679*Met+0.02652*Ile-0.03206*Leu+0.01949*Phe | 0.7443 |

FIG. 83 (Continued)

| No | Formula | ROC_AUC |
|---|---|---|
| 176 | 1.43006−0.07525*Asn−0.10534*Met−0.01641*Leu | 0.7401 |
| 177 | 2.34325−0.06037*Asn−0.08938*Met−0.02111*Leu | 0.7401 |
| 178 | 2.72774−0.09007*Met+0.03920*Ile−0.04420*Leu+0.03016*Tyr+0.05062*Phe−0.05152*Trp | 0.7398 |
| 179 | 1.91148+0.05040*Asn−0.00846*Val−0.10881*Met+0.04014*Ile−0.03744*Leu+0.01252*Lys | 0.7345 |
| 180 | 2.69128−0.00945*Val+0.04010*Ile−0.03618*Leu+0.02202*Tyr−0.04998*Trp+0.01237*Lys | 0.7344 |
| 181 | 4.09229−0.01661*Val+0.02476*Ile+0.02644*Tyr−0.06476*Trp | 0.7311 |
| 182 | 2.06990−0.09369*Met+0.03951*Ile−0.04137*Leu+0.03288*Tyr−0.04527*Trp+0.01490*Lys | 0.7258 |
| 183 | 2.47473+0.02875*Ile−0.02735*Leu+0.02422*Tyr−0.05131*Trp | 0.7241 |
| 184 | 1.37475+0.03236*Asn+0.03215*Ile−0.04241*Leu | 0.7213 |
| 185 | −0.01201+0.05055*Asn−0.13020*Met+0.03800*Ile−0.05345*Leu+0.04249*Phe+0.01160*Lys | 0.7172 |
| 186 | 4.79398−0.01399*Val+0.02658*Ile−0.05559*Trp | 0.7171 |
| 187 | 2.72693+0.02872*Ile−0.02806*Leu+0.02716*Phe−0.05276*Trp | 0.7163 |
| 188 | 2.10978−0.00655*Val+0.04056*Ile−0.04420*Leu+0.04294*Phe−0.05526*Trp+0.01261*Lys | 0.7109 |
| 189 | 3.76811+0.03531*Ile−0.03216*Leu−0.03842*Trp | 0.7107 |
| 190 | 2.65812+0.03649*Ile−0.04310*Leu+0.04855*Phe−0.05114*Trp | 0.7099 |
| 191 | 1.80082−0.07864*Met+0.04127*Ile−0.04860*Leu+0.05360*Phe−0.05174*Trp+0.01509*Lys | 0.7079 |
| 192 | 3.33185+0.02905*Ile−0.02229*Leu−0.04540*Trp | 0.7075 |
| 193 | 2.19976+0.03663*Ile−0.03952*Leu−0.04429*Trp+0.01323*Lys | 0.7046 |
| 194 | 3.12748−0.01082*Val+0.03487*Ile−0.02512*Leu | 0.6843 |
| 195 | 1.41186+0.02935*Ile−0.03561*Leu+0.01196*Phe | 0.6840 |
| 196 | 3.28657−0.01542*Leu+0.02778*Phe−0.05334*Trp | 0.6830 |
| 197 | 2.05018−0.00841*Val+0.03966*Ile−0.04265*Leu+0.01143*Lys | 0.6768 |
| 198 | 3.20423−0.02568*Leu+0.04738*Phe−0.05022*Trp | 0.6765 |
| 199 | 1.40585+0.03555*Ile−0.05125*Leu+0.03552*Phe | 0.6757 |
| 200 | 1.79952−0.06951*Met+0.03899*Ile−0.04521*Leu+0.01398*Lys | 0.6709 |

| ROC_AUC | 0.8 | | 0.75 | | 0.7 | |
|---|---|---|---|---|---|---|
| RANK | AMINO ACID | FREQUENCY OF APPEARANCE | AMINO ACID | FREQUENCY OF APPEARANCE | AMINO ACID | FREQUENCY OF APPEARANCE |
| 1 | Ala | 2187 | Ala | 9466 | Trp | 14341 |
| 2 | Trp | 1841 | Trp | 8581 | Leu | 13728 |
| 3 | Val | 1082 | Leu | 7264 | Ala | 13675 |
| 4 | Met | 952 | Asn | 6832 | Val | 13290 |
| 5 | Leu | 934 | His | 6519 | Met | 13035 |
| 6 | Asn | 772 | Val | 6490 | His | 12638 |
| 7 | His | 689 | Met | 6471 | Asn | 12422 |
| 8 | Thr | 444 | Pro | 5231 | Pro | 11581 |
| 9 | Arg | 431 | Thr | 4531 | Thr | 11252 |
| 10 | Pro | 419 | Ile | 4127 | Arg | 10154 |
| 11 | Ile | 398 | Glu | 4091 | Ile | 10121 |
| 12 | Orn | 392 | Arg | 4066 | Glu | 10083 |
| 13 | Phe | 371 | Orn | 3834 | Tyr | 10020 |
| 14 | Glu | 368 | ABA | 3740 | Ser | 9954 |
| 15 | Ser | 347 | Lys | 3608 | ABA | 9911 |
| 16 | Tyr | 347 | Gln | 3604 | Orn | 9766 |
| 17 | Cit | 340 | Tyr | 3604 | Lys | 9592 |
| 18 | Lys | 336 | Ser | 3563 | Gln | 9539 |
| 19 | Gln | 320 | Cit | 3547 | Phe | 9524 |
| 20 | ABA | 314 | Gly | 3474 | Gly | 9449 |
| 21 | Gly | 306 | Phe | 3383 | Cit | 9415 |

| No | Formula | ROC_AUC |
|---|---|---|
| 1 | 6.78981+0.05102*Ser+0.01259*Gln-0.05243*Gly+0.05778*Cit-0.02344*Val-0.05969*Trp | 0.8484 |
| 2 | 9.12485+0.05074*Ser+0.01384*Gln-0.05068*Gly-0.01997*Val-0.06332*Trp-0.01056*Lys | 0.8467 |
| 3 | 7.08400+0.04813*Ser+0.01376*Gln-0.04992*Gly-0.02535*Val+0.03194*Tyr-0.08301*Trp | 0.8439 |
| 4 | 9.62164+0.05104*Ser-0.02170*Glu+0.01295*Gln-0.05352*Gly-0.02026*Val-0.07047*Trp | 0.8439 |
| 5 | 8.45821+0.04716*Ser+0.01328*Gln-0.05263*Gly-0.02459*Val+0.05210*Met-0.07573*Trp | 0.8399 |
| 6 | 8.14276+0.04363*Ser+0.02480*Asn+0.01278*Gln-0.05121*Gly-0.02239*Val-0.06968*Trp | 0.8387 |
| 7 | 7.88323+0.04688*Ser+0.01181*Gln-0.05139*Gly-0.02457*Val+0.02811*His-0.07254*Trp | 0.8387 |
| 8 | 8.13840+0.04663*Ser+0.01359*Gln-0.05196*Gly+0.04218*ABA-0.02342*Val-0.07228*Trp | 0.8382 |
| 9 | 3.97626+0.02173*Ser+0.00499*Gln-0.02379*Gly+0.04100*Cit-0.01143*Val-0.02762*Trp | 0.8382 |
| 10 | 5.61660+0.04688*Ser+0.01016*Gln-0.04844*Gly+0.06619*Cit-0.01983*Val-0.01223*Lys | 0.8376 |
| 11 | 7.82558+0.04882*Ser+0.01270*Gln-0.05005*Gly-0.02269*Val+0.01792*Phe-0.07583*Trp | 0.8376 |
| 12 | 8.15461+0.04197*Ser-0.02989*Glu+0.01088*Gln-0.04340*Gly-0.06649*Trp-0.01596*Lys | 0.8365 |
| 13 | 8.20547+0.04952*Ser+0.01313*Gln-0.05257*Gly-0.02294*Val-0.06633*Trp+0.00983*Orn | 0.8359 |
| 14 | 6.37216+0.04105*Ser+0.00945*Gln-0.04625*Gly-0.02035*Val+0.03821*His-0.01839*Lys | 0.8359 |
| 15 | 8.15873+0.04980*Ser+0.01292*Gln+0.00252*Pro-0.05172*Gly-0.02251*Val-0.06680*Trp | 0.8359 |
| 16 | 3.83363+0.02234*Ser+0.00483*Gln-0.02318*Gly+0.04706*Cit-0.01033*Val-0.00979*Lys | 0.8359 |
| 17 | 8.12658+0.04794*Ser-0.01296*Gln-0.05191*Gly+0.00222*Ala-0.02287*Val-0.07040*Trp | 0.8348 |
| 18 | 5.01984+0.04487*Ser+0.00898*Gln-0.04937*Gly-0.00072*Ala+0.06303*Cit-0.02180*Val | 0.8348 |
| 19 | 8.28337+0.04896*Ser+0.01268*Gln-0.05048*Gly-0.02512*Val+0.01218*Leu-0.07655*Trp | 0.8348 |
| 20 | 8.30799+0.04743*Ser+0.01292*Gln-0.05091*Gly-0.02407*Val+0.01034*Ile-0.06764*Trp | 0.8342 |
| 21 | 4.93589+0.04546*Ser+0.00894*Gln-0.04960*Gly+0.06413*Cit-0.02052*Val-0.00762*Ile | 0.8336 |
| 22 | 4.62156+0.04276*Ser+0.00834*Gln-0.04945*Gly+0.05936*Cit-0.02278*Val+0.01217*His | 0.8336 |
| 23 | 5.58391+0.04572*Ser+0.00953*Gln-0.05063*Gly+0.06274*Cit-0.02162*Val-0.01570*Phe | 0.8330 |
| 24 | 5.63449+0.04526*Ser-0.01221*Glu+0.00866*Gln-0.05062*Gly+0.05751*Cit-0.02061*Val | 0.8330 |
| 25 | 4.99123+0.04428*Ser+0.00868*Gln-0.04824*Gly+0.06913*Cit-0.02116*Val-0.01169*Orn | 0.8325 |

FIG. 87 (Continued)

| No | Formula | ROC_AUC |
|---|---|---|
| 26 | 8.35849+0.04881*Ser+0.01275*Gln-0.05104*Gly-0.02200*Val-0.06440*Trp | 0.8325 |
| 27 | 4.94367+0.04596*Ser-0.00709*Asn+0.00906*Gln-0.04961*Gly+0.06401*Cit-0.02192*Val | 0.8325 |
| 28 | 8.18108+0.00302*Thr+0.04673*Ser+0.01270*Gln-0.05076*Gly-0.02175*Val-0.06527*Trp | 0.8325 |
| 29 | 5.12074+0.04410*Ser+0.00894*Gln-0.00228*Pro-0.04930*Gly+0.06459*Cit-0.02176*Val | 0.8319 |
| 30 | 5.12219-0.00375*Thr+0.04717*Ser+0.00896*Gln-0.04988*Gly+0.06372*Cit-0.02226*Val | 0.8313 |
| 31 | 4.95009+0.04498*Ser+0.00891*Gln-0.04949*Gly+0.06389*Cit-0.00972*ABA-0.02175*Val | 0.8313 |
| 32 | 5.11497+0.04574*Ser+0.00899*Gln-0.04909*Gly+0.06756*Cit-0.02099*Val-0.00902*Arg | 0.8302 |
| 33 | 3.56360+0.02142*Ser+0.00414*Gln-0.02416*Gly+0.04543*Cit-0.01177*Val-0.01074*Phe | 0.8302 |
| 34 | 4.52567+0.04352*Ser+0.00890*Gln-0.04912*Gly+0.05978*Cit-0.02247*Val+0.00766*Tyr | 0.8296 |
| 35 | 4.92008+0.04535*Ser+0.00898*Gln-0.04926*Gly+0.06512*Cit-0.02141*Val-0.01629*Met | 0.8291 |
| 36 | 4.87925+0.04425*Ser+0.00895*Gln-0.04952*Gly+0.06230*Cit-0.02194*Val | 0.8285 |
| 37 | 5.03939+0.04488*Ser+0.00921*Gln-0.04974*Gly+0.06285*Cit-0.02073*Val-0.00531*Leu | 0.8285 |
| 38 | 3.37760+0.02035*Ser+0.00395*Gln-0.00222*Pro-0.02373*Gly+0.04674*Cit-0.01199*Val | 0.8268 |
| 39 | 3.34853+0.02191*Ser+0.00398*Gln-0.02330*Gly+0.04919*Cit-0.01162*Val-0.00796*Arg | 0.8262 |
| 40 | 3.69084+0.02240*Ser+0.00415*Gln-0.02382*Gly-0.00257*Ala+0.04687*Cit-0.01149*Val | 0.8256 |
| 41 | 3.34517+0.02133*Ser+0.00366*Gln-0.02243*Gly+0.05661*Cit-0.01061*Val-0.02218*Orn | 0.8251 |
| 42 | 3.09076+0.02003*Ser+0.00393*Gln-0.02372*Gly+0.04275*Cit+0.00508*ABA-0.01221*Val | 0.8251 |
| 43 | 3.19096+0.02226*Ser+0.00401*Gln-0.02338*Gly+0.04841*Cit-0.01120*Val-0.02763*Met | 0.8251 |
| 44 | 3.32498+0.02142*Ser+0.00420*Gln-0.02406*Gly+0.04536*Cit-0.01176*Val-0.00621*His | 0.8245 |
| 45 | 3.41633+0.02066*Ser-0.00436*Glu+0.00376*Gln-0.02416*Gly+0.04233*Cit-0.01152*Val | 0.8239 |
| 46 | 3.27495+0.02262*Ser+0.00386*Gln-0.02404*Gly+0.04746*Cit-0.00982*Val-0.01289*Ile | 0.8234 |
| 47 | 6.41378+0.03644*Ser-0.02858*Glu+0.00871*Gln-0.04242*Gly-0.06787*Trp | 0.8222 |
| 48 | 4.11625+0.03651*Ser+0.00960*Gln-0.03810*Gly+0.05226*Cit-0.05203*Trp-0.01522*Lys | 0.8222 |
| 49 | 3.52372+0.02155*Ser+0.00417*Gln-0.02440*Gly+0.04565*Cit-0.01004*Val-0.00893*Leu | 0.8205 |
| 50 | 7.02005+0.04389*Ser+0.01050*Gln-0.04697*Gly-0.01865*Val-0.01146*Lys | 0.8199 |

FIG. 88

| No | Formula | ROC_AUC |
|---|---|---|
| 51 | 2.68133+0.01971*Ser+0.00378*Gln−0.02303*Gly+0.03979*Cit−0.01281*Val+0.00968*Tyr | 0.8199 |
| 52 | 3.31376+0.03851*Ser+0.00834*Gln−0.04099*Gly+0.05729*Cit−0.02262*Ile−0.04808*Trp | 0.8194 |
| 53 | 2.30153−0.01991*Ser+0.00378*Gln−0.02087*Gly+0.04712*Cit−0.01782*Ile−0.02351*Trp | 0.8160 |
| 54 | 6.42312+0.04236*Ser−0.03378*Gly+0.05906*Cit−0.01669*Val+0.01875*Tyr−0.03985*Trp | 0.8142 |
| 55 | 2.65572+0.01849*Ser+0.00468*Gln−0.01961*Gly+0.04554*Cit−0.02442*Trp−0.01032*Lys | 0.8142 |
| 56 | 5.47242+0.04063*Ser+0.00916*Gln−0.04711*Gly−0.02215*Val+0.01487*Tyr | 0.8137 |
| 57 | 6.34583−0.00102*Thr+0.04285*Ser+0.00931*Gln−0.04808*Gly−0.02103*Val | 0.8131 |
| 58 | 6.90955+0.04292*Ser+0.00975*Gln−0.04891*Gly−0.02052*Val−0.01330*Phe | 0.8131 |
| 59 | 2.69867+0.03343*Ser+0.00788*Gln−0.03822*Gly+0.05309*Cit−0.01841*Met−0.05167*Trp | 0.8125 |
| 60 | 6.16110+0.01053*Gln−0.03429*Gly+0.03724*Cit−0.01669*Val+0.02620*Tyr−0.05509*Trp | 0.8125 |
| 61 | 7.38881+0.01708*Thr+0.01093*Gln−0.03730*Gly−0.01460*Val−0.05784*Trp | 0.8125 |
| 62 | 6.17700+0.04159*Ser+0.00935*Gln−0.04812*Gly+0.00877*ABA−0.02118*Val | 0.8120 |
| 63 | 7.61323+0.00924*Gln−0.03519*Gly−0.01673*Val+0.03252*His−0.05703*Trp | 0.8120 |
| 64 | 7.04258+0.04318*Ser−0.03499*Gly+0.06332*Cit−0.01803*Val+0.01026*Leu−0.04072*Trp | 0.8120 |
| 65 | 2.21589+0.03157*Ser+0.00792*Gln−0.03770*Gly+0.04719*Cit+0.00932*Tyr−0.05963*Trp | 0.8114 |
| 66 | 3.51796+0.02988*Ser−0.03646*Asn+0.00421*Gln−0.02482*Gly+0.05413*Cit−0.01173*Val | 0.8114 |
| 67 | 6.26325+0.00888*Gln−0.03370*Gly+0.05247*Cit−0.01254*Val−0.00982*Lys | 0.8108 |
| 68 | 3.99605+0.02171*Ser−0.01807*Gly+0.03940*Cit−0.01061*Val−0.01937*Tyr−0.02886*Trp | 0.8103 |
| 69 | 6.27072+0.04213*Ser+0.00930*Gln−0.04801*Gly−0.02096*Val | 0.8097 |
| 70 | 2.62792+0.03209*Ser+0.00797*Gln−0.03847*Gly+0.04957*Cit+0.00320*ABA−0.05582*Trp | 0.8097 |
| 71 | 4.10692+0.01885*Ser+0.00460*Gln−0.02261*Gly−0.01251*Val | 0.8097 |
| 72 | 3.69027+0.00514*Gln−0.01743*Gly+0.03544*Cit−0.00942*Val+0.01957*Tyr−0.01110*Lys | 0.8097 |
| 73 | 2.47866+0.03214*Ser+0.00791*Gln−0.03824*Gly+0.04980*Cit+0.00583*Phe−0.05901*Trp | 0.8091 |
| 74 | 2.04134+0.01784*Ser+0.00387*Gln−0.01929*Gly+0.04766*Cit−0.02983*Trp−0.00867*Arg | 0.8085 |
| 75 | 6.42916+0.04284*Ser−0.03487*Gly+0.07409*Cit−0.01461*Val−0.00822*Lys | 0.8080 |

FIG. 88 (Continued)

| No | Formula | ROC_AUC |
|---|---|---|
| 76 | 2.64706+0.03233*Ser+0.00793*Gln-0.03847*Gly+0.05005*Cit-0.05521*Trp | 0.8074 |
| 77 | 5.92307+0.04186*Ser-0.03565*Gly+0.07935*Cit-0.01551*Val-0.01624*Orn | 0.8074 |
| 78 | 6.65829+0.04297*Ser-0.03460*Gly+0.06556*Cit-0.01586*Val+0.01373*Phe-0.03991*Trp | 0.8068 |
| 79 | 6.99121+0.04354*Ser-0.03516*Gly+0.06733*Cit-0.00447*ABA-0.01539*Val-0.03033*Trp | 0.8068 |
| 80 | 7.02315+0.04278*Ser-0.03523*Gly+0.06511*Cit-0.01567*Val+0.00764*Met-0.03221*Trp | 0.8068 |
| 81 | 3.91361-0.01530*Thr+0.03196*Ser+0.00407*Gln-0.02515*Gly+0.05137*Cit-0.01307*Val | 0.8068 |
| 82 | 3.38799+0.00423*Gln-0.00417*Pro-0.01885*Gly+0.03941*Cit-0.01109*Val+0.01655*Tyr | 0.8068 |
| 83 | 6.95733+0.04348*Ser-0.03514*Gly+0.06734*Cit-0.01503*Val-0.00226*Ile-0.03018*Trp | 0.8057 |
| 84 | 4.59232+0.00506*Gln-0.01742*Gly+0.05466*Cit-0.00655*Val-0.02121*Orn-0.00873*Lys | 0.8051 |
| 85 | 6.97627+0.04314*Ser-0.03508*Gly+0.06657*Cit-0.01543*Val-0.03088*Trp | 0.8040 |
| 86 | 4.87607+0.04298*Ser-0.03467*Gly+0.07123*Cit-0.01655*Val-0.04656*Met+0.02093*Tyr | 0.8040 |
| 87 | 7.00205-0.00076*Thr+0.04362*Ser-0.03513*Gly+0.06684*Cit-0.01546*Val-0.03046*Trp | 0.8034 |
| 88 | 7.05840+0.04303*Ser-0.00105*Pro-0.03502*Gly+0.06792*Cit-0.01538*Val-0.03019*Trp | 0.8028 |
| 89 | 1.82448+0.01769*Ser-0.00377*Gln-0.01936*Gly+0.04586*Cit-0.02568*Met-0.02666*Trp | 0.8028 |
| 90 | -0.11981+0.00820*Ala-0.08596*Met-0.02960*Leu+0.04381*Phe-0.05551*Trp | 0.8019 |
| 91 | 2.11936+0.02109*Ser+0.00285*Gln-0.02010*Gly+0.06421*Cit-0.02013*Ile-0.02474*Orn | 0.8017 |
| 92 | 2.14349+0.01732*Ser+0.00384*Gln-0.01965*Gly-0.00204*Ala+0.04422*Cit-0.02667*Trp | 0.8017 |
| 93 | 5.85263+0.04221*Ser-0.03666*Gly-0.00043*Ala+0.07116*Cit-0.01632*Val | 0.8011 |
| 94 | 3.80876+0.02444*Ser-0.01723*Gly+0.07104*Cit-0.01367*Ile-0.02530*Orn-0.00808*Lys | 0.8000 |
| 95 | 3.29320+0.00444*Gln-0.01905*Gly+0.03624*Cit-0.01063*Val+0.01362*Tyr-0.00575*His | 0.8000 |
| 96 | 5.64172+0.00814*Gln-0.03586*Gly+0.05215*Cit-0.01470*Val | 0.7994 |
| 97 | 3.85969+0.00537*Gln-0.01788*Gly+0.02818*Cit-0.01069*Val+0.02209*Tyr-0.03685*Trp | 0.7994 |
| 98 | 5.87410+0.04330*Ser-0.03694*Gly+0.07310*Cit-0.01486*ABA-0.01622*Val | 0.7994 |
| 99 | 4.82378+0.02371*Ser-0.01975*Gly-0.00146*Ala+0.05019*Cit-0.00918*Val-0.01616*Trp | 0.7994 |
| 100 | -0.73085+0.06009*Asn+0.00824*Ala-0.11096*Met-0.02079*Leu-0.05105*Trp | 0.7990 |

FIG. 89

| No | Formula | ROC_AUC |
|---|---|---|
| 101 | 5.77866+0.04260*Ser 0.03647*Gly+0.07287*Cit-0.01599*Val-0.01218*Met | 0.7989 |
| 102 | 2.44163+0.01908*Ser+0.00349*Gln-0.02151*Gly-0.00209*Ala+0.04983*Cit-0.01365*Leu | 0.7983 |
| 103 | 5.97869+0.04215*Ser-0.03679*Gly+0.07082*Cit-0.01619*Val-0.00456*Phe | 0.7983 |
| 104 | 3.33843+0.00398*Gln-0.01761*Gly+0.04817*Cit-0.00943*Val+0.01283*Tyr-0.02159*Orn | 0.7983 |
| 105 | 4.20392-0.01244*Asn+0.00431*Gln-0.01819*Gly+0.05579*Cit-0.00801*Val-0.02041*Orn | 0.7983 |
| 106 | 4.76506+0.02403*Ser-0.00701*Glu-0.02110*Gly-0.00236*Ala+0.05039*Cit-0.00873*Val | 0.7983 |
| 107 | 1.98232+0.01714*Ser+0.00406*Gln-0.01993*Gly+0.04336*Cit-0.00671*His-0.02985*Trp | 0.7977 |
| 108 | 3.35921-0.02401*Asn+0.00435*Gln-0.01817*Gly+0.03909*Cit-0.01051*Val+0.01800*Tyr | 0.7972 |
| 109 | 5.76481+0.04195*Ser-0.03682*Gly+0.07082*Cit-0.01644*Val | 0.7972 |
| 110 | -1.29111+0.00631*Ala+0.04047*Ile-0.05064*Leu+0.03828*Phe-0.06347*Trp | 0.7967 |
| 111 | 8.10371+0.03483*Ser-0.02815*Glu-0.03211*Gly-0.04983*Trp | 0.7966 |
| 112 | 5.97942-0.00374*Thr+0.04445*Ser-0.03701*Gly+0.07196*Cit-0.01657*Val | 0.7960 |
| 113 | 3.64778+0.00417*Gln-0.01839*Gly+0.05079*Cit+0.02422*ABA-0.00897*Val-0.02230*Orn | 0.7960 |
| 114 | -2.42705+0.05766*Asn+0.00758*Ala-0.13157*Met+0.02305*Phe-0.07357*Trp | 0.7955 |
| 115 | 3.84204+0.02224*Ser-0.02041*Gly+0.04892*Cit-0.01039*Val | 0.7954 |
| 116 | 4.18456+0.03116*Ser+0.00841*Gln-0.03749*Gly-0.06109*Trp | 0.7949 |
| 117 | 2.57726+0.00421*Gln-0.01376*Gly+0.05365*Cit+0.01723*Tyr-0.02744*Orn-0.01274*Lys | 0.7949 |
| 118 | 4.44429+0.00904*Gln-0.02669*Gly+0.03049*Cit+0.02407*Tyr-0.05192*Trp-0.01509*Lys | 0.7943 |
| 119 | 3.78130+0.00436*Gln-0.01979*Gly+0.04004*Cit-0.00999*Val | 0.7943 |
| 120 | -2.13016+0.03643*Asn+0.00658*Ala-0.03207*Leu+0.03560*Phe-0.06551*Trp | 0.7938 |
| 121 | -1.99198+0.00694*Ala-0.03439*Leu+0.03595*Phe-0.06536*Trp+0.00798*Lys | 0.7935 |
| 122 | -0.17392+0.06065*Asn+0.00868*Ala-0.01064*Val-0.11651*Met-0.06030*Trp | 0.7934 |
| 123 | 9.08127+0.03988*Ser-0.03256*Gly-0.01432*Val-0.03956*Trp | 0.7932 |
| 124 | 2.98686+0.03347*Ser-0.02695*Gly+0.06101*Cit-0.05525*Met+0.02133*Tyr-0.03823*Trp | 0.7932 |
| 125 | -1.30729+0.01422*Glu+0.00664*Ala-0.03472*Leu+0.04060*Phe-0.06302*Trp | 0.7929 |

FIG. 89 (Continued)

| No | Formula | ROC_AUC |
|---|---|---|
| 126 | 4.32032+0.02404*Ser-0.02011*Gly-0.00190*Ala+0.05348*Cit-0.00944*Val-0.00991*Met | 0.7920 |
| 127 | -1.69920-0.00668*Ala-0.03257*Leu+0.03703*Phe+0.01223*His-0.06284*Trp | 0.7917 |
| 128 | 4.52776+0.02387*Ser-0.02035*Gly-0.00205*Ala+0.05266*Cit-0.00956*Val-0.00432*Phe | 0.7915 |
| 129 | 6.18893+0.03195*Asn+0.00864*Gln-0.03736*Gly-0.01644*Val | 0.7915 |
| 130 | -1.66480+0.05740*Asn+0.00663*Ala-0.13400*Met+0.03962*Ile-0.05072*Leu | 0.7909 |
| 131 | 3.88320+0.00727*Gln-0.02893*Gly+0.05113*Cit-0.01345*Lys | 0.7897 |
| 132 | 3.62032-0.00701*Thr+0.00426*Gln-0.01841*Gly+0.03693*Cit-0.01099*Val+0.01412*Tyr | 0.7892 |
| 133 | -1.55001+0.03678*Asn+0.00617*Ala+0.03861*Ile-0.04323*Leu-0.05816*Trp | 0.7887 |
| 134 | 1.89621+0.01734*Ser+0.00307*Gln-0.01995*Gly-0.00287*Ala+0.04921*Cit-0.00983*Phe | 0.7886 |
| 135 | -1.69102+0.00656*Ala+0.04280*Ile-0.04851*Leu-0.06033*Trp+0.01034*Lys | 0.7883 |
| 136 | 1.54331+0.01819*Ser+0.00299*Gln-0.01937*Gly-0.00224*Ala+0.05172*Cit-0.03004*Met | 0.7875 |
| 137 | 3.97920+0.00745*Gln-0.02993*Gly+0.04491*Cit-0.04406*Trp | 0.7869 |
| 138 | 3.43052+0.03117*Ser-0.04599*Asn-0.01961*Gly+0.05216*Cit-0.01119*Val+0.02049*Tyr | 0.7869 |
| 139 | 2.03350+0.02478*Ser-0.03421*Asn+0.00393*Gln-0.02056*Gly+0.05067*Cit-0.02666*Trp | 0.7869 |
| 140 | 0.56396+0.00863*Ala-0.01135*Val-0.08979*Met+0.02927*Phe-0.06657*Trp | 0.7865 |
| 141 | 2.04946-0.01131*Thr+0.02393*Ser+0.00359*Gln-0.02026*Gly+0.04744*Cit-0.02677*Trp | 0.7863 |
| 142 | 0.57102+0.00790*Ala-0.08215*Met+0.04237*Ile-0.04001*Leu-0.04982*Trp | 0.7859 |
| 143 | 3.82393+0.03176*Ser-0.02938*Gly+0.05906*Cit-0.03739*Trp | 0.7846 |
| 144 | 3.73105+0.03256*Ser-0.02894*Gly+0.06793*Cit-0.01224*Lys | 0.7846 |
| 145 | 3.64960+0.00463*Gln-0.01824*Gly-0.01193*Val+0.01769*Tyr | 0.7835 |
| 146 | 4.99356-0.01364*Thr+0.03240*Ser-0.02091*Gly+0.05592*Cit-0.01031*Val-0.01280*Trp | 0.7818 |
| 147 | 0.08652+0.00921*Ala-0.01215*Val-0.10864*Met-0.06602*Trp+0.01357*Lys | 0.7816 |
| 148 | 0.47013+0.00720*Ala-0.00929*Val+0.04456*Ile-0.03494*Leu-0.05699*Trp | 0.7811 |
| 149 | 0.87853+0.02767*Ser+0.00534*Gln-0.03729*Gly+0.05665*Cit | 0.7806 |
| 150 | 5.11656+0.02060*Ser-0.01853*Gly-0.01045*Val | 0.7806 |

FIG. 90

| No | Formula | ROC_AUC |
|---|---|---|
| 151 | 2.58419+0.01784*Ser−0.01692*Gly+0.04669*Cit−0.02497*Trp | 0.7801 |
| 152 | 3.41730+0.03295*Ser−0.03192*Gly+0.06751*Cit−0.01372*Leu | 0.7795 |
| 153 | −1.68205+0.00697*Ala−0.12512*Met+0.04318*Ile−0.05716*Leu+0.01353*Lys | 0.7795 |
| 154 | 6.76758+0.00851*Gln−0.03485*Gly−0.01442*Val | 0.7778 |
| 155 | 2.61085+0.00416*Gln−0.01670*Gly+0.03842*Cit−0.02969*Trp | 0.7778 |
| 156 | 4.62127+0.03083*Ser−0.03251*Asn−0.02078*Gly−0.00147*Ala+0.05944*Cit−0.00936*Val | 0.7761 |
| 157 | 1.71517+0.01755*Ser+0.00316*Gln−0.01994*Gly−0.00291*Ala+0.04969*Cit−0.00638*His | 0.7755 |
| 158 | 4.84953−0.01483*Gly+0.05889*Cit−0.00615*Val−0.02184*Orn | 0.7749 |
| 159 | 2.54431+0.03050*Ser−0.03076*Gly−0.00150*Ala+0.06460*Cit | 0.7744 |
| 160 | 7.47701+0.03886*Ser−0.03423*Gly−0.01547*Val | 0.7738 |
| 161 | 2.14323+0.02933*Ser−0.03123*Gly+0.06384*Cit | 0.7715 |
| 162 | 1.86417+0.01946*Ser−0.01716*Gly+0.05539*Cit−0.04278*Met | 0.7709 |
| 163 | 1.81141+0.02513*Ser−0.03569*Asn+0.00312*Gln−0.02056*Gly−0.00244*Ala+0.05653*Cit | 0.7698 |
| 164 | 3.96781−0.01361*Gly+0.04943*Cit−0.00843*Lys | 0.7687 |
| 165 | 2.30928+0.01847*Ser−0.01762*Gly−0.00297*Ala+0.05220*Cit | 0.7687 |
| 166 | 2.56273+0.03232*Ser−0.03038*Gly+0.06965*Cit−0.04098*Met | 0.7687 |
| 167 | 5.71308+0.03277*Ser−0.02642*Glu−0.03407*Gly | 0.7681 |
| 168 | 2.12086+0.00308*Gln−0.01591*Gly+0.05700*Cit−0.02590*Orn | 0.7675 |
| 169 | −1.42317+0.05839*Asn−0.11795*Met+0.04532*Ile−0.05912*Leu+0.04073*Phe | 0.7655 |
| 170 | 6.71308−0.02611*Gly+0.06080*Cit−0.01016*Val | 0.7647 |
| 171 | 2.34191+0.00579*Gln−0.03093*Gly+0.05165*Cit | 0.7647 |
| 172 | 5.56495−0.02252*Gly+0.05341*Cit−0.03177*Trp | 0.7641 |
| 173 | 5.38508+0.00785*Gln−0.02912*Gly−0.05086*Trp | 0.7641 |
| 174 | 5.44460−0.02232*Gly+0.06000*Cit−0.00950*Lys | 0.7635 |
| 175 | 2.48236+0.00353*Gln−0.01788*Gly+0.04648*Cit−0.01739*Ile | 0.7635 |

FIG. 90 (Continued)

| No | Formula | ROC_AUC |
|---|---|---|
| 176 | 3.94309−0.01396*Gly+0.06301*Cit−0.01128*Ile−0.02337*Orn | 0.7630 |
| 177 | 2.96389−0.01414*Gly+0.05058*Cit−0.00710*Arg | 0.7624 |
| 178 | 1.37369+0.01619*Ser−0.01767*Gly+0.04842*Cit | 0.7624 |
| 179 | −1.15444+0.04907*Ile−0.05590*Leu+0.04005*Phe−0.05661*Trp+0.00952*Lys | 0.7623 |
| 180 | 3.73345−0.01376*Gly+0.04414*Cit−0.02278*Trp | 0.7618 |
| 181 | 4.69329−0.01596*Gly+0.04597*Cit−0.00778*Val | 0.7601 |
| 182 | 4.14810−0.01340*Asn−0.01487*Gly+0.05127*Cit−0.00935*Leu | 0.7595 |
| 183 | 4.05085−0.01375*Gly−0.00129*Ala+0.04582*Cit−0.01950*Trp | 0.7578 |
| 184 | 4.81305−0.02450*Gly+0.06007*Cit−0.00747*Leu | 0.7561 |
| 185 | 1.45900+0.00305*Gln−0.01718*Gly+0.04200*Cit | 0.7561 |
| 186 | 4.73261−0.02383*Gly+0.06392*Cit−0.01081*Arg | 0.7556 |
| 187 | −1.48020+0.05352*Asn−0.11907*Met+0.04789*Ile−0.05429*Leu+0.01052*Lys | 0.7550 |
| 188 | 3.83156−0.01528*Gly+0.04855*Cit−0.01056*Leu | 0.7538 |
| 189 | 4.22943−0.02408*Gly+0.06101*Cit−0.01552*Met | 0.7533 |
| 190 | 3.16998−0.01820*Asn−0.01429*Gly+0.05010*Cit | 0.7527 |
| 191 | 3.23189−0.01363*Gly+0.06092*Cit−0.02565*Orn | 0.7527 |
| 192 | 2.99317−0.01412*Gly+0.05017*Cit−0.02671*Met | 0.7487 |
| 193 | 3.55140−0.01508*Gly+0.05070*Cit−0.01482*Ile | 0.7464 |
| 194 | 2.04429+0.02581*Ser−0.03914*Asn−0.01826*Gly+0.05798*Cit | 0.7453 |
| 195 | 3.08803−0.01469*Gly+0.04726*Cit−0.00922*Phe | 0.7396 |
| 196 | 3.39134−0.01448*Gly−0.00225*Ala+0.04840*Cit | 0.7368 |
| 197 | 3.08058−0.00592*Thr−0.01439*Gly+0.04810*Cit | 0.7356 |
| 198 | 2.51081+0.05928*Cit−0.04536*Trp−0.02773*Orn | 0.7026 |
| 199 | 2.95869+0.04377*Cit−0.00604*Val−0.04618*Trp | 0.6883 |
| 200 | 3.54170−0.00972*Val+0.03648*Tyr−0.06393*Trp | 0.6821 |

FIG. 92

| No | Formula | ROC_AUC |
|---|---|---|
| 1 | 5.98134+0.03070*Ser+0.00620*Gln−0.03718*Gly+0.05108*Cit−0.01641*Val−0.03504*Trp | 0.8439 |
| 2 | 8.13811+0.03042*Ser+0.00743*Gln−0.03427*Gly−0.01476*Val−0.03563*Trp−0.01063*Lys | 0.8416 |
| 3 | 7.24671+0.02955*Ser+0.00664*Gln−0.03556*Gly−0.01647*Val−0.03997*Trp+0.00283*Orn | 0.8387 |
| 4 | 8.71692+0.03451*Ser−0.02491*Glu+0.00661*Gln−0.03917*Gly−0.01374*Val−0.04675*Trp | 0.8387 |
| 5 | 7.26431+0.02934*Ser+0.00661*Gln−0.03521*Gly+0.00232*ABA−0.01629*Val−0.03992*Trp | 0.8370 |
| 6 | 7.28338+0.02958*Ser+0.00662*Gln−0.03529*Gly−0.01627*Val−0.03959*Trp | 0.8365 |
| 7 | 6.33470+0.02830*Ser+0.00645*Gln−0.03364*Gly−0.01832*Val+0.02456*Tyr−0.04877*Trp | 0.8359 |
| 8 | 7.35107+0.02951*Ser+0.00665*Gln−0.00054*Pro−0.03528*Gly−0.01623*Val−0.03960*Trp | 0.8359 |
| 9 | 7.23379+0.02949*Ser+0.00664*Gln−0.03538*Gly−0.01637*Val−0.03963*Trp+0.00097*Arg | 0.8353 |
| 10 | 6.85268+0.03013*Ser+0.00662*Gln−0.03514*Gly−0.01750*Val+0.02343*Phe−0.05476*Trp | 0.8353 |
| 11 | 3.61460+0.01696*Ser+0.00399*Gln−0.02201*Gly+0.04150*Cit−0.01026*Val−0.02399*Trp | 0.8353 |
| 12 | 7.28014+0.02807*Ser+0.00667*Gln−0.03619*Gly−0.01776*Val+0.03747*Met−0.04514*Trp | 0.8348 |
| 13 | 7.23578+0.02940*Ser+0.00642*Gln−0.03489*Gly−0.01844*Val+0.00875*Leu−0.04678*Trp | 0.8348 |
| 14 | 7.08480+0.02491*Ser+0.02670*Asn+0.00685*Gln−0.03588*Gly−0.01716*Val−0.04581*Trp | 0.8348 |
| 15 | 7.01251+0.00536*Thr+0.02637*Ser+0.00683*Gln−0.03529*Gly−0.01615*Val−0.04244*Trp | 0.8342 |
| 16 | 6.70388+0.02823*Ser+0.00592*Gln−0.03631*Gly−0.01858*Val+0.02797*His−0.04732*Trp | 0.8342 |
| 17 | 5.85773+0.03129*Ser+0.00669*Gln−0.03760*Gly+0.05468*Cit−0.01553*Val−0.01198*Lys | 0.8336 |
| 18 | 7.24438+0.02869*Ser+0.00658*Gln−0.03521*Gly−0.01738*Val+0.00668*Ile−0.04111*Trp | 0.8325 |
| 19 | 5.24487+0.02904*Ser−0.02684*Glu+0.00489*Gln−0.03600*Gly+0.04049*Cit−0.04881*Trp | 0.8313 |
| 20 | 5.02573+0.03095*Ser+0.00556*Gln−0.03842*Gly+0.05781*Cit−0.01659*Val−0.00664*Arg | 0.8313 |
| 21 | 7.05456+0.02885*Ser+0.00669*Gln−0.03569*Gly+0.00150*Ala−0.01678*Val−0.04252*Trp | 0.8308 |
| 22 | 4.33036+0.02935*Ser+0.00527*Gln−0.03967*Gly+0.05174*Cit−0.01880*Val+0.01626*His | 0.8308 |
| 23 | 4.83882+0.03036*Ser+0.00581*Gln−0.03898*Gly+0.05481*Cit−0.01656*Val−0.00288*Leu | 0.8302 |
| 24 | 3.54109+0.01808*Ser+0.00428*Gln−0.02193*Gly+0.04482*Cit−0.00971*Val−0.00899*Lys | 0.8302 |
| 25 | 4.99782+0.03279*Ser+0.00580*Gln−0.03976*Gly+0.05732*Cit−0.02402*ABA−0.01694*Val | 0.8291 |

FIG. 92 (Continued)

| No | Formula | ROC_AUC |
|---|---|---|
| 26 | 6.58048+0.02848*Ser+0.00652*Gln-0.03698*Gly-0.01809*Val+0.04240*His-0.02011*Lys | 0.8285 |
| 27 | 4.78633+0.03120*Ser+0.00575*Gln-0.03904*Gly+0.05685*Cit-0.01621*Val-0.00653*Ile | 0.8279 |
| 28 | 4.85153+0.03023*Ser+0.00573*Gln-0.03890*Gly+0.05463*Cit-0.01715*Val-0.00257*Phe | 0.8279 |
| 29 | 4.37569+0.02972*Ser+0.00563*Gln-0.03845*Gly+0.05203*Cit-0.01813*Val+0.00849*Tyr | 0.8274 |
| 30 | 4.78471+0.03061*Ser+0.00557*Gln-0.03792*Gly+0.06311*Cit-0.01635*Val-0.01300*Orn | 0.8274 |
| 31 | 2.94230+0.01715*Ser+0.00363*Gln-0.02268*Gly+0.04443*Cit-0.01082*Val-0.00587*Phe | 0.8274 |
| 32 | 2.88702+0.01775*Ser+0.00353*Gln-0.02228*Gly+0.04714*Cit-0.01069*Val-0.00547*Arg | 0.8268 |
| 33 | 4.76582+0.03072*Ser+0.00571*Gln-0.03870*Gly+0.05611*Cit-0.01690*Val-0.01000*Met | 0.8262 |
| 34 | 4.97981+0.03003*Ser+0.00584*Gln-0.00213*Pro-0.03894*Gly+0.05607*Cit-0.01719*Val | 0.8262 |
| 35 | 6.58647+0.02913*Ser-0.03060*Glu+0.00527*Gln-0.03526*Gly-0.05331*Trp | 0.8251 |
| 36 | 4.77192-0.00034*Thr+0.03047*Ser+0.00570*Gln-0.03895*Gly+0.05466*Cit-0.01734*Val | 0.8251 |
| 37 | 2.91870+0.01668*Ser+0.00367*Gln-0.00171*Pro-0.02270*Gly+0.04558*Cit-0.01111*Val | 0.8251 |
| 38 | 4.75034+0.03026*Ser+0.00571*Gln-0.03896*Gly+0.05459*Cit-0.01733*Val | 0.8239 |
| 39 | 4.77178+0.03032*Ser+0.00571*Gln-0.03892*Gly-0.00010*Ala+0.05463*Cit-0.01729*Val | 0.8239 |
| 40 | 4.73001+0.02990*Ser+0.00199*Asn+0.00573*Gln-0.03901*Gly+0.05416*Cit-0.01741*Val | 0.8239 |
| 41 | 3.07466+0.01779*Ser+0.00365*Gln-0.02251*Gly-0.00167*Ala+0.04516*Cit-0.01052*Val | 0.8234 |
| 42 | 2.77505+0.01791*Ser+0.00341*Gln-0.02163*Gly+0.05630*Cit-0.00973*Val-0.01884*Orn | 0.8228 |
| 43 | 2.74811+0.01809*Ser+0.00362*Gln-0.02232*Gly+0.04720*Cit-0.01031*Val-0.02110*Met | 0.8228 |
| 44 | 3.06056+0.01797*Ser-0.00599*Glu+0.00346*Gln-0.02351*Gly+0.04194*Cit-0.01046*Val | 0.8228 |
| 45 | 2.70812+0.01685*Ser+0.00358*Gln-0.02270*Gly+0.04356*Cit+0.00155*ABA-0.01122*Val | 0.8222 |
| 46 | 2.83393+0.01868*Ser+0.00359*Gln-0.02295*Gly+0.04773*Cit-0.00913*Val-0.01182*Ile | 0.8211 |
| 47 | 2.83489+0.01734*Ser+0.00370*Gln-0.02278*Gly+0.04479*Cit-0.01091*Val-0.00365*His | 0.8199 |
| 48 | 3.05741+0.01761*Ser+0.00374*Gln-0.02308*Gly+0.04527*Cit-0.00914*Val-0.00800*Leu | 0.8194 |
| 49 | 4.38375+0.02465*Ser+0.00578*Gln-0.03059*Gly+0.05104*Cit-0.03534*Trp-0.01374*Lys | 0.8171 |
| 50 | 2.24928+0.01610*Ser+0.00350*Gln-0.02204*Gly+0.04006*Cit-0.01211*Val-0.01057*Tyr | 0.8165 |

FIG. 93

| No | Formula | ROC_AUC |
|---|---|---|
| 51 | 6.21562+0.03394*Ser-0.03047*Gly+0.04845*Cit-0.01516*Val+0.01816*Tyr-0.03695*Trp | 0.8148 |
| 52 | 2.15931+0.01641*Ser+0.00321*Gln-0.02008*Gly+0.04875*Cit-0.01759*Ile-0.02206*Trp | 0.8148 |
| 53 | 3.44197+0.02674*Ser+0.00490*Gln-0.03280*Gly+0.05745*Cit-0.01872*Ile-0.03519*Trp | 0.8142 |
| 54 | 3.42237+0.02408*Ser+0.00502*Gln-0.03264*Gly+0.05210*Cit-0.01028*Leu-0.03168*Trp | 0.8131 |
| 55 | 6.99040+0.03305*Ser-0.02096*Glu+0.00601*Gln-0.04072*Gly-0.01534*Val | 0.8125 |
| 56 | 7.08839+0.03000*Ser+0.00706*Gln-0.03581*Gly-0.01551*Val-0.01195*Lys | 0.8125 |
| 57 | 3.68414+0.02457*Ser+0.00437*Gln-0.03071*Gly+0.05672*Cit-0.03957*Trp-0.01278*Arg | 0.8120 |
| 58 | 7.03762+0.00750*Gln-0.03217*Gly-0.01498*Val+0.04481*His-0.01976*Lys | 0.8114 |
| 59 | 5.96189+0.00723*Gln-0.03035*Gly+0.04154*Cit-0.01463*Val+0.02061*Tyr-0.04212*Trp | 0.8114 |
| 60 | 7.41009+0.00815*Gln-0.03071*Gly+0.04886*Cit-0.01128*Val-0.02994*Trp-0.00997*Lys | 0.8114 |
| 61 | 7.42002+0.03200*Ser-0.03138*Gly-0.01639*Val+0.03324*His-0.04391*Trp | 0.8108 |
| 62 | 6.44762+0.03551*Ser-0.03167*Gly+0.05316*Cit-0.01465*Val+0.01968*Phe-0.04241*Trp | 0.8103 |
| 63 | 6.91495+0.03156*Ser-0.02811*Glu-0.03134*Gly+0.01655*His-0.05281*Trp | 0.8097 |
| 64 | 5.19554+0.02810*Ser+0.00591*Gln-0.03640*Gly-0.01875*Val+0.01545*Tyr | 0.8097 |
| 65 | 3.65987+0.01837*Ser-0.01779*Gly+0.03890*Cit-0.00998*Val+0.01865*Tyr-0.02826*Trp | 0.8097 |
| 66 | 5.95458+0.02870*Ser+0.00608*Gln-0.03716*Gly-0.01767*Val+0.00208*Ile | 0.8091 |
| 67 | 6.73114+0.03472*Ser-0.03156*Gly+0.05312*Cit-0.01597*Val+0.00913*Leu-0.03735*Trp | 0.8091 |
| 68 | 6.45488+0.00781*Gln-0.03215*Gly+0.05189*Cit-0.01194*Val-0.01109*Lys | 0.8085 |
| 69 | 6.58131+0.03566*Ser-0.03210*Gly+0.05786*Cit-0.01295*Val-0.00869*Lys | 0.8080 |
| 70 | 3.00673+0.02403*Ser+0.00457*Gln-0.03110*Gly+0.05422*Cit-0.02289*Met-0.03716*Trp | 0.8080 |
| 71 | 6.76849+0.03507*Ser-0.03186*Gly+0.05470*Cit-0.01362*Val-0.02954*Trp | 0.8074 |
| 72 | 3.65304+0.01567*Ser+0.00426*Gln-0.02147*Gly-0.01161*Val | 0.8074 |
| 73 | 5.98221+0.02898*Ser+0.00609*Gln-0.03717*Gly-0.01731*Val | 0.8068 |
| 74 | 2.93503+0.02258*Ser+0.00454*Gln-0.03118*Gly+0.05034*Cit-0.04124*Trp | 0.8068 |
| 75 | 2.99278+0.02277*Ser+0.00453*Gln-0.03114*Gly-0.00028*Ala+0.05050*Cit-0.04064*Trp | 0.8068 |

FIG. 93 (Continued)

| No | Formula | ROC_AUC |
|---|---|---|
| 76 | 6.59014+0.00720*Gln−0.03145*Gly+0.04735*Cit−0.01459*Val+0.00719*Leu−0.03975*Trp | 0.8068 |
| 77 | 6.75920+0.00024*Thr+0.03493*Ser−0.03185*Gly+0.05464*Cit−0.01361*Val−0.02967*Trp | 0.8068 |
| 78 | 4.21853+0.00484*Gln−0.01825*Gly+0.05471*Cit−0.00667*Val−0.01810*Orn−0.00854*Lys | 0.8063 |
| 79 | 2.90780+0.02185*Ser+0.00371*Asn+0.00457*Gln−0.03118*Gly+0.04944*Cit−0.04223*Trp | 0.8057 |
| 80 | 3.26498+0.02236*Ser+0.00472*Gln−0.00278*Pro−0.03123*Gly+0.05230*Cit−0.04106*Trp | 0.8057 |
| 81 | 3.17103+0.02331*Ser−0.03202*Asn+0.00356*Gln−0.02291*Gly+0.05156*Cit−0.01034*Val | 0.8057 |
| 82 | 1.89911+0.01139*Ala−0.09251*Met−0.02785*Leu+0.05291*Phe−0.06526*Trp | 0.8054 |
| 83 | 2.75463+0.02255*Ser+0.00451*Gln−0.03098*Gly+0.04978*Cit+0.00690*Phe−0.04590*Trp | 0.8051 |
| 84 | 2.77658+0.00399*Gln−0.01847*Gly+0.04918*Cit−0.00943*Val+0.01308*Tyr−0.01782*Orn | 0.8051 |
| 85 | 3.59804+0.00411*Gln−0.01856*Gly+0.05750*Cit−0.00756*Val−0.01866*Orn−0.00550*Arg | 0.8051 |
| 86 | 2.56486+0.01444*Ser+0.00378*Gln−0.01843*Gly+0.04416*Cit−0.02253*Trp−0.00951*Lys | 0.8051 |
| 87 | 1.82027+0.01248*Ser+0.00308*Gln−0.00146*Pro−0.01866*Gly+0.04423*Cit−0.02855*Trp | 0.8046 |
| 88 | 6.60339+0.00736*Gln−0.03179*Gly+0.04848*Cit−0.01279*Val−0.03373*Trp | 0.8040 |
| 89 | 1.63858+0.01268*Ser+0.00300*Gln−0.01862*Gly+0.04238*Cit+0.00141*Phe−0.03005*Trp | 0.8034 |
| 90 | 2.91827+0.00424*Gln−0.00353*Pro−0.01949*Gly+0.04017*Cit−0.01109*Val+0.01627*Tyr | 0.8028 |
| 91 | 1.81442−0.01330*Ser+0.00317*Gln−0.01885*Gly+0.04405*Cit−0.00471*His−0.02754*Trp | 0.8028 |
| 92 | 1.98871+0.01409*Ser+0.00299*Gln−0.01825*Gly+0.04751*Cit−0.02774*Trp−0.00786*Arg | 0.8028 |
| 93 | 3.47489−0.01298*Thr+0.02542*Ser+0.00343*Gln−0.02323*Gly+0.04917*Cit−0.01166*Val | 0.8017 |
| 94 | 5.54941+0.00690*Gln−0.03349*Gly+0.05195*Cit−0.01348*Val−0.00359*Phe | 0.8011 |
| 95 | 1.98277+0.01372*Ser+0.00307*Gln−0.01871*Gly−0.00163*Ala+0.04425*Cit−0.02548*Trp | 0.8011 |
| 96 | 3.53600+0.00459*Gln−0.01820*Gly+0.03158*Cit−0.01037*Val+0.02110*Tyr−0.03308*Trp | 0.8006 |
| 97 | 0.73280+0.00948*Ala+0.03289*Ile−0.04692*Leu+0.04528*Phe−0.06883*Trp | 0.8004 |
| 98 | 2.66336+0.02197*Ser+0.00446*Gln−0.03051*Gly+0.04827*Cit+0.00600*Tyr−0.04386*Trp | 0.8000 |
| 99 | 1.63413+0.01812*Ser+0.00276*Gln−0.01988*Gly+0.06517*Cit−0.01915*Ile−0.02101*Orn | 0.8000 |
| 100 | 3.66840−0.01266*Asn+0.00423*Gln−0.01894*Gly+0.05597*Cit−0.00770*Val−0.01712*Orn | 0.8000 |

FIG. 94

| No | Formula | ROC_AUC |
|---|---|---|
| 101 | 1.70039+0.01438*Ser+0.00306*Gln−0.01858*Gly+0.04697*Cit−0.02475*Met−0.02439*Trp | 0.7994 |
| 102 | 1.15872+0.01136*Ser+0.00293*Gln−0.01743*Gly+0.03804*Cit+0.01199*Tyr−0.03471*Trp | 0.7994 |
| 103 | 0.07744+0.05640*Asn+0.01021*Ala−0.15431*Met+0.03594*Phe−0.07941*Trp | 0.7984 |
| 104 | 2.81026+0.00429*Gln−0.01956*Gly+0.03839*Cit−0.01057*Val+0.01429*Tyr−0.00513*His | 0.7983 |
| 105 | 1.68214+0.05490*Asn+0.01086*Ala−0.11333*Met−0.01769*Leu−0.05438*Trp | 0.7982 |
| 106 | 4.31648+0.02037*Ser−0.01921*Gly−0.00082*Ala+0.04703*Cit−0.00841*Val−0.01856*Trp | 0.7972 |
| 107 | 0.61523+0.02150*Glu+0.00952*Ala−0.03855*Leu+0.05031*Phe−0.06717*Trp | 0.7971 |
| 108 | 5.39254+0.00687*Gln−0.03355*Gly+0.05176*Cit+0.00133*ABA−0.01377*Val | 0.7966 |
| 109 | 5.40935+0.00688*Gln−0.03357*Gly+0.05190*Cit−0.01373*Val | 0.7960 |
| 110 | 0.50794+0.02443*Asn+0.00925*Ala−0.03201*Leu+0.04243*Phe−0.06975*Trp | 0.7955 |
| 111 | 0.21536+0.00935*Ala−0.03544*Leu+0.04242*Phe−0.07135*Trp+0.00920*Lys | 0.7954 |
| 112 | 5.66461+0.03440*Ser−0.03373*Gly+0.05745*Cit−0.01460*Val | 0.7949 |
| 113 | 5.34279+0.00696*Gln−0.02721*Gly+0.04891*Cit−0.03363*Trp−0.01245*Lys | 0.7949 |
| 114 | 2.54676+0.05584*Asn+0.01082*Ala−0.00983*Val−0.12236*Met−0.06096*Trp | 0.7947 |
| 115 | 7.76197+0.03395*Ser−0.02959*Glu−0.03110*Gly−0.04750*Trp | 0.7943 |
| 116 | 8.22621+0.03417*Ser−0.02944*Gly−0.01327*Val−0.03403*Trp | 0.7937 |
| 117 | 4.62638+0.00683*Gln−0.02518*Gly+0.04242*Cit+0.01952*Tyr−0.04131*Trp−0.01472*Lys | 0.7937 |
| 118 | 0.66311+0.00943*Ala−0.03274*Leu+0.04242*Phe+0.01097*His−0.06855*Trp | 0.7933 |
| 119 | 4.01113+0.03079*Ser−0.02216*Glu−0.03394*Gly+0.04910*Cit | 0.7932 |
| 120 | 3.33158+0.00425*Gln−0.02034*Gly+0.04185*Cit−0.00967*Val | 0.7932 |
| 121 | 2.95323−0.02410*Asn−0.00423*Gln−0.01881*Gly+0.04099*Cit−0.01032*Val+0.01827*Tyr | 0.7926 |
| 122 | 3.15776−0.00693*Thr+0.00419*Gln−0.01915*Gly+0.03908*Cit−0.01094*Val+0.01520*Tyr | 0.7926 |
| 123 | 2.75769+0.00417*Gln−0.01952*Gly+0.04012*Cit−0.00912*Val−0.01046*Ile+0.01495*Tyr | 0.7926 |
| 124 | 2.09944+0.02015*Ser−0.02913*Asn+0.00336*Gln−0.01924*Gly+0.05338*Cit−0.00939*Lys | 0.7926 |
| 125 | 0.79846+0.00514*Pro+0.00903*Ala−0.03365*Leu+0.04462*Phe−0.06754*Trp | 0.7923 |

FIG. 94 (Continued)

| No | Formula | ROC_AUC |
|---|---|---|
| 126 | 4.36548+0.02269*Ser+0.00571*Gln−0.03019*Gly−0.01516*Lys | 0.7909 |
| 127 | 5.98278+0.03079*Asn+0.00715*Gln−0.03406*Gly−0.01572*Val | 0.7909 |
| 128 | 2.81812+0.01116*Ala−0.01010*Val−0.10044*Met+0.03639*Phe−0.07296*Trp | 0.7906 |
| 129 | 3.39247+0.01975*Ser−0.02014*Gly+0.04769*Cit−0.00962*Val | 0.7903 |
| 130 | 4.12624+0.00649*Gln−0.02860*Gly+0.05235*Cit−0.01387*Lys | 0.7897 |
| 131 | 3.05273+0.02630*Ser−0.04256*Asn−0.01917*Gly+0.05093*Cit−0.01028*Val+0.01988*Tyr | 0.7886 |
| 132 | 1.10858+0.01542*Ser+0.00271*Gln−0.01897*Gly−0.00153*Ala+0.05155*Cit−0.03078*Met | 0.7886 |
| 133 | 3.43962+0.00555*Gln−0.02702*Gly+0.04501*Cit+0.01018*Tyr−0.04368*Trp | 0.7880 |
| 134 | 3.93531+0.02698*Ser−0.02788*Gly+0.05321*Cit−0.03622*Trp | 0.7875 |
| 135 | 1.92289−0.00942*Thr+0.01864*Ser+0.00276*Gln−0.01900*Gly+0.04709*Cit−0.02433*Trp | 0.7869 |
| 136 | 4.40361+0.02543*Ser−0.02802*Asn−0.01963*Gly+0.05334*Cit−0.00816*Val−0.01555*Trp | 0.7869 |
| 137 | 2.78291+0.00995*Ala−0.00893*Val+0.03563*Ile−0.03061*Leu−0.05790*Trp | 0.7861 |
| 138 | 1.35213+0.01667*Ser−0.01416*Gly+0.04701*Cit−0.06049*Met+0.02546*Tyr−0.02580*Trp | 0.7858 |
| 139 | 3.75570−0.00570*Gln−0.02780*Gly+0.04786*Cit+0.00723*Phe−0.04402*Trp | 0.7852 |
| 140 | 2.01799+0.01909*Ser−0.03091*Asn+0.00296*Gln−0.01918*Gly+0.05058*Cit−0.02352*Trp | 0.7852 |
| 141 | 4.10284+0.02857*Ser−0.02820*Gly+0.05723*Cit−0.01205*Lys | 0.7829 |
| 142 | 3.16522+0.00457*Gln−0.01847*Gly−0.01183*Val+0.01833*Tyr | 0.7829 |
| 143 | 3.97906+0.02613*Ser−0.03050*Asn−0.02018*Gly−0.00077*Ala+0.05579*Cit−0.00849*Val | 0.7829 |
| 144 | 3.94599+0.00573*Gln−0.02800*Gly+0.04844*Cit−0.03915*Trp | 0.7823 |
| 145 | 1.27341+0.01445*Ser+0.00281*Gln−0.01936*Gly−0.00228*Ala+0.04878*Cit−0.00543*His | 0.7806 |
| 146 | 4.61967−0.01194*Thr+0.02755*Ser−0.02010*Gly+0.05147*Cit−0.00945*Val−0.01405*Trp | 0.7806 |
| 147 | 1.26732+0.02151*Ser+0.00384*Gln−0.03268*Gly+0.05446*Cit | 0.7801 |
| 148 | 2.52967+0.01780*Ser−0.01901*Gly+0.05080*Cit−0.01349*Leu | 0.7783 |
| 149 | 2.37024+0.01561*Ser−0.01691*Gly+0.04615*Cit−0.02564*Trp | 0.7772 |
| 150 | 2.36825+0.00365*Gln−0.01718*Gly+0.04101*Cit−0.02864*Trp | 0.7766 |

FIG. 95

| No | Formula | ROC_AUC |
|---|---|---|
| 151 | 7.02986+0.03334*Ser−0.03147*Gly−0.01438*Val | 0.7761 |
| 152 | 6.55628+0.00719*Gln−0.03208*Gly−0.01385*Val | 0.7755 |
| 153 | 4.03196−0.01337*Gly+0.06197*Cit−0.02119*Orn−0.00763*Lys | 0.7755 |
| 154 | 2.77409+0.02838*Ser−0.02928*Gly+0.06279*Cit−0.04082*Met | 0.7744 |
| 155 | 2.76467+0.02658*Ser−0.02950*Gly−0.00155*Ala+0.05704*Cit | 0.7738 |
| 156 | 2.30614+0.02542*Ser−0.02985*Gly+0.05651*Cit | 0.7715 |
| 157 | 1.56762+0.00310*Gln−0.01679*Gly+0.05802*Cit−0.02193*Orn | 0.7715 |
| 158 | 5.50544+0.03102*Ser−0.02630*Glu−0.03288*Gly | 0.7709 |
| 159 | 1.51403+0.01766*Ser−0.01730*Gly+0.05454*Cit−0.03930*Met | 0.7698 |
| 160 | 3.54323−0.01431*Gly+0.04832*Cit−0.00787*Lys | 0.7675 |
| 161 | 6.65303−0.02619*Gly+0.05498*Cit−0.00973*Val | 0.7670 |
| 162 | 1.81877+0.01644*Ser−0.01756*Gly−0.00241*Ala+0.05021*Cit | 0.7664 |
| 163 | 1.51861+0.02039*Ser−0.03348*Asn+0.00262*Gln−0.01963*Gly−0.00175*Ala+0.05491*Cit | 0.7658 |
| 164 | 2.87382+0.02224*Ser−0.02971*Asn−0.01746*Gly−0.00089*Ala+0.05468*Cit−0.01822*Trp | 0.7658 |
| 165 | 5.16318+0.00609*Gln−0.02639*Gly−0.04351*Trp | 0.7641 |
| 166 | 1.04876+0.01470*Ser−0.01771*Gly+0.04812*Cit | 0.7635 |
| 167 | 1.26162+0.03766*Ile−0.04937*Leu+0.04613*Phe−0.05594*Trp+0.01225*Lys | 0.7635 |
| 168 | 2.96640+0.05875*Asn−0.08049*Met+0.03379*Ile−0.02898*Leu−0.03716*Trp | 0.7631 |
| 169 | 5.60299−0.02299*Gly+0.05516*Cit−0.00954*Lys | 0.7630 |
| 170 | 4.39664−0.02364*Gly+0.06658*Cit−0.01819*Orn | 0.7630 |
| 171 | 3.46234−0.01453*Gly+0.04503*Cit−0.02399*Trp | 0.7630 |
| 172 | 2.04558+0.00355*Gln−0.01858*Gly+0.04872*Cit−0.01710*Ile | 0.7630 |
| 173 | 1.05599+0.05674*Asn−0.11700*Met+0.03588*Ile−0.04737*Leu+0.04373*Phe | 0.7629 |
| 174 | 5.54067−0.02278*Gly+0.05176*Cit−0.03191*Trp | 0.7624 |
| 175 | 2.31368+0.00502*Gln−0.02977*Gly+0.05245*Cit | 0.7624 |

FIG. 95 (Continued)

| No | Formula | ROC_AUC |
|---|---|---|
| 176 | 1.64193+0.03378*Asn+0.03370*Ile−0.04304*Leu+0.04588*Phe−0.05408*Trp | 0.7621 |
| 177 | 4.26734−0.01668*Gly+0.04631*Cit−0.00744*Val | 0.7601 |
| 178 | 3.84933−0.01366*Asn−0.01570*Gly+0.05172*Cit−0.00939*Leu | 0.7595 |
| 179 | 3.27337−0.05603*Met+0.03887*Ile−0.04151*Leu+0.05427*Phe−0.04736*Trp | 0.7594 |
| 180 | 2.58120−0.01486*Gly+0.05092*Cit−0.00670*Arg | 0.7590 |
| 181 | 4.90018−0.02486*Gly+0.05548*Cit−0.00755*Leu | 0.7584 |
| 182 | 3.51511−0.01605*Gly+0.04887*Cit−0.01065*Leu | 0.7550 |
| 183 | 1.04849+0.00302*Gln−0.01774*Gly+0.04393*Cit | 0.7544 |
| 184 | 0.90049+0.05040*Asn−0.10850*Met+0.03628*Ile−0.04322*Leu+0.01213*Lys | 0.7523 |
| 185 | 2.83086−0.01853*Asn−0.01503*Gly+0.05112*Cit | 0.7516 |
| 186 | 2.70224−0.01442*Gly+0.06092*Cit−0.02161*Orn | 0.7504 |
| 187 | 2.59457−0.01487*Gly+0.05084*Cit−0.02470*Met | 0.7504 |
| 188 | 3.03755+0.05707*Asn−0.00801*Val−0.09387*Met+0.03759*Ile−0.03088*Leu | 0.7488 |
| 189 | 1.79896+0.02250*Ser−0.03709*Asn−0.01817*Gly+0.05709*Cit | 0.7476 |
| 190 | 1.61002−0.01229*Thr+0.02230*Ser−0.01816*Gly+0.05312*Cit | 0.7476 |
| 191 | 3.14961−0.01577*Gly+0.05136*Cit−0.01417*Ile | 0.7464 |
| 192 | 3.21521−0.00849*Val+0.04049*Ile−0.03370*Leu−0.04445*Trp+0.01361*Lys | 0.7462 |
| 193 | 2.83637−0.01510*Gly−0.00180*Ala+0.04842*Cit | 0.7413 |
| 194 | 2.32070−0.01538*Gly+0.04763*Cit−0.00224*His | 0.7413 |
| 195 | 2.67389−0.01533*Gly+0.04795*Cit−0.00856*Phe | 0.7407 |
| 196 | 2.66896−0.00549*Thr−0.01508*Gly+0.04891*Cit | 0.7345 |
| 197 | 2.01270+0.05421*Cit−0.04296*Trp−0.02084*Orn | 0.7037 |
| 198 | 2.81847+0.03958*Cit−0.00565*Val−0.04578*Trp | 0.6923 |
| 199 | 3.12684−0.00930*Val+0.03579*Tyr−0.06032*Trp | 0.6860 |
| 200 | 0.63711+0.03236*Cit+0.02399*Tyr−0.05819*Trp | 0.6826 |

| ROC_AUC | 0.8 | | 0.75 | | 0.7 | |
|---|---|---|---|---|---|---|
| RANK | AMINO ACID | FREQUENCY OF APPEARANCE | AMINO ACID | FREQUENCY OF APPEARANCE | AMINO ACID | FREQUENCY OF APPEARANCE |
| 1 | Gly | 674 | Gly | 10338 | Gly | 15504 |
| 2 | Val | 449 | Cit | 3841 | Lys | 8963 |
| 3 | Gln | 448 | Trp | 3420 | Trp | 8571 |
| 4 | Ser | 445 | Ser | 3234 | Tyr | 7447 |
| 5 | Trp | 287 | Val | 3166 | Cit | 7096 |
| 6 | Cit | 264 | Lys | 3115 | His | 6889 |
| 7 | Lys | 232 | Gln | 3088 | Orn | 6363 |
| 8 | Glu | 206 | His | 2955 | Thr | 6250 |
| 9 | His | 183 | Glu | 2788 | Val | 6137 |
| 10 | Thr | 89 | Leu | 2412 | Ser | 6133 |
| 11 | Tyr | 83 | Thr | 2395 | Glu | 5865 |
| 12 | Orn | 77 | Arg | 2305 | Phe | 5614 |
| 13 | Phe | 73 | Tyr | 2243 | Met | 5609 |
| 14 | Asn | 72 | Phe | 2193 | Arg | 5505 |
| 15 | Arg | 72 | Ile | 2184 | Gln | 5502 |
| 16 | Met | 70 | Met | 2174 | Asn | 5439 |
| 17 | Ile | 70 | Asn | 2172 | ABA | 5418 |
| 18 | Leu | 67 | ABA | 2149 | Pro | 5382 |
| 19 | Pro | 61 | Ala | 2130 | Leu | 5358 |
| 20 | Ala | 61 | Pro | 2106 | Ala | 5308 |
| 21 | ABA | 61 | Orn | 2100 | Ile | 5249 |

| No | Formula | ROC_AUC |
|---|---|---|
| 1 | −0.74740+0.09273*Asn+0.02241*Glu+0.01196*Ala−0.01415*Val−0.12983*Met−0.05678*Trp | 0.8220 |
| 2 | 1.80583+0.07894*Asn+0.01254*Ala−0.04321*Cit−0.01244*Val−0.12642*Met−0.05951*Trp | 0.8194 |
| 3 | −1.77085+0.08486*Asn+0.02369*Glu+0.01110*Ala−0.00970*Val−0.12804*Met−0.02389*Leu | 0.8153 |
| 4 | −0.96501+0.07255*Asn+0.01134*Ala−0.13031*Met+0.02623*Ile−0.03006*Leu−0.04335*Trp | 0.8150 |
| 5 | −1.60146+0.08059*Asn+0.01981*Glu+0.01137*Ala−0.11896*Met−0.02365*Leu−0.04157*Trp | 0.8146 |
| 6 | 1.14677+0.08533*Asn+0.01289*Ala−0.01247*Val−0.11760*Met−0.05640*Trp−0.01642*Arg | 0.8145 |
| 7 | −2.00115+0.05710*Asn+0.01165*Ala−0.13068*Met−0.02456*Leu+0.03362*His−0.04194*Trp | 0.8142 |
| 8 | −1.55746+0.06723*Asn+0.00900*Gly+0.01158*Ala−0.04583*Cit−0.14351*Met−0.06260*Trp | 0.8139 |
| 9 | −3.21868+0.05301*Asn+0.01002*Ala−0.14761*Met+0.02827*Ile−0.04431*Leu+0.03775*His | 0.8134 |
| 10 | −2.60461+0.07825*Asn+0.01906*Glu+0.00997*Ala−0.13243*Met+0.02177*Ile−0.04024*Leu | 0.8134 |
| 11 | −0.93419+0.06808*Asn+0.01188*Ala−0.01264*Val−0.14075*Met+0.02845*His−0.05647*Trp | 0.8131 |
| 12 | −0.00793+0.08222*Asn+0.01187*Ala−0.01491*Val−0.14436*Met+0.02213*Ile−0.05935*Trp | 0.8129 |
| 13 | −1.19882+0.06908*Asn+0.01217*Ala−0.13616*Met−0.02494*Leu+0.02946*Phe−0.05041*Trp | 0.8126 |
| 14 | −0.16793+0.07816*Asn+0.00432*Pro+0.01156*Ala−0.01186*Val−0.13354*Met−0.05376*Trp | 0.8124 |
| 15 | −1.44486+0.08071*Asn−0.00456*Gln+0.00979*Gly+0.01137*Ala−0.14602*Met−0.05591*Trp | 0.8121 |
| 16 | −4.02210+0.07570*Asn+0.02289*Glu+0.00705*Gly+0.01051*Ala−0.13601*Met−0.03020*Leu | 0.8120 |
| 17 | 0.59979+0.07084*Asn+0.01196*Ala−0.03921*Cit−0.11733*Met−0.01897*Leu−0.04754*Trp | 0.8119 |
| 18 | −3.85139+0.06338*Asn+0.02130*Glu+0.01021*Ala−0.13663*Met−0.03672*Leu+0.03616*His | 0.8117 |
| 19 | 1.36972+0.08871*Asn−0.00309*Gln+0.01218*Ala−0.01140*Val−0.12875*Met−0.05382*Trp | 0.8117 |
| 20 | −0.08271+0.07611*Asn+0.01235*Ala+0.02919*ABA−0.01234*Val−0.13553*Met−0.05577*Trp | 0.8114 |
| 21 | −1.02847+0.07501*Asn+0.00566*Gly+0.01244*Ala−0.01085*Val−0.13681*Met−0.05531*Trp | 0.8114 |
| 22 | −0.85917+0.07788*Asn+0.01300*Glu+0.01073*Ala−0.03690*Cit−0.13557*Met−0.06165*Trp | 0.8113 |
| 23 | −2.91017+0.07622*Asn+0.02128*Glu+0.01052*Ala−0.13599*Met−0.03585*Leu+0.01861*Phe | 0.8113 |
| 24 | 0.24305+0.07727*Asn+0.01255*Ala−0.00947*Val−0.12301*Met−0.01099*Leu−0.04742*Trp | 0.8113 |
| 25 | −0.96418+0.07436*Asn+0.01108*Ala−0.01049*Val−0.14167*Met+0.03238*Ile−0.03175*Leu | 0.8111 |

FIG. 99 (Continued)

| No | Formula | ROC_AUC |
|---|---|---|
| 26 | −0.19379+0.07833*Asn+0.01234*Ala−0.01229*Val−0.14228*Met+0.01868*Phe−0.06163*Trp | 0.8106 |
| 27 | 0.09289+0.07891*Asn+0.01224*Ala−0.01183*Val−0.13659*Met+0.00383*Tyr−0.05518*Trp | 0.8083 |
| 28 | −2.70586+0.06640*Asn+0.00448*Gly+0.01063*Ala−0.14567*Met+0.02361*Ile−0.03598*Leu | 0.8083 |
| 29 | 0.14338+0.07911*Asn+0.01232*Ala−0.01171*Val−0.13238*Met−0.05437*Trp | 0.8074 |
| 30 | 0.12175+0.07902*Asn+0.01232*Ala−0.01174*Val−0.13275*Met−0.05437*Trp+0.00075*Orn | 0.8074 |
| 31 | 0.35448−0.00381*Ser+0.08357*Asn+0.01232*Ala−0.01169*Val−0.13187*Met−0.05472*Trp | 0.8073 |
| 32 | −2.08435+0.06717*Asn+0.01059*Ala−0.14660*Met+0.02431*Ile−0.04051*Leu+0.01377*Phe | 0.8072 |
| 33 | −0.13442+0.07693*Asn+0.01224*Ala−0.01176*Val−0.13581*Met−0.05568*Trp+0.00287*Lys | 0.8071 |
| 34 | −0.05066+0.07170*Asn+0.01117*Ala−0.04054*Cit−0.13702*Met−0.06044*Trp | 0.8061 |
| 35 | −2.45442+0.07785*Asn+0.02050*Glu+0.01053*Ala−0.12954*Met−0.03144*Leu | 0.8061 |
| 36 | −1.15040+0.06797*Asn+0.01185*Ala−0.12931*Met−0.02061*Leu−0.04395*Trp+0.00456*Lys | 0.8059 |
| 37 | −1.99557+0.06791*Asn+0.00414*Pro+0.01000*Ala−0.14033*Met+0.02155*Ile−0.03744*Leu | 0.8058 |
| 38 | −0.72531+0.07116*Asn+0.01198*Ala−0.12527*Met−0.01958*Leu−0.04256*Trp | 0.8054 |
| 39 | −1.44998−0.00640*Ser+0.07598*Asn+0.01061*Ala−0.14057*Met+0.02572*Ile−0.03827*Leu | 0.8049 |
| 40 | −2.13528+0.06620*Asn+0.01045*Ala−0.14450*Met+0.02498*Ile−0.03855*Leu+0.00339*Lys | 0.8037 |
| 41 | −2.83570+0.06723*Asn+0.00740*Gly+0.01148*Ala−0.14921*Met−0.05727*Trp | 0.8035 |
| 42 | −1.79428+0.06862*Asn+0.01059*Ala−0.14141*Met+0.02478*Ile−0.03753*Leu | 0.8030 |
| 43 | −1.81239+0.00058*Thr+0.06793*Asn+0.01055*Ala−0.14178*Met+0.02471*Ile−0.03742*Leu | 0.8029 |
| 44 | −1.73226+0.06900*Asn+0.01056*Ala−0.14037*Met+0.02501*Ile−0.03748*Leu−0.00213*Orn | 0.8029 |
| 45 | −1.19470+0.06252*Asn+0.01329*Glu+0.00751*Ala−0.10238*Met−0.02250*Leu−0.05201*Trp | 0.8028 |
| 46 | −2.17814+0.01034*Ala−0.12548*Met−0.03032*Ile−0.04651*Leu+0.04753*His | 0.8028 |
| 47 | −1.76623+0.06876*Asn+0.01063*Ala−0.13980*Met+0.02477*Ile−0.03733*Leu−0.00159*Tyr | 0.8028 |
| 48 | −2.27612+0.07906*Asn+0.01532*Glu+0.01064*Ala−0.14098*Met−0.05806*Trp | 0.8027 |
| 49 | −1.97959+0.06646*Asn+0.01054*Asn−0.01908*ABA−0.14375*Met+0.02415*Ile−0.03774*Leu | 0.8019 |
| 50 | −1.35662+0.05369*Asn+0.00771*Ala−0.11271*Met−0.02141*Leu+0.01404*His−0.05016*Trp | 0.8012 |

FIG. 100

| No | Formula | ROC_AUC |
|---|---|---|
| 51 | −0.84180+0.05559*Asn+0.00729*Ala−0.11427*Met+0.03891*Ile−0.03769*Leu−0.05073*Trp | 0.8011 |
| 52 | −2.37452+0.08743*Asn+0.02067*Glu+0.01020*Ala−0.01470*Val−0.15312*Met | 0.8010 |
| 53 | −2.90837+0.05396*Asn+0.01080*Ala−0.14262*Met−0.03204*Leu+0.03465*His | 0.8009 |
| 54 | −1.72105+0.07064*Asn+0.01118*Ala−0.15080*Met+0.01191*Phe−0.06072*Trp | 0.7976 |
| 55 | −0.18262+0.00793*Ala−0.08371*Met−0.02877*Leu+0.04336*Phe−0.05539*Trp | 0.7968 |
| 56 | 0.45123+0.01214*Ala−0.10772*Met+0.02608*Ile−0.03594*Leu+0.03001*Phe−0.04709*Trp | 0.7966 |
| 57 | −1.45540+0.07147*Asn+0.01120*Ala−0.14414*Met−0.05608*Trp | 0.7962 |
| 58 | −1.53166+0.05747*Asn+0.00763*Ala−0.11650*Met−0.02923*Leu+0.04250*Phe−0.05797*Trp | 0.7957 |
| 59 | −1.90063+0.06624*Asn+0.01117*Ala−0.14274*Met−0.03078*Leu+0.01521*Phe | 0.7956 |
| 60 | −1.01479+0.05626*Asn+0.00665*Ala−0.00801*Val−0.12907*Met+0.04173*Ile−0.04235*Leu | 0.7937 |
| 61 | −0.76506+0.05802*Asn+0.00796*Ala−0.10793*Met−0.01995*Leu−0.05067*Trp | 0.7937 |
| 62 | −0.92448+0.05857*Asn+0.00815*Ala−0.01149*Val−0.12107*Met+0.02879*Phe−0.06831*Trp | 0.7935 |
| 63 | −1.56605+0.06781*Asn+0.01118*Ala−0.13711*Met−0.02730*Leu | 0.7934 |
| 64 | 0.99478+0.00768*Gly+0.01298*Ala−0.11369*Met−0.02311*Leu+0.03240*Phe−0.05187*Trp | 0.7929 |
| 65 | −1.27407+0.00601*Ala+0.03836*Ile−0.04884*Leu+0.03767*Phe−0.06268*Trp | 0.7918 |
| 66 | −1.29966+0.05650*Asn−0.00095*Gln+0.00641*Ala−0.12855*Met+0.03807*Ile−0.04865*Leu | 0.7907 |
| 67 | 2.07863+0.01244*Ala−0.01010*Val−0.09114*Met+0.03361*Ile−0.02447*Leu−0.04286*Trp | 0.7907 |
| 68 | −1.75309+0.05461*Asn−0.00128*Pro+0.00616*Ala−0.13075*Met+0.03718*Ile−0.04866*Leu | 0.7902 |
| 69 | −2.40719+0.05581*Asn−0.00736*Ala−0.12866*Met+0.02300*Phe−0.07282*Trp | 0.7901 |
| 70 | −1.81048+0.05383*Asn+0.00642*Ala−0.13130*Met+0.03715*Ile−0.04893*Leu+0.00461*Orn | 0.7894 |
| 71 | −1.83489+0.01113*Ala−0.11891*Met−0.03328*Leu+0.04448*His | 0.7893 |
| 72 | −1.76394+0.05432*Asn+0.00635*Ala−0.13130*Met+0.03800*Ile−0.04888*Leu+0.00140*Arg | 0.7892 |
| 73 | −2.08787+0.03462*Asn+0.00634*Ala−0.03131*Leu+0.03534*Phe−0.06494*Trp | 0.7887 |
| 74 | −0.94178+0.05507*Asn+0.00742*Ala−0.12203*Met−0.02154*Leu+0.01772*Tyr−0.05429*Trp | 0.7887 |
| 75 | −1.55704−0.00186*Ser+0.05621*Asn+0.00634*Ala−0.12898*Met+0.03810*Ile−0.04902*Leu | 0.7886 |

FIG. 100 (Continued)

| No | Formula | ROC_AUC |
|---|---|---|
| 76 | -0.23193+0.05880*Asn+0.00840*Ala-0.01029*Val-0.11271*Met-0.05969*Trp | 0.7884 |
| 77 | -1.32365+0.01351*Glu+0.00641*Ala-0.03380*Leu+0.04017*Phe-0.06254*Trp | 0.7878 |
| 78 | -1.88253+0.00662*Ala-0.03327*Leu+0.03615*Phe-0.06424*Trp+0.00688*Lys | 0.7878 |
| 79 | -1.46793+0.07471*Asn+0.01070*Ala-0.01227*Val-0.15750*Met | 0.7872 |
| 80 | 0.04590+0.01169*Ala-0.10606*Met+0.02772*Ile-0.03275*Leu-0.04260*Trp+0.00826*Lys | 0.7871 |
| 81 | -1.85752+0.05295*Asn+0.00601*Ala-0.13984*Met+0.03790*Ile-0.05034*Leu+0.01131*Tyr | 0.7864 |
| 82 | -1.71317+0.00643*Ala-0.03198*Leu+0.03680*Phe+0.01231*His-0.06246*Trp | 0.7862 |
| 83 | -1.73556+0.05705*Asn+0.00702*Ala-0.12342*Met-0.03050*Leu | 0.7861 |
| 84 | 0.66261+0.01269*Ala-0.10226*Met-0.02555*Leu+0.03053*Phe-0.04693*Trp | 0.7860 |
| 85 | 0.97673+0.01197*Ala-0.09614*Met+0.02670*Ile-0.03059*Leu-0.03915*Trp | 0.7859 |
| 86 | -1.53904+0.05163*Asn+0.00793*Ala-0.12210*Met-0.02245*Leu-0.05322*Trp+0.00937*Lys | 0.7859 |
| 87 | -0.17578+0.01245*Ala-0.11143*Met-0.02722*Leu+0.03034*Phe-0.04988*Trp+0.00764*Lys | 0.7858 |
| 88 | -2.42489+0.05554*Asn+0.00658*Ala-0.13475*Met-0.03864*Leu+0.03485*Phe | 0.7855 |
| 89 | -1.69621+0.05495*Asn+0.00637*Ala-0.13004*Met+0.03802*Ile-0.04888*Leu | 0.7850 |
| 90 | 0.77152+0.01103*Ala-0.01057*Val+0.02988*Ile-0.03207*Leu+0.01812*Phe-0.05202*Trp | 0.7846 |
| 91 | -1.31205-0.00840*Thr+0.06283*Asn+0.00661*Ala-0.12415*Met+0.03906*Ile-0.04980*Leu | 0.7838 |
| 92 | -2.52636+0.04809*Asn+0.00628*Ala-0.14336*Met+0.03985*Ile-0.05288*Leu+0.00924*Lys | 0.7831 |
| 93 | -2.35556+0.05295*Asn+0.00592*Ala-0.14088*Met+0.03764*Ile-0.05677*Leu+0.03451*Phe | 0.7830 |
| 94 | -0.95207+0.01087*Ala-0.11958*Met+0.02592*Ile-0.04380*Leu+0.01567*Phe+0.00618*Lys | 0.7814 |
| 95 | 0.50697+0.00760*Ala-0.08013*Met+0.04081*Ile-0.03851*Leu-0.04930*Trp | 0.7810 |
| 96 | -1.70828+0.05651*Asn+0.00761*Ala-0.12160*Met-0.06536*Trp | 0.7808 |
| 97 | 0.27207+0.01130*Ala-0.00877*Val-0.10941*Met+0.03249*Ile-0.03570*Leu+0.00618*Lys | 0.7805 |
| 98 | -1.10026+0.00748*Ala-0.09344*Met-0.03091*Leu+0.04279*Phe+0.01983*His-0.05513*Trp | 0.7795 |
| 99 | -1.13655+0.00620*Ala-0.10846*Met+0.03933*Ile-0.05728*Leu+0.03669*Phe | 0.7794 |
| 100 | -1.85679+0.01040*Ala-0.03139*Leu+0.03854*His-0.04544*Trp | 0.7793 |

FIG. 101

| No | Formula | ROC_AUC |
|---|---|---|
| 101 | −0.65185+0.05875*Asn+0.01026*Ala−0.01373*Val−0.06501*Trp | 0.7787 |
| 102 | −0.36243+0.00723*Ala−0.09049*Met+0.04109*Ile−0.04787*Leu+0.04399*Phe−0.05584*Trp | 0.7780 |
| 103 | −2.32030+0.06970*Asn+0.00920*Ala−0.03246*Cit−0.16483*Met | 0.7777 |
| 104 | −3.06081+0.04967*Asn+0.00655*Ala−0.14493*Met−0.04065*Leu+0.03326*Phe+0.00751*Lys | 0.7771 |
| 105 | −4.10351+0.07579*Asn+0.01365*Glu+0.00878*Ala−0.16672*Met | 0.7768 |
| 106 | −0.61018+0.01090*Ala−0.11364*Met+0.02651*Ile−0.04032*Leu+0.00634*Lys | 0.7768 |
| 107 | −1.90692+0.05788*Asn+0.00695*Ala−0.01273*Val−0.14040*Met | 0.7768 |
| 108 | 0.54479+0.01084*Ala−0.01095*Val+0.03144*Ile−0.03056*Leu−0.04944*Trp+0.00537*Lys | 0.7766 |
| 109 | −1.99281+0.05459*Asn+0.00712*Ala−0.12642*Met−0.03164*Leu+0.01018*Orn | 0.7765 |
| 110 | 1.29151+0.01202*Ala−0.01315*Val−0.11232*Met+0.01983*Ile−0.05906*Trp+0.00625*Lys | 0.7761 |
| 111 | 0.16876+0.01120*Ala−0.10629*Met+0.02594*Ile−0.03823*Leu | 0.7751 |
| 112 | −2.49729+0.05073*Asn+0.00700*Ala−0.13610*Met−0.03318*Leu+0.00844*Lys | 0.7747 |
| 113 | −1.61495+0.00659*Ala−0.11855*Met+0.04134*Ile−0.05442*Leu+0.01196*Lys | 0.7741 |
| 114 | −2.63168+0.04180*Asn+0.01735*Glu+0.00578*Ala−0.03509*Leu+0.03804*Phe−0.06681*Trp | 0.7740 |
| 115 | −0.96690+0.00854*Ser+0.00804*Ala−0.09251*Met−0.02898*Leu+0.04478*Phe−0.05582*Trp | 0.7732 |
| 116 | 0.78049+0.00749*Ala−0.10533*Met+0.04354*Ile−0.04381*Leu−0.05316*Trp+0.01315*Lys | 0.7713 |
| 117 | −2.16272+0.05041*Asn+0.00670*Ala+0.02384*Cit−0.13470*Met+0.03474*Ile−0.04766*Leu | 0.7713 |
| 118 | 0.38838+0.00826*Ala−0.00567*Val−0.08101*Met−0.02242*Leu+0.04176*Phe−0.05664*Trp | 0.7710 |
| 119 | −2.13130+0.03048*Asn+0.00560*Ala+0.03630*Ile−0.04815*Leu+0.03518*Phe−0.06524*Trp | 0.7707 |
| 120 | −0.47889+0.01076*Glu+0.00756*Ala−0.07719*Met−0.03149*Leu+0.04531*Phe−0.05624*Trp | 0.7707 |
| 121 | 0.32913+0.00697*Ala−0.00765*Val−0.09332*Met+0.04310*Ile−0.04293*Leu | 0.7695 |
| 122 | −0.47632+0.00453*Pro+0.00725*Ala−0.08893*Met−0.02988*Leu+0.04502*Phe−0.05555*Trp | 0.7694 |
| 123 | −2.14807+0.00683*Ala−0.12155*Met−0.04120*Leu+0.03449*Phe+0.01042*Lys | 0.7691 |
| 124 | −3.28864+0.06879*Asn+0.00940*Ala−0.17019*Met | 0.7688 |
| 125 | −0.43957+0.00651*Ala−0.00825*Val+0.04227*Ile−0.04135*Leu+0.03525*Phe−0.06379*Trp | 0.7670 |

FIG. 101 (Continued)

| No | Formula | ROC_AUC |
|---|---|---|
| 126 | −0.53065+0.00787*Ala+0.03446*ABA−0.09015*Met−0.03097*Leu+0.04351*Phe−0.05573*Trp | 0.7663 |
| 127 | −0.24549+0.00030*Gly+0.00792*Ala−0.08430*Met−0.02868*Leu+0.04343*Phe−0.05544*Trp | 0.7654 |
| 128 | −0.22039+0.00008*Gln+0.00792*Ala−0.08393*Met−0.02879*Leu+0.04336*Phe−0.05540*Trp | 0.7641 |
| 129 | 0.40956+0.01173*Ala−0.10218*Met−0.02740*Leu | 0.7636 |
| 130 | −0.59699+0.00814*Ala−0.09164*Met−0.02937*Leu+0.04222*Phe−0.05634*Trp+0.01388*Orn | 0.7634 |
| 131 | −3.07253+0.00923*Ala−0.03995*Leu+0.03808*His | 0.7631 |
| 132 | −1.22543+0.00787*Ala−0.10460*Met−0.03168*Leu+0.04122*Phe−0.05816*Trp+0.01117*Lys | 0.7627 |
| 133 | −1.53271+0.01330*Glu+0.00566*Ala+0.03838*Ile−0.05199*Leu+0.04025*Phe−0.06319*Trp | 0.7623 |
| 134 | −4.10033+0.05439*Asn+0.00587*Ala−0.15107*Met | 0.7620 |
| 135 | −0.67394+0.00678*Ala−0.01007*Val+0.04545*Ile−0.03801*Leu−0.06096*Trp+0.00976*Lys | 0.7610 |
| 136 | −0.40870+0.00750*Ala−0.10084*Met−0.02986*Leu+0.01793*Tyr+0.04109*Phe−0.05878*Trp | 0.7608 |
| 137 | −1.45754+0.05567*Asn−0.11442*Met+0.04368*Ile−0.05729*Leu+0.03954*Phe | 0.7605 |
| 138 | −0.94080+0.00694*Ala−0.00830*Val−0.11720*Met+0.04518*Ile−0.04795*Leu+0.01244*Lys | 0.7603 |
| 139 | −0.51969+0.00646*Ala−0.00642*Val−0.10564*Met+0.04213*Ile−0.05133*Leu+0.03411*Phe | 0.7598 |
| 140 | −0.59754+0.00784*Ala−0.09223*Met−0.02911*Leu+0.04381*Phe−0.05494*Trp+0.00677*Arg | 0.7597 |
| 141 | 1.04344+0.01105*Ala−0.01204*Val−0.05972*Trp | 0.7592 |
| 142 | 0.53978+0.01167*Ala−0.10900*Met−0.05330*Trp | 0.7588 |
| 143 | 0.16981+0.01115*Ala−0.02505*Leu−0.04403*Trp | 0.7585 |
| 144 | −1.41418+0.03802*Asn+0.00662*Ala−0.02444*Leu−0.05679*Trp | 0.7585 |
| 145 | 0.22321+0.08833*Asn−0.08743*Met+0.03893*Ile−0.03092*Leu−0.03102*Trp | 0.7581 |
| 146 | −1.01790+0.00673*Ala−0.02486*Leu+0.01483*His−0.05467*Trp | 0.7580 |
| 147 | −1.78070+0.00665*Ala−0.12024*Met+0.04022*Ile−0.05433*Leu+0.00591*Orn+0.01165*Lys | 0.7577 |
| 148 | 0.67675+0.00823*Ala−0.07369*Met−0.01950*Leu−0.04892*Trp | 0.7564 |
| 149 | −0.34144+0.00668*Ala−0.09514*Met+0.03950*Ile−0.04917*Leu | 0.7561 |
| 150 | −2.14360+0.00580*Ala+0.03980*Ile−0.05236*Leu+0.03580*Phe−0.06550*Trp+0.00757*Lys | 0.7558 |

FIG. 102

| No | Formula | ROC AUC |
|---|---|---|
| 151 | −1.31836+0.00628*Ala−0.11135*Met+0.03796*Ile−0.05696*Leu+0.03577*Phe+0.00647*Orn | 0.7550 |
| 152 | −2.22495+0.00612*Ala−0.12808*Met+0.04079*Ile−0.06133*Leu+0.03378*Phe+0.01088*Lys | 0.7550 |
| 153 | −1.84127+0.00619*Ala−0.12982*Met+0.04112*Ile−0.05598*Leu+0.01298*Tyr+0.01159*Lys | 0.7547 |
| 154 | −0.27677+0.00730*Ala−0.08864*Met−0.02977*Leu | 0.7539 |
| 155 | −0.41635+0.00641*Ala+0.03873*Ile−0.04149*Leu−0.05469*Trp | 0.7536 |
| 156 | −0.76464+0.00746*Ala−0.09508*Met−0.03141*Leu+0.01482*Orn | 0.7530 |
| 157 | −1.41816−0.00328*Thr+0.00670*Ala−0.11455*Met+0.04191*Ile−0.05500*Leu+0.01221*Lys | 0.7524 |
| 158 | −2.68061+0.04835*Asn+0.00917*Ala−0.03566*Leu | 0.7520 |
| 159 | −1.72390+0.01788*Glu+0.00956*Ala+0.02151*ABA−0.03730*Leu | 0.7516 |
| 160 | 0.52295+0.00965*Ala−0.04235*Cit−0.06675*Trp | 0.7514 |
| 161 | −1.47729+0.05142*Asn−0.11408*Met+0.04616*Ile−0.05226*Leu+0.00954*Lys | 0.7498 |
| 162 | −1.08374+0.00685*Ala−0.10199*Met−0.03802*Leu+0.03674*Phe | 0.7494 |
| 163 | −0.79824+0.08190*Asn−0.10133*Met+0.03614*Ile−0.03955*Leu+0.01625*Phe | 0.7488 |
| 164 | 0.33652+0.08832*Asn−0.00851*Val−0.09502*Met+0.04228*Ile−0.03070*Leu | 0.7483 |
| 165 | −0.82775+0.00826*Ala+0.02269*Cit−0.09368*Met−0.02923*Leu+0.04087*Phe−0.05085*Trp | 0.7481 |
| 166 | −1.05164+0.07943*Asn−0.10178*Met+0.03647*Ile−0.03773*Leu+0.00573*Lys | 0.7466 |
| 167 | −0.62382+0.08320*Asn−0.10402*Met+0.03655*Ile−0.03702*Leu+0.00754*Tyr | 0.7464 |
| 168 | −1.07375+0.00678*Ala−0.03076*Leu+0.03767*Phe−0.06182*Trp | 0.7446 |
| 169 | −0.46637+0.08417*Asn−0.09576*Met+0.03673*Ile−0.03606*Leu | 0.7443 |
| 170 | −1.50492+0.00730*Ala−0.11158*Met−0.03375*Leu+0.01139*Lys | 0.7435 |
| 171 | 0.23273+0.00750*Ala−0.01113*Val−0.06539*Trp | 0.7423 |
| 172 | −0.65367+0.05698*Asn−0.09473*Met+0.04591*Ile−0.04904*Leu+0.04607*Phe−0.04844*Trp | 0.7421 |
| 173 | −0.20739+0.00715*Ala−0.02311*Leu−0.05393*Trp | 0.7385 |
| 174 | −0.21531+0.00781*Ala−0.08851*Met−0.06367*Trp | 0.7383 |
| 175 | −1.22462+0.00697*Ala−0.02633*Leu−0.05702*Trp+0.00805*Lys | 0.7373 |

FIG. 102 (Continued)

| No | Formula | ROC_AUC |
|---|---|---|
| 176 | -1.70795+0.01140*Glu+0.00560*Ala-0.03733*Leu | 0.7350 |
| 177 | -2.75163+0.03322*Asn+0.00590*Ala-0.07535*Trp | 0.7334 |
| 178 | -0.40038+0.00716*Ala-0.01228*Val-0.10564*Met | 0.7325 |
| 179 | -0.60906+0.05768*Asn-0.09786*Met+0.04410*Ile-0.04804*Leu | 0.7318 |
| 180 | -1.66854+0.00521*Ala+0.03637*Ile-0.05350*Leu | 0.7313 |
| 181 | -2.18972+0.04982*Asn-0.12681*Met+0.04531*Ile-0.06063*Leu+0.03778*Phe+0.00848*Lys | 0.7287 |
| 182 | -0.04153+0.08423*Asn-0.09091*Met-0.03710*Trp | 0.7281 |
| 183 | -0.05358+0.08263*Asn-0.08637*Met-0.01902*Leu | 0.7202 |
| 184 | -0.47586+0.05930*Asn-0.08714*Met-0.02598*Leu | 0.7169 |
| 185 | -2.32368+0.00546*Ala-0.04115*Leu+0.02615*Phe | 0.7165 |
| 186 | -1.38886+0.06571*Asn-0.03315*Ile-0.04154*Leu | 0.7135 |
| 187 | -0.47735-0.08374*Met+0.05080*Ile-0.05457*Leu+0.04596*Phe-0.04974*Trp+0.01228*Lys | 0.7041 |
| 188 | -1.66247+0.03782*Asn+0.04020*Ile-0.05231*Leu | 0.6984 |
| 189 | -0.44043-0.08621*Met+0.04758*Ile-0.05314*Leu+0.01224*Lys | 0.6895 |
| 190 | 0.72189+0.03705*Ile-0.03494*Leu-0.03160*Trp+0.00866*Lys | 0.6893 |
| 191 | 0.70034-0.06438*Met+0.03758*Ile-0.03745*Leu+0.00951*Lys | 0.6886 |
| 192 | 1.32107+0.03633*Ile-0.03664*Leu+0.02471*Phe-0.03390*Trp | 0.6851 |
| 193 | 0.77856-0.00692*Val+0.04009*Ile-0.03679*Leu+0.00719*Lys | 0.6834 |
| 194 | -0.44371+0.03470*Ile-0.04467*Leu+0.01395*Phe+0.00706*Lys | 0.6809 |
| 195 | -0.07353+0.03530*Ile-0.04112*Leu+0.00740*Lys | 0.6805 |
| 196 | -1.43528+0.04336*Ile-0.05575*Leu+0.00826*Lys | 0.6793 |
| 197 | 1.89724+0.03724*Ile-0.03144*Leu-0.02829*Trp | 0.6785 |
| 198 | 0.83417-0.06031*Met+0.04511*Ile-0.04731*Leu | 0.6776 |
| 199 | 1.90866-0.05137*Met+0.03753*Ile-0.03402*Leu | 0.6757 |
| 200 | 0.52664+0.03498*Ile-0.04164*Leu+0.01581*Phe | 0.6703 |

FIG. 104

| No | Formula | ROC_AUC |
|----|---------|---------|
| 1 | 1.00630+0.07789*Asn+0.01247*Ala-0.01035*Val-0.14326*Met-0.05306*Trp | 0.8379 |
| 2 | 0.55775+0.07798*Asn+0.01149*Ala-0.03709*Cit-0.14632*Met-0.05887*Trp | 0.8341 |
| 3 | 0.14539+0.07324*Asn+0.01242*Ala-0.13649*Met-0.01812*Leu-0.04335*Trp | 0.8312 |
| 4 | -1.88344+0.07684*Asn+0.02152*Glu+0.01116*Ala-0.12853*Met-0.03057*Leu | 0.8305 |
| 5 | -1.08023+0.06685*Asn+0.01118*Ala-0.14651*Met+0.02620*Ile-0.03659*Leu | 0.8303 |
| 6 | -1.87342+0.07189*Asn+0.00728*Gly+0.01169*Ala-0.16161*Met-0.05587*Trp | 0.8298 |
| 7 | -1.39255+0.07947*Asn+0.01422*Glu+0.01115*Ala-0.15196*Met-0.05448*Trp | 0.8297 |
| 8 | 0.18437+0.08163*Asn+0.01210*Ala-0.14117*Met-0.05596*Trp-0.01598*Arg | 0.8284 |
| 9 | -1.47271+0.01079*Ala-0.13047*Met+0.03096*Ile-0.04491*Leu+0.04722*His | 0.8272 |
| 10 | -2.05510+0.05528*Asn+0.01106*Ala-0.15131*Met-0.03051*Leu+0.03482*His | 0.8266 |
| 11 | -0.85057+0.07411*Asn+0.01151*Ala-0.16321*Met+0.01301*Phe-0.05935*Trp | 0.8245 |
| 12 | 0.15837+0.08591*Asn+0.01994*Glu+0.01194*Ala-0.01250*Val-0.13483*Met-0.05252*Trp | 0.8219 |
| 13 | 2.19576+0.08180*Asn+0.01232*Ala-0.03832*Cit-0.01060*Val-0.13287*Met-0.05740*Trp | 0.8209 |
| 14 | -0.81838+0.08011*Asn+0.01964*Glu+0.01194*Ala-0.12548*Met-0.02305*Leu-0.04007*Trp | 0.8154 |
| 15 | -0.98444+0.05989*Asn+0.01186*Ala-0.14662*Met-0.02288*Leu+0.03371*His-0.04226*Trp | 0.8149 |
| 16 | 1.80213+0.08559*Asn+0.01294*Ala-0.01052*Val-0.12755*Met-0.05441*Trp-0.01661*Arg | 0.8146 |
| 17 | -0.02829+0.07113*Asn+0.01199*Ala-0.14197*Met+0.02563*Ile-0.02877*Leu-0.04284*Trp | 0.8144 |
| 18 | -1.11143+0.08070*Asn+0.02379*Glu+0.01137*Ala-0.00840*Val-0.12570*Met-0.02384*Leu | 0.8144 |
| 19 | 1.58465+0.01252*Ala-0.09726*Met+0.02817*Ile-0.03057*Leu-0.03830*Trp | 0.8142 |
| 20 | -0.82660+0.07560*Asn+0.00815*Gly+0.01152*Ala-0.04010*Cit-0.15172*Met-0.06060*Trp | 0.8140 |
| 21 | 1.33787+0.01292*Ala-0.10090*Met-0.02491*Leu+0.03129*Phe-0.04634*Trp | 0.8133 |
| 22 | -2.30898+0.05209*Asn+0.01055*Ala-0.15804*Met+0.02861*Ile-0.04260*Leu+0.03708*His | 0.8132 |
| 23 | -0.41725+0.06820*Asn+0.01091*Ala-0.03748*Cit-0.15768*Met+0.02532*His-0.06033*Trp | 0.8131 |
| 24 | 1.23281+0.07690*Asn+0.01225*Ala-0.03655*Cit-0.12718*Met-0.01784*Leu-0.04770*Trp | 0.8131 |
| 25 | 0.97882+0.07772*Asn+0.01201*Ala-0.01316*Val-0.15289*Met+0.01978*Ile-0.05736*Trp | 0.8130 |

FIG. 104 (Continued)

| No | Formula | ROC_AUC |
|---|---|---|
| 26 | −0.30702+0.07250*Asn+0.01233*Ala−0.14666*Met−0.02388*Leu+0.02991*Phe−0.05059*Trp | 0.8130 |
| 27 | −0.17074+0.07569*Asn+0.00577*Gly+0.01243*Ala−0.00947*Val−0.14874*Met−0.05417*Trp | 0.8129 |
| 28 | 0.01346+0.06737*Asn+0.01189*Ala−0.01091*Val−0.15508*Met+0.02763*His−0.05451*Trp | 0.8128 |
| 29 | 0.65704+0.07750*Asn+0.00565*Pro+0.01169*Ala−0.01078*Val−0.14839*Met−0.05270*Trp | 0.8127 |
| 30 | −0.58676+0.07870*Asn−0.00401*Gln+0.00983*Gly+0.01177*Ala−0.15844*Met−0.05484*Trp | 0.8126 |
| 31 | −3.12397+0.06283*Asn+0.02249*Glu+0.01055*Ala−0.13883*Met−0.03573*Leu+0.03656*His | 0.8122 |
| 32 | 0.67755+0.07781*Asn+0.01231*Ala−0.01077*Val−0.15227*Met+0.01739*Phe−0.05929*Trp | 0.8122 |
| 33 | 2.00339+0.08240*Asn−0.00245*Gln+0.01247*Ala−0.00989*Val−0.14072*Met−0.05224*Trp | 0.8122 |
| 34 | −0.24178−0.08191*Asn+0.01177*Glu+0.01109*Ala−0.03350*Cit−0.14386*Met−0.05834*Trp | 0.8120 |
| 35 | −1.99116−0.07453*Asn+0.02053*Glu+0.01078*Ala−0.13422*Met+0.02418*Ile−0.04031*Leu | 0.8119 |
| 36 | −3.42260−0.07536*Asn+0.02411*Glu+0.00701*Gly+0.01099*Ala−0.13515*Met−0.02928*Leu | 0.8119 |
| 37 | −1.02627+0.07137*Asn+0.00604*Gly+0.01237*Ala−0.14326*Met−0.01611*Leu−0.04563*Trp | 0.8115 |
| 38 | 0.77214+0.07525*Asn+0.01248*Ala+0.02867*ABA−0.01107*Val−0.14555*Met−0.05429*Trp | 0.8114 |
| 39 | −0.19409+0.06960*Asn+0.01136*Ala−0.008884*Val−0.14607*Met+0.03163*Ile−0.03122*Leu | 0.8113 |
| 40 | 1.08476+0.07654*Asn+0.01274*Ala−0.00819*Val−0.13465*Met−0.01045*Leu−0.04688*Trp | 0.8111 |
| 41 | 0.96699+0.07754*Asn+0.01242*Ala−0.01046*Val−0.14591*Met+0.00272*Tyr−0.05350*Trp | 0.8100 |
| 42 | −2.02484+0.06527*Asn+0.00466*Gly+0.01111*Ala−0.15182*Met+0.02576*Ile−0.03517*Leu | 0.8088 |
| 43 | 0.94989+0.07753*Asn+0.01249*Ala−0.01045*Val−0.14399*Met−0.05322*Trp+0.00210*Orn | 0.8085 |
| 44 | 1.20053−0.00337*Ser+0.08126*Asn+0.01249*Ala−0.01029*Val−0.14294*Met−0.05332*Trp | 0.8084 |
| 45 | 0.80465+0.07689*Asn+0.01236*Ala−0.01039*Val−0.14549*Met−0.05370*Trp+0.00194*Lys | 0.8082 |
| 46 | −1.39657+0.06614*Asn+0.01107*Ala−0.15196*Met+0.02587*Ile−0.04002*Leu+0.01512*Phe | 0.8081 |
| 47 | 1.43510+0.04978*Asn+0.01036*Ala−0.11386*Met+0.03072*Ile−0.03100*Leu−0.05299*Trp | 0.8072 |
| 48 | −0.20145+0.07129*Asn+0.01226*Ala−0.13964*Met−0.01913*Leu−0.04393*Trp+0.00361*Lys | 0.8069 |
| 49 | −2.26979−0.07159*Asn+0.00756*Gly+0.01152*Ala−0.17020*Met+0.01527*Phe−0.06145*Trp | 0.8061 |
| 50 | −0.76993−0.00532*Ser+0.07211*Asn+0.01120*Ala−0.14602*Met+0.02695*Ile−0.03702*Leu | 0.8050 |

FIG. 105

| No | Formula | ROC_AUC |
|---|---|---|
| 51 | 1.46297+0.04843*Asn+0.00892*Ala-0.00874*Val-0.12718*Met+0.03537*Ile-0.03483*Leu | 0.8043 |
| 52 | -1.28717+0.06501*Asn+0.01116*Ala+0.01763*ABA-0.14802*Met+0.02589*Ile-0.03697*Leu | 0.8043 |
| 53 | -1.40097+0.06505*Asn+0.01102*Ala-0.14940*Met+0.02647*Ile-0.03768*Leu+0.00319*Lys | 0.8041 |
| 54 | 1.85039+0.01104*Ala-0.00960*Val+0.03038*Ile-0.02873*Leu-0.04564*Trp | 0.8040 |
| 55 | 0.80692+0.05334*Asn+0.01057*Ala-0.13299*Met-0.02664*Leu-0.05203*Phe-0.06523*Trp | 0.8040 |
| 56 | -1.08175+0.06684*Asn+0.01118*Ala-0.14658*Met+0.02620*Ile-0.03660*Leu+0.00008*Tyr | 0.8038 |
| 57 | 2.50117-0.05256*Asn+0.01031*Ala-0.01235*Val-0.12701*Met+0.01805*Ile-0.06374*Trp | 0.8028 |
| 58 | 1.70822+0.05459*Asn+0.01037*Ala-0.00995*Val-0.14151*Met+0.03635*Phe-0.07258*Trp | 0.8025 |
| 59 | 1.89066+0.01104*Ala-0.09033*Met-0.02706*Leu+0.05179*Phe-0.06430*Trp | 0.8001 |
| 60 | 0.17406+0.04609*Asn+0.00890*Ala-0.13103*Met+0.03059*Ile-0.04098*Leu+0.00890*Orn | 0.7990 |
| 61 | 0.80619-0.00615*Ser+0.05387*Asn+0.00874*Ala-0.12513*Met+0.03202*Ile-0.04126*Leu | 0.7984 |
| 62 | -0.44651+0.04822*Asn+0.00852*Ala-0.14663*Met+0.03316*Ile-0.05063*Leu+0.04001*Phe | 0.7977 |
| 63 | 0.66251-0.00712*Thr+0.05528*Asn+0.00907*Ala-0.12072*Met+0.03093*Ile-0.04092*Leu | 0.7977 |
| 64 | 1.12022+0.01244*Ala-0.10774*Met+0.02739*Ile-0.03602*Leu+0.03002*Phe-0.04563*Trp | 0.7972 |
| 65 | -0.55664+0.07429*Asn+0.01165*Ala-0.15608*Met-0.05463*Trp | 0.7969 |
| 66 | 0.77301+0.00914*Ala+0.03164*Ile-0.04552*Leu+0.04423*Phe-0.06763*Trp | 0.7953 |
| 67 | 0.61301+0.04785*Asn+0.01015*Ala-0.01064*Val+0.02812*Ile-0.02828*Leu-0.05022*Trp | 0.7944 |
| 68 | -0.09807+0.00711*Gly+0.01284*Ala-0.11043*Met-0.02262*Leu+0.03177*Phe-0.04928*Trp | 0.7938 |
| 69 | 1.49934+0.01081*Ala-0.09836*Met+0.03521*Ile-0.04332*Leu+0.05367*Phe-0.06409*Trp | 0.7935 |
| 70 | 0.24559+0.00669*Gly+0.01246*Ala-0.10588*Met+0.02744*Ile-0.02802*Leu-0.04097*Trp | 0.7935 |
| 71 | 0.65699+0.05159*Asn+0.00892*Ala-0.12298*Met-0.02677*Leu | 0.7935 |
| 72 | 0.55046+0.05193*Asn+0.00882*Ala-0.00522*Val-0.14055*Met-0.03005*Leu+0.03554*Phe | 0.7932 |
| 73 | 0.12741+0.05447*Asn+0.00990*Ala-0.15035*Met+0.03530*Phe-0.07804*Trp | 0.7930 |
| 74 | 1.68467+0.05297*Asn+0.01052*Ala-0.11010*Met-0.01709*Leu-0.05359*Trp | 0.7928 |
| 75 | -0.91535+0.06896*Asn+0.01162*Ala-0.14097*Met-0.02580*Leu | 0.7927 |

FIG. 105 (Continued)

| No | Formula | ROC_AUC |
|---|---|---|
| 76 | 1.07181+0.01057*Ala−0.10278*Met−0.02907*Leu+0.04978*Phe+0.02040*His−0.06375*Trp | 0.7925 |
| 77 | 0.81221+0.04777*Asn+0.01028*Ala−0.12036*Met−0.02125*Leu−0.05618*Trp+0.01052*Lys | 0.7923 |
| 78 | 2.65939+0.01281*Ala−0.00907*Val−0.09439*Met+0.03380*Ile−0.02445*Leu−0.04190*Trp | 0.7922 |
| 79 | 1.82070+0.04973*Asn+0.01025*Ala−0.01067*Val−0.13030*Met−0.06404*Trp+0.00897*Lys | 0.7922 |
| 80 | −0.47208+0.04317*Asn+0.00845*Ala−0.13717*Met+0.03333*Ile−0.04612*Leu+0.00993*Lys | 0.7919 |
| 81 | 0.64517+0.02077*Glu+0.00921*Ala−0.03750*Leu+0.04922*Phe−0.06610*Trp | 0.7918 |
| 82 | 0.56148+0.02331*Asn+0.00894*Ala−0.03117*Leu+0.04157*Phe−0.06864*Trp | 0.7902 |
| 83 | 0.15445+0.04563*Asn+0.00887*Ala+0.01498*Cit−0.13139*Met+0.02901*Ile−0.03953*Leu | 0.7899 |
| 84 | 0.30302+0.00903*Ala−0.03434*Leu+0.04165*Phe−0.07004*Trp+0.00856*Lys | 0.7898 |
| 85 | 2.54600+0.05397*Asn+0.01051*Ala−0.00965*Val−0.11880*Met−0.05993*Trp | 0.7896 |
| 86 | 0.85777+0.01218*Ala−0.10548*Met+0.02860*Ile−0.03256*Leu−0.03960*Trp+0.00666*Lys | 0.7893 |
| 87 | −0.37839+0.04929*Asn+0.00883*Ala−0.14584*Met−0.03558*Leu+0.03727*Phe+0.00893*Orn | 0.7885 |
| 88 | 2.12428+0.01318*Ala−0.00612*Val−0.09732*Met−0.01886*Leu+0.02952*Phe−0.04840*Trp | 0.7880 |
| 89 | 0.69339+0.00910*Ala−0.03195*Leu+0.04152*Phe+0.01086*His−0.06751*Trp | 0.7880 |
| 90 | −1.14090+0.01136*Ala−0.12132*Met−0.03191*Leu+0.04544*His | 0.7877 |
| 91 | 1.46718−0.00745*Pro+0.01016*Ala−0.10288*Met−0.02981*Leu+0.05365*Phe−0.06227*Trp | 0.7875 |
| 92 | 0.98731+0.05387*Asn+0.01005*Ala−0.12803*Met−0.06559*Trp | 0.7874 |
| 93 | −0.77332+0.07282*Asn+0.01096*Ala−0.01092*Val−0.16010*Met | 0.7874 |
| 94 | 0.64388+0.01259*Ala−0.10869*Met−0.02666*Leu+0.03135*Phe−0.04760*Trp+0.00638*Lys | 0.7873 |
| 95 | 0.90408+0.00939*Ala+0.01721*ABA−0.03141*Leu+0.04234*Phe−0.06679*Trp | 0.7872 |
| 96 | 1.35605+0.01796*Glu+0.01065*Ala−0.08129*Met−0.03337*Leu+0.05611*Phe−0.06337*Trp | 0.7864 |
| 97 | 0.07969−0.00580*Thr+0.05725*Asn+0.00895*Ala−0.13630*Met−0.03519*Leu+0.03673*Phe | 0.7858 |
| 98 | 1.47880+0.01086*Ala−0.00926*Val+0.02946*Ile−0.03247*Leu+0.01766*Phe−0.05005*Trp | 0.7847 |
| 99 | −0.39696+0.03520*Asn+0.02487*Glu+0.00836*Ala−0.03970*Leu+0.04789*Phe−0.06744*Trp | 0.7846 |
| 100 | 2.52103+0.01114*Ala−0.00469*Val−0.08902*Met−0.02237*Leu+0.04934*Phe−0.06398*Trp | 0.7844 |

FIG. 106

| No | Formula | ROC_AUC |
|---|---|---|
| 101 | 1.41418+0.00539*Ser+0.01099*Ala-0.09626*Met-0.02722*Leu+0.05285*Phe-0.06402*Trp | 0.7841 |
| 102 | 1.19043+0.01040*Ala-0.09284*Met+0.03517*Ile-0.03853*Leu-0.05539*Trp+0.01298*Lys | 0.7838 |
| 103 | -0.87967+0.04737*Asn+0.00843*Ala-0.15021*Met-0.03887*Leu+0.03728*Phe+0.00853*Lys | 0.7838 |
| 104 | -0.15135+0.05164*Asn+0.00869*Ala-0.14184*Met-0.03532*Leu+0.03820*Phe | 0.7831 |
| 105 | 0.74275+0.01164*Ala-0.00754*Val-0.10877*Met+0.03362*Ile-0.03478*Leu+0.00542*Lys | 0.7823 |
| 106 | 0.41306+0.04834*Asn+0.00876*Ala-0.12668*Met+0.03148*Ile-0.04091*Leu | 0.7821 |
| 107 | -0.48064+0.01132*Ala-0.11769*Met+0.02853*Ile-0.04329*Leu+0.01709*Phe+0.00572*Lys | 0.7817 |
| 108 | 0.52051+0.00895*Ala-0.10846*Met+0.03547*Ile-0.05196*Leu+0.04009*Phe | 0.7817 |
| 109 | 1.20081+0.05291*Asn+0.00829*Ala-0.01231*Val-0.14499*Met | 0.7812 |
| 110 | 1.80518+0.00146*Thr+0.01096*Ala-0.09284*Met-0.02707*Leu+0.05219*Phe-0.06442*Trp | 0.7806 |
| 111 | 1.55299+0.01099*Ala+0.02226*ABA-0.09302*Met-0.02797*Leu+0.05090*Phe-0.06321*Trp | 0.7804 |
| 112 | 1.71066+0.00087*Gly+0.01104*Ala-0.09188*Met-0.02677*Leu+0.05193*Phe-0.06461*Trp | 0.7800 |
| 113 | 0.28138+0.01920*Asn+0.00872*Ala+0.03017*Ile-0.04528*Leu+0.04281*Phe-0.06852*Trp | 0.7799 |
| 114 | 1.69142+0.00930*Ala-0.00701*Val+0.03467*Ile-0.03986*Leu+0.04084*Phe-0.06709*Trp | 0.7798 |
| 115 | 0.80198+0.01071*Ala-0.10625*Met-0.03156*Leu+0.05112*Phe-0.06716*Trp+0.01183*Lys | 0.7797 |
| 116 | -0.72131+0.01016*Ala-0.03094*Leu+0.03499*His-0.04253*Trp | 0.7795 |
| 117 | 1.44229+0.00910*Ala-0.00705*Val-0.10709*Met+0.03847*Ile-0.04623*Leu+0.03667*Phe | 0.7788 |
| 118 | 0.39877+0.04989*Asn+0.00989*Ala-0.01264*Val-0.06139*Trp | 0.7780 |
| 119 | -0.62175+0.01129*Ala-0.13492*Met+0.03652*His-0.05325*Trp | 0.7776 |
| 120 | 1.52042+0.01116*Ala-0.09811*Met-0.02749*Leu+0.05039*Phe-0.06342*Trp+0.01157*Orn | 0.7776 |
| 121 | -1.73023+0.07140*Asn+0.00982*Ala-0.02883*Cit-0.16768*Met | 0.7773 |
| 122 | 1.65011+0.00056*Gln+0.01100*Ala-0.09173*Met-0.02730*Leu+0.05194*Phe-0.06456*Trp | 0.7772 |
| 123 | 1.29767+0.07871*Asn-0.09144*Met+0.03307*Ile-0.02404*Leu-0.03065*Trp | 0.7767 |
| 124 | 1.62096+0.01085*Ala-0.09879*Met-0.02685*Leu+0.05127*Phe-0.06493*Trp+0.00635*Arg | 0.7766 |
| 125 | 0.25940+0.02027*Glu+0.00889*Ala+0.03089*Ile-0.05188*Leu+0.05005*Phe-0.06621*Trp | 0.7764 |

FIG. 106 (Continued)

| No | Formula | ROC_AUC |
|---|---|---|
| 126 | 0.55087+0.01177*Ala−0.10377*Met+0.02855*Ile−0.03751*Leu | 0.7745 |
| 127 | 0.24184+0.00878*Ala−0.10522*Met+0.03565*Ile−0.04808*Leu+0.01147*Lys | 0.7743 |
| 128 | 1.58770+0.01051*Ala−0.11253*Met−0.02870*Leu+0.02158*Tyr+0.04919*Phe−0.06642*Trp | 0.7741 |
| 129 | 1.38425+0.00919*Ala−0.08837*Met+0.03379*Ile−0.04223*Leu | 0.7735 |
| 130 | −0.13212+0.04708*Asn+0.00864*Ala−0.13229*Met−0.03073*Leu+0.00900*Lys | 0.7723 |
| 131 | 1.30066+0.00893*Ala−0.00910*Val−0.10621*Met+0.03976*Ile−0.04193*Leu+0.01184*Lys | 0.7720 |
| 132 | −0.55406+0.00856*Ala−0.12410*Met+0.03721*Ile−0.05732*Leu+0.03899*Phe+0.01103*Lys | 0.7715 |
| 133 | 0.19640+0.00910*Ala−0.11540*Met+0.03420*Ile−0.05167*Leu+0.03888*Phe+0.01096*Orn | 0.7708 |
| 134 | −0.13799+0.00895*Ala−0.11360*Met+0.03418*Ile−0.04795*Leu+0.01270*Orn+0.01121*Lys | 0.7692 |
| 135 | 1.32273+0.02727*Asn+0.00913*Ala−0.02263*Leu−0.05852*Trp | 0.7687 |
| 136 | 2.01402+0.01053*Ala−0.01096*Val−0.11208*Met+0.03315*Phe−0.07526*Trp+0.00941*Lys | 0.7687 |
| 137 | −0.06101+0.00882*Ala−0.11445*Met−0.03980*Leu+0.03706*Phe+0.01016*Lys | 0.7685 |
| 138 | −2.48053+0.06885*Asn+0.01005*Ala−0.17417*Met | 0.7682 |
| 139 | 2.75678+0.01099*Ala−0.06785*Met−0.01755*Leu−0.05272*Trp | 0.7672 |
| 140 | 1.71461+0.00946*Ala+0.03058*Ile−0.03577*Leu−0.05660*Trp | 0.7668 |
| 141 | −0.16892+0.00867*Ala+0.03261*Ile−0.04990*Leu+0.04258*Phe−0.07026*Trp+0.00906*Lys | 0.7667 |
| 142 | 0.02537+0.07417*Asn−0.10511*Met+0.03259*Ile−0.03461*Leu+0.02007*Phe | 0.7665 |
| 143 | 1.27027+0.07777*Asn−0.00781*Val−0.09613*Met+0.03802*Ile−0.02514*Leu | 0.7664 |
| 144 | 0.73175−0.00452*Ser+0.07970*Asn−0.09673*Met+0.03377*Ile−0.03033*Leu | 0.7664 |
| 145 | 0.28987+0.07380*Asn−0.10536*Met+0.03314*Ile−0.03111*Leu+0.00807*Tyr | 0.7653 |
| 146 | 1.45260+0.01108*Ala+0.01905*Cit−0.09947*Met−0.02671*Leu+0.05017*Phe−0.06219*Trp | 0.7647 |
| 147 | 4.83583−0.01283*Gly−0.00411*Ile−0.02495*Trp | 0.7634 |
| 148 | −1.92199+0.00919*Ala−0.03892*Leu+0.03457*His | 0.7628 |
| 149 | 0.78732+0.01226*Ala−0.09623*Met−0.02575*Leu | 0.7620 |
| 150 | 1.18139+0.00947*Ala−0.03062*Leu+0.04323*Phe−0.06756*Trp | 0.7616 |

FIG. 107

| No | Formula | ROC_AUC |
|---|---|---|
| 151 | 3.54323−0.01431*Gly+0.04832*Cit−0.00787*Lys | 0.7615 |
| 152 | −0.24857+0.07123*Asn−0.10474*Met+0.03348*Ile−0.03245*Leu+0.00663*Lys | 0.7614 |
| 153 | 0.91156+0.00917*Ala−0.10040*Met−0.03561*Leu+0.03816*Phe | 0.7610 |
| 154 | 1.12176+0.01222*Ala−0.10950*Met−0.05042*Trp | 0.7604 |
| 155 | 1.69779+0.01088*Ala−0.01130*Val−0.05631*Trp | 0.7596 |
| 156 | 0.17845+0.00906*Ala+0.01767*Cit−0.11591*Met+0.03235*Ile−0.04994*Leu+0.03884*Phe | 0.7591 |
| 157 | 1.30338+0.03640*Ile−0.04793*Leu+0.04533*Phe−0.05527*Trp+0.01164*Lys | 0.7589 |
| 158 | 1.22356+0.01037*Ala−0.10706*Met+0.03479*Phe−0.07729*Trp | 0.7588 |
| 159 | 0.95778+0.01124*Ala−0.02486*Leu−0.04205*Trp | 0.7586 |
| 160 | 1.05767+0.05468*Asn−0.11385*Met+0.03491*Ile−0.04625*Leu+0.04264*Phe | 0.7576 |
| 161 | 3.51511−0.01605*Gly+0.04887*Cit−0.01065*Leu | 0.7551 |
| 162 | 2.83086−0.01853*Asn−0.01503*Gly+0.05112*Cit | 0.7532 |
| 163 | 1.04849+0.00302*Gln−0.01774*Gly+0.04393*Cit | 0.7531 |
| 164 | 1.14680+0.00973*Ala−0.03993*Cit−0.06289*Trp | 0.7530 |
| 165 | −1.17153+0.02068*Glu+0.01012*Ala+0.0223*ABA−0.03706*Leu | 0.7522 |
| 166 | −1.55170+0.04110*Asn+0.00933*Ala−0.03482*Leu | 0.7511 |
| 167 | 1.08831+0.00927*Ala−0.02601*Leu−0.05993*Trp+0.00940*Lys | 0.7504 |
| 168 | 0.91220−0.08860*Met+0.03955*Ile−0.05396*Leu+0.04146*Phe+0.01281*Lys | 0.7483 |
| 169 | 0.92793+0.04874*Asn−0.10518*Met+0.03524*Ile−0.04199*Leu+0.01151*Lys | 0.7472 |
| 170 | 2.70224−0.01442*Gly+0.06092*Cit−0.02161*Orn | 0.7460 |
| 171 | 4.26734−0.01668*Gly+0.04631*Cit−0.00744*Val | 0.7452 |
| 172 | 0.46527+0.07522*Asn−0.09723*Met+0.03312*Ile−0.02998*Leu | 0.7449 |
| 173 | 3.23247+0.01678*Ser−0.01441*Glu−0.01841*Gly | 0.7417 |
| 174 | 3.14961−0.01577*Gly+0.05136*Cit−0.01417*Ile | 0.7400 |
| 175 | 2.02633+0.05705*Asn−0.10176*Met+0.03493*Ile−0.03890*Leu+0.05341*Phe−0.04885*Trp | 0.7392 |

FIG. 107 (Continued)

| No | Formula | ROC_AUC |
|---|---|---|
| 176 | 2.02101+0.05500*Asn-0.09156*Met+0.03317*Ile-0.03575*Leu | 0.7383 |
| 177 | 1.92692+0.04874*Asn-0.00837*Val-0.10548*Met+0.03906*Ile-0.03628*Leu+0.01188*Lys | 0.7313 |
| 178 | 1.04876+0.01470*Ser-0.01771*Gly+0.04812*Cit | 0.7282 |
| 179 | 1.14066+0.08212*Asn-0.09486*Met-0.03753*Trp | 0.7274 |
| 180 | 0.04087+0.04871*Asn-0.12624*Met+0.03684*Ile-0.05192*Leu+0.04144*Phe+0.01099*Lys | 0.7245 |
| 181 | 2.82259+0.01502*Ser-0.01554*Gly-0.00183*Ala | 0.7203 |
| 182 | 0.75272+0.07833*Asn-0.08770*Met-0.01586*Leu | 0.7200 |
| 183 | -0.21107+0.05371*Asn+0.02918*Ile-0.03638*Leu | 0.7139 |
| 184 | 1.81738-0.07635*Met+0.03994*Ile-0.04711*Leu+0.05260*Phe-0.05119*Trp+0.01438*Lys | 0.6997 |
| 185 | 5.47511-0.01443*Gly-0.00719*Val-0.00611*Orn | 0.6988 |
| 186 | 1.77311-0.00663*Val-0.08719*Met+0.04246*Ile-0.04866*Leu+0.03825*Phe+0.01314*Lys | 0.6892 |
| 187 | 1.52761+0.03357*Ile-0.03168*Leu-0.03035*Trp+0.00839*Lys | 0.6892 |
| 188 | 1.21589-0.06078*Met+0.03648*Ile-0.03417*Leu+0.00964*Lys | 0.6866 |
| 189 | 1.80020-0.06751*Met+0.03796*Ile-0.04403*Leu+0.01333*Lys | 0.6865 |
| 190 | 2.10250+0.03271*Ile-0.03379*Leu+0.02709*Phe-0.03479*Trp | 0.6857 |
| 191 | 1.46048-0.00668*Val+0.03751*Ile-0.03322*Leu+0.00711*Lys | 0.6841 |
| 192 | 2.06920-0.00832*Val-0.03866*Ile-0.04151*Leu+0.01087*Lys | 0.6819 |
| 193 | 0.26556+0.03230*Ile-0.04134*Leu+0.01489*Phe+0.00693*Lys | 0.6818 |
| 194 | 0.65589+0.03308*Ile-0.03761*Leu+0.00728*Lys | 0.6791 |
| 195 | 2.65634+0.03402*Ile-0.02824*Leu-0.02747*Trp | 0.6775 |
| 196 | 3.23281-0.01328*Gly-0.01662*Leu+0.02496*Tyr | 0.6774 |
| 197 | 0.22328+0.03536*Ile-0.05557*Leu+0.03188*Phe+0.00944*Lys | 0.6762 |
| 198 | 5.24536-0.01551*Gly-0.00841*Val-0.01577*Met | 0.6755 |
| 199 | 2.40443-0.04590*Met+0.03619*Ile-0.03063*Leu | 0.6740 |
| 200 | 1.22841+0.03263*Ile-0.03844*Leu+0.01659*Phe | 0.6695 |

| ROC_AUC | 0.8 | | 0.75 | | 0.7 | |
|---|---|---|---|---|---|---|
| RANK | AMINO ACID | FREQUENCY OF APPEARANCE | AMINO ACID | FREQUENCY OF APPEARANCE | AMINO ACID | FREQUENCY OF APPEARANCE |
| 1 | Ala | 213 | Ala | 7996 | Ala | 15131 |
| 2 | Met | 203 | Leu | 4324 | Asn | 11738 |
| 3 | Asn | 186 | Trp | 3898 | Leu | 11518 |
| 4 | Trp | 115 | Met | 3862 | His | 10530 |
| 5 | Leu | 106 | Asn | 3292 | Met | 10456 |
| 6 | His | 61 | His | 2701 | Trp | 10376 |
| 7 | Val | 57 | Val | 2601 | Pro | 9587 |
| 8 | Glu | 52 | Glu | 2511 | Cit | 9144 |
| 9 | Cit | 41 | Cit | 2435 | Glu | 9143 |
| 10 | Ile | 41 | Pro | 2304 | Val | 9083 |
| 11 | Arg | 32 | Ile | 2120 | Gly | 8575 |
| 12 | Gly | 31 | Gly | 2103 | Ile | 8303 |
| 13 | Pro | 24 | Arg | 1950 | Thr | 8224 |
| 14 | Gln | 23 | Gln | 1943 | Gln | 7990 |
| 15 | Phe | 19 | Thr | 1765 | Arg | 7569 |
| 16 | ABA | 15 | Tyr | 1748 | ABA | 7518 |
| 17 | Ser | 13 | ABA | 1694 | Lys | 7407 |
| 18 | Orn | 12 | Ser | 1665 | Tyr | 7354 |
| 19 | Lys | 12 | Phe | 1658 | Phe | 7349 |
| 20 | Thr | 11 | Orn | 1645 | Ser | 7149 |
| 21 | Tyr | 11 | Lys | 1615 | Orn | 7064 |

METHOD OF EVALUATING PROSTATIC DISEASE

This application is a Continuation of PCT/JP2009/061349, filed Jun. 22, 2009, which claims priority from Japanese patent application JP 2008-162613 filed Jun. 20, 2008. The contents of each of the aforementioned application are incorporated herein by reference in their entirety.

BACKGROUND OF THE INVENTION

1. Field of the Invention

The present invention relates to a method of evaluating prostatic disease including at least one of prostatic cancer and prostatic hypertrophy, which utilizes a concentration of an amino acid in blood (plasma).

2. Description of the Related Art

Prostatic cancer has the rate of a predictive value of the number of deaths from cancer by organ is 3.90 in 2015 as compared with in 1990, which is the highest rate of all cancers. Therefore, to reduce increase in future death rate, it need to be diagnosed with high precision in an early stage.

At present, the diagnosis of prostatic cancer is performed by prostate-specific antigen (PSA), rectal examination, and transrectal ultrasonography. An abnormal case is subjected to prostate six sextant biopsies by transrectal ultrasonic guide for definitive diagnosis.

However, PSA, which occurs, not only in prostatic cancer tissue, but also in prostatic hypertrophy tissue, is difficult to discriminate between prostatic cancer in an early stage and prostatic hypertrophy, with the biopsy positive predictive value being as low as 3% to 4%. In addition, rectal examination and transrectal ultrasonography have lower sensitivity and biopsy positive predictive value than PSA. Further, prostate six sextant biopsies by transrectal ultrasonic guide, which is definitive diagnosis, is a high-invasiveness examination so that it is not realistic to subject all patients who are suspected of having prostatic cancer to it. Therefore, from the viewpoint of the physical load on patients and the cost effectiveness, desirably, subjects having a high possibility of occurrence of prostatic cancer are selected by a method with less invasiveness and mental pain, the selected subjects are diagnosed, and the subjects who have obtained definitive diagnosis are to be treated.

It is known that blood amino acid concentration is changed by occurrence of cancer. For instance, Cynober (see "Cynober, L. ed., Metabolic and therapeutic aspects of amino acids in clinical nutrition. 2nd ed., CRC Press.") has reported that the consumption amount in cancer cells of each of glutamine mainly as an oxidative energy source, arginine as the precursor of nitrogen oxide or polyamine, and methionine subjected to activation of methionine take-in ability by cancer cells is increased. In addition, Vissers et al. (see "Vissers, Y. L J., et. al., Plasma arginine concentration are reduced in cancer patients: evidence for arginine deficiency?, The American Journal of Clinical Nutrition, 2005 81, p. 1142-1146"), Kubota (see "Kubota, A., Meguid, M. M., and Hitch, D. C., Amino acid profiles correlate diagnostically with organ site in three kinds of malignant tumors., Cancer, 1991, 69, p 2343-2348"), Park (see "Park, K. G., et al., Arginine metabolism in benign and malignant disease of breast and colon: evidence for possible inhibition of tumor-infiltrating macrophages., Nutrition, 1991 7, p. 185-188"), Proenza et al. (see "Proenza, A. M., J. Oliver, A. Palou and P. Roca, Breast and lung cancer are associated with a decrease in blood cell amino acid content. J Nutr Biochem, 2003. 14(3): p. 133-8"), and Cascino (see "Cascino, A., M. Muscaritoli, C. Cangiano, L. Conversano, A. Laviano, S. Ariemma, M. M. Meguid and F. Rossi Fanelli, Plasma amino acid imbalance in patients with lung and breast cancer. Anticancer Res, 1995. 15(2): p. 507-10") have reported that the plasma amino acid composition of cancer patients is different from that of healthy subjects.

WO 2004/052191 and WO 2006/098192 disclose a method for associating amino acid concentration with biological state. WO 2008/016111 discloses a method for evaluating the state of lung cancer using an amino acid concentration.

However, there is a problem that diagnosing methods and apparatuses, which use a plurality of amino acids as explanatory variables to diagnose the presence or absence of occurrence of prostatic cancer, prostatic hypertrophy, and other prostatic diseases, have not developed from the viewpoint of time and cost, and have not been practically used. In addition, there is a problem that even when the presence or absence of occurrence of prostatic cancer, prostatic hypertrophy, and other prostatic diseases is discriminated by an index formula group for discriminating lung cancer disclosed in WO 2008/016111, sufficient discriminative ability cannot be obtained due to different discriminated targets.

SUMMARY OF THE INVENTION

It is an object of the present invention to at least partially solve the problems in the conventional technology. The present invention has been made in view of the problems described above, and an object of the present invention is to provide a method of evaluating prostatic disease, which can evaluate the state of prostatic disease accurately, by using, of blood amino acid concentrations, the amino acid concentration associated with the state of prostatic disease.

The present inventors have earnestly studied the problems to solve them, have identified amino acids useful for 2-group discrimination between prostatic disease and prostatic disease-free and the like, have found that multivariate discriminants (index formulae or correlation equations) containing the concentrations of the identified amino acids, as explanatory variables, significantly correlate with the state of prostatic disease, and have completed the present invention. Specifically, the present inventors have searched for more specific index formulae with respect to prostatic disease, have been able to obtain index formulae which are more suitable for evaluating the state of prostatic disease than the index formulae disclosed in WO 2004/052191, WO 2006/098192, and WO 2008/016111, and have completed the present invention.

To solve the problem and achieve the object described above, a method of evaluating prostatic disease according to one aspect of the present invention includes a measuring step of measuring amino acid concentration data on a concentration value of an amino acid in blood collected from a subject to be evaluated, and a concentration value criterion evaluating step of evaluating a state of prostatic disease including at least one of prostatic cancer and prostatic hypertrophy in the subject, based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject measured at the measuring step.

Another aspect of the present invention is the method of evaluating prostatic disease, wherein the concentration value criterion evaluating step further includes a concentration value criterion discriminating step of discriminating between the prostatic disease and a prostatic disease-free, between the prostatic cancer and a prostatic cancer-free, or between the prostatic cancer and the prostatic hypertrophy in the subject, based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject measured at the measuring step.

Still another aspect of the present invention is the method of evaluating prostatic disease, wherein the concentration value criterion evaluating step further includes (I) a discriminant value calculating step of calculating a discriminant value that is a value of a multivariate discriminant with a concentration of the amino acid as an explanatory variable, based on both (i) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject measured at the measuring step and (ii) the previously established multivariate discriminant, and (II) a discriminant value criterion evaluating step of evaluating the state of the prostatic disease in the subject based on the discriminant value calculated at the discriminant value calculating step. The multivariate discriminant contains at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable.

Still another aspect of the present invention is the method of evaluating prostatic disease, wherein the discriminant value criterion evaluating step further includes a discriminant value criterion discriminating step of discriminating between the prostatic disease and a prostatic disease-free, between the prostatic cancer and a prostatic cancer-free, or between the prostatic cancer and the prostatic hypertrophy in the subject, based on the discriminant value calculated at the discriminant value calculating step.

Still another aspect of the present invention is the method of evaluating prostatic disease, wherein the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the method of evaluating prostatic disease, wherein (I) at the discriminant value calculating step, the discriminant value is calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the subject measured at the measuring step and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) at the discriminant value criterion discriminating step, the discrimination between the prostatic disease and the prostatic disease-free in the subject is conducted based on the discriminant value calculated at the discriminant value calculating step. Still another aspect of the present invention is the method of evaluating prostatic disease, wherein the multivariate discriminant is the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(\text{Tau/ABA})+b_1(\text{Thr/Cit})+c_1(\text{Glu/Ser})+d_1(\text{Pro/Asn})+e_1 \quad \text{(formula 1)}$$

wherein $a_1$, $b_1$, $c_1$, $d_1$, and $e_1$ in the formula 1 is arbitrary real number.

Still another aspect of the present invention is the method of evaluating prostatic disease, wherein (I) at the discriminant value calculating step, the discriminant value is calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the subject measured at the measuring step and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) at the discriminant value criterion discriminating step, the discrimination between the prostatic cancer and the prostatic cancer-free in the subject is conducted based on the discriminant value calculated at the discriminant value calculating step. Still another aspect of the present invention is the method of evaluating prostatic disease, wherein the multivariate discriminant is the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau/Trp})+b_2(\text{Thr/Ser})+c_2(\text{Glu/Asn})+d_2(\text{Orn/Gln})+e_2 \quad \text{(formula 2)}$$

$$a_3(\text{Tau/Met})+b_3(\text{Ser/Cit})+c_3(\text{Asn/Thr})+d_3(\text{Glu/Pro})+e_3 \quad \text{(formula 3)}$$

$$a_4(\text{Thr/Orn})+b_4(\text{Ser/Ile})+c_4(\text{Asn/Glu})+d_4(\text{Gln/Tau})+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number.

Still another aspect of the present invention is the method of evaluating prostatic disease, wherein (I) at the discriminant value calculating step, the discriminant value is calculated based on both (i) the concentration value of at least one of Thr, Ser, Gly, Cit, Val, His, Trp, and Lys contained in the amino acid concentration data of the subject measured at the measuring step and (ii) the multivariate discriminant containing at least one of Thr, Ser, Gly, Cit, Val, His, Trp, and Lys as the explanatory variable, and (II) at the discriminant value criterion discriminating step, the discrimination between the prostatic cancer and the prostatic hypertrophy in the subject is conducted based on the discriminant value calculated at the discriminant value calculating step. Still another aspect of the present invention is the method of evaluating prostatic disease, wherein the multivariate discriminant is the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(Ser/Gln)+b_5(Glu/Tau)+c_5(Ala/Asn)+d_5(Val/Thr)+e_5 \quad \text{(formula 5)}$$

wherein $a_5$, $b_5$, $c_5$, $d_5$, and $e_5$ in the formula 5 is arbitrary real number.

A prostatic disease-evaluating apparatus according to one aspect of the present invention includes a control unit and a memory unit to evaluate a state of prostatic disease including at least one of prostatic cancer and prostatic hypertrophy in a subject to be evaluated. The control unit includes (I) a discriminant value-calculating unit that calculates a discriminant value that is a value of a multivariate discriminant with a concentration of an amino acid as an explanatory variable, based on both (i) a concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in a previously obtained amino acid concentration data of the subject on the concentration value of the amino acid and (ii) the multivariate discriminant stored in the memory unit, and (II) a discriminant value criterion-evaluating unit that evaluates the state of the prostatic disease in the subject based on the discriminant value calculated by the discriminant value-calculating unit. The multivariate discriminant contains at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable.

Another aspect of the present invention is the prostatic disease-evaluating apparatus, wherein the discriminant value criterion-evaluating unit further includes a discriminant value criterion-discriminating unit that discriminates between the prostatic disease and a prostatic disease-free, between the prostatic cancer and a prostatic cancer-free, or between the prostatic cancer and the prostatic hypertrophy in the subject, based on the discriminant value calculated by the discriminant value-calculating unit.

Still another aspect of the present invention is the prostatic disease-evaluating apparatus, wherein the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the prostatic disease-evaluating apparatus, wherein (I) the discriminant value-calculating unit calculates the discriminant value based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the subject and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) the discriminant value criterion-discriminating unit discriminates between the prostatic disease and the prostatic disease-free in the subject based on the discriminant value calculated by the discriminant value-calculating unit. Still another aspect of the present invention is the prostatic disease-evaluating apparatus, wherein the multivariate discriminant is the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(Tau/ABA)+b_1(Thr/Cit)+c_1(Glu/Ser)+d_1(Pro/Asn)+e_1 \quad \text{(formula 1)}$$

wherein $a_1$, $b_1$, $c_1$, $d_1$, and $e_1$ in the formula 1 is arbitrary real number.

Still another aspect of the present invention is the prostatic disease-evaluating apparatus, wherein (I) the discriminant value-calculating unit calculates the discriminant value based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the subject and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) the discriminant value criterion-discriminating unit discriminates between the prostatic cancer and the prostatic cancer-free in the subject based on the discriminant value calculated by the discriminant value-calculating unit. Still another aspect of the present invention is the prostatic disease-evaluating apparatus, wherein the multivariate discriminant is the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(Tau/Trp)+b_2(Thr/Ser)+c_2(Glu/Asn)+d_2(Orn/Gln)+e_2 \quad \text{(formula 2)}$$

$$a_3(Tau/Met)+b_3(Ser/Cit)+c_3(Asn/Thr)+d_3(Glu/Pro)+e_3 \quad \text{(formula 3)}$$

$$a_4(Thr/Orn)+b_4(Ser/Ile)+c_4(Asn/Glu)+d_4(Gln/Tau)+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number.

Still another aspect of the present invention is the prostatic disease-evaluating apparatus, wherein (I) the discriminant value-calculating unit calculates the discriminant value based on both (i) the concentration value of at least one of Thr, Ser, Gly, Cit, Val, His, Trp, and Lys contained in the amino acid concentration data of the subject and (ii) the multivariate discriminant containing at least one of Thr, Ser, Gly, Cit, Val, His, Trp, and Lys as the explanatory variable, and (II) the discriminant value criterion-discriminating unit discriminates between the prostatic cancer and the prostatic hypertrophy in the subject based on the discriminant value calculated by the discriminant value-calculating unit. Still another aspect of the present invention is the prostatic disease-evaluating apparatus, wherein the multivariate discriminant is the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(Ser/Gln)+b_5(Glu/Tau)+c_5(Ala/Asn)+ d_5(Val/Thr)+e_5 \quad \text{(formula 5)}$$

wherein $a_5$, $b_5$, $c_5$, $d_5$, and $e_5$ in the formula 5 is arbitrary real number.

Still another aspect of the present invention is the prostatic disease-evaluating apparatus, wherein the control unit further includes a multivariate discriminant-preparing unit that prepares the multivariate discriminant stored in the memory unit, based on prostatic disease state information containing the amino acid concentration data and prostatic disease state index data on an index for indicating the state of prostatic disease, stored in the memory unit. The multivariate discriminant-preparing unit further includes (i) a candidate multivariate discriminant-preparing unit that prepares a candidate multivariate discriminant that is a candidate of the multivariate discriminant, based on a predetermined discriminant-preparing method from the prostatic disease state information, (ii) a candidate multivariate discriminant-verifying unit that verifies the candidate multivariate discriminant prepared by the candidate multivariate discriminant-preparing unit, based on a predetermined verifying method, and (iii) an explanatory variable-selecting unit that selects the explanatory variable of the candidate multivariate discriminant based on a predetermined explanatory variable-selecting method from a verification result obtained by the candidate multivariate discriminant-verifying unit, thereby selecting a combination of the amino acid concentration data contained in the prostatic disease state information used in preparing the candidate multivariate discriminant. The multivariate discriminant-preparing unit prepares the multivariate discriminant by selecting the candidate multivariate discriminant used as the multivariate discriminant, from a plurality of the candidate multivariate discriminants, based on the verification results accumulated by repeatedly executing the candidate multivariate discriminant-preparing unit, the candidate multivariate discriminant-verifying unit, and the explanatory variable-selecting unit.

A prostatic disease-evaluating method according to one aspect of the present invention is a method of evaluating a state of prostatic disease including at least one of prostatic cancer and prostatic hypertrophy in a subject to be evaluated. The method is carried out with an information processing apparatus including a control unit and a memory unit. The method includes (I) a discriminant value calculating step of calculating a discriminant value that is a value of a multivariate discriminant with a concentration of an amino acid as an explanatory variable, based on both (i) a concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in a previously obtained amino acid concentration data of the subject on the concentration value of the amino acid and (ii) the multivariate discriminant stored in the memory unit, and (II) a discriminant value criterion evaluating step of evaluating the state of the prostatic disease in the subject based on the discriminant value calculated at the discriminant value calculating step. The multivariate discriminant contains at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable. The steps (I) and (II) are executed by the control unit.

Another aspect of the present invention is the prostatic disease-evaluating method, wherein the discriminant value criterion evaluating step further includes a discriminant value criterion discriminating step of discriminating between the prostatic disease and a prostatic disease-free, between the prostatic cancer and a prostatic cancer-free, or between the prostatic cancer and the prostatic hypertrophy in the subject, based on the discriminant value calculated at the discriminant value calculating step.

Still another aspect of the present invention is the prostatic disease-evaluating method, wherein the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

Still another aspect of the present invention is the prostatic disease-evaluating method, wherein (I) at the discriminant value calculating step, the discriminant value is calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the subject and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) at the discriminant value criterion discriminating step, the discrimination between the prostatic disease and the prostatic disease-free in the subject is conducted based on the discriminant value calculated at the discriminant value calculating step. Still another aspect of the present invention is the prostatic disease-evaluating method, wherein the multivariate discriminant is the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(Tau/ABA)+b_1(Thr/Cit)+c_1(Glu/Ser)+ d_1(Pro/Asn)+e_1 \quad \text{(formula 1)}$$

wherein $a_1$, $b_1$, $c_1$, $d_1$, and $e_1$ in the formula 1 is arbitrary real number.

Still another aspect of the present invention is the prostatic disease-evaluating method, wherein (I) at the discriminant value calculating step, the discriminant value is calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the subject and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) at the discriminant value criterion discriminating step, the discrimination between the prostatic cancer and the prostatic cancer-free in the subject is conducted based on the discriminant value calculated at the discriminant value calculating step. Still another aspect of the present invention is the prostatic disease-evaluating method, wherein the multivariate discriminant is the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau}/\text{Trp})+b_2(\text{Thr}/\text{Ser})+c_2(\text{Glu}/\text{Asn})+d_2(\text{Orn}/\text{Gln})+e_2 \quad \text{(formula 2)}$$

$$a_3(\text{Tau}/\text{Met})+b_3(\text{Ser}/\text{Cit})+c_3(\text{Asn}/\text{Thr})+d_3(\text{Glu}/\text{Pro})+e_3 \quad \text{(formula 3)}$$

$$a_4(\text{Thr}/\text{Orn})+b_4(\text{Ser}/\text{Ile})+c_4(\text{Asn}/\text{Glu})+d_4(\text{Gln}/\text{Tau})+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number.

Still another aspect of the present invention is the prostatic disease-evaluating method, wherein (I) at the discriminant value calculating step, the discriminant value is calculated based on both (i) the concentration value of at least one of Thr, Ser, Gly, Cit, Val, His, Trp, and Lys contained in the amino acid concentration data of the subject and (ii) the multivariate discriminant containing at least one of Thr, Ser, Gly, Cit, Val, His, Trp, and Lys as the explanatory variable, and (II) at the discriminant value criterion discriminating step, the discrimination between the prostatic cancer and the prostatic hypertrophy in the subject is conducted based on the discriminant value calculated at the discriminant value calculating step. Still another aspect of the present invention is the prostatic disease-evaluating method, wherein the multivariate discriminant is the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(\text{Ser}/\text{Gln})+b_5(\text{Glu}/\text{Tau})+c_5(\text{Ala}/\text{Asn})+d_5(\text{Val}/\text{Thr})+e_5 \quad \text{(formula 5)}$$

wherein $a_5$, $b_5$, $c_5$, $d_5$, and $e_5$ in the formula 5 is arbitrary real number.

Still another aspect of the present invention is the prostatic disease-evaluating method, wherein the method further includes a multivariate discriminant preparing step of preparing the multivariate discriminant stored in the memory unit, based on prostatic disease state information containing the amino acid concentration data and prostatic disease state index date on an index for indicating the state of prostatic disease, stored in the memory unit. The multivariate discriminant preparing step is executed by the control unit. The multivariate discriminant preparing step further includes (i) a candidate multivariate discriminant preparing step of preparing a candidate multivariate discriminant that is a candidate of the multivariate discriminant, based on a predetermined discriminant-preparing method from the prostatic disease state information, (ii) a candidate multivariate discriminant verifying step of verifying the candidate multivariate discriminant prepared at the candidate multivariate preparing step, based on a predetermined verifying method, and (iii) an explanatory variable selecting step of selecting the explanatory variable of the candidate multivariate discriminant based on a predetermined explanatory variable-selecting method from a verification result obtained at the candidate multivariate discriminant verifying step, thereby selecting a combination of the amino acid concentration data contained in the prostatic disease state information used in preparing the candidate multivariate discriminant. At the multivariate discriminant preparing step, the multivariate discriminant is prepared by selecting the candidate multivariate discriminant used as the multivariate discriminant, from a plurality of the candidate multivariate discriminants, based on the verification results accumulated by repeatedly executing the candidate multivariate discriminant preparing step, the candidate multivariate discriminant verifying step, and the explanatory variable selecting step.

A prostatic disease-evaluating system according to one aspect of the present invention includes (i) a prostatic disease-evaluating apparatus including a control unit and a memory unit to evaluate a state of prostatic disease including at least one of prostatic cancer and prostatic hypertrophy in a subject to be evaluated, and (ii) an information communication terminal apparatus that provides amino acid concentration data of the subject on a concentration value of an amino acid. The apparatuses are connected to each other communicatively via a network. The information communication terminal apparatus includes an amino acid concentration data-sending unit that transmits the amino acid concentration data of the subject to the prostatic disease-evaluating apparatus, and an evaluation result-receiving unit that receives an evaluation result of the subject on the state of prostatic disease transmitted from the prostatic disease-evaluating apparatus. The control unit of the prostatic disease-evaluating apparatus includes (I) an amino acid concentration data-receiving unit that receives the amino acid concentration data of the subject transmitted from the information communication terminal apparatus, (II) a discriminant value-calculating unit that calculates a discriminant value that is a value of a multivariate discriminant with a concentration of the amino acid as an explanatory variable, based on both (i) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject received by the amino acid concentration data-receiving unit and (ii) the multivariate discriminant stored in the memory unit, (III) a discriminant value criterion-evaluating unit that evaluates the state of the prostatic disease in the subject based on the discriminant value calculated by the discriminant value-calculating unit, and (IV) an evaluation result-sending unit that transmits the evaluation result of the subject obtained by the discriminant value criterion-evaluating unit to the information communication terminal apparatus. The multivariate discriminant contains at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable.

A prostatic disease-evaluating program product according to one aspect of the present invention makes an information processing apparatus including a control unit and a memory unit execute a method of evaluating a state of prostatic disease including at least one of prostatic cancer and prostatic hypertrophy in a subject to be evaluated. The method includes (I) a discriminant value calculating step of calculating a discriminant value that is a value of a multivariate discriminant with a concentration of an amino acid as an explanatory variable, based on both (i) a concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in a previously obtained amino acid concentration data of the subject on the concentration value of the amino acid and (ii) the multivariate discriminant stored in the memory unit, and (II) a discriminant value criterion evaluating step of evaluating the state of the prostatic disease in the subject based on the discriminant value calculated at the discriminant value calculating step. The multivariate discriminant contains at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable. The steps (I) and (II) are executed by the control unit.

The present invention also relates to a recording medium, the recording medium according to one aspect of the present invention includes the prostatic disease-evaluating program product described above.

According to the present invention, (i) the amino acid concentration data on the concentration value of the amino acid in blood collected from the subject is measured, and (ii) the state of prostatic disease including at least one of prostatic cancer and prostatic hypertrophy in the subject is evaluated based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the measured amino acid concentration data of the subject. Thus, the concentrations of the amino acids which among amino acids in blood, are related to the state of prostatic disease can be utilized to bring about the effect of enabling an accurate evaluation of the state of prostatic disease. Specifically, an examinee likely to contract prostatic disease can be narrowed by one sample in a short time to bring about the effect of enabling the reduction of temporal, physical and financial burden of the examinee. Specifically, whether a certain sample is with prostatic disease can be evaluated accurately by the concentrations of a plurality of the amino acids to bring about the effect of enabling to make the examination efficient and high accurate.

According to the present invention, the discrimination between the prostatic disease and the prostatic disease-free, between the prostatic cancer and the prostatic cancer-free, or between the prostatic cancer and the prostatic hypertrophy in the subject is conducted based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the measured amino acid concentration data of the subject. Thus, the concentrations of the amino acids which among amino acids in blood, are useful for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling accurately these 2-group discriminations.

According to the present invention, (I) the discriminant value that is the value of the multivariate discriminant with the concentration of the amino acid as the explanatory variable is calculated based on both (i) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the measured amino acid concentration data of the subject and (ii) the previously established multivariate discriminant containing at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable, and (II) the state of prostatic disease in the subject is evaluated based on the calculated discriminant value. Thus, the discriminant values obtained in the multivariate discriminants correlated significantly with the state of prostatic disease can be utilized to bring about the effect of enabling an accurate evaluation of the state of prostatic disease. Specifically, an examinee likely to contract prostatic disease can be narrowed by one sample in a short time to bring about the effect of enabling the reduction of temporal, physical and financial burden of the examinee. Specifically, whether a certain sample is with prostatic disease can be evaluated accurately by the concentrations of a plurality of the amino acids and the discriminants with the concentrations of the amino acids as the explanatory variables to bring about the effect of enabling to make the examination efficient and high accurate.

According to the present invention, the discrimination between the prostatic disease and the prostatic disease-free, between the prostatic cancer and the prostatic cancer-free, or between the prostatic cancer and the prostatic hypertrophy in the subject is conducted based on the calculated discriminant value. Thus, the discriminant values obtained in the multivariate discriminants useful for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling accurately these 2-group discriminations.

According to the present invention, the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, the discriminant values obtained in the multivariate discriminants useful particularly for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling more accurately these 2-group discriminations.

According to the present invention, (I) the discriminant value is calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the subject and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) the discrimination between the prostatic disease and the prostatic disease-free in the subject is conducted based on the calculated discriminant value. Thus, the discriminant values obtained in the multivariate discriminants useful particularly for the 2-group discrimination of the prostatic disease and the prostatic disease-free, can be utilized to bring about the effect of enabling more accurately the 2-group discrimination. According to the present invention, the multivariate discriminant is the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(\text{Tau}/\text{ABA})+b_1(\text{Thr}/\text{Cit})+c_1(\text{Glu}/\text{Ser})+d_1(\text{Pro}/\text{Asn})+e_1 \quad \text{(formula 1)}$$

wherein $a_1$, $b_1$, $c_1$, $d_1$, and $e_1$ in the formula 1 is arbitrary real number. Thus, the discriminant values obtained in the multivariate discriminants useful particularly for the 2-group discrimination of the prostatic disease and the prostatic disease-free, can be utilized to bring about the effect of enabling more accurately the 2-group discrimination.

According to the present invention, (I) the discriminant value is calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the subject and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) the discrimination between the prostatic cancer and the prostatic cancer-free in the subject is conducted based on the calculated discriminant value. Thus, the discriminant values obtained in the multivariate discriminants useful particularly for the 2-group discrimination of the prostatic cancer and the prostatic cancer-free, can be utilized to bring about the effect of enabling more accurately the 2-group discrimination. According to the present invention, the multivariate discriminant is the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau}/\text{Trp})+b_2(\text{Thr}/\text{Ser})+c_2(\text{Glu}/\text{Asn})+d_2(\text{Orn}/\text{Gln})+e_2 \quad \text{(formula 2)}$$

$$a_3(\text{Tau}/\text{Met})+b_3(\text{Ser}/\text{Cit})+c_3(\text{Asn}/\text{Thr})+d_3(\text{Glu}/\text{Pro})+e_3 \quad \text{(formula 3)}$$

$$a_4(\text{Thr}/\text{Orn})+b_4(\text{Ser}/\text{Ile})+c_4(\text{Asn}/\text{Glu})+d_4(\text{Gln}/\text{Tau})+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number. Thus, the discriminant values obtained in the multivariate discriminants useful particularly for the 2-group discrimination of the prostatic cancer and the prostatic cancer-free, can be utilized to bring about the effect of enabling more accurately the 2-group discrimination.

According to the present invention, (I) the discriminant value is calculated based on both (i) the concentration value of at least one of Thr, Ser, Gly, Cit, Val, His, Trp, and Lys contained in the amino acid concentration data of the subject and (ii) the multivariate discriminant containing at least one of Thr, Ser, Gly, Cit, Val, His, Trp, and Lys as the explanatory variable, and (II) the discrimination between the prostatic cancer and the prostatic hypertrophy in the subject is conducted based on the calculated discriminant value. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination. According to the present invention, the multivariate discriminant is the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(\text{Ser}/\text{Gln})+b_5(\text{Glu}/\text{Tau})+c_5(\text{Ala}/\text{Asn})+d_5(\text{Val}/\text{Thr})+e_5 \quad \text{(formula 5)}$$

wherein $a_5$, $b_5$, $c_5$, $d_5$, and $e_5$ in the formula 5 is arbitrary real number. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination.

According to the present invention, the multivariate discriminant stored in the memory unit is prepared based on the prostatic disease state information containing the amino acid concentration data and the prostatic disease state index data on the index for indicating the state of prostatic disease, stored in the memory unit. Specifically, (1) the candidate multivariate discriminant is prepared based on the predetermined discriminant-preparing method from the prostatic disease state information, (2) the prepared candidate multivariate discriminant is verified based on the predetermined verifying method, (3) the explanatory variables of the candidate multivariate discriminant are selected based on the predetermined explanatory variable-selecting method from the verification results, thereby selecting the combination of the amino acid concentration data contained in the prostatic disease state information used in preparing of the candidate multivariate discriminant, and (4) the candidate multivariate discriminant used as the multivariate discriminant is selected from a plurality of the candidate multivariate discriminants based on the verification results accumulated by repeatedly executing (1), (2) and (3), thereby preparing the multivariate discriminant. Thus, the effect of being able to prepare the multivariate discriminant most appropriate for evaluating the state of prostatic disease is brought about.

According to the present invention, the prostatic disease-evaluating program recorded on the recording medium is read and executed by the computer, thereby allowing the computer to execute the prostatic disease-evaluating program, thus bringing about the effect of obtaining the same effect as in the prostatic disease-evaluating program.

When the state of prostatic disease is evaluated in the present invention, concentrations of other metabolites, gene expression level, protein expression level, age and sex of the subject, presence or absence of smoking, digitalized electrocardiogram waveform, or the like may be used in addition to the amino acid concentration. When the state of prostatic disease is evaluated in the present invention, the concentrations of the other metabolites, the gene expression level, the protein expression level, the age and sex of the subject, the presence or absence of the smoking, the digitalized electrocardiogram waveform, or the like may be used as the explanatory variables in the multivariate discriminant in addition to the amino acid concentration.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a chart showing an example of information stored in a user information file 106a;

FIG. 8 is a chart showing an example of information stored in an amino acid concentration data file 106b;

FIG. 9 is a chart showing an example of information stored in a prostatic disease state information file 106c;

FIG. 10 is a chart showing an example of information stored in a designated prostatic disease state information file 106d;

FIG. 11 is a chart showing an example of information stored in a candidate multivariable discriminant file 106e1;

FIG. 12 is a chart showing an example of information stored in a verification result file 106e2;

FIG. 13 is a chart showing an example of information stored in a selected prostatic disease state information file 106e3;

FIG. 14 is a chart showing an example of information stored in a multivariable discriminant file 106e4;

FIG. 15 is a chart showing an example of information stored in a discriminant value file 106f;

FIG. 24 is a chart showing a list of discriminants having the same discrimination performance as that of an index formula 1;

FIG. 25 is a chart showing a list of discriminants having the same discrimination performance as that of the index formula 1;

FIG. 27 is a chart showing a list of discriminants having the same discrimination performance as that of an index formula 2;

FIG. 28 is a chart showing a list of discriminants having the same discrimination performance as that of the index formula 2;

FIG. 30 is a chart showing a list of discriminants having the same discrimination performance as that of an index formula 3;

FIG. 31 is a chart showing a list of discriminants having the same discrimination performance as that of the index formula 3;

FIG. 34 is a chart showing a list of discriminants having the same discrimination performance as that of an index formula 4;

FIG. 35 is a chart showing a list of discriminants having the same discrimination performance as that of the index formula 4;

FIG. 37 is a chart showing a list of discriminants having the same discrimination performance as that of an index formula 5;

FIG. 38 is a chart showing a list of discriminants having the same discrimination performance as that of the index formula 5;

FIG. 40 is a chart showing a list of discriminants having the same discrimination performance as that of an index formula 6;

FIG. 41 is a chart showing a list of discriminants having the same discrimination performance as that of the index formula 6;

FIG. 44 is a chart showing a list of discriminants having the same discrimination performance as that of an index formula 7;

FIG. 45 is a chart showing a list of discriminants having the same discrimination performance as that of the index formula 7;

FIG. 47 is a chart showing a list of discriminants having the same discrimination performance as that of an index formula 8;

FIG. 48 is a chart showing a list of discriminants having the same discrimination performance as that of the index formula 8;

FIG. 50 is a chart showing a list of discriminants having the same discrimination performance as that of an index formula 9;

FIG. 51 is a chart showing a list of discriminants having the same discrimination performance as that of the index formula 9;

FIG. 54 is a chart showing a list of discriminants having the same discrimination performance as that of an index formula 10;

FIG. 55 is a chart showing a list of discriminants having the same discrimination performance as that of the index formula 10;

FIG. 57 is a chart showing a list of discriminants having the same discrimination performance as that of an index formula 11;

FIG. 58 is a chart showing a list of discriminants having the same discrimination performance as that of the index formula 11;

FIG. 60 is a chart showing a list of discriminants having the same discrimination performance as that of an index formula 12;

FIG. 61 is a chart showing a list of discriminants having the same discrimination performance as that of the index formula 12;

FIG. 64 is a chart showing a list of discriminants having the same discrimination performance as that of an index formula 13;

FIG. 65 is a chart showing a list of discriminants having the same discrimination performance as that of the index formula 13;

FIG. 67 is a chart showing a list of discriminants having the same discrimination performance as that of an index formula 14;

FIG. 68 is a chart showing a list of discriminants having the same discrimination performance as that of the index formula 14;

FIG. 70 is a chart showing a list of discriminants having the same discrimination performance as that of an index formula 15;

FIG. 71 is a chart showing a list of discriminants having the same discrimination performance as that of the index formula 15;

FIG. 75 is a chart showing a list of discriminants having the same discrimination performance as that of an index formula 16;

FIG. 76 is a chart showing a list of discriminants having the same discrimination performance as that of the index formula 16;

FIG. 77 is a chart showing a list of discriminants having the same discrimination performance as that of the index formula 16;

FIG. 78 is a chart showing a list of discriminants having the same discrimination performance as that of the index formula 16;

FIG. 80 is a chart showing a list of discriminants having the same discrimination performance as that of an index formula 17;

FIG. 81 is a chart showing a list of discriminants having the same discrimination performance as that of the index formula 17;

FIG. 82 is a chart showing a list of discriminants having the same discrimination performance as that of the index formula 17;

FIG. 83 is a chart showing a list of discriminants having the same discrimination performance as that of the index formula 17;

FIG. 87 is a chart showing a list of discriminants having the same discrimination performance as that of an index formula 18;

FIG. 88 is a chart showing a list of discriminants having the same discrimination performance as that of the index formula 18;

FIG. 89 is a chart showing a list of discriminants having the same discrimination performance as that of the index formula 18;

FIG. 90 is a chart showing a list of discriminants having the same discrimination performance as that of the index formula 18;

FIG. 92 is a chart showing a list of discriminants having the same discrimination performance as that of an index formula 19;

FIG. 93 is a chart showing a list of discriminants having the same discrimination performance as that of the index formula 19;

FIG. 94 is a chart showing a list of discriminants having the same discrimination performance as that of the index formula 19;

FIG. 95 is a chart showing a list of discriminants having the same discrimination performance as that of the index formula 19;

FIG. 99 is a chart showing a list of discriminants having the same discrimination performance as that of an index formula 20;

FIG. 100 is a chart showing a list of discriminants having the same discrimination performance as that of the index formula 20;

FIG. 101 is a chart showing a list of discriminants having the same discrimination performance as that of the index formula 20;

FIG. 102 is a chart showing a list of discriminants having the same discrimination performance as that of the index formula 20;

FIG. 104 is a chart showing a list of discriminants having the same discrimination performance as that of an index formula 21;

FIG. 105 is a chart showing a list of discriminants having the same discrimination performance as that of the index formula 21;

FIG. 106 is a chart showing a list of discriminants having the same discrimination performance as that of the index formula 21;

FIG. 107 is a chart showing a list of discriminants having the same discrimination performance as that of the index formula 21;

DETAILED DESCRIPTION OF THE PREFERRED EMBODIMENTS

Hereinafter, an embodiment (first embodiment) of the method of evaluating prostatic disease of the present invention and an embodiment (second embodiment) of the prostatic disease-evaluating apparatus, the prostatic disease-evaluating method, the prostatic disease-evaluating system, the prostatic disease-evaluating program and the recording medium of the present invention are described in detail with reference to the drawings. The present invention is not limited to these embodiments.

First Embodiment 1-1. Outline of the Invention

Figure 1:
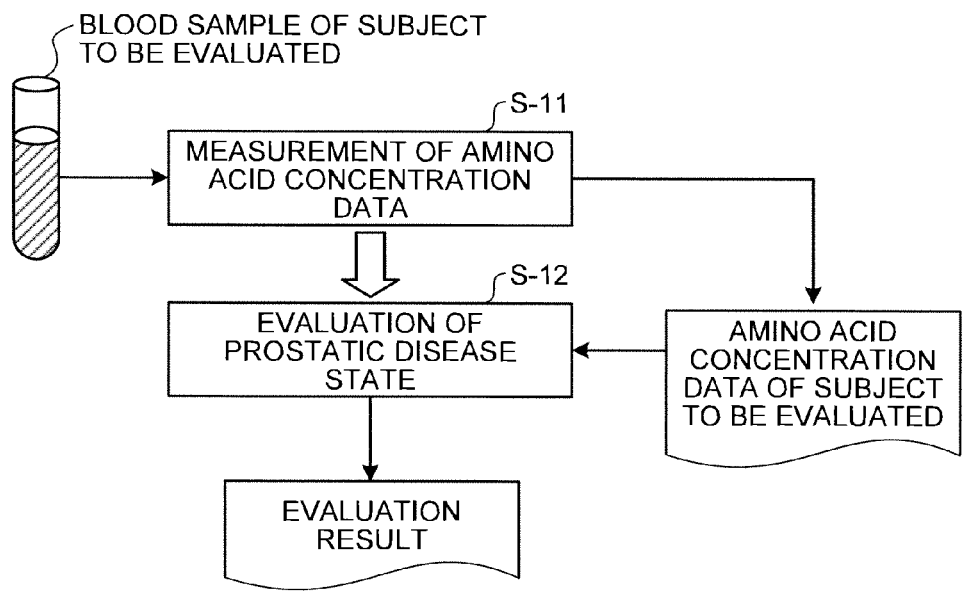
FIG. 1 is a principle configurational diagram showing a basic principle of the present invention.

Here, an outline of the method of evaluating prostatic disease of the present invention will be described with reference to FIG. 1. FIG. 1 is a principle configurational diagram showing a basic principle of the present invention.

In the present invention, amino acid concentration data on a concentration value of an amino acid in blood collected from a subject (for example, an individual such as animal or human) to be evaluated is first measured (step S-11). Concentrations of amino acids in blood are analyzed in the following manner. A blood sample is collected in a heparin-treated tube, and then the blood plasma is separated by centrifugation of the collected blood sample. All blood plasma samples separated are frozen and stored at −70° C. before a measurement of amino acid concentrations. Before the measurement of amino acid concentrations, the blood plasma samples are deproteinized by adding sulfosalicylic acid to a concentration of 3%. An amino acid analyzer by high-performance liquid chromatography (HPLC) by using ninhydrin reaction in the post column is used for the measurement of amino acid concentrations. The unit of the amino acid concentration may be for example molar concentration, weight concentration, or these concentrations which are subjected to addition, subtraction, multiplication or division by an arbitrary constant.

In the present invention, a state of prostatic disease including at least one of prostatic cancer and prostatic hypertrophy in the subject is evaluated based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject measured in step S-11 (step S-12).

According to the present invention described above, (i) the amino acid concentration data on the concentration value of the amino acid in blood collected from the subject is measured, and (ii) the state of prostatic disease including at least one of prostatic cancer and prostatic hypertrophy in the subject is evaluated based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the measured amino acid concentration data of the subject. Thus, the concentrations of the amino acids which among amino acids in blood, are related to the state of prostatic disease can be utilized to bring about the effect of enabling an accurate evaluation of the state of prostatic disease. Specifically, an examinee likely to contract prostatic disease can be narrowed by one sample in a short time to bring about the effect of enabling the reduction of temporal, physical and financial burden of the examinee. Specifically, whether a certain sample is with prostatic disease can be evaluated accurately by the concentrations of a plurality of the amino acids to bring about the effect of enabling to make the examination efficient and high accurate.

Before step S-12 is executed, data such as defective and outliers may be removed from the amino acid concentration data of the subject measured in step S-11. Thereby, the state of prostatic disease can be more accurately evaluated.

In step S-12, the discrimination between the prostatic disease and the prostatic disease-free, between the prostatic cancer and the prostatic cancer-free, or between the prostatic cancer and the prostatic hypertrophy in the subject may be conducted based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject measured in step S-11. Thus, the concentrations of the amino acids which among amino acids in blood, are useful for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling accurately these 2-group discriminations.

In step S-12, (I) a discriminant value that is a value of a multivariate discriminant with a concentration of the amino acid as an explanatory variable may be calculated based on both (i) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject measured in step S-11 and (ii) the previously established multivariate discriminant containing at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable, and (II) the state of prostatic disease in the subject may be evaluated based on the calculated discriminant value. Thus, the discriminant values obtained in the multivariate discriminants correlated significantly with the state of prostatic disease can be utilized to bring about the effect of enabling an accurate evaluation of the state of prostatic disease. Specifically, an examinee likely to contract prostatic disease can be narrowed by one sample in a short time to bring about the effect of enabling the reduction of temporal, physical and financial burden of the examinee. Specifically, whether a certain sample is with prostatic disease can be evaluated accurately by the concentrations of a plurality of the amino acids and the discriminants with the concentrations of the amino acids as the explanatory variables to bring about the effect of enabling to make the examination efficient and high accurate.

In step S-12, the discrimination between the prostatic disease and the prostatic disease-free, between the prostatic cancer and the prostatic cancer-free, or between the prostatic cancer and the prostatic hypertrophy in the subject may be conducted based on the calculated discriminant value. Specifically, the discriminant value may be compared with a previously established threshold (cutoff value), thereby discriminating between the prostatic disease and the prostatic disease-free, between the prostatic cancer and the prostatic cancer-free, or between the prostatic cancer and the prostatic hypertrophy. Thus, the discriminant values obtained in the multivariate discriminants useful for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling accurately these 2-group discriminations.

The multivariate discriminant may be any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, the discriminant values obtained in the multivariate discriminants useful particularly for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling more accurately these 2-group discriminations.

In step S-12, (I) the discriminant value may be calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the subject measured in step S-11 and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) the discrimination between the prostatic disease and the prostatic disease-free in the subject may be conducted based on the calculated discriminant value. Thus, the discriminant values obtained in the multivariate discriminants useful particularly for the 2-group discrimination of the prostatic disease and the prostatic disease-free, can be utilized to bring about the effect of enabling more accurately the 2-group discrimination. The multivariate discriminant to be used in this case may be the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(\text{Tau}/\text{ABA})+b_1(\text{Thr}/\text{Cit})+c_1(\text{Glu}/\text{Ser})+d_1(\text{Pro}/\text{Asn})+e_1 \qquad \text{(formula 1)}$$

wherein $a_1$, $b_1$, $c_1$, $d_1$, and $e_1$ in the formula 1 is arbitrary real number. Thus, the discriminant values obtained in the multivariate discriminants useful particularly for the 2-group discrimination of the prostatic disease and the prostatic disease-free, can be utilized to bring about the effect of enabling more accurately the 2-group discrimination.

In step S-12, (I) the discriminant value may be calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the subject measured in step S-11 and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) the discrimination between the prostatic cancer and the prostatic cancer-free in the subject may be conducted based on the calculated discriminant value. Thus, the discriminant values obtained in the multivariate discriminants useful particularly for the 2-group discrimination of the prostatic cancer and the prostatic cancer-free, can be utilized to bring about the effect of enabling more accurately the 2-group discrimination. The multivariate discriminant to be used in this case may be the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau/Trp}) + b_2(\text{Thr/Ser}) + c_2(\text{Glu/Asn}) + d_2(\text{Orn/Gln}) + e_2 \quad \text{(formula 2)}$$

$$a_3(\text{Tau/Met}) + b_3(\text{Ser/Cit}) + c_3(\text{Asn/Thr}) + d_3(\text{Glu/Pro}) + e_3 \quad \text{(formula 3)}$$

$$a_4(\text{Thr/Orn}) + b_4(\text{Ser/Ile}) + c_4(\text{Asn/Glu}) + d_4(\text{Gln/Tau}) + e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number. Thus, the discriminant values obtained in the multivariate discriminants useful particularly for the 2-group discrimination of the prostatic cancer and the prostatic cancer-free, can be utilized to bring about the effect of enabling more accurately the 2-group discrimination.

In step S-12, (I) the discriminant value may be calculated based on both (i) the concentration value of at least one of Thr, Ser, Gly, Cit, Val, His, Trp, and Lys contained in the amino acid concentration data of the subject measured in step S-11 and (ii) the multivariate discriminant containing at least one of Thr, Ser, Gly, Cit, Val, His, Trp, and Lys as the explanatory variable, and (II) the discrimination between the prostatic cancer and the prostatic hypertrophy in the subject may be conducted based on the calculated discriminant value. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination. The multivariate discriminant to be used in this case may be the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(\text{Ser/Gln}) + b_5(\text{Glu/Tau}) + c_5(\text{Ala/Asn}) + d_5(\text{Val/Thr}) + e_5 \quad \text{(formula 5)}$$

wherein $a_5$, $b_5$, $c_5$, $d_5$, and $e_5$ in the formula 5 is arbitrary real number. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination.

The multivariate discriminant described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the state of prostatic disease, regardless of the unit of the amino acid concentration in the amino acid concentration data as input data.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions α, β, γ etc. (for example, α+β) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

When the state of prostatic disease is evaluated in the present invention, the concentrations of the other metabolites, the gene expression level, the protein expression level, the age and sex of the subject, the presence or absence of the smoking, the digitalized electrocardiogram waveform, or the like may be used in addition to the amino acid concentration.

When the state of prostatic disease is evaluated in the present invention, the concentrations of the other metabolites, the gene expression level, the protein expression level, the age and sex of the subject, the presence or absence of the smoking, the digitalized electrocardiogram waveform, or the like may be used as the explanatory variables in the multivariate discriminant in addition to the amino acid concentration.

Figure 2:
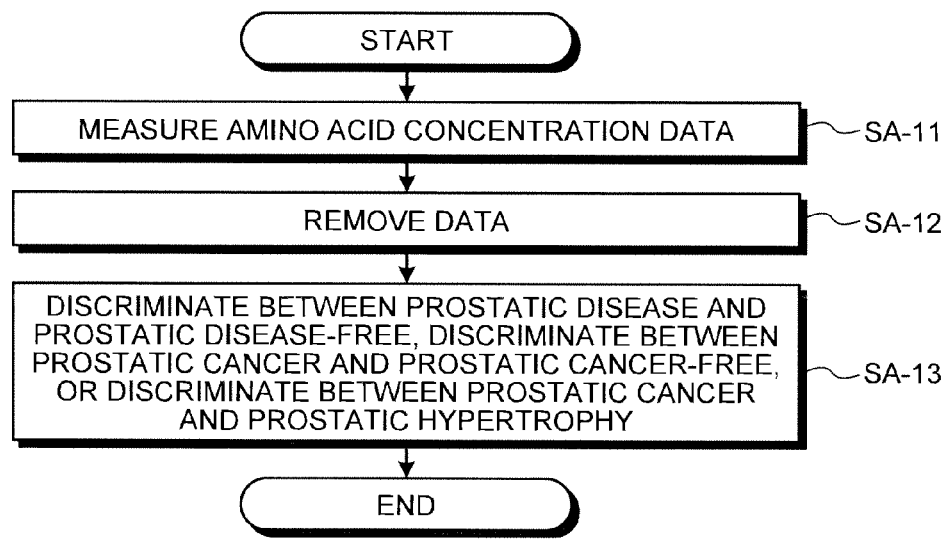
FIG. 2 is a flowchart showing one example of a method of evaluating prostatic disease according to a first embodiment.

1-2. Method of Evaluating Prostatic Disease in Accordance with the First Embodiment Herein, the method of evaluating prostatic disease according to the first embodiment is described with reference to FIG. 2. FIG. 2 is a flowchart showing one example of the method of evaluating prostatic disease according to the first embodiment.

The amino acid concentration data on the concentration values of the amino acids is measured from blood collected from an individual such as animal or human (step SA-11). The measurement of the concentration values of the amino acids is conducted by the method described above.

Data such as defective and outliers is then removed from the amino acid concentration data of the individual measured in step SA-11 (step SA-12).

Then, any one of the discriminations described in the following 11. to 13. is conducted in the individual, based on the amino acid concentration data of the individual from which the data such as the defective and the outliers have been removed in step SA-12 or the previously established multivariate discriminant with the concentration of the amino acid as the explanatory variable (the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.) (step SA-13).

11. Discrimination Between Prostatic Disease and Prostatic Disease-Free (A) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data is compared with a previously established threshold (cutoff value), thereby discriminating between the prostatic disease and the prostatic disease-free, or (B) (I) the discriminant value is calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) the calculated discriminant value is compared with a previously established threshold (cutoff value), thereby discriminating between the prostatic disease and the prostatic disease-free in the individual.

12. Discrimination Between Prostatic Cancer and Prostatic Cancer-Free (A) the discrimination between the prostatic cancer and the prostatic cancer-free in the subject is conducted based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data, or (B) (I) the discriminant value is calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) the calculated discriminant value is compared with a previously established threshold (cutoff value), thereby discriminating between the prostatic cancer and the prostatic cancer-free in the individual.

13. Discrimination Between Prostatic Cancer and Prostatic Hypertrophy (A) the discrimination between the prostatic cancer and the prostatic hypertrophy in the subject is conducted based on the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data, or (B) (I) the discriminant value is calculated based on both (i) the concentration value of at least one of Thr, Ser, Gly, Cit, Val, His, Trp, and Lys contained in the amino acid concentration data and (ii) the multivariate discriminant containing at least one of Thr, Ser, Gly, Cit, Val, His, Trp, and Lys as the explanatory variable, and (II) the calculated discriminant value is compared with a previously established threshold (cutoff value), thereby discriminating between the prostatic cancer and the prostatic hypertrophy in the individual.

1-3. Summary of the First Embodiment and Other Embodiments

In the method of evaluating prostatic disease as described above in detail, (1) the amino acid concentration data is measured from blood collected from the individual, (2) the data such as the defective and the outliers is removed from the measured amino acid concentration data of the individual, and (3) any one of the discriminations described in 11. to 13. above is conducted based on (i) the amino acid concentration data of the individual from which the data such as the defective and the outliers have been removed or (ii) the previously established multivariate discriminant with the concentration of the amino acid as the explanatory variable. Thus, the concentrations of the amino acids which among amino acids in blood, are useful for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling accurately these 2-group discriminations. The discriminant values obtained in the multivariate discriminants useful particularly for the 2-group discrimination of the prostatic disease and the prostatic disease-free, can be utilized to bring about the effect of enabling more accurately the 2-group discrimination. The discriminant values obtained in the multivariate discriminants useful particularly for the 2-group discrimination of the prostatic cancer and the prostatic cancer-free, can be utilized to bring about the effect of enabling more accurately the 2-group discrimination. The discriminant values obtained in the multivariate discriminants useful particularly for the 2-group discrimination of the prostatic cancer and the prostatic hypertrophy, can be utilized to bring about the effect of enabling more accurately the 2-group discrimination.

When the discrimination described in 11. above is conducted in step SA-13, the multivariate discriminant may be the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(Tau/ABA)+b_1(Thr/Cit)+c_1(Glu/Ser)+d_1(Pro/Asn)+e_1 \quad \text{(formula 1)}$$

wherein $a_1$, $b_1$, $c_1$, $d_1$, and $e_1$ in the formula 1 is arbitrary real number. Thus, the discriminant values obtained in the multivariate discriminants useful particularly for the 2-group discrimination of the prostatic disease and the prostatic disease-free, can be utilized to bring about the effect of enabling more accurately the 2-group discrimination.

When the discrimination described in 12. above is conducted in step SA-13, the multivariate discriminant may be the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(Tau/Trp)+b_2(Thr/Ser)+c_2(Glu/Asn)+d_2(Orn/Gln)+e_2 \quad \text{(formula 2)}$$

$$a_3(Tau/Met)+b_3(Ser/Cit)+c_3(Asn/Thr)+d_3(Glu/Pro)+e_3 \quad \text{(formula 3)}$$

$$a_4(Thr/Orn)+b_4(Ser/Ile)+c_4(Asn/Glu)+d_4(Gln/Tau)+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number. Thus, the discriminant values obtained in the multivariate discriminants useful particularly for the 2-group discrimination of the prostatic cancer and the prostatic cancer-free, can be utilized to bring about the effect of enabling more accurately the 2-group discrimination.

When the discrimination described in 13. above is conducted in step SA-13, the multivariate discriminant may be the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(Ser/Gln)+b_5(Glu/Tau)+c_5(Ala/Asn)+d_5(Val/Thr)+e_5 \quad \text{(formula 5)}$$

wherein $a_5$, $b_5$, $c_5$, $d_5$, and $e_5$ in the formula 5 is arbitrary real number. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination.

The multivariate discriminant described above can be prepared by a method described in International Publication WO 2004/052191 that is an international application filed by the present applicant or by a method (multivariate discriminant-preparing processing described in the second embodiment described later) described in International Publication WO 2006/098192 that is an international application filed by the present applicant. Any multivariate discriminants obtained by these methods can be preferably used in the evaluation of the state of prostatic disease, regardless of the unit of the amino acid concentration in the amino acid concentration data as input data.

Second Embodiment 2-1. Outline of the Invention

Figure 3:
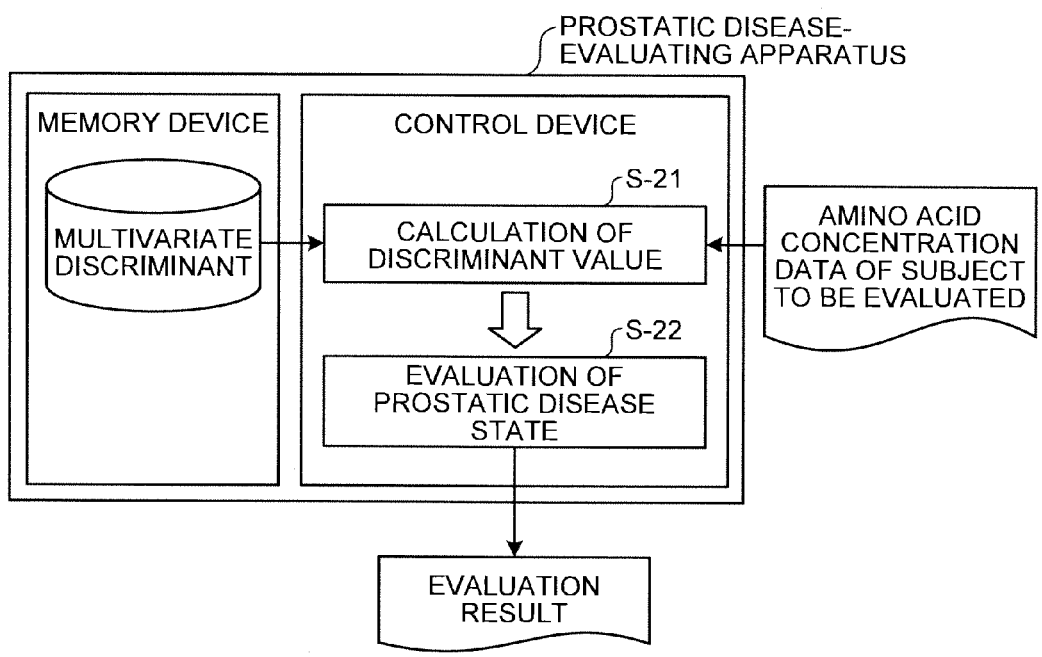
FIG. 3 is a principle configurational diagram showing a basic principle of the present invention.

Herein, an outline of the prostatic disease-evaluating apparatus, the prostatic disease-evaluating method, the prostatic disease-evaluating system, the prostatic disease-evaluating program and the recording medium of the present invention are described in detail with reference to FIG. 3. FIG. 3 is a principle configurational diagram showing a basic principle of the present invention.

In the present invention, a discriminant value that is a value of a multivariate discriminant with a concentration of an amino acid as an explanatory variable is calculated in a control device, based on both (i) a concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in previously obtained amino acid concentration data on the concentration value of the amino acid of a subject (for example, an individual such as animal or human) to be evaluated and (ii) the multivariate discriminant containing at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable, stored in a memory device (step S-21).

In the present invention, a state of prostatic disease including at least one of prostatic cancer and prostatic hypertrophy in the subject is evaluated in the control device based on the discriminant value calculated in step S-21 (step S-22).

According to the present invention described above, (I) the discriminant value that is the value of the multivariate discriminant with the concentration of the amino acid as the explanatory variable is calculated based on both (i) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the previously obtained amino acid concentration data on the concentration value of the amino acid of the subject and (ii) the multivariate discriminant stored in the memory device containing at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable, and (II) the state of prostatic disease in the subject is evaluated based on the calculated discriminant value. Thus, the discriminant values obtained in the multivariate discriminants correlated significantly with the state of prostatic disease can be utilized to bring about the effect of enabling an accurate evaluation of the state of prostatic disease. Specifically, an examinee likely to contract prostatic disease can be narrowed by one sample in a short time to bring about the effect of enabling the reduction of temporal, physical and financial burden of the examinee. Specifically, whether a certain sample is with prostatic disease can be evaluated accurately by the concentrations of a plurality of the amino acids and the discriminants with the concentrations of the amino acids as the explanatory variables to bring about the effect of enabling to make the examination efficient and high accurate.

In step S-22, the discrimination between the prostatic disease and the prostatic disease-free, between the prostatic cancer and the prostatic cancer-free, or between the prostatic cancer and the prostatic hypertrophy in the subject may be conducted based on the discriminant value calculated in step S-21. Thus, the discriminant values obtained in the multivariate discriminants useful for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling accurately these 2-group discriminations.

The multivariate discriminant may be any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree. Thus, the discriminant values obtained in the multivariate discriminants useful particularly for the 2-group discrimination of the prostatic disease and the prostatic disease-free, the 2-group discrimination of the prostatic cancer and the prostatic cancer-free, or the 2-group discrimination of the prostatic cancer and the prostatic hypertrophy, can be utilized to bring about the effect of enabling more accurately these 2-group discriminations.

(I) In step S-21, the discriminant value may be calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and (II) in step S-22, the discrimination between the prostatic disease and the prostatic disease-free in the subject may be conducted based on the calculated discriminant value. Thus, the discriminant values obtained in the multivariate discriminants useful particularly for the 2-group discrimination of the prostatic disease and the prostatic disease-free, can be utilized to bring about the effect of enabling more accurately the 2-group discrimination. The multivariate discriminant to be used in this case may be the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(Tau/ABA)+b_1(Thr/Cit)+c_1(Glu/Ser)+d_1(Pro/Asn)+e_1 \quad \text{(formula 1)}$$

wherein $a_1$, $b_1$, $c_1$, $d_1$, and $e_1$ in the formula 1 is arbitrary real number. Thus, the discriminant values obtained in the multivariate discriminants useful particularly for the 2-group discrimination of the prostatic disease and the prostatic disease-free, can be utilized to bring about the effect of enabling more accurately the 2-group discrimination.

(I) In step S-21, the discriminant value may be calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and (II) in step S-22, the discrimination between the prostatic cancer and the prostatic cancer-free in the subject may be conducted based on the calculated discriminant value. Thus, the discriminant values obtained in the multivariate discriminants useful particularly for the 2-group discrimination of the prostatic cancer and the prostatic cancer-free, can be utilized to bring about the effect of enabling more accurately the 2-group discrimination. The multivariate discriminant to be used in this case may be the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(Tau/Trp)+b_2(Thr/Ser)+c_2(Glu/Asn)+d_2(Orn/Gln)+e_2 \quad \text{(formula 2)}$$

$$a_3(Tau/Met)+b_3(Ser/Cit)+c_3(Asn/Thr)+d_3(Glu/Pro)+e_3 \quad \text{(formula 3)}$$

$$a_4(Thr/Orn)+b_4(Ser/Ile)+c_4(Asn/Glu)+d_4(Gln/Tau)+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number. Thus, the discriminant values obtained in the multivariate discriminants useful particularly for the 2-group discrimination of the prostatic cancer and the prostatic cancer-free, can be utilized to bring about the effect of enabling more accurately the 2-group discrimination.

(I) In step S-21, the discriminant value may be calculated based on both (i) the concentration value of at least one of Thr, Ser, Gly, Cit, Val, His, Trp, and Lys contained in the amino acid concentration data and (ii) the multivariate discriminant containing at least one of Thr, Ser, Gly, Cit, Val, His, Trp, and Lys as the explanatory variable, and (II) in step S-22, the discrimination between the prostatic cancer and the prostatic hypertrophy in the subject may be conducted based on the calculated discriminant value. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination. The multivariate discriminant to be used in this case may be the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(Ser/Gln)+b_5(Glu/Tau)+c_5(Ala/Asn)+d_5(Val/Thr)+e_5 \quad \text{(formula 5)}$$

wherein $a_5$, $b_5$, $c_5$, $d_5$, and $e_5$ in the formula 5 is arbitrary real number. Thus, the discriminant values obtained in the multivariate discriminants useful for the 2-group discrimination of the prostatic cancer and the prostatic hypertrophy, can be utilized to bring about the effect of enabling more accurately the 2-group discrimination.

The multivariate discriminant described above can be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in the evaluation of the state of prostatic disease, regardless of the unit of the amino acid concentration in the amino acid concentration data as input data.

The multivariate discriminant refers to a form of equation used generally in multivariate analysis and includes, for example, multiple regression equation, multiple logistic regression equation, linear discriminant function, Mahalanobis' generalized distance, canonical discriminant function, support vector machine, and decision tree. The multivariate discriminant also includes an equation shown by the sum of different forms of the multivariate discriminants. In the multiple regression equation, multiple logistic regression equation and canonical discriminant function, a coefficient and constant term are added to each explanatory variable, and the coefficient and constant term in this case are preferably real numbers, more preferably values in the range of 99% confidence interval for the coefficient and constant term obtained from data for discrimination, more preferably in the range of 95% confidence interval for the coefficient and constant term obtained from data for discrimination. The value of each coefficient and the confidence interval thereof may be those multiplied by a real number, and the value of each constant term and the confidence interval thereof may be those having an arbitrary actual constant added or subtracted or those multiplied or divided by an arbitrary actual constant.

In the fractional expression, the numerator of the fractional expression is expressed by the sum of the amino acids A, B, C etc. and the denominator of the fractional expression is expressed by the sum of the amino acids a, b, c etc. The fractional expression also includes the sum of the fractional expressions $\alpha$, $\beta$, $\gamma$ etc. (for example, $\alpha+\beta$) having such constitution. The fractional expression also includes divided fractional expressions. The amino acids used in the numerator or denominator may have suitable coefficients respectively. The amino acids used in the numerator or denominator may appear repeatedly. Each fractional expression may have a suitable coefficient. A value of a coefficient for each explanatory variable and a value for a constant term may be any real numbers. In combinations where explanatory variables in the numerator and explanatory variables in the denominator in the fractional expression are switched with each other, the positive (or negative) sign is generally reversed in correlation with objective explanatory variables, but because their correlation is maintained, such combinations can be assumed to be equivalent to one another in discrimination, and thus the fractional expression also includes combinations where explanatory variables in the numerator and explanatory variables in the denominator in the fractional expression are switched with each other.

When the state of prostatic disease is evaluated in the present invention, the concentrations of the other metabolites, the gene expression level, the protein expression level, the age and sex of the subject, the presence or absence of the smoking, the digitalized electrocardiogram waveform, or the like may be used in addition to the amino acid concentration. When the state of prostatic disease is evaluated in the present invention, the concentrations of the other metabolites, the gene expression level, the protein expression level, the age and sex of the subject, the presence or absence of the smoking, the digitalized electrocardiogram waveform, or the like may be used as the explanatory variables in the multivariate discriminant in addition to the amino acid concentration.

Here, the summary of the multivariate discriminant-preparing processing (steps 1 to 4) is described in detail.

First, a candidate multivariate discriminant (e.g., $y=a_1x_1+a_2x_2+ \ldots +a_nx_n$, y: prostatic disease state index data, $x_i$: amino acid concentration data, $a_i$: constant, i=1, 2, ..., n) that is a candidate for the multivariate discriminant is prepared in the control device based on a predetermined discriminant-preparing method from prostatic disease state information stored in the memory device containing the amino acid concentration data and prostatic disease state index data on an index for indicating the state of prostatic disease (step 1). Data containing defective and outliers may be removed in advance from the prostatic disease state information.

In step 1, a plurality of the candidate multivariate discriminants may be prepared from the prostatic disease state information by using a plurality of the different discriminant-preparing methods (including those for multivariate analysis such as principal component analysis, discriminant analysis, support vector machine, multiple regression analysis, logistic regression analysis, k-means method, cluster analysis, and decision tree). Specifically, a plurality of the candidate multivariate discriminants may be prepared simultaneously and concurrently by using a plurality of different algorithms with the prostatic disease state information which is multivariate data composed of the amino acid concentration data and the prostatic disease state index data obtained by analyzing blood samples from a large number of healthy subjects and prostatic disease patients. For example, the two different candidate multivariate discriminants may be formed by performing discriminant analysis and logistic regression analysis simultaneously with the different algorithms. Alternatively, the candidate multivariate discriminant may be formed by converting the prostatic disease state information with the candidate multivariate discriminant prepared by performing principal component analysis and then performing discriminant analysis of the converted prostatic disease state information. In this way, it is possible to finally prepare the multivariate discriminant suitable for diagnostic condition.

The candidate multivariate discriminant prepared by principal component analysis is a linear expression consisting of amino acid explanatory variables maximizing the variance of all amino acid concentration data. The candidate multivariate discriminant prepared by discriminant analysis is a high-powered expression (including exponential and logarithmic expressions) consisting of amino acid explanatory variables minimizing the ratio of the sum of the variances in respective groups to the variance of all amino acid concentration data. The candidate multivariate discriminant prepared by using support vector machine is a high-powered expression (including kernel function) consisting of amino acid explanatory variables maximizing the boundary between groups. The candidate multivariate discriminant prepared by multiple regression analysis is a high-powered expression consisting of amino acid explanatory variables minimizing the sum of the distances from all amino acid concentration data. The candidate multivariate discriminant prepared by logistic regression analysis is a fraction expression having, as a component, the natural logarithm having a linear expression consisting of amino acid explanatory variables maximizing the likelihood as the exponent. The k-means method is a method of searching k pieces of neighboring amino acid concentration data in various groups, designating the group containing the greatest number of the neighboring points as its data-belonging group, and selecting the amino acid explanatory variable that makes the group to which input amino acid concentration data belong agree well with the designated group. The cluster analysis is a method of clustering (grouping) the points closest in entire amino acid concentration data. The decision tree is a method of ordering amino acid explanatory variables and predicting the group of amino acid concentration data from the pattern possibly held by the higher-ordered amino acid explanatory variable.

Returning to the description of the multivariate discriminant-preparing processing, the candidate multivariate discriminant prepared in step 1 is verified (mutually verified) in the control device based on a particular verifying method (step 2). The verification of the candidate multivariate discriminant is performed on each other to each candidate multivariate discriminant prepared in step 1.

In step 2, at least one of discrimination rate, sensitivity, specificity, information criterion, and the like of the candidate multivariate discriminant may be verified by at least one of the bootstrap method, holdout method, leave-one-out method, and the like. In this way, it is possible to prepare the candidate multivariate discriminant higher in predictability or reliability, by taking the prostatic disease state information and the diagnostic condition into consideration.

The discrimination rate is the rate of the prostatic disease states judged correct according to the present invention in all input data. The sensitivity is the rate of the prostatic disease states judged correct according to the present invention in the prostatic disease states declared prostatic disease in the input data. The specificity is the rate of the prostatic disease states judged correct according to the present invention in the prostatic disease states declared healthy in the input data. The information criterion is the sum of the number of the amino acid explanatory variables in the candidate multivariate discriminant prepared in step 1 and the difference in number between the prostatic disease states evaluated according to the present invention and those declared in input data. The predictability is the average of the discrimination rate, sensitivity, or specificity obtained by repeating verification of the candidate multivariate discriminant. Alternatively, the reliability is the variance of the discrimination rate, sensitivity, or specificity obtained by repeating verification of the candidate multivariate discriminant.

Returning to the description of the multivariate discriminant-preparing processing, a combination of the amino acid concentration data contained in the prostatic disease state information used in preparing the candidate multivariate discriminant is selected by selecting the explanatory variable of the candidate multivariate discriminant in the control device based on a predetermined explanatory variable-selecting method from the verification result obtained in step 2 (step 3). The selection of the amino acid explanatory variable is performed on each candidate multivariate discriminant prepared in step 1. In this way, it is possible to select the amino acid explanatory variable of the candidate multivariate discriminant properly. The step 1 is executed once again by using the prostatic disease state information including the amino acid concentration data selected in step 3.

In step 3, the amino acid explanatory variable of the candidate multivariate discriminant may be selected based on at least one of the stepwise method, best path method, local search method, and genetic algorithm from the verification result obtained in step 2.

The best path method is a method of selecting an amino acid explanatory variable by optimizing an evaluation index of the candidate multivariate discriminant while eliminating the amino acid explanatory variables contained in the candidate multivariate discriminant one by one.

Returning to the description of the multivariate discriminant-preparing processing, the steps 1, 2 and 3 are repeatedly performed in the control device, and based on verification results thus accumulated, the candidate multivariate discriminant used as the multivariate discriminant is selected from a plurality of the candidate multivariate discriminants, thereby preparing the multivariate discriminant (step 4). In the selection of the candidate multivariate discriminant, there are cases where the optimum multivariate discriminant is selected from the candidate multivariate discriminants prepared in the same discriminant-preparing method or the optimum multivariate discriminant is selected from all candidate multivariate discriminants.

As described above, in the multivariate discriminant-preparing processing, the processing for the preparation of the candidate multivariate discriminants, the verification of the candidate multivariate discriminants, and the selection of the explanatory variables in the candidate multivariate discriminants are performed based on the prostatic disease state information in a series of operations in a systematized manner, whereby the multivariate discriminant most appropriate for evaluating each prostatic disease state can be prepared.

2-2. System Configuration

Hereinafter, the configuration of the prostatic disease-evaluating system according to the second embodiment (hereinafter referred to sometimes as the present system) will be described with reference to FIGS. 4 to 20. This system is merely one example, and the present invention is not limited thereto.

Figure 4:
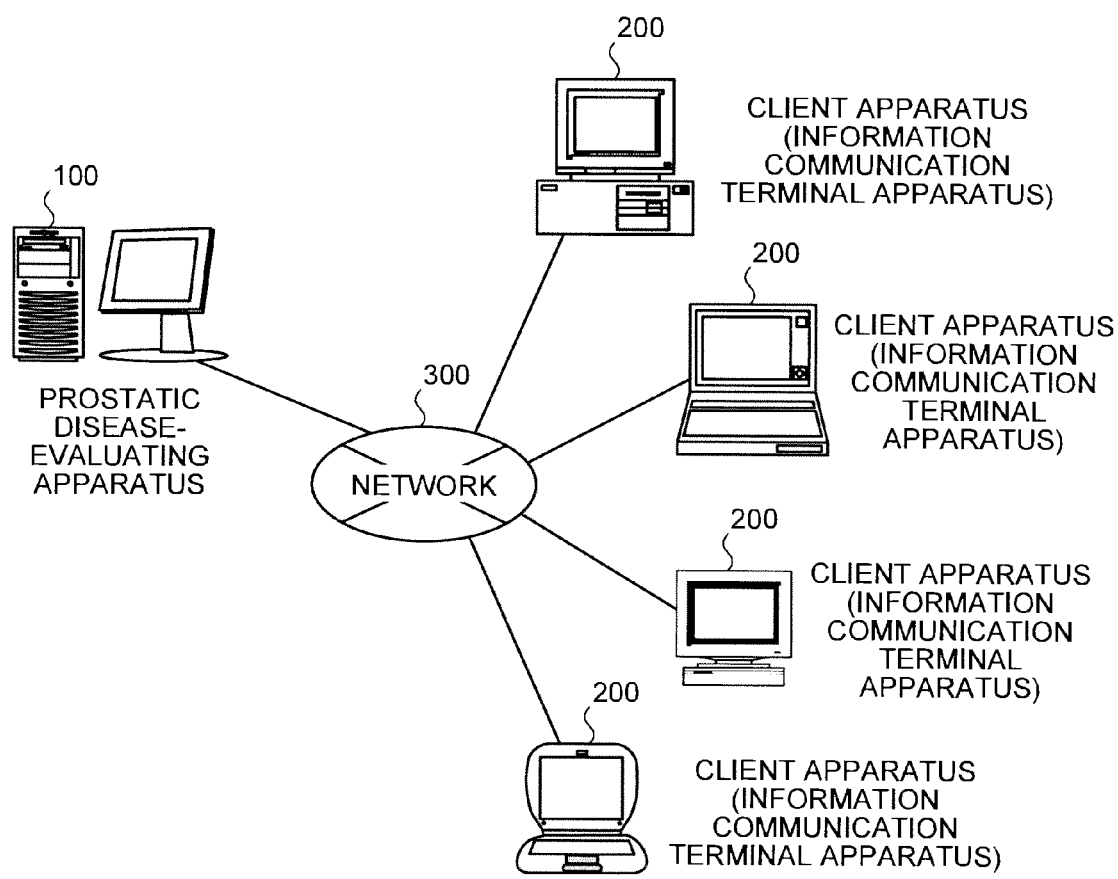
FIG. 4 is a diagram showing an example of an entire configuration of a present system.
Figure 5:
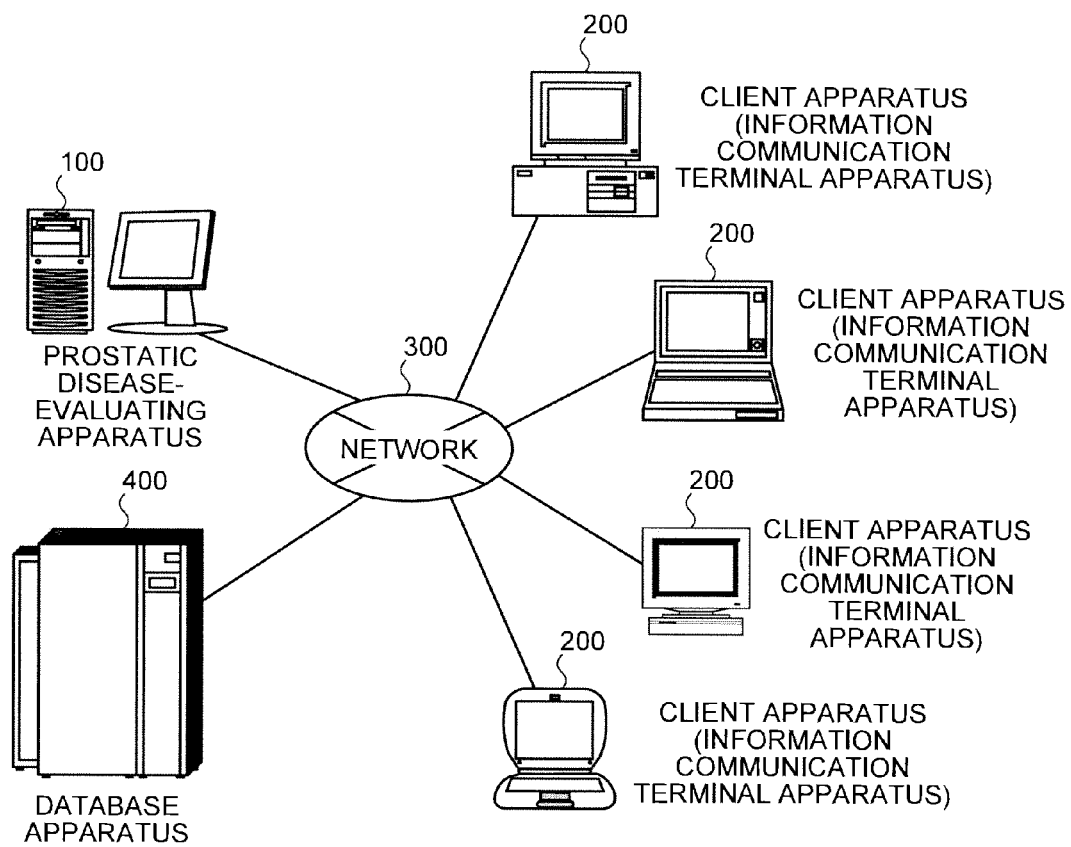
FIG. 5 is a diagram showing another example of an entire configuration of the present system.

First, an entire configuration of the present system will be described with reference to FIGS. 4 and 5. FIG. 4 is a diagram showing an example of the entire configuration of the present system. FIG. 5 is a diagram showing another example of the entire configuration of the present system. As shown in FIG. 4, the present system is constituted in which the prostatic disease-evaluating apparatus 100 that evaluates the state of prostatic disease in the subject, and the client apparatus 200 (corresponding to the information communication terminal apparatus of the present invention) that provides the amino acid concentration data of the subject on the concentration values of the amino acids, are communicatively connected to each other via a network 300.

In the present system as shown in FIG. 5, in addition to the prostatic disease-evaluating apparatus 100 and the client apparatus 200, the database apparatus 400 storing, for example, the prostatic disease state information used in preparing the multivariate discriminant and the multivariate discriminant used in evaluating the state of prostatic disease in the prostatic disease-evaluating apparatus 100, may be communicatively connected via the network 300. In this configuration, the information on the state of prostatic disease etc. are provided via the network 300 from the prostatic disease-evaluating apparatus 100 to the client apparatuses 200 and the database apparatus 400, or from the client apparatuses 200 and the database apparatus 400 to the prostatic disease-evaluating apparatus 100. The "information on the state of prostatic disease" is information on the measured values of particular items of the state of prostatic disease of human. The information on the state of prostatic disease is generated in the prostatic disease-evaluating apparatus 100, client apparatus 200, or other apparatuses (e.g., various measuring apparatuses) and stored mainly in the database apparatus 400.

Figure 6:
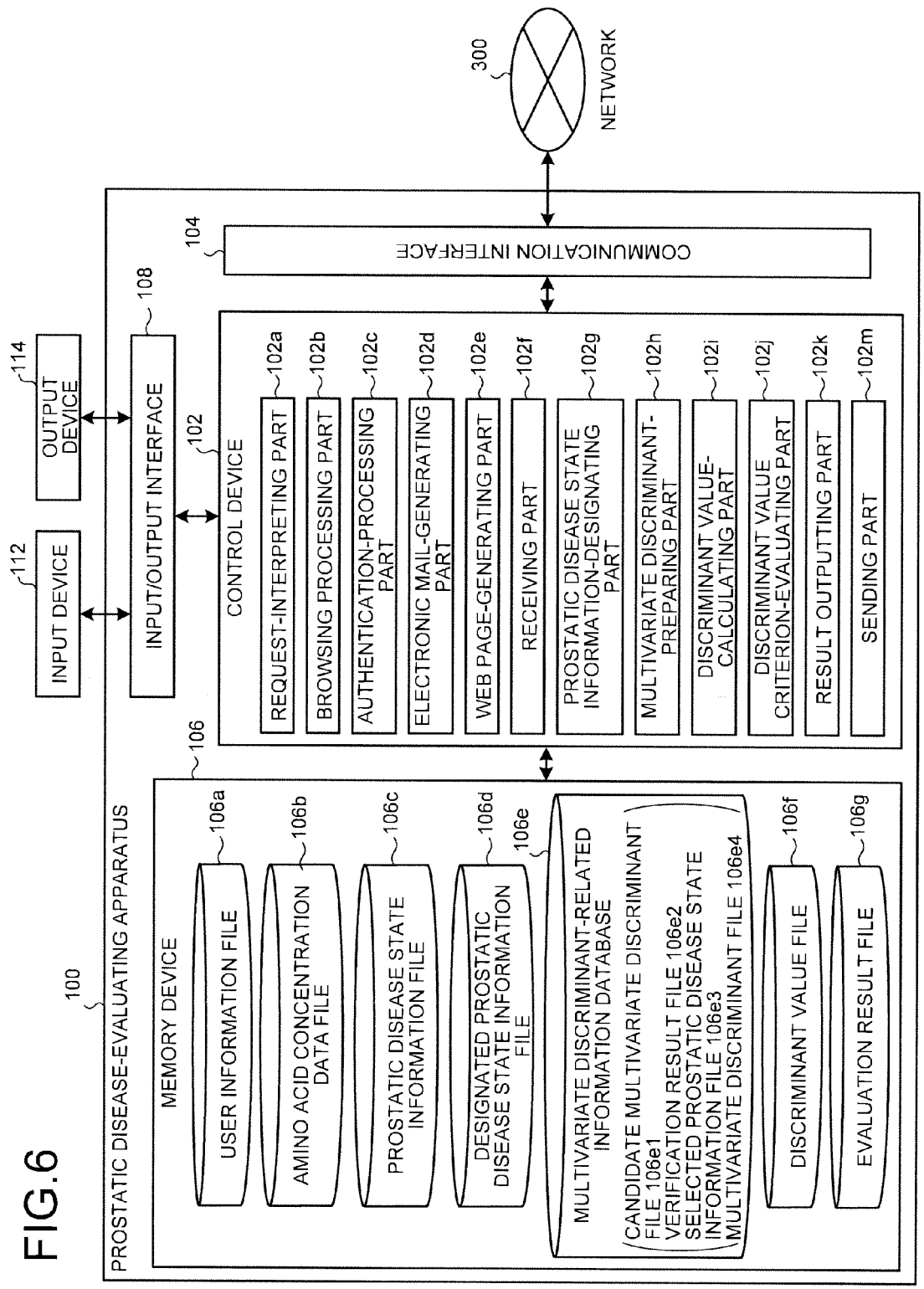
FIG. 6 is a block diagram showing an example of a configuration of a prostatic disease-evaluating apparatus 100 in the present system.

Now, the configuration of the prostatic disease-evaluating apparatus 100 in the present system will be described with reference to FIGS. 6 to 18. FIG. 6 is a block diagram showing an example of the configuration of the prostatic disease-evaluating apparatus 100 in the present system, showing conceptually only the region relevant to the present invention.

The prostatic disease-evaluating apparatus 100 includes (a) a control device 102, such as CPU (Central Processing Unit), that integrally controls the prostatic disease-evaluating apparatus 100, (b) a communication interface 104 that connects the prostatic disease-evaluating apparatus 100 to the network 300 communicatively via communication apparatuses such as a router and wired or wireless communication lines such as a private line, (c) a memory device 106 that stores various databases, tables, files and others, and (d) an input/output interface 108 connected to an input device 112 and an output device 114, and these parts are connected to each other communicatively via any communication channel. The prostatic disease-evaluating apparatus 100 may be present together with various analyzers (e.g., amino acid analyzer) in a same housing. A typical configuration of disintegration/integration of the prostatic disease-evaluating apparatus 100 is not limited to that shown in the figure, and all or a part of it may be disintegrated or integrated functionally or physically in any unit, for example, according to various loads applied. For example, a part of the processing may be performed via CGI (Common Gateway Interface).

The memory device 106 is a storage means, and examples thereof include memory apparatuses such as RAM (Random Access Memory) and ROM (Read Only Memory), fixed disk drives such as a hard disk, a flexible disk, an optical disk, and the like. The memory device 106 stores computer programs giving instructions to the CPU for various processings, together with OS (Operating System). As shown in the figure, the memory device 106 stores the user information file 106a, the amino acid concentration data file 106b, the prostatic disease state information file 106c, the designated prostatic disease state information file 106d, a multivariate discriminant-related information database 106e, the discriminant value file 106f and the evaluation result file 106g.

The user information file 106a stores user information on users. FIG. 7 is a chart showing an example of information stored in the user information file 106a. As shown in FIG. 7, the information stored in the user information file 106a includes user ID (identification) for identifying a user uniquely, user password for authentication of the user, user name, organization ID for uniquely identifying an organization of the user, department ID for uniquely identifying a department of the user organization, department name, and electronic mail address of the user that are correlated to one another.

Returning to FIG. 6, the amino acid concentration data file 106b stores the amino acid concentration data on the concentration values of the amino acids. FIG. 8 is a chart showing an example of information stored in the amino acid concentration data file 106b. As shown in FIG. 8, the information stored in the amino acid concentration data file 106b includes individual number for uniquely identifying an individual (sample) as a subject to be evaluated and amino acid concentration data that are correlated to one another. In FIG. 8, the amino acid concentration data is assumed to be numerical values, i.e., on a continuous scale, but the amino acid concentration data may be expressed on a nominal scale or an ordinal scale. In the case of the nominal or ordinal scale, any number may be allocated to each state for analysis. The amino acid concentration data may be combined with other biological information (e.g., the concentrations of metabolites other than the amino acids, the gene expression level, the protein expression level, the age and sex of the subject, the presence or absence of the smoking, and the digitalized electrocardiogram waveform).

Returning to FIG. 6, the prostatic disease state information file 106c stores the prostatic disease state information used in preparing the multivariate discriminant. FIG. 9 is a chart showing an example of information stored in the prostatic disease state information file 106c. As shown in FIG. 9, the information stored in the prostatic disease state information file 106c includes individual (sample) number, prostatic disease state index data (T) corresponding to prostatic disease state index (index $T_1$, index $T_2$, index $T_3$ . . . ), and amino acid concentration data that are correlated to one another. In FIG. 9, the prostatic disease state index data and the amino acid concentration data are assumed to be numerical values, i.e., on a continuous scale, but the prostatic disease state index data and the amino acid concentration data may be expressed on a nominal scale or an ordinal scale. In the case of the nominal or ordinal scale, any number may be allocated to each state for analysis. The prostatic disease state index data is a single known condition index serving as a marker of the state of prostatic disease, and numerical data may be used.

Returning to FIG. 6, the designated prostatic disease state information file 106d stores the prostatic disease state information designated in a prostatic disease state information-designating part 102g described below. FIG. 10 is a chart showing an example of information stored in the designated prostatic disease state information file 106d. As shown in FIG. 10, the information stored in the designated prostatic disease state information file 106d includes individual number, designated prostatic disease state index data, and designated amino acid concentration data that are correlated to one another.

Returning to FIG. 6, the multivariate discriminant-related information database 106e is composed of (i) the candidate multivariate discriminant file 106e1 storing the candidate multivariate discriminant prepared in a candidate multivariate discriminant-preparing part 102h1 described below, (ii) the verification result file 106e2 storing the verification results obtained in a candidate multivariate discriminant-verifying part 102h2 described below, (iii) the selected prostatic disease state information file 106e3 storing the prostatic disease state information containing the combination of the amino acid concentration data selected in an explanatory variable-selecting part 102h3 described below, and (iv) the multivariate discriminant file 106e4 storing the multivariate discriminant prepared in the multivariate discriminant-preparing part 102h described below.

The candidate multivariate discriminant file 106e1 stores the candidate multivariate discriminants prepared in the candidate multivariate discriminant-preparing part 102h1 described below. FIG. 11 is a chart showing an example of information stored in the candidate multivariate discriminant file 106e1. As shown in FIG. 11, the information stored in the candidate multivariate discriminant file 106e1 includes rank, and candidate multivariate discriminant (e.g., $F_1$ (Gly, Leu, Phe, . . . ), $F_2$ (Gly, Leu, Phe, . . . ), or $F_3$ (Gly, Leu, Phe, . . . ) in FIG. 11) that are correlated to each other.

Returning to FIG. 6, the verification result file 106e2 stores the verification results obtained in the candidate multivariate discriminant-verifying part 102h2 described below. FIG. 12 is a chart showing an example of information stored in the verification result file 106e2.

As shown in FIG. 12, the information stored in the verification result file 106e2 includes rank, candidate multivariate discriminant (e.g., $F_k$ (Gly, Leu, Phe, . . . ), $F_m$ (Gly, Leu, Phe, . . . ), $F_1$ (Gly, Leu, Phe, . . . ) in FIG. 12), and verification result of each candidate multivariate discriminant (e.g., evaluation value of each candidate multivariate discriminant) that are correlated to one another.

Returning to FIG. 6, the selected prostatic disease state information file 106e3 stores the prostatic disease state information including the combination of the amino acid concentration data corresponding to the explanatory variables selected in the explanatory variable-selecting part 102h3 described below. FIG. 13 is a chart showing an example of information stored in the selected prostatic disease state information file 106e3. As shown in FIG. 13, the information stored in the selected prostatic disease state information file 106e3 includes individual number, prostatic disease state index data designated in the prostatic disease state information-designating part 102g described below, and amino acid concentration data selected in the explanatory variable-selecting part 102h3 described below that are correlated to one another.

Returning to FIG. 6, the multivariate discriminant file 106e4 stores the multivariate discriminants prepared in the multivariate discriminant-preparing part 102h described below. FIG. 14 is a chart showing an example of information stored in the multivariate discriminant file 106e4. As shown in FIG. 14, the information stored in the multivariate discriminant file 106e4 includes rank, multivariate discriminant (e.g., $F_p$ (Phe, . . . ), $F_p$ (Gly, Leu, Phe), $F_k$ (Gly, Leu, Phe, . . . ) in FIG. 14), a threshold corresponding to each discriminant-preparing method, and verification result of each multivariate discriminant (e.g., evaluation value of each multivariate discriminant) that are correlated to one another.

Returning to FIG. 6, the discriminant value file 106f stores the discriminant value calculated in a discriminant value-calculating part 102i described below. FIG. 15 is a chart showing an example of information stored in the discriminant value file 106f. As shown in FIG. 15, the information stored in the discriminant value file 106f includes individual number for uniquely identifying the individual (sample) as the subject, rank (number for uniquely identifying the multivariate discriminant), and discriminant value that are correlated to one another.

Figures 16, 17:
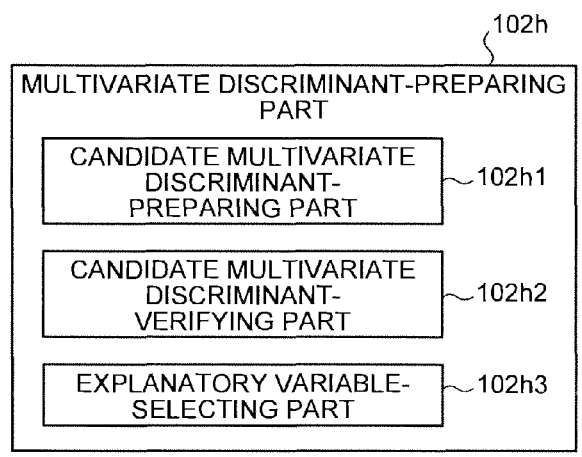
FIG. 16 is a chart showing an example of information stored in an evaluation result file 106g.
FIG. 17 is a block diagram showing a configuration of a multivariable discriminant-preparing part 102h.

Returning to FIG. 6, the evaluation result file 106g stores the evaluation results obtained in the discriminant value criterion-evaluating part 102j described below (specifically the discrimination results obtained in a discriminant value criterion-discriminating part 102j1 described below). FIG. 16 is a chart showing an example of information stored in the evaluation result file 106g. The information stored in the evaluation result file 106g includes individual number for uniquely identifying the individual (sample) as the subject, previously obtained amino acid concentration data of the subject, discriminant value calculated by multivariate discriminant, and evaluation result on the state of prostatic disease that are correlated to one another.

Returning to FIG. 6, the memory device 106 stores various Web data for providing the client apparatuses 200 with web site information, CGI programs, and others as information other than the information described above. The Web data include data for displaying the Web pages described below and others, and the data are generated as, for example, a HTML (HyperText Markup Language) or XML (Extensible Markup Language) text file. Files for components and files for operation for generation of the Web data, and other temporary files, and the like are also stored in the memory device 106. In addition, the memory device 106 may store as needed sound files of sounds for transmission to the client apparatuses 200 in WAVE format or AIFF (Audio Interchange File Format) format and image files of still images or motion pictures in JPEG (Joint Photographic Experts Group) format or MPEG2 (Moving Picture Experts Group phase 2) format.

The communication interface 104 allows communication between the prostatic disease-evaluating apparatus 100 and the network 300 (or communication apparatus such as a router). Thus, the communication interface 104 has a function to communicate data via a communication line with other terminals.

The input/output interface 108 is connected to the input device 112 and the output device 114. A monitor (including a home television), a speaker, or a printer may be used as the output device 114 (hereinafter, the output device 114 may be described as a monitor 114). A keyboard, a mouse, a microphone, or a monitor functioning as a pointing device together with a mouse may be used as the input device 112.

The control device 102 has an internal memory storing control programs such as OS (Operating System), programs for various processing procedures, and other needed data, and performs various information processings according to these programs. As shown in the figure, the control device 102 includes mainly a request-interpreting part 102a, a browsing processing part 102b, an authentication-processing part 102c, an electronic mail-generating part 102d, a Web page-generating part 102e, a receiving part 102f, the prostatic disease state information-designating part 102g, the multivariate discriminant-preparing part 102h, the discriminant value-calculating part 102i, the discriminant value criterion-evaluating part 102j, a result outputting part 102k and a sending part 102m. The control device 102 performs data processings such as removal of data including defective, removal of data including many outliers, and removal of explanatory variables for the defective-including data in the prostatic disease state information transmitted from the database apparatus 400 and in the amino acid concentration data transmitted from the client apparatus 200.

The request-interpreting part 102a interprets the requests transmitted from the client apparatus 200 or the database apparatus 400 and sends the requests to other parts in the control device 102 according to results of interpreting the requests. Upon receiving browsing requests for various screens transmitted from the client apparatus 200, the browsing processing part 102b generates and transmits web data for these screens. Upon receiving authentication requests transmitted from the client apparatus 200 or the database apparatus 400, the authentication-processing part 102c performs authentication. The electronic mail-generating part 102d generates electronic mails including various kinds of information. The Web page-generating part 102e generates Web pages for users to browse with the client apparatus 200.

The receiving part 102f receives, via the network 300, information (specifically, the amino acid concentration data, the prostatic disease state information, the multivariate discriminant etc.) transmitted from the client apparatus 200 and the database apparatus 400. The prostatic disease state information-designating part 102g designates objective prostatic disease state index data and objective amino acid concentration data in preparing the multivariate discriminant.

The multivariate discriminant-preparing part 102h generates the multivariate discriminants based on the prostatic disease state information received in the receiving part 102f and the prostatic disease state information designated in the prostatic disease state information-designating part 102g. Specifically, the multivariate discriminant-preparing part 102h generates the multivariate discriminant by selecting the candidate multivariate discriminant used as the multivariate discriminant from a plurality of the candidate multivariate discriminants, based on verification results accumulated by repeating processings in the candidate multivariate discriminant-preparing part 102h1, the candidate multivariate discriminant-verifying part 102h2, and the explanatory variable-selecting part 102h3 from the prostatic disease state information.

If the multivariate discriminants are stored previously in a predetermined region of the memory device 106, the multivariate discriminant-preparing part 102h may generate the multivariate discriminant by selecting the desired multivariate discriminant out of the memory device 106. Alternatively, the multivariate discriminant-preparing part 102h may generate the multivariate discriminant by selecting and downloading the desired multivariate discriminant from the multivariate discriminants previously stored in another computer apparatus (e.g., the database apparatus 400).

Hereinafter, a configuration of the multivariate discriminant-preparing part 102h will be described with reference to FIG. 17. FIG. 17 is a block diagram showing the configuration of the multivariate discriminant-preparing part 102h, and only a part in the configuration related to the present invention is shown conceptually. The multivariate discriminant-preparing part 102h has the candidate multivariate discriminant-preparing part 102h1, the candidate multivariate discriminant-verifying part 102h2, and the explanatory variable-selecting part 102h3, additionally. The candidate multivariate discriminant-preparing part 102h1 generates the candidate multivariate discriminant that is a candidate of the multivariate discriminant, from the prostatic disease state information based on a predetermined discriminant-preparing method. The candidate multivariate discriminant-preparing part 102h1 may generate a plurality of the candidate multivariate discriminants from the prostatic disease state information, by using a plurality of the different discriminant-preparing methods. The candidate multivariate discriminant-verifying part 102h2 verifies the candidate multivariate discriminant prepared in the candidate multivariate discriminant-preparing part 102h1 based on a particular verifying method. The candidate multivariate discriminant-verifying part 102h2 may verify at least one of the discrimination rate, sensitivity, specificity, and information criterion of the candidate multivariate discriminants based on at least one of the bootstrap method, holdout method, and leave-one-out method. The explanatory variable-selecting part 102h3 selects the combination of the amino acid concentration data contained in the prostatic disease state information used in preparing the candidate multivariate discriminant, by selecting the explanatory variables of the candidate multivariate discriminant based on a particular explanatory variable-selecting method from the verification results obtained in the candidate multivariate discriminant-verifying part 102h2. The explanatory variable-selecting part 102h3 may select the explanatory variables of the candidate multivariate discriminant based on at least one of the stepwise method, best path method, local search method, and genetic algorithm from the verification results.

Returning to FIG. 6, the discriminant value-calculating part 102i calculates the discriminant value that is the value of the multivariate discriminant, based on both (i) the concentration value of at least one of Tau, Thr, Ser, Asn, Glu, Pro, Gly, Ala, Cit, ABA, Val, Met, Ile, Leu, Phe, His, Trp, Orn, Lys, and Cys2 contained in the amino acid concentration data of the subject received in the receiving part 102f and (ii) the multivariate discriminant containing at least one of Tau, Thr, Ser, Asn, Glu, Pro, Gly, Ala, Cit, ABA, Val, Met, Ile, Leu, Phe, His, Trp, Orn, Lys, and Cys2 as the explanatory variable prepared in the multivariate discriminant-preparing part 102h.

The multivariate discriminant may be any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

When the discriminant value criterion-discriminating part 102j1 discriminates between the prostatic disease and the prostatic disease-free, the discriminant value-calculating part 102i may calculate the discriminant value based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the subject received in the receiving part 102f and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable prepared in the multivariate discriminant-preparing part 102h. The multivariate discriminant to be used in this case may be the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(\text{Tau}/\text{ABA})+b_1(\text{Thr}/\text{Cit})+c_1(\text{Glu}/\text{Ser})+d_1(\text{Pro}/\text{Asn})+e_1 \quad \text{(formula 1)}$$

wherein $a_1$, $b_1$, $c_1$, $d_1$, and $e_1$ in the formula 1 is arbitrary real number.

When the discriminant value criterion-discriminating part 102j1 discriminates between the prostatic cancer and the prostatic cancer-free, the discriminant value-calculating part 102i may calculate the discriminant value based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the subject received in the receiving part 102f and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable prepared in the multivariate discriminant-preparing part 102h. The multivariate discriminant to be used in this case may be the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau/Trp}) + b_2(\text{Thr/Ser}) + c_2(\text{Glu/Asn}) + d_2(\text{Orn/Gln}) + e_2 \quad \text{(formula 2)}$$

$$a_3(\text{Tau/Met}) + b_3(\text{Ser/Cit}) + c_3(\text{Asn/Thr}) + d_3(\text{Glu/Pro}) + e_3 \quad \text{(formula 3)}$$

$$a_4(\text{Thr/Orn}) + b_4(\text{Ser/Ile}) + c_4(\text{Asn/Glu}) + d_4(\text{Gln/Tau}) + e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number.

When the discriminant value criterion-discriminating part 102j1 discriminates between the prostatic cancer and the prostatic hypertrophy, the discriminant value-calculating part 102i may calculate the discriminant value based on both (i) the concentration value of at least one of Thr, Ser, Gly, Cit, Val, His, Trp, and Lys contained in the amino acid concentration data of the subject received in the receiving part 102f and (ii) the multivariate discriminant containing at least one of Thr, Ser, Gly, Cit, Val, His, Trp, and Lys as the explanatory variable prepared in the multivariate discriminant-preparing part 102h. The multivariate discriminant to be used in this case may be the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(\text{Ser/Gln}) + b_5(\text{Glu/Tau}) + c_5(\text{Ala/Asn}) + d_5(\text{Val/Thr}) + e_5 \quad \text{(formula 5)}$$

wherein $a_5$, $b_5$, $c_5$, $d_5$, and $e_5$ in the formula 5 is arbitrary real number.

Figure 18:
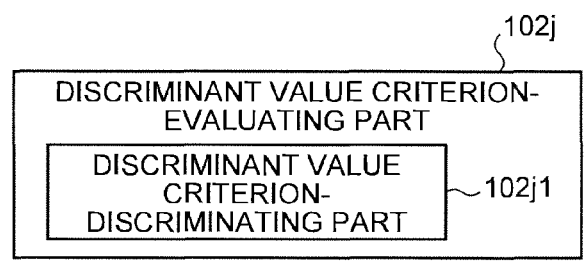
FIG. 18 is a block diagram showing a configuration of a discriminant value criterion-evaluating part 102j.

The discriminant value criterion-evaluating part 102j evaluates the state of prostatic disease in the subject based on the discriminant value calculated in the discriminant value-calculating part 102i. The discriminant value criterion-evaluating part 102j further includes the discriminant value criterion-discriminating part 102j1. Now, the configuration of the discriminant value criterion-evaluating part 102j will be described with reference to FIG. 18. FIG. 18 is a block diagram showing the configuration of the discriminant value criterion-evaluating part 102j, and only a part in the configuration related to the present invention is shown conceptually. The discriminant value criterion-discriminating part 102j1 conducts "the discrimination between prostatic disease and prostatic disease-free", "the discrimination between prostatic cancer and prostatic cancer-free", or "the discrimination between prostatic cancer and prostatic hypertrophy", based on the discriminant value calculated in the discriminant value-calculating part 102i.

Returning to FIG. 6, the result outputting part 102k outputs, into the output device 114, the processing results in each processing part in the control device 102 (the evaluation results obtained in the discriminant value criterion-evaluating part 102j (specifically, the discrimination results obtained in the discriminant value criterion-discriminating part 102j1)) etc.

The sending part 102m transmits the evaluation results to the client apparatus 200 that is a sender of the amino acid concentration data of the subject, and transmits the multivariate discriminant prepared in the prostatic disease-evaluating apparatus 100 and the evaluation results to the database apparatus 400.

Figure 19:
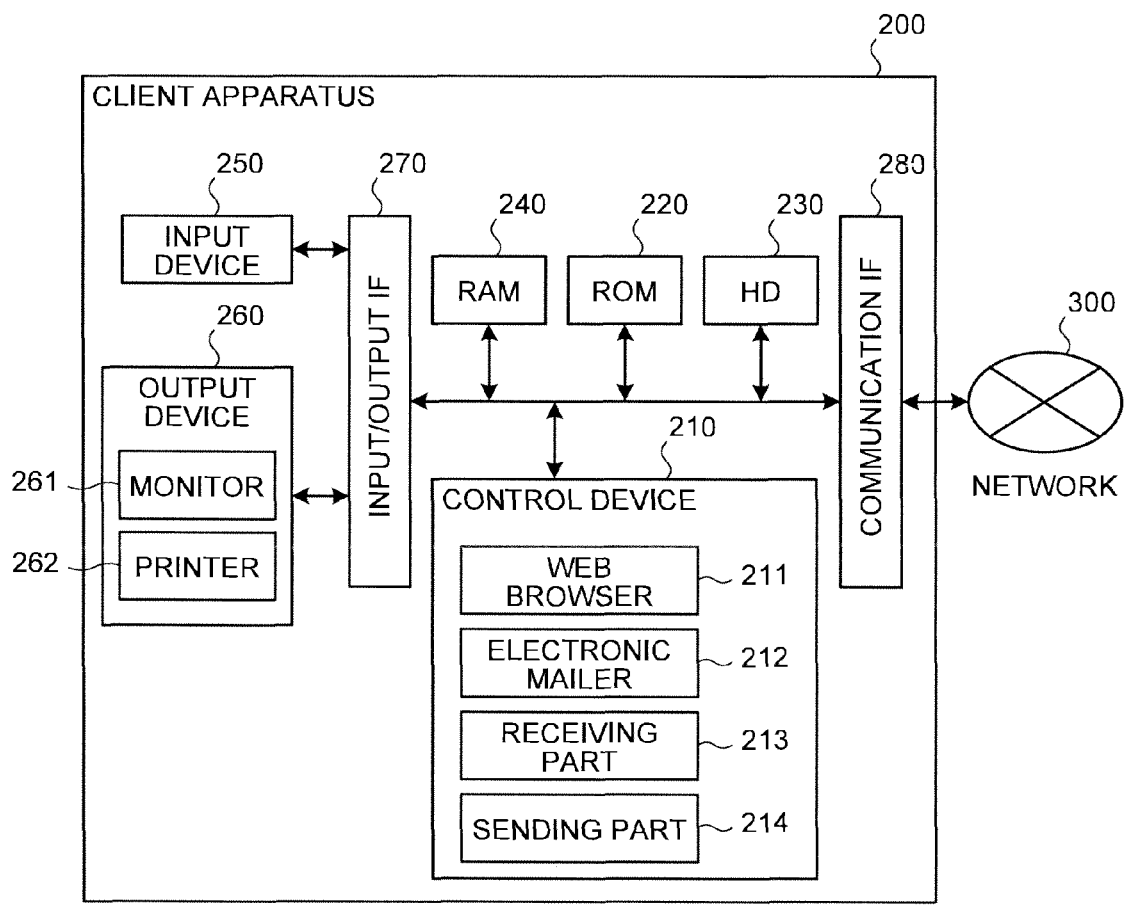
FIG. 19 is a block diagram showing an example of a configuration of a client apparatus 200 in the present system.

Hereinafter, a configuration of the client apparatus 200 in the present system will be described with reference to FIG. 19. FIG. 19 is a block diagram showing an example of the configuration of the client apparatus 200 in the present system, and only the part in the configuration relevant to the present invention is shown conceptually.

The client apparatus 200 includes a control device 210, ROM 220, HD (Hard Disk) 230, RAM 240, an input device 250, an output device 260, an input/output IF 270, and a communication IF 280 that are connected communicatively to one another through a communication channel.

The control device 210 has a Web browser 211, an electronic mailer 212, a receiving part 213, and a sending part 214. The Web browser 211 performs browsing processings of interpreting Web data and displaying the interpreted Web data on a monitor 261 described below. The Web browser 211 may have various plug-in softwares, such as stream player, having functions to receive, display and feedback streaming screen images. The electronic mailer 212 sends and receives electronic mails using a particular protocol (e.g., SMTP (Simple Mail Transfer Protocol) or POPS (Post Office Protocol version 3)). The receiving part 213 receives various kinds of information, such as the evaluation results transmitted from the prostatic disease-evaluating apparatus 100, via the communication IF 280. The sending part 214 sends various kinds of information such as the amino acid concentration data of the subject, via the communication IF 280, to the prostatic disease-evaluating apparatus 100.

The input device 250 is for example a keyboard, a mouse or a microphone. The monitor 261 described below also functions as a pointing device together with a mouse. The output device 260 is an output means for outputting information received via the communication IF 280, and includes the monitor 261 (including home television) and a printer 262. In addition, the output device 260 may have a speaker or the like additionally. The input/output IF 270 is connected to the input device 250 and the output device 260.

The communication IF 280 connects the client apparatus 200 to the network 300 (or communication apparatus such as a router) communicatively. In other words, the client apparatuses 200 are connected to the network 300 via a communication apparatus such as a modem, TA (Terminal Adapter) or a router, and a telephone line, or a private line. In this way, the client apparatuses 200 can access to the prostatic disease-evaluating apparatus 100 by using a particular protocol.

The client apparatus 200 may be realized by installing softwares (including programs, data and others) for a Web data-browsing function and an electronic mail-processing function to an information processing apparatus (for example, an information processing terminal such as a known personal computer, a workstation, a family computer, Internet TV (Television), PHS (Personal Handyphone System) terminal, a mobile phone terminal, a mobile unit communication terminal or PDA (Personal Digital Assistants)) connected as needed with peripheral devices such as a printer, a monitor, and an image scanner.

All or a part of processings of the control device 210 in the client apparatus 200 may be performed by CPU and programs read and executed by the CPU. Computer programs for giving instructions to the CPU and executing various processings together with the OS (Operating System) are recorded in the ROM 220 or HD 230. The computer programs, which are executed as they are loaded in the RAM 240, constitute the control device 210 with the CPU. The computer programs may be stored in application program servers connected via any network to the client apparatus 200, and the client apparatus 200 may download all or a part of them as needed. All or any part of processings of the control device 210 may be realized by hardware such as wired-logic.

Hereinafter, the network 300 in the present system will be described with reference to FIGS. 4 and 5. The network 300 has a function to connect the prostatic disease-evaluating apparatus 100, the client apparatuses 200, and the database apparatus 400 mutually, communicatively to one another, and is for example the Internet, an intranet, or LAN (Local Area Network (both wired/wireless)). The network 300 may be VAN (Value Added Network), a personal computer communication network, a public telephone network (including both analog and digital), a leased line network (including both analog and digital), CATV (Community Antenna Television) network, a portable switched network or a portable packet-switched network (including IMT2000 (International Mobile Telecommunication 2000) system, GSM (Global System for Mobile Communications) system, or PDC (Personal Digital Cellular)/PDC-P system), a wireless calling network, a local wireless network such as Bluetooth (registered trademark), PHS network, a satellite communication network (including CS (Communication Satellite), BS (Broadcasting Satellite), ISDB (Integrated Services Digital Broadcasting), and the like), or the like.

Figure 20:
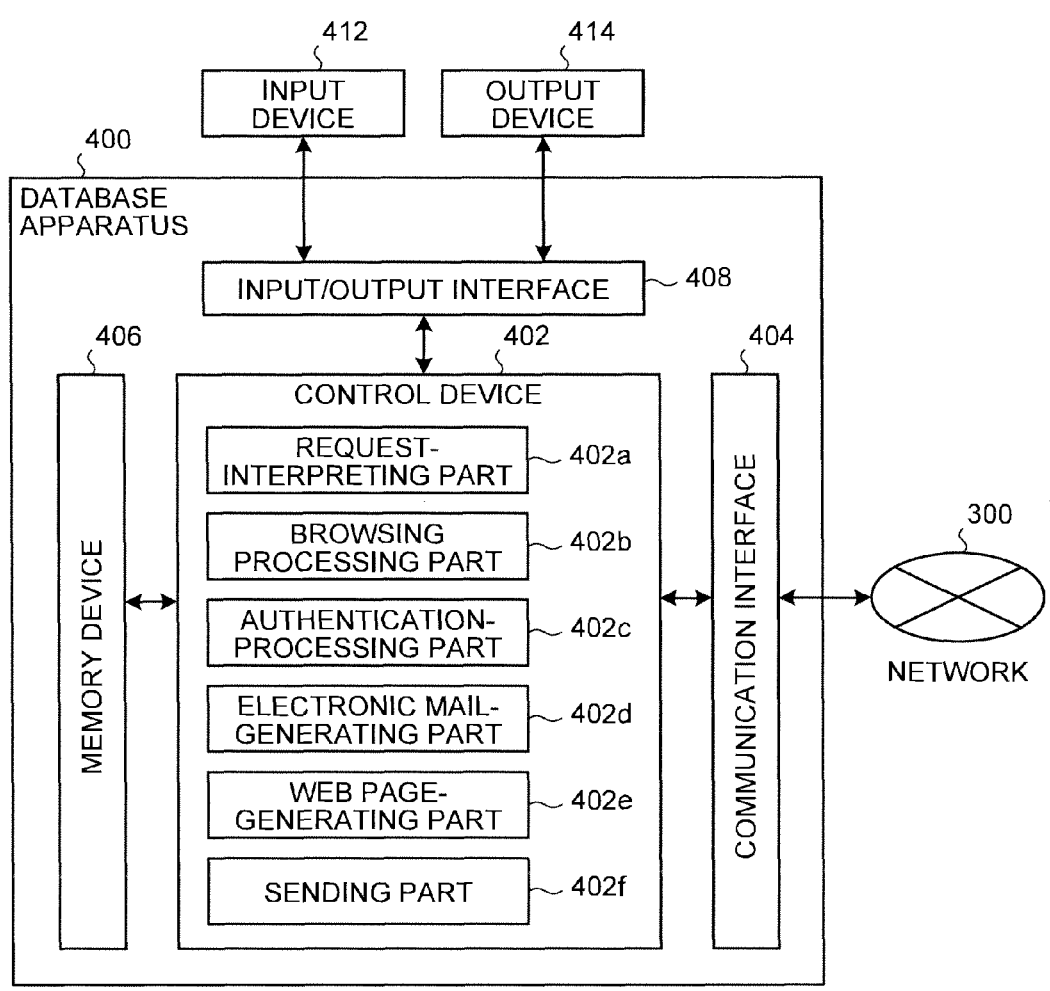
FIG. 20 is a block diagram showing an example of a configuration of a database apparatus 400 in the present system.

Hereinafter, the configuration of the database apparatus 400 in the present system will be described with reference to FIG. 20. FIG. 20 is a block diagram showing an example of the configuration of the database apparatus 400 in the present system, showing conceptually only the region relevant to the present invention.

The database apparatus 400 has functions to store, for example, the prostatic disease state information used in preparing the multivariate discriminants in the prostatic disease-evaluating apparatus 100 or in the database apparatus 400, the multivariate discriminants prepared in the prostatic disease-evaluating apparatus 100, and the evaluation results obtained in the prostatic disease-evaluating apparatus 100. As shown in FIG. 20, the database apparatus 400 includes (a) a control device 402, such as CPU, which integrally controls the entire database apparatus 400, (b) a communication interface 404 connecting the database apparatus to the network 300 communicatively via a communication apparatus such as a router and via wired or wireless communication circuits such as a private line, (c) a memory device 406 storing various databases, tables and files (for example, files for Web pages), and (d) an input/output interface 408 connected to an input device 412 and an output device 414, and these parts are connected communicatively to each other via any communication channel.

The memory device 406 is a storage means, and may be, for example, memory apparatus such as RAM or ROM, a fixed disk drive such as a hard disk, a flexible disk, an optical disk, and the like. The memory device 406 stores, for example, various programs used in various processings. The communication interface 404 allows communication between the database apparatus 400 and the network 300 (or a communication apparatus such as a router). Thus, the communication interface 404 has a function to communicate data via a communication line with other terminals. The input/output interface 408 is connected to the input device 412 and the output device 414. A monitor (including a home television), a speaker, or a printer may be used as the output device 414 (hereinafter, the output device 414 may be described as a monitor 414). A keyboard, a mouse, a microphone, or a monitor functioning as a pointing device together with a mouse may be used as the input device 412.

The control device 402 has an internal memory storing control programs such as OS (Operating System), programs for various processing procedures, and other needed data, and performs various information processings according to these programs. As shown in the figure, the control device 402 includes mainly a request-interpreting part 402a, a browsing processing part 402b, an authentication-processing part 402c, an electronic mail-generating part 402d, a Web page-generating part 402e, and a sending part 402f.

The request-interpreting part 402a interprets the requests transmitted from the prostatic disease-evaluating apparatus 100 and sends the requests to other parts in the control device 402 according to results of interpreting the requests. Upon receiving browsing requests for various screens transmitted from the prostatic disease-evaluating apparatus 100, the browsing processing part 402b generates and transmits web data for these screens. Upon receiving authentication requests transmitted from the prostatic disease-evaluating apparatus 100, the authentication-processing part 402c performs authentication. The electronic mail-generating part 402d generates electronic mails including various kinds of information. The Web page-generating part 402e generates Web pages for users to browse with the client apparatus 200. The sending part 402f transmits various kinds of information such as the prostatic disease state information and the multivariate discriminants to the prostatic disease-evaluating apparatus 100.

2-3. Processing in the Present System

Figure 21:
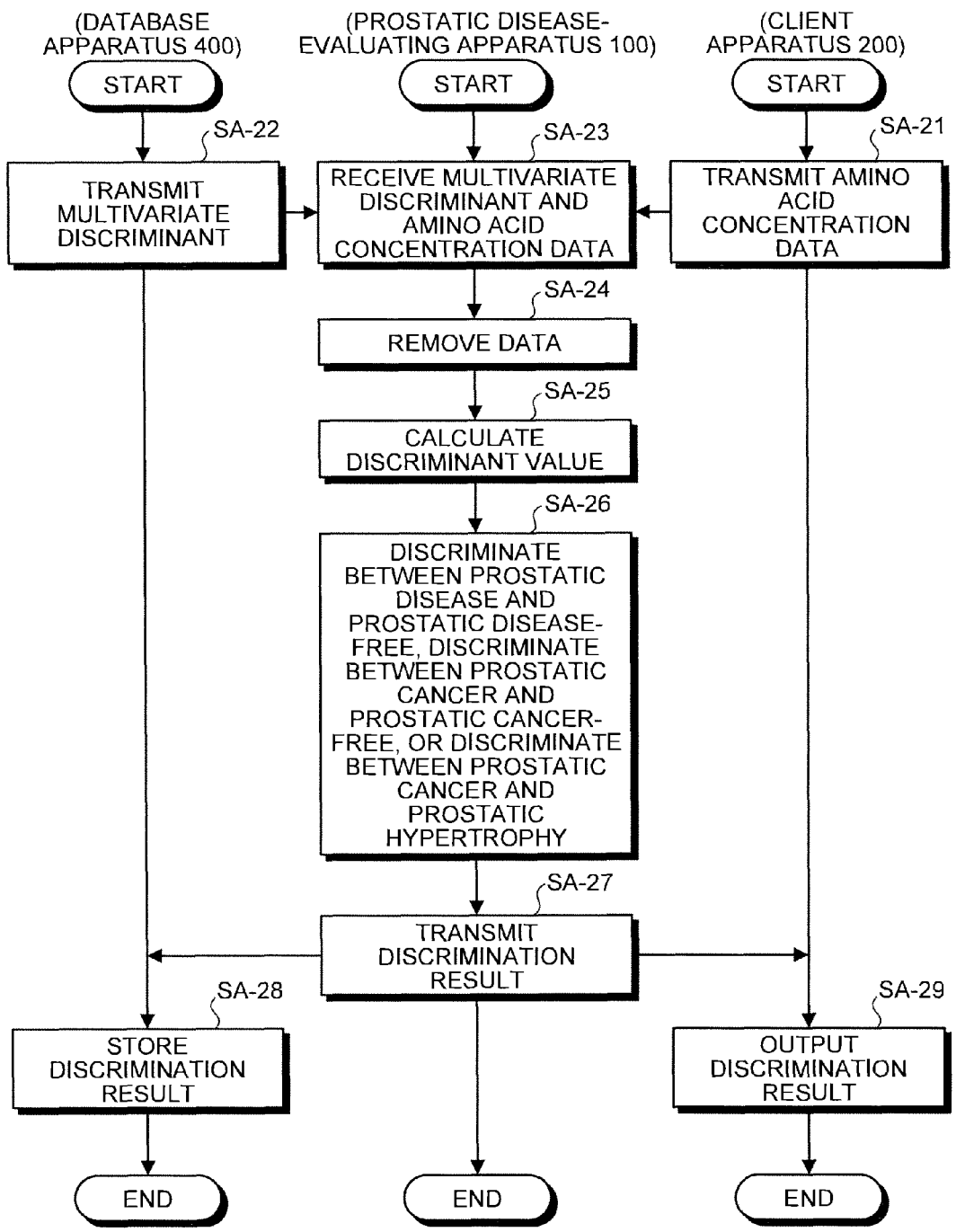
FIG. 21 is a flowchart showing an example of a prostatic disease evaluation service processing performed in the present system.

Here, an example of a prostatic disease evaluation service processing performed in the present system constituted as described above will be described with reference to FIG. 21. FIG. 21 is a flowchart showing the example of the prostatic disease evaluation service processing.

The amino acid concentration data used in the present processing is data concerning the concentration values of amino acids obtained by analyzing blood previously collected from an individual. Hereinafter, the method of analyzing blood amino acid will be described briefly. First, a blood sample is collected in a heparin-treated tube, and then the blood plasma is separated by centrifugation of the tube. All blood plasma samples separated are frozen and stored at −70° C. before a measurement of an amino acid concentration. Before the measurement of the amino acid concentration, the blood plasma samples are deproteinized by adding sulfosalicylic acid to a concentration of 3%. An amino acid analyzer by high-performance liquid chromatography (HPLC) by using ninhydrin reaction in the post column is used for the measurement of the amino acid concentration.

First, the client apparatus 200 accesses the prostatic disease-evaluating apparatus 100 when the user specifies the Web site address (such as URL) provided from the prostatic disease-evaluating apparatus 100, via the input device 250 on the screen displaying the Web browser 211. Specifically, when the user instructs update of the Web browser 211 screen on the client apparatus 200, the Web browser 211 sends the Web site address provided from the prostatic disease-evaluating apparatus 100 by a particular protocol to the prostatic disease-evaluating apparatus 100, thereby transmitting requests demanding a transmission of Web page corresponding to an amino acid concentration data transmission screen to the prostatic disease-evaluating apparatus 100 based on a routing of the address.

Then, upon receipt of the request transmitted from the client apparatus 200, the request-interpreting part 102a in the prostatic disease-evaluating apparatus 100 analyzes the transmitted requests and sends the requests to other parts in the control device 102 according to analytical results. Specifically, when the transmitted requests are requests to send the Web page corresponding to the amino acid concentration data transmission screen, mainly the browsing processing part 102b in the prostatic disease-evaluating apparatus 100 obtains the Web data for display of the Web page stored in a predetermined region of the memory device 106 and sends the obtained Web data to the client apparatus 200. More specifically, upon receiving the requests to transmit the Web page corresponding to the amino acid concentration data transmission screen by the user, the control device 102 in the prostatic disease-evaluating apparatus 100 demands inputs of user ID and user password from the user. If the user ID and password are input, the authentication-processing part 102c in the prostatic disease-evaluating apparatus 100 examines the input user ID and password by comparing them with the user ID and user password stored in the user information file 106a for authentication. Only when the user is authenticated, the browsing processing part 102b in the prostatic disease-evaluating apparatus 100 sends the Web data for displaying the Web page corresponding to the amino acid concentration data transmission screen to the client apparatus 200. The client apparatus 200 is identified with the IP (Internet Protocol) address transmitted from the client apparatus 200 together with the transmission requests.

Then, the client apparatus 200 receives, in the receiving part 213, the Web data (for displaying the Web page corresponding to the amino acid concentration data transmission screen) transmitted from the prostatic disease-evaluating apparatus 100, interprets the received Web data with the Web browser 211, and displays the amino acid concentration data transmission screen on the monitor 261.

When the user inputs and selects, via the input device 250, for example the amino acid concentration data of the individual on the amino acid concentration data transmission screen displayed on the monitor 261, the sending part 214 of the client apparatus 200 transmits an identifier for identifying input information and selected items to the prostatic disease-evaluating apparatus 100, thereby transmitting the amino acid concentration data of the individual as the subject to the prostatic disease-evaluating apparatus 100 (step SA-21). In step SA-21, the transmission of the amino acid concentration data may be realized for example by using an existing file transfer technology such as FTP (File Transfer Protocol).

Then, the request-interpreting part 102a of the prostatic disease-evaluating apparatus 100 interprets the identifier transmitted from the client apparatus 200 thereby interpreting the requests from the client apparatus 200, and requests the database apparatus 400 to send the multivariate discriminant for the evaluation of the state of prostatic disease.

Then, the request-interpreting part 402a in the database apparatus 400 interprets the transmission requests from the prostatic disease-evaluating apparatus 100 and transmits, to the prostatic disease-evaluating apparatus 100, the multivariate discriminant containing at least one of Tau, Thr, Ser, Asn, Glu, Pro, Gly, Ala, Cit, ABA, Val, Met, Ile, Leu, Phe, His, Trp, Orn, Lys, and Cys2 as the explanatory variables stored in a predetermined region of the memory device 406 (for example, the multivariate discriminant is the updated newest multivariate discriminant. the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.) (step SA-22).

When the discrimination between prostatic disease and prostatic disease-free is conducted in step SA-26 described below, in step SA-22, the multivariate discriminant transmitted to the prostatic disease-evaluating apparatus 100 may be the multivariate discriminant containing at least one of Tau, Thr, Asn, Glu, Pro, Gly, Ala, Cit, ABA, Val, Met, Ile, Leu, His, Trp, Lys, and Cys2 as the explanatory variable. Specifically, the multivariate discriminant may be the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(\text{Tau/ABA})+b_1(\text{Thr/Cit})+c_1(\text{Glu/Ser})+d_1(\text{Pro/Asn})+e_1 \quad \text{(formula 1)}$$

wherein $a_1$, $b_1$, $c_1$, $d_1$, and $e_1$ in the formula 1 is arbitrary real number.

When the discrimination between prostatic cancer and prostatic cancer-free is conducted in step SA-26 described below, in step SA-22, the multivariate discriminant transmitted to the prostatic disease-evaluating apparatus 100 may be the multivariate discriminant containing at least one of Tau, Thr, Asn, Glu, Pro, Ala, Cit, ABA, Val, Met, Ile, Leu, Phe, His, Trp, Orn, and Cys2 as the explanatory variable. Specifically, the multivariate discriminant may be the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau/Trp})+b_2(\text{Thr/Ser})+c_2(\text{Glu/Asn})+d_2(\text{Orn/Gln})+e_2 \quad \text{(formula 2)}$$

$$a_3(\text{Tau/Met})+b_3(\text{Ser/Cit})+c_3(\text{Asn/Thr})+d_3(\text{Glu/Pro})+e_3 \quad \text{(formula 3)}$$

$$a_4(\text{Thr/Orn})+b_4(\text{Ser/Ile})+c_4(\text{Asn/Glu})+d_4(\text{Gln/Tau})+e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number.

When the discrimination between prostatic cancer and prostatic hypertrophy is conducted in step SA-26 described below, in step SA-22, the multivariate discriminant transmitted to the prostatic disease-evaluating apparatus 100 may be the multivariate discriminant containing at least one of Thr, Ser, Gly, Cit, Val, His, Trp, and Lys as the explanatory variable. Specifically, the multivariate discriminant may be the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(\text{Ser/Gln}) + b_5(\text{Glu/Tau}) + c_5(\text{Ala/Asn}) + d_5(\text{Val/Thr}) + e_5 \quad \text{(formula 5)}$$

wherein $a_5$, $b_5$, $c_5$, $d_5$, and $e_5$ in the formula 5 is arbitrary real number.

Returning to FIG. 21, The prostatic disease-evaluating apparatus 100 receives, in the receiving part 102f, the amino acid concentration data of the individual transmitted from the client apparatuses 200 and the multivariate discriminant transmitted from the database apparatus 400, and stores the received amino acid concentration data in a predetermined memory region of the amino acid concentration data file 106b and the received multivariate discriminant in a predetermined memory region of the multivariate discriminant file 106e4 (step SA-23).

Then, the control device 102 in the prostatic disease-evaluating apparatus 100 removes data such as defective and outliers from the amino acid concentration data of the individual received in step SA-23 (step SA-24).

Then, the prostatic disease-evaluating apparatus 100 calculates, in the discriminant value-calculating part 102i, the discriminant value that is the value of the multivariate discriminant, based on both (i) the multivariate discriminant received in step SA-23 and (ii) the amino acid concentration data of the individual from which the data such as the defective and outliers have been removed in step SA-24 (step SA-25), compares, in the discriminant value criterion-discriminating part 102j1, the discriminant value calculated in step SA-25 with a previously established threshold (cutoff value), thereby conducting any one of the discriminations described in the following 21. to 23. in the individual, and stores the discrimination results in a predetermined memory region of the evaluation result file 106g (step SA-26).

21. Discrimination Between Prostatic Disease and Prostatic Disease-Free

In step SA-25, the discriminant value is calculated based on both (i) the concentration value of at least one of Tau, Thr, Asn, Glu, Pro, Gly, Ala, Cit, ABA, Val, Met, Ile, Leu, His, Trp, Lys, and Cys2 contained in the amino acid concentration data of the individual and (ii) the multivariate discriminant containing at least one of Tau, Thr, Asn, Glu, Pro, Gly, Ala, Cit, ABA, Val, Met, Ile, Leu, His, Trp, Lys, and Cys2 as the explanatory variable, and in step SA-26, the calculated discriminant value is compared with a previously established threshold (cutoff value), thereby discriminating between the prostatic disease and the prostatic disease-free in the individual.

22. Discrimination Between Prostatic Cancer and Prostatic Cancer-Free

In step SA-25, the discriminant value is calculated based on both (i) the concentration value of at least one of Tau, Thr, Asn, Glu, Pro, Ala, Cit, ABA, Val, Met, Ile, Leu, Phe, His, Trp, Orn, and Cys2 contained in the amino acid concentration data of the individual and (ii) the multivariate discriminant containing at least one of Tau, Thr, Asn, Glu, Pro, Ala, Cit, ABA, Val, Met, Ile, Leu, Phe, His, Trp, Orn, and Cys2 as the explanatory variable, and in step SA-26, the calculated discriminant value is compared with a previously established threshold (cutoff value), thereby discriminating between the prostatic cancer and the prostatic cancer-free in the individual.

23. Discrimination Between Prostatic Cancer and Prostatic Hypertrophy

In step SA-25, the discriminant value is calculated based on both (i) the concentration value of at least one of Thr, Ser, Gly, Cit, Val, His, Trp, and Lys contained in the amino acid concentration data of the individual and (ii) the multivariate discriminant containing at least one of Thr, Ser, Gly, Cit, Val, His, Trp, and Lys as the explanatory variable, and in step SA-26, the calculated discriminant value is compared with a previously established threshold (cutoff value), thereby discriminating between the prostatic cancer and the prostatic hypertrophy in the individual.

Returning to FIG. 21, the sending part 102m in the prostatic disease-evaluating apparatus 100 sends, to the client apparatus 200 that has sent the amino acid concentration data and to the database apparatus 400, the discrimination results obtained in step SA-26 (step SA-27). Specifically, the prostatic disease-evaluating apparatus 100 first generates a Web page for displaying the discrimination results in the Web page-generating part 102e and stores the Web data corresponding to the generated Web page in a predetermined memory region of the memory device 106. Then, the user is authenticated as described above by inputting a predetermined URL (Uniform Resource Locator) into the Web browser 211 of the client apparatus 200 via the input device 250, and the client apparatus 200 sends a Web page browsing request to the prostatic disease-evaluating apparatus 100. The prostatic disease-evaluating apparatus 100 then interprets the browsing request transmitted from the client apparatus 200 in the browsing processing part 102b and reads the Web data corresponding to the Web page for displaying the discrimination results, out of the predetermined memory region of the memory device 106. The sending part 102m in the prostatic disease-evaluating apparatus 100 then sends the read-out Web data to the client apparatus 200 and simultaneously sends the Web data or the discrimination results to the database apparatus 400.

In step SA-27, the control device 102 in the prostatic disease-evaluating apparatus 100 may notify the discrimination results to the user client apparatus 200 by electronic mail. Specifically, the electronic mail-generating part 102d in the prostatic disease-evaluating apparatus 100 first acquires the user electronic mail address by referencing the user information stored in the user information file 106a based on the user ID and the like at the transmission timing. The electronic mail-generating part 102d in the prostatic disease-evaluating apparatus 100 then generates electronic mail data with the acquired electronic mail address as its mail address, including the user name and the discrimination results. The sending part 102m in the prostatic disease-evaluating apparatus 100 then sends the generated electronic mail data to the user client apparatus 200.

Also in step SA-27, the prostatic disease-evaluating apparatus 100 may send the discrimination results to the user client apparatus 200 by using, for example, an existing file transfer technology such as FTP.

Returning to FIG. 21, the control device 402 in the database apparatus 400 receives the discrimination results or the Web data transmitted from the prostatic disease-evaluating apparatus 100 and stores (accumulates) the received discrimination results or the received Web data in a predetermined memory region of the memory device 406 (step SA-28).

The receiving part 213 of the client apparatus 200 receives the Web data transmitted from the prostatic disease-evaluating apparatus 100, and the received Web data is interpreted with the Web browser 211, to display on the monitor 261 the Web page screen displaying the discrimination result of the individual (step SA-29). When the discrimination results are sent from the prostatic disease-evaluating apparatus 100 by electronic mail, the electronic mail transmitted from the prostatic disease-evaluating apparatus 100 is received at any timing, and the received electronic mail is displayed on the monitor 261 with the known function of the electronic mailer 212 in the client apparatus 200.

In this way, the user can confirm the discrimination results on prostatic disease of the individual, by browsing the Web page displayed on the monitor 261. The user may print out the content of the Web page displayed on the monitor 261 by the printer 262.

When the discrimination results are transmitted by electronic mail from the prostatic disease-evaluating apparatus 100, the user reads the electronic mail displayed on the monitor 261, whereby the user can confirm the discrimination results on prostatic disease of the individual. The user may print out the content of the electronic mail displayed on the monitor 261 by the printer 262.

Given the foregoing description, the explanation of the prostatic disease evaluation service processing is finished.

2-4. Summary of the Second Embodiment and Other Embodiments

According to the prostatic disease-evaluating system described above in detail, the client apparatus 200 sends the amino acid concentration data of the individual to the prostatic disease-evaluating apparatus 100. Upon receiving the requests from the prostatic disease-evaluating apparatus 100, the database apparatus 400 transmits the multivariate discriminant for the discrimination of prostatic disease to the prostatic disease-evaluating apparatus 100. By the prostatic disease-evaluating apparatus 100, (1) the amino acid concentration data is received from the client apparatus 200, and the multivariate discriminant is received from the database apparatus 400 simultaneously, (2) the discriminant value is calculated based on both the received amino acid concentration data and the received multivariate discriminant, (3) the calculated discriminant value is compared with the previously established threshold, thereby conducting any one of the discriminations described in 21. to 23. above in the individual, and (4) the discrimination results are transmitted to the client apparatus 200 and database apparatus 400. Then, the client apparatus 200 receives and displays the discrimination results transmitted from the prostatic disease-evaluating apparatus 100, and the database apparatus 400 receives and stores the discrimination results transmitted from the prostatic disease-evaluating apparatus 100. Thus, the discriminant values obtained in the multivariate discriminants useful particularly for the 2-group discrimination of the prostatic disease and the prostatic disease-free, can be utilized to bring about the effect of enabling more accurately the 2-group discrimination. The discriminant values obtained in the multivariate discriminants useful particularly for the 2-group discrimination of the prostatic cancer and the prostatic cancer-free, can be utilized to bring about the effect of enabling more accurately the 2-group discrimination. The discriminant values obtained in the multivariate discriminants useful particularly for the 2-group discrimination of the prostatic cancer and the prostatic hypertrophy, can be utilized to bring about the effect of enabling more accurately the 2-group discrimination.

When the discrimination described in 21. above is conducted in step SA-26, the multivariate discriminant may be the fractional expression of formula 1, the logistic regression equation with Tau, Glu, Pro, Ala, Cit, and ABA as the explanatory variables, the logistic regression equation with Asn, Glu, Ala, Val, Met, and Trp as the explanatory variables, the linear discriminant with Tau, Glu, Gly, Cit, ABA, and Val as the explanatory variables, or the linear discriminant with Asn, Glu, Ala, Val, Met, and Trp as the explanatory variables:

$$a_1(\text{Tau/ABA}) + b_1(\text{Thr/Cit}) + c_1(\text{Glu/Ser}) + d_1(\text{Pro/Asn}) + e_1 \quad \text{(formula 1)}$$

wherein $a_1$, $b_1$, $c_1$, $d_1$, and $e_1$ in the formula 1 is arbitrary real number. Thus, the discriminant values obtained in the multivariate discriminants useful particularly for the 2-group discrimination of the prostatic disease and the prostatic disease-free, can be utilized to bring about the effect of enabling more accurately the 2-group discrimination.

When the discrimination described in 22. above is conducted in step SA-26, the multivariate discriminant may be the fractional expression of formula 2, the fractional expression of formula 3, the fractional expression of formula 4, the logistic regression equation with Tau, Ala, ABA, Trp, Orn, and Arg as the explanatory variables, the logistic regression equation with Tau, Glu, Cit, ABA, Val, and Orn as the explanatory variables, the logistic regression equation with Tau, Thr, Ala, Trp, Orn, and Arg as the explanatory variables, the logistic regression equation with Asn, Ala, Val, Met, Trp, and Arg as the explanatory variables, the linear discriminant with Tau, Ala, ABA, Trp, Orn, and Arg as the explanatory variables, the linear discriminant with Tau, Glu, Ala, Cit, Met, and Orn as the explanatory variables, the linear discriminant with Tau, Thr, Ser, Ala, Orn, and Arg as the explanatory variables, or the linear discriminant with Asn, Ala, Val, Met, Tyr, and Trp as the explanatory variables:

$$a_2(\text{Tau/Trp}) + b_2(\text{Thr/Ser}) + c_2(\text{Glu/Asn}) + d_2(\text{Orn/Gln}) + e_2 \quad \text{(formula 2)}$$

$$a_3(\text{Tau/Met}) + b_3(\text{Ser/Cit}) + c_3(\text{Asn/Thr}) + d_3(\text{Glu/Pro}) + e_3 \quad \text{(formula 3)}$$

$$a_4(\text{Thr/Orn}) + b_4(\text{Ser/Ile}) + c_4(\text{Asn/Glu}) + d_4(\text{Gln/Tau}) + e_4 \quad \text{(formula 4)}$$

wherein $a_2$, $b_2$, $c_2$, $d_2$, and $e_2$ in the formula 2 is arbitrary real number, $a_3$, $b_3$, $c_3$, $d_3$, and $e_3$ in the formula 3 is arbitrary real number, and $a_4$, $b_4$, $c_4$, $d_4$, and $e_4$ in the formula 4 is arbitrary real number. Thus, the discriminant values obtained in the multivariate discriminants useful particularly for the 2-group discrimination of the prostatic cancer and the prostatic cancer-free, can be utilized to bring about the effect of enabling more accurately the 2-group discrimination.

When the discrimination described in 23. above is conducted in step SA-26, the multivariate discriminant may be the fractional expression of formula 5, the logistic regression equation with Thr, Ala, Val, Tyr, Trp, and Lys as the explanatory variables, the logistic regression equation with Ser, Gln, Gly, Cit, Val, and Trp as the explanatory variables, the linear discriminant with Thr, Ala, Val, Tyr, Trp, and Lys as the explanatory variables, or the linear discriminant with Ser, Gln, Gly, Cit, Val, and Trp as the explanatory variables:

$$a_5(\text{Ser/Gln}) + b_5(\text{Glu/Tau}) + c_5(\text{Ala/Asn}) + d_5(\text{Val/Thr}) + e_5 \quad \text{(formula 5)}$$

wherein $a_5$, $b_5$, $c_5$, $d_5$, and $e_5$ in the formula 5 is arbitrary real number. Thus, the discriminant values obtained in the multivariate discriminants useful particularly for the 2-group discrimination of the prostatic cancer and the prostatic hypertrophy, can be utilized to bring about the effect of enabling more accurately the 2-group discrimination.

The multivariate discriminant described above can be prepared by a method described in International Publication WO 2004/052191 that is an international application filed by the present applicant or by a method (multivariate discriminant-preparing processing described later) described in International Publication WO 2006/098192 that is an international application filed by the present applicant. Any multivariate discriminants obtained by these methods can be preferably used in the evaluation of the state of prostatic disease, regardless of the unit of the amino acid concentration in the amino acid concentration data as input data.

In addition to the second embodiment described above, the prostatic disease-evaluating apparatus, the prostatic disease-evaluating method, the prostatic disease-evaluating system, the prostatic disease-evaluating program product and the recording medium according to the present invention can be practiced in various different embodiments within the technological scope of the claims. For example, among the processings described in the second embodiment above, all or a part of the processings described above as performed automatically may be performed manually, and all or a part of the manually conducted processings may be performed automatically by known methods. In addition, the processing procedure, control procedure, specific name, various registered data, information including parameters such as retrieval condition, screen, and database configuration shown in the description above or drawings may be modified arbitrarily, unless specified otherwise. For example, the components of the prostatic disease-evaluating apparatus 100 shown in the figures are conceptual and functional and may not be the same physically as those shown in the figure. In addition, all or an arbitrary part of the operational function of each component and each device in the prostatic disease-evaluating apparatus 100 (in particular, the operational functions executed in the control device 102) may be executed by the CPU (Central Processing Unit) or the programs executed by the CPU, and may be realized as wired-logic hardware.

The "program" is a data processing method written in any language or by any description method and may be of any format such as source code or binary code. The "program" may not be limited to a program configured singly, and may include a program configured decentrally as a plurality of modules or libraries, and a program to achieve the function together with a different program such as OS (Operating System). The program is stored on a recording medium and read mechanically as needed by the prostatic disease-evaluating apparatus 100. Any well-known configuration or procedure may be used as specific configuration, reading procedure, installation procedure after reading, and the like for reading the programs recorded on the recording medium in each apparatus.

The "recording media" includes any "portable physical media", "fixed physical media", and "communication media". Examples of the "portable physical media" include flexible disk, magnetic optical disk, ROM, EPROM (Erasable Programmable Read Only Memory), EEPROM (Electronically Erasable and Programmable Read Only Memory), CD-ROM (Compact Disk Read Only Memory), MO (Magneto-Optical disk), DVD (Digital Versatile Disk), and the like. Examples of the "fixed physical media" include ROM, RAM, HD, and the like which are installed in various computer systems. The "communication media" for example stores the program for a short period of time such as communication line and carrier wave when the program is transmitted via a network such as LAN (Local Area Network), WAN (Wide Area Network), or the Internet.

Figure 22:
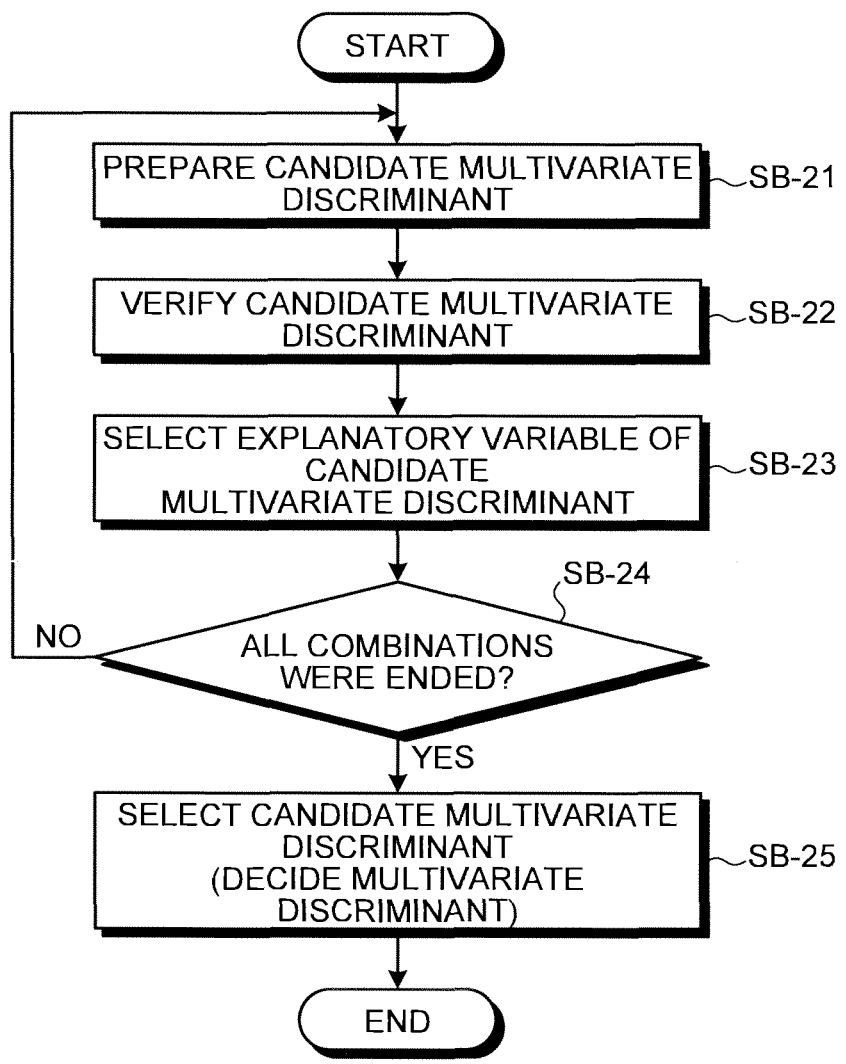
FIG. 22 is a flowchart showing an example of a multivariate discriminant-preparing processing performed in the prostatic disease-evaluating apparatus 100 in the present system.

Finally, an example of the multivariate discriminant-preparing processing performed in the prostatic disease-evaluating apparatus 100 is described in detail with reference to FIG. 22. FIG. 22 is a flowchart showing an example of the multivariate discriminant-preparing processing. The multivariate discriminant-preparing processing may be performed in the database apparatus 400 handling the prostatic disease state information.

In the present description, the prostatic disease-evaluating apparatus 100 stores the prostatic disease state information previously obtained from the database apparatus 400 in a predetermined memory region of the prostatic disease state information file 106c. The prostatic disease-evaluating apparatus 100 shall store, in a predetermined memory region of the designated prostatic disease state information file 106d, the prostatic disease state information including the prostatic disease state index data and amino acid concentration data designated previously in the prostatic disease state information-designating part 102g.

The candidate multivariate discriminant-preparing part 102h1 in the multivariate discriminant-preparing part 102h first prepares the candidate multivariate discriminants according to a predetermined discriminant-preparing method from the prostatic disease state information stored in a predetermine memory region of the designated prostatic disease state information file 106d, and stores the prepared candidate multivariate discriminants in a predetermined memory region of the candidate multivariate discriminant file 106e1 (step SB-21). Specifically, the candidate multivariate discriminant-preparing part 102h1 in the multivariate discriminant-preparing part 102h first selects a desired method out of a plurality of different discriminant-preparing methods (including those for multivariate analysis such as principal component analysis, discriminant analysis, support vector machine, multiple regression analysis, logistic regression analysis, k-means method, cluster analysis, and decision tree) and determines the form of the candidate multivariate discriminant to be prepared based on the selected discriminant-preparing method. The candidate multivariate discriminant-preparing part 102h1 in the multivariate discriminant-preparing part 102h then performs various calculation corresponding to the selected function-selecting method (e.g., average or variance), based on the prostatic disease state information. The candidate multivariate discriminant-preparing part 102h1 in the multivariate discriminant-preparing part 102h then determines the parameters for the calculation result and the determined candidate multivariate discriminant. In this way, the candidate multivariate discriminant is generated based on the selected discriminant-preparing method. When the candidate multivariate discriminants are generated simultaneously and concurrently (in parallel) by using a plurality of different discriminant-preparing methods in combination, the processings described above may be executed concurrently for each selected discriminant-preparing method. Alternatively when the candidate multivariate discriminants are generated in series by using a plurality of different discriminant-preparing methods in combination, for example, the candidate multivariate discriminants may be generated by converting the prostatic disease state information with the candidate multivariate discriminants prepared by performing principal component analysis and performing discriminant analysis of the converted prostatic disease state information.

The candidate multivariate discriminant-verifying part 102h2 in the multivariate discriminant-preparing part 102h verifies (mutually verifies) the candidate multivariate discriminant prepared in step SB-21 according to a particular verifying method and stores the verification result in a predetermined memory region of the verification result file 106e2 (step SB-22). Specifically, the candidate multivariate discriminant-verifying part 102h2 in the multivariate discriminant-preparing part 102h first generates the verification data to be used in verification of the candidate multivariate discriminant, based on the prostatic disease state information stored in a predetermined memory region of the designated prostatic disease state information file 106d, and verifies the candidate multivariate discriminant according to the generated verification data. If a plurality of the candidate multivariate discriminants is generated by using a plurality of different discriminant-preparing methods in step SB-21, the candidate multivariate discriminant-verifying part 102h2 in the multivariate discriminant-preparing part 102h verifies each candidate multivariate discriminant corresponding to each discriminant-preparing method according to a particular verifying method. Here in step SB-22, at least one of the discrimination rate, sensitivity, specificity, information criterion, and the like of the candidate multivariate discriminant may be verified based on at least one method of the bootstrap method, holdout method, leave-one-out method, and the like. Thus, it is possible to select the candidate multivariate discriminant higher in predictability or reliability, by taking the prostatic disease state information and diagnostic condition into consideration.

Then, the explanatory variable-selecting part 102h3 in the multivariate discriminant-preparing part 102h selects the combination of the amino acid concentration data contained in the prostatic disease state information used in preparing the candidate multivariate discriminant by selecting the explanatory variable of the candidate multivariate discriminant from the verification result obtained in step SB-22 according to a predetermined explanatory variable-selecting method, and stores the prostatic disease state information including the selected combination of the amino acid concentration data in a predetermined memory region of the selected prostatic disease state information file 106e3 (step SB-23). When a plurality of the candidate multivariate discriminants is generated by using a plurality of different discriminant-preparing methods in step SB-21 and each candidate multivariate discriminant corresponding to each discriminant-preparing method is verified according to a predetermined verifying method in step SB-22, the explanatory variable-selecting part 102h3 in the multivariate discriminant-preparing part 102h selects the explanatory variable of the candidate multivariate discriminant for each candidate multivariate discriminant corresponding to the verification result obtained in step SB-22, according to a predetermined explanatory variable-selecting method in step SB-23. Here in step SB-23, the explanatory variable of the candidate multivariate discriminant may be selected from the verification results according to at least one of the stepwise method, best path method, local search method, and genetic algorithm. The best path method is a method of selecting an explanatory variable by optimizing an evaluation index of the candidate multivariate discriminant while eliminating the explanatory variables contained in the candidate multivariate discriminant one by one. In step SB-23, the explanatory variable-selecting part 102h3 in the multivariate discriminant-preparing part 102h may select the combination of the amino acid concentration data based on the prostatic disease state information stored in a predetermined memory region of the designated prostatic disease state information file 106d.

The multivariate discriminant-preparing part 102h then judges whether all combinations of the amino acid concentration data contained in the prostatic disease state information stored in a predetermined memory region of the designated prostatic disease state information file 106d are processed, and if the judgment result is "End" (Yes in step SB-24), the processing advances to the next step (step SB-25), and if the judgment result is not "End" (No in step SB-24), it returns to step SB-21. The multivariate discriminant-preparing part 102h may judge whether the processing is performed a predetermined number of times, and if the judgment result is "End" (Yes in step SB-24), the processing may advance to the next step (step SB-25), and if the judgment result is not "End" (No in step SB-24), it may return to step SB-21. The multivariate discriminant-preparing part 102h may judge whether the combination of the amino acid concentration data selected in step SB-23 is the same as the combination of the amino acid concentration data contained in the prostatic disease state information stored in a predetermined memory region of the designated prostatic disease state information file 106d or the combination of the amino acid concentration data selected in the previous step SB-23, and if the judgment result is "the same" (Yes in step SB-24), the processing may advance to the next step (step SB-25) and if the judgment result is not "the same" (No in step SB-24), it may return to step SB-21. If the verification result is specifically the evaluation value for each multivariate discriminant, the multivariate discriminant-preparing part 102h may advance to step SB-25 or return to step SB-21, based on the comparison of the evaluation value with a particular threshold corresponding to each discriminant-preparing method.

Then, the multivariate discriminant-preparing part 102h determines the multivariate discriminant by selecting the candidate multivariate discriminant used as the multivariate discriminant based on the verification results from a plurality of the candidate multivariate discriminants, and stores the determined multivariate discriminant (the selected candidate multivariate discriminant) in particular memory region of the multivariate discriminant file 106e4 (step SB-25). Here, in step SB-25, for example, there are cases where the optimal multivariate discriminant is selected from the candidate multivariate discriminants prepared in the same discriminant-preparing method or the optimal multivariate discriminant is selected from all candidate multivariate discriminants.

Given the foregoing description, the explanation of the multivariate discriminant-preparing processing is finished.

Example 1

Figure 23:
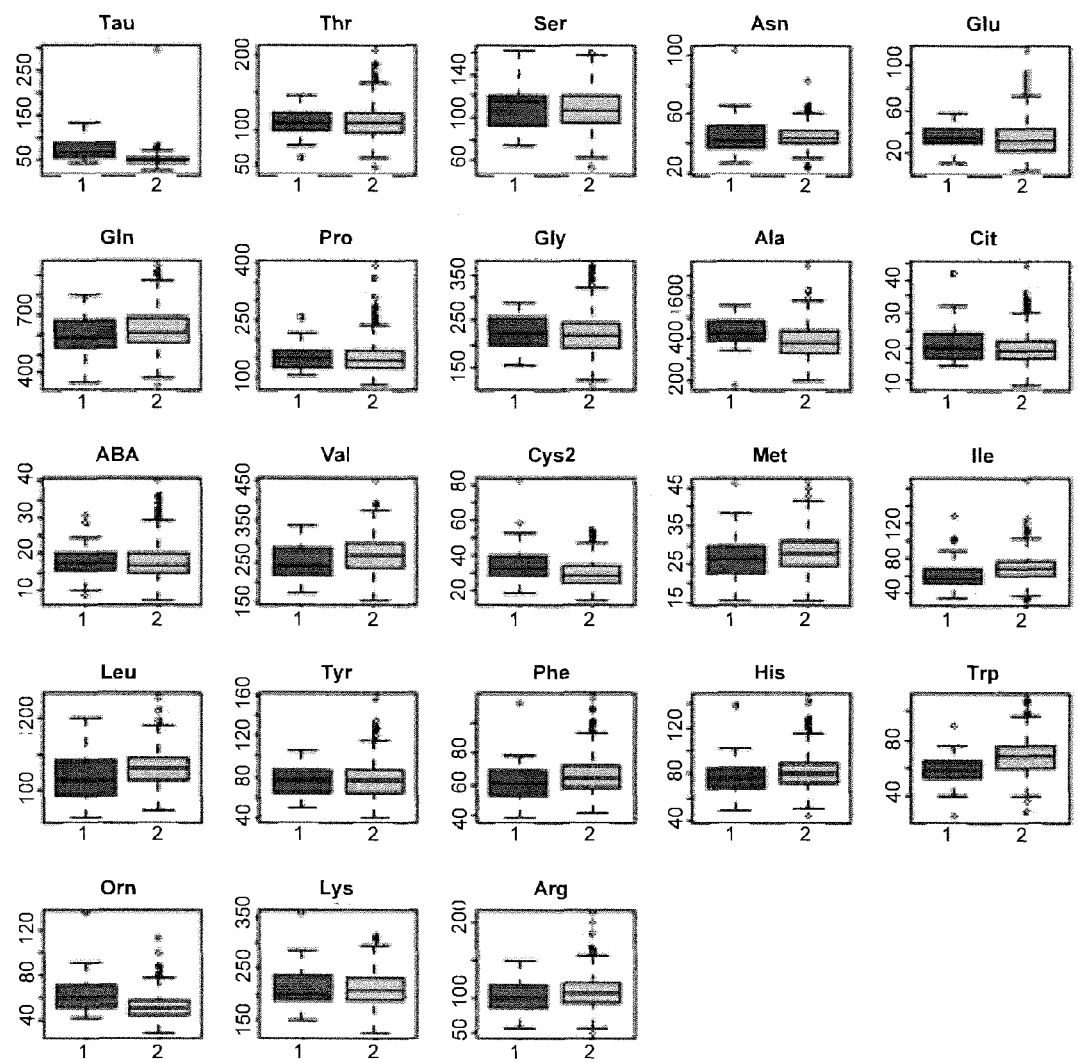
FIG. 23 is boxplots showing distributions of amino acid explanatory variables in a prostatic cancer group and a prostatic cancer-free group.

Blood amino acid concentrations are measured from the blood samples of a prostatic cancer patient group subjected to prostatic cancer diagnosis by prostatic biopsy and the blood samples of a prostatic cancer-free group by the amino acid analysis method. FIG. 23 is boxplots showing the distribution of the amino acid explanatory variables of the prostatic cancer group and the prostatic cancer-free group (on the horizontal axis, the prostatic cancer-free group: 1, and the prostatic cancer group: 2). The t-test between the two groups is conducted for the discrimination between the prostatic cancer group and the prostatic cancer-free group.

Ala, Tau, Cys2, and Orn of the prostatic cancer group are increased more significantly than those of the prostatic cancer-free group, and Leu, Trp, Val, and Ile are decreased more significantly than those of the prostatic cancer-free group. From this result, it is found that the amino acid explanatory variables Ala, Tau, Cys2, Orn, Leu, Trp, Val, and Ile have 2-group discriminative ability between the prostatic cancer group and the prostatic cancer-free group.

Example 2

The sample data used in Example 1 is used. Indices which maximize 2-group discriminative ability between the prostatic cancer group and the prostatic cancer-free group are earnestly searched for, by using the method described in International publication WO 2004/052191 which is an international application by the present applicant. As a result, index formula 1 is obtained among a plurality of index formulae having equivalent ability. Other than this, a plurality of multivariate discriminants having discriminative ability equivalent to index formula 1 are obtained. They are shown in FIGS. 24 and 25. The value of each coefficient in the formulae shown in FIGS. 24 and 25 may be multiplied by a real number or by adding an arbitrary constant term thereto.

$$0.24(Tau)/(Trp)-0.03(Thr)/(Ser)-0.002(Glu)/(Asn)+2.13(Orn)/(Gln)+0.72 \quad \text{Index formula 1}$$

Figure 26:
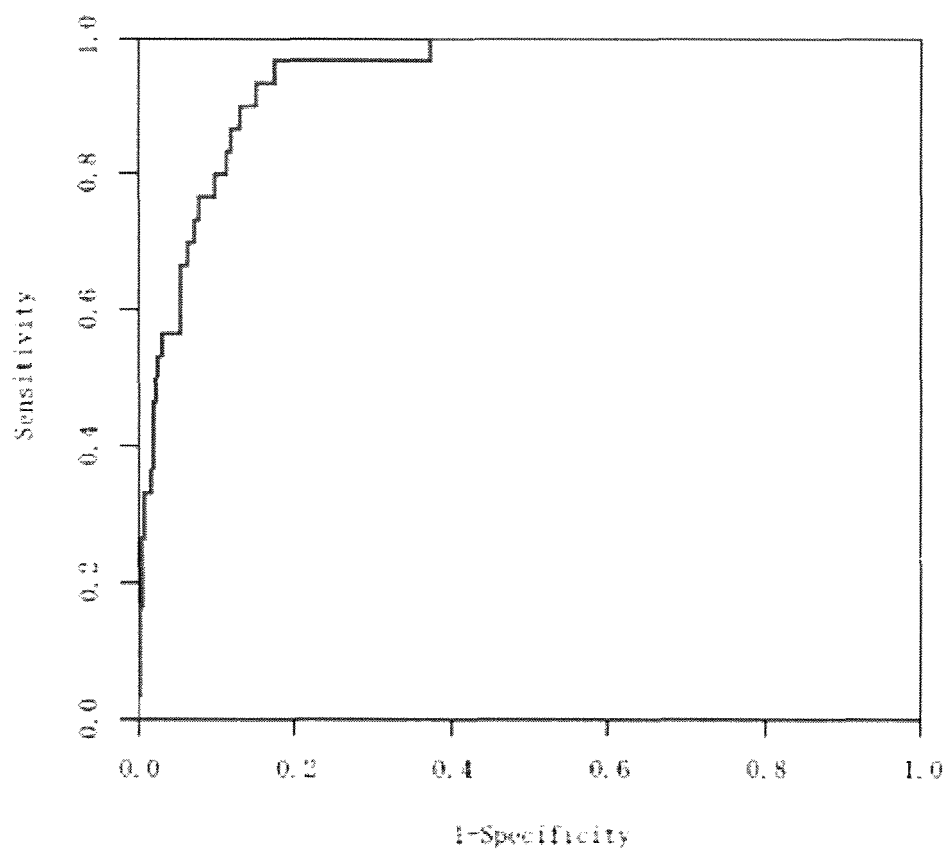
FIG. 26 is a graph showing area under the ROC curve of each amino acid explanatory variable in the 2-group discrimination between the prostatic cancer group and the prostatic cancer-free group.

To examine the prostatic cancer diagnostic ability using index formula 1, 2-group discrimination between the prostatic cancer group and the prostatic cancer-free group is evaluated by the area under the ROC curve (see FIG. 26). As a result, an AUC of 0.941±0.012 (in 95% confidence interval, 0.917 to 0.966) is obtained. In addition, the optimum cutoff value of 2-group discrimination between the prostatic cancer group and the prostatic cancer-free group using index formula 1 is calculated with the symptom prevalence of the prostatic cancer group of 5%. As a result, the cutoff value is 1.086, and 96.67% sensitivity, 80.25% specificity, 20.48% positive predictive value, 99.78% negative predictive value, and 81.07% correct diagnosis rate are obtained. From these results, it is found that index formula 1 is useful, with high diagnostic ability.

Example 3

The sample data used in Example 1 is used. Indices which maximize 2-group discriminative ability between the prostatic cancer group and the prostatic cancer-free group are searched for, by logistic analysis (explanatory variable coverage method according to the ROC maximum criterion). As a result, as index formula 2, a logistic regression equation having Tau, Ala, ABA, Trp, Orn, and Arg (the numeral coefficients of the amino acid explanatory variables Tau, Ala, ABA, Trp, Orn, and Arg, and the constant terms are 0.0519, 0.0137, 0.0792, −0.1079, 0.0795, −0.0201, and −8.5123 in order) is obtained. Other than this, a plurality of logistic regression equations having discriminative ability equivalent to index formula 2 are obtained. They are shown in FIGS. 27 and 28. The value of each coefficient in the equations shown in FIGS. 27 and 28 may be multiplied by a real number.

Figure 29:
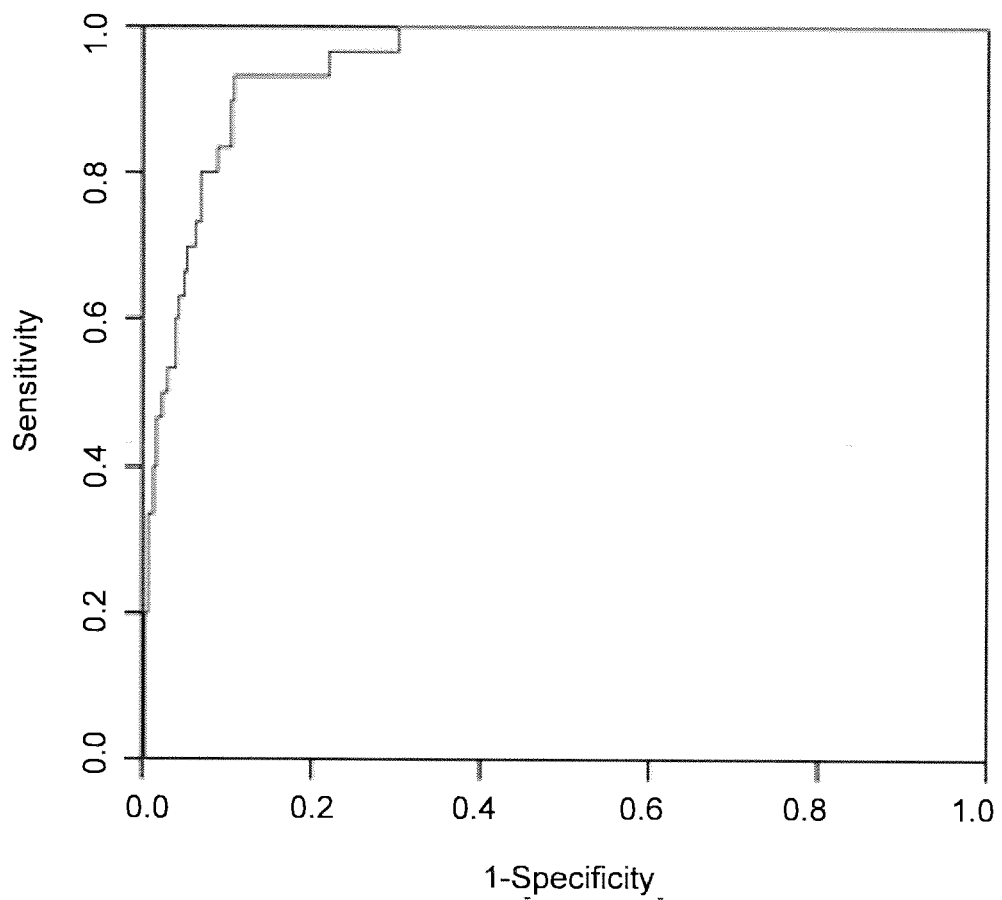
FIG. 29 is a graph showing area under the ROC curve of each amino acid explanatory variable in the 2-group discrimination between the prostatic cancer group and the prostatic cancer-free group.

To examine the prostatic cancer diagnostic ability using index formula 2, 2-group discrimination between the prostatic cancer group and the prostatic cancer-free group is evaluated by area under the ROC curve (see FIG. 29). As a result, an AUC of 0.950±0.011 (in 95% confidence interval, 0.929 to 0.971) is obtained. In addition, the optimum cutoff value of 2-group discrimination between the prostatic cancer group and the prostatic cancer-free group using index formula 2 is calculated with the symptom prevalence of the prostatic cancer group of 5%. As a result, the cutoff value is 0.060, and 90.00% sensitivity, 89.24% specificity, 30.57% positive predictive value, 99.41% negative predictive value, and 89.28% correct diagnosis rate are obtained. From these results, it is found that index formula 2 is useful, with high diagnostic ability.

Example 4

The sample data used in Example 1 is used. Indices which maximize 2-group discriminative ability between the prostatic cancer group and the prostatic cancer-free group are searched for, by linear discriminant analysis (explanatory variable coverage method). As a result, as index formula 3, a linear discriminant function having Tau, Ala, ABA, Trp, Orn, and Arg (the numeral coefficients of the amino acid explanatory variables Tau, Ala, ABA, Trp, Orn, and Arg are 5.713e−01, 6.033e−02, 2.377e−01, −5.546e−01, 5.431e−01, −1.042e−01, and −3.573e+01 in order) is obtained. Other than this, a plurality of linear discriminant functions having discriminative ability equivalent to index formula 3 are obtained. They are shown in FIGS. 30 and 31. The value of each coefficient in the functions shown in FIGS. 30 and 31 may be multiplied by a real number or by adding an arbitrary constant term thereto.

Figure 32:
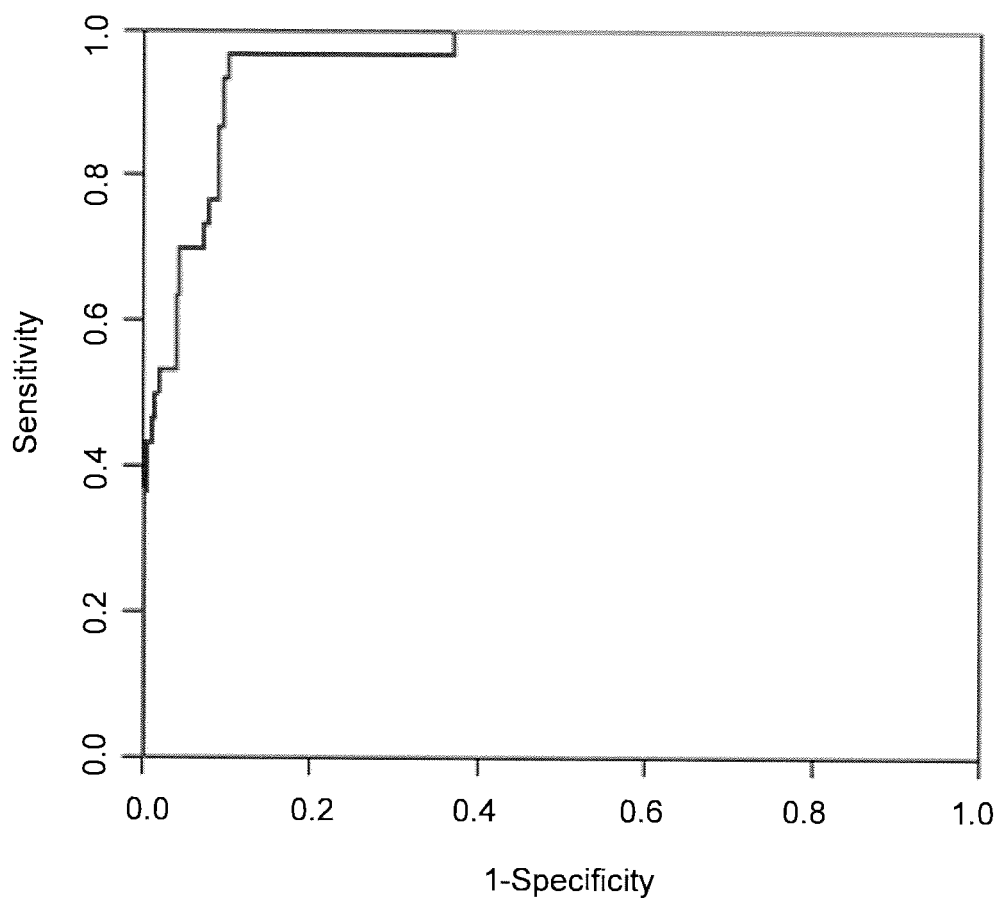
FIG. 32 is a graph showing area under the ROC curve of each amino acid explanatory variable in the 2-group discrimination between the prostatic cancer group and the prostatic cancer-free group.

To examine the prostatic cancer diagnostic ability using index formula 3, 2-group discrimination between the prostatic cancer group and the prostatic cancer-free group is evaluated by area under the ROC curve (see FIG. 32). As a result, an AUC of 0.954±0.010 (in 95% confidence interval, 0.934 to 0.974) is obtained. In addition, the optimum cutoff value of 2-group discrimination between the prostatic cancer group and the prostatic cancer-free group using index formula 3 is calculated with the symptom prevalence of the prostatic cancer group of 5%. As a result, the cutoff value is 11.15, and 93.33% sensitivity, 90.12% specificity, 33.22% positive predictive value, 99.61% negative predictive value, and 90.28% correct diagnosis rate are obtained. From these results, it is found that index formula 3 is useful, with high diagnostic ability.

Example 5

Figure 33:
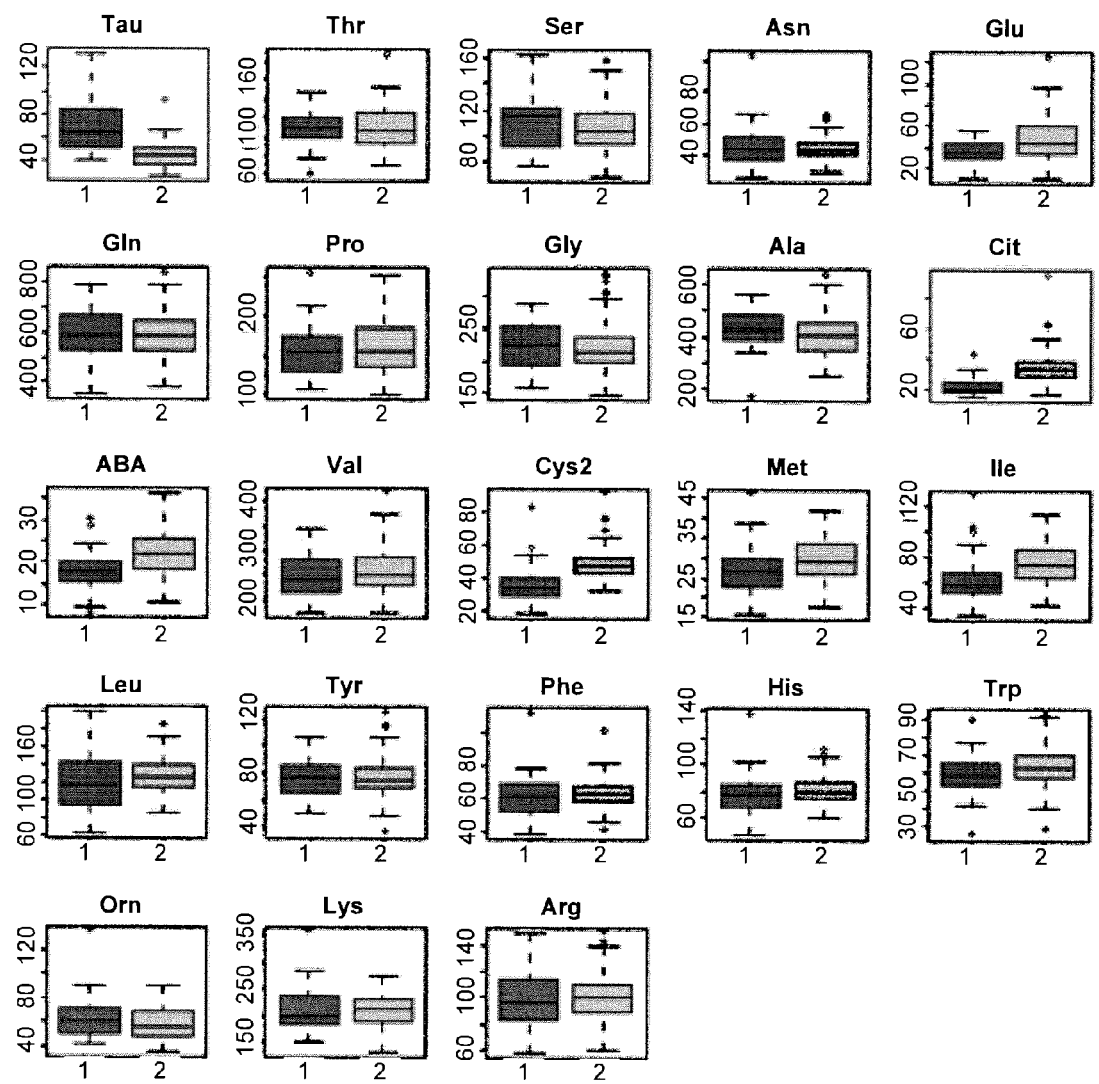
FIG. 33 is boxplots showing distributions of amino acid explanatory variables in a prostatic cancer group and a prostatic cancer-free group.

Blood amino acid concentrations are measured from the blood samples of a prostatic cancer patient group subjected to prostatic cancer diagnosis by prostatic biopsy and the blood samples of a prostatic cancer-free group by the amino acid analysis method. FIG. 33 is boxplots showing the distribution of the amino acid explanatory variables of the prostatic cancer group and the prostatic cancer-free group (on the horizontal axis, the prostatic cancer-free group: 1, and the prostatic cancer group: 2). The t-test between the two groups is conducted for the discrimination between the prostatic cancer group and the prostatic cancer-free group.

Tau of the prostatic cancer group is increased more significantly than that of the prostatic cancer-free group, and Glu, Cit, ABA, Cys2, Met, Ile, and Trp are decreased more significantly than those of the prostatic cancer-free group. From this result, it is found that the amino acid explanatory variables Tau, Glu, Cit, ABA, Cys2, Met, Ile, and Trp have 2-group discriminative ability between the prostatic cancer group and the prostatic cancer-free group.

Example 6

The sample data used in Example 5 is used. Indices which maximize 2-group discriminative ability between the prostatic cancer group and the prostatic cancer-free group are earnestly searched for, by using the method described in International publication WO 2004/052191 which is an international application by the present applicant. As a result, index formula 4 is obtained among a plurality of index formulae having equivalent ability. Other than this, a plurality of multivariate discriminants having discriminative ability equivalent to index formula 4 are obtained. They are shown in FIGS. 34 and 35. The value of each coefficient in the formulae shown in FIGS. 34 and 35 may be multiplied by a real number or by adding an arbitrary constant term thereto.

$$0.19(Tau)/(Met)+0.13(Ser)/(Cit)+0.25(Asn)/(Thr)-0.75(Glu)/(Pro)+0.50 \quad \text{Index formula 4}$$

Figure 36:
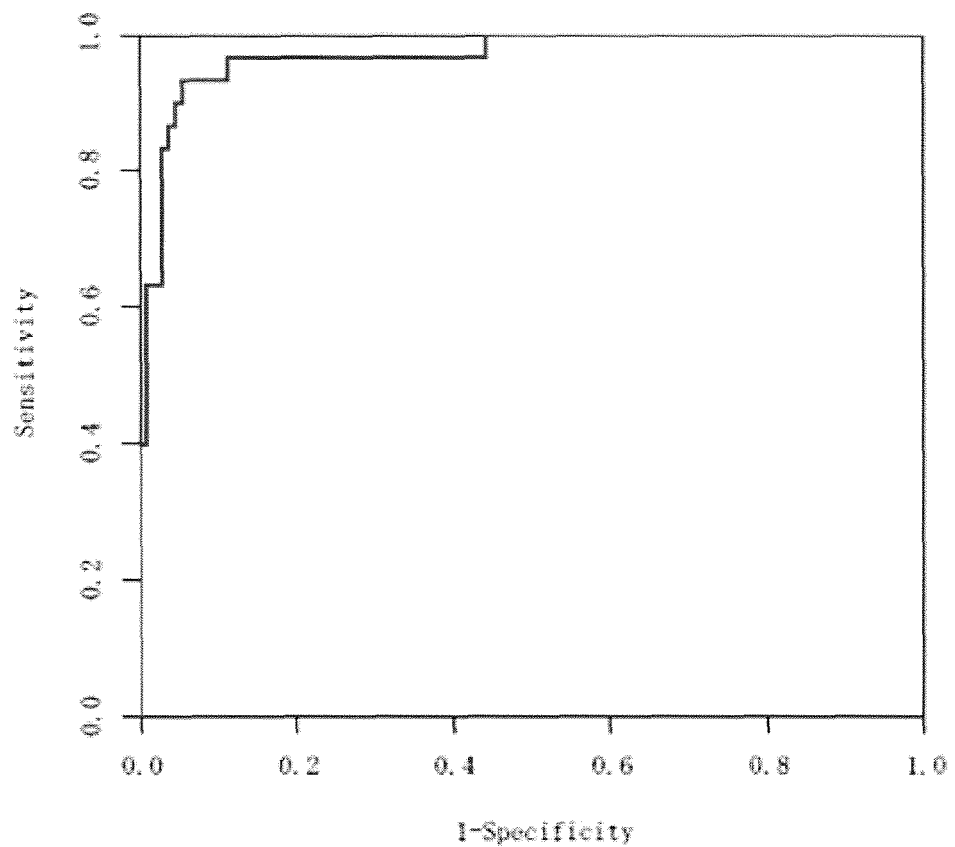
FIG. 36 is a graph showing area under the ROC curve of each amino acid explanatory variable in the 2-group discrimination between the prostatic cancer group and the prostatic cancer-free group.

To examine the prostatic cancer diagnostic ability using index formula 4, 2-group discrimination between the prostatic cancer group and the prostatic cancer-free group is evaluated by the area under the ROC curve (see FIG. 36). As a result, an AUC of 0.969±0.013 (in 95% confidence interval, 0.943 to 0.995) is obtained. In addition, the optimum cutoff value of 2-group discrimination between the prostatic cancer group and the prostatic cancer-free group using index formula 1 is calculated with the symptom prevalence of the prostatic cancer group of 22%. As a result, the cutoff value is 1.264, and 96.67% sensitivity, 88.68% specificity, 70.66% positive predictive value, 98.95% negative predictive value, and 90.44% correct diagnosis rate are obtained. From these results, it is found that index formula 4 is useful, with high diagnostic ability.

Example 7

The sample data used in Example 5 is used. Indices which maximize 2-group discriminative ability between the prostatic cancer group and the prostatic cancer-free group are searched for, by logistic analysis (explanatory variable coverage method according to the ROC maximum criterion). As a result, as index formula 5, a logistic regression equation having Tau, Glu, Cit, ABA, Val, and Orn (the numeral coefficients of the amino acid explanatory variables Tau, Glu, Cit, ABA, Val, and Orn, and the constant terms are 0.0760, −0.1100, −0.4990, −0.3076, 0.0418, 0.0992, and 0.8657 in order) is obtained. Other than this, a plurality of logistic regression equations having discriminative ability equivalent to index formula 5 are obtained. They are shown in FIGS. 37 and 38. The value of each coefficient in the equations shown in FIGS. 37 and 38 may be multiplied by a real number.

Figure 39:
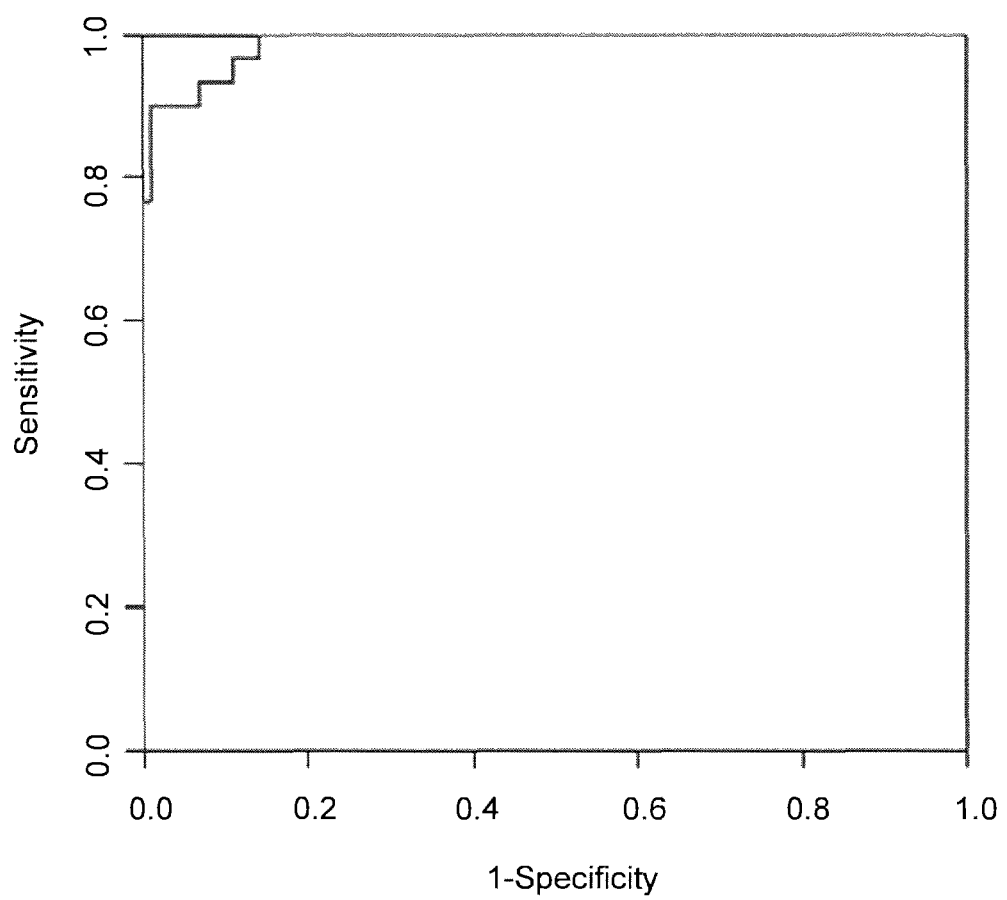
FIG. 39 is a graph showing area under the ROC curve of each amino acid explanatory variable in the 2-group discrimination between the prostatic cancer group and the prostatic cancer-free group.

To examine the prostatic cancer diagnostic ability using index formula 5, 2-group discrimination between the prostatic cancer group and the prostatic cancer-free group is evaluated by area under the ROC curve (see FIG. 39). As a result, an AUC of 0.988±0.008 (in 95% confidence interval, 0.972 to 1) is obtained. In addition, the optimum cutoff value of 2-group discrimination between the prostatic cancer group and the prostatic cancer-free group using index formula 5 is calculated with the symptom prevalence of the prostatic cancer group of 22%. As a result, the cutoff value is 0.269, and 93.33% sensitivity, 92.93% specificity, 78.83% positive predictive value, 98.02% negative predictive value, and 93.02% correct diagnosis rate are obtained. From these results, it is found that index formula 5 is useful, with high diagnostic ability.

Example 8

The sample data used in Example 5 is used. Indices which maximize 2-group discriminative ability between the prostatic cancer group and the prostatic cancer-free group are searched for, by linear discriminant analysis (explanatory variable coverage method). As a result, as index formula 6, a linear discriminant function having Tau, Glu, Ala, Cit, Met, and Orn (the numeral coefficients of the amino acid explanatory variables Tau, Glu, Ala, Cit, Met, and Orn are −3.776e−01, 2.843e−01, −2.857e−02, 5.645e−01, 6.426e−01, −2.102e−01, and −5.599e+00 in order) is obtained. Other than this, a plurality of linear discriminant functions having discriminative ability equivalent to index formula 6 are obtained. They are shown in FIGS. 40 and 41. The value of each coefficient in the functions shown in FIGS. 40 and 41 may be multiplied by a real number or by adding an arbitrary constant term thereto.

Figure 42:
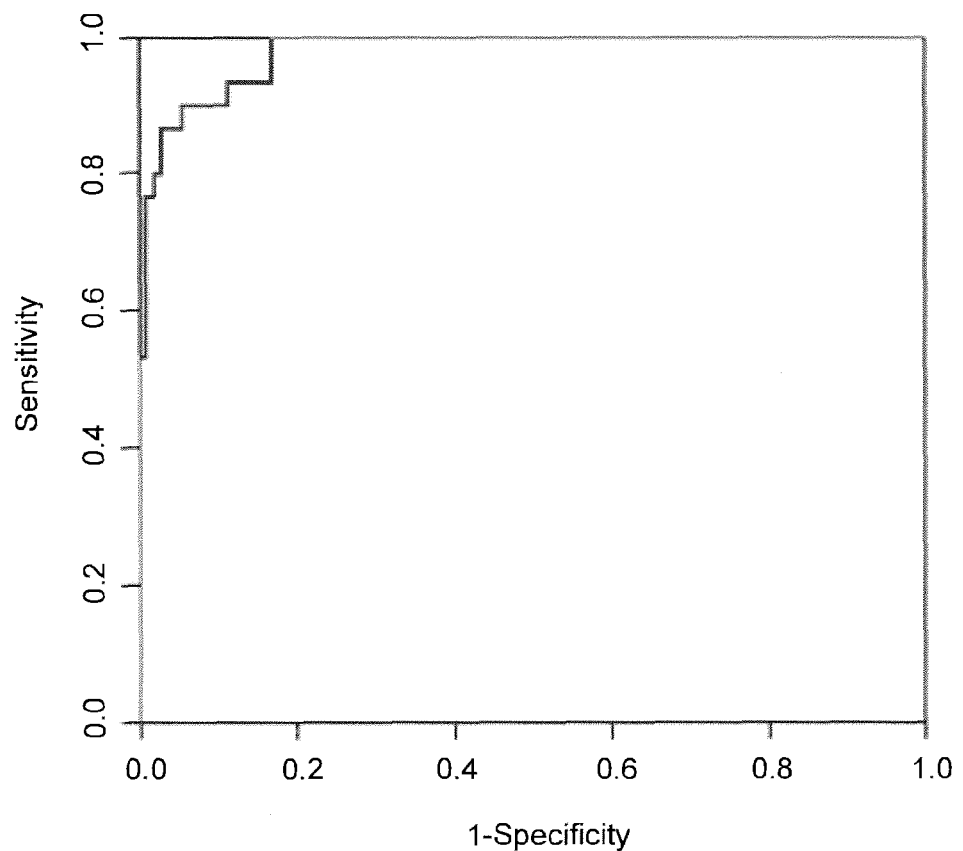
FIG. 42 is a graph showing area under the ROC curve of each amino acid explanatory variable in the 2-group discrimination between the prostatic cancer group and the prostatic cancer-free group.

To examine the prostatic cancer diagnostic ability using index formula 6, 2-group discrimination between the prostatic cancer group and the prostatic cancer-free group is evaluated by area under the ROC curve (see FIG. 42). As a result, an AUC of 0.978±0.011 (in 95% confidence interval, 0.957 to 1) is obtained. In addition, the optimum cutoff value of 2-group discrimination between the prostatic cancer group and the prostatic cancer-free group using index formula 6 is calculated with the symptom prevalence of the prostatic cancer group of 22%. As a result, the cutoff value is −4.27, and 93.33% sensitivity, 84.22% specificity, 69.93% positive predictive value, 97.92% negative predictive value, and 89.70% correct diagnosis rate are obtained. From these results, it is found that index formula 6 is useful, with high diagnostic ability.

Example 9

Figure 43:
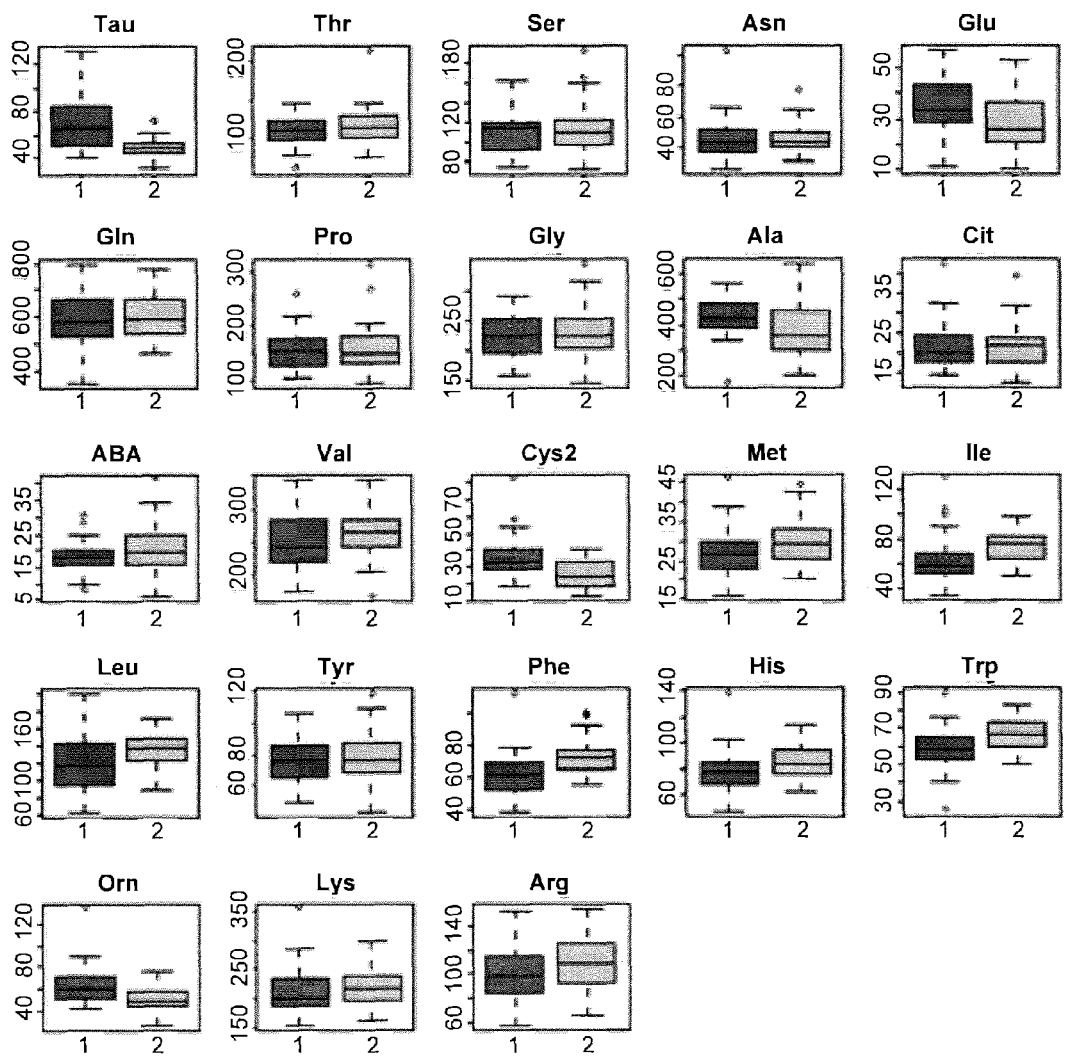
FIG. 43 is boxplots showing distributions of amino acid explanatory variables in a prostatic cancer group and a prostatic cancer-free group.

Blood amino acid concentrations are measured from the blood samples of a prostatic cancer patient group subjected to prostatic cancer diagnosis by prostatic biopsy and the blood samples of a prostatic cancer-free group by the amino acid analysis method. FIG. 43 is boxplots showing the distribution of the amino acid explanatory variables of the prostatic cancer group and the prostatic cancer-free group (on the horizontal axis, the prostatic cancer-free group: 1, and the prostatic cancer group: 2). The t-test between the two groups is conducted for the discrimination between the prostatic cancer group and the prostatic cancer-free group.

Tau, Glu, Ala, Cys2, and Orn of the prostatic cancer group are increased more significantly than those of the prostatic cancer-free group, and Met, Ile, Leu, Phe, and Trp are decreased more significantly than those of the prostatic cancer-free group. From this result, it is found that the amino acid explanatory variables Tau, Glu, Ala, Cys2, Orn, Met, Ile, Leu, Phe, and Trp have 2-group discriminative ability between the prostatic cancer group and the prostatic cancer-free group.

Example 10

The sample data used in Example 9 is used. Indices which maximize 2-group discriminative ability between the prostatic cancer group and the prostatic cancer-free group are earnestly searched for, by using the method described in International publication WO 2004/052191 which is an international application by the present applicant. As a result, index formula 7 is obtained among a plurality of index formulae having equivalent ability. Other than this, a plurality of multivariate discriminants having discriminative ability equivalent to index formula 7 are obtained. They are shown in FIGS. 44 and 45. The value of each coefficient in the formulae shown in FIGS. 44 and 45 may be multiplied by a real number or by adding an arbitrary constant term thereto.

$$-0.34(Thr)/(Orn)+0.25(Ser)/(Ile)-0.03(Asn)/(Glu)-0.08(Gln)/(Tau)+2.62 \quad \text{Index formula 7}$$

Figure 46:
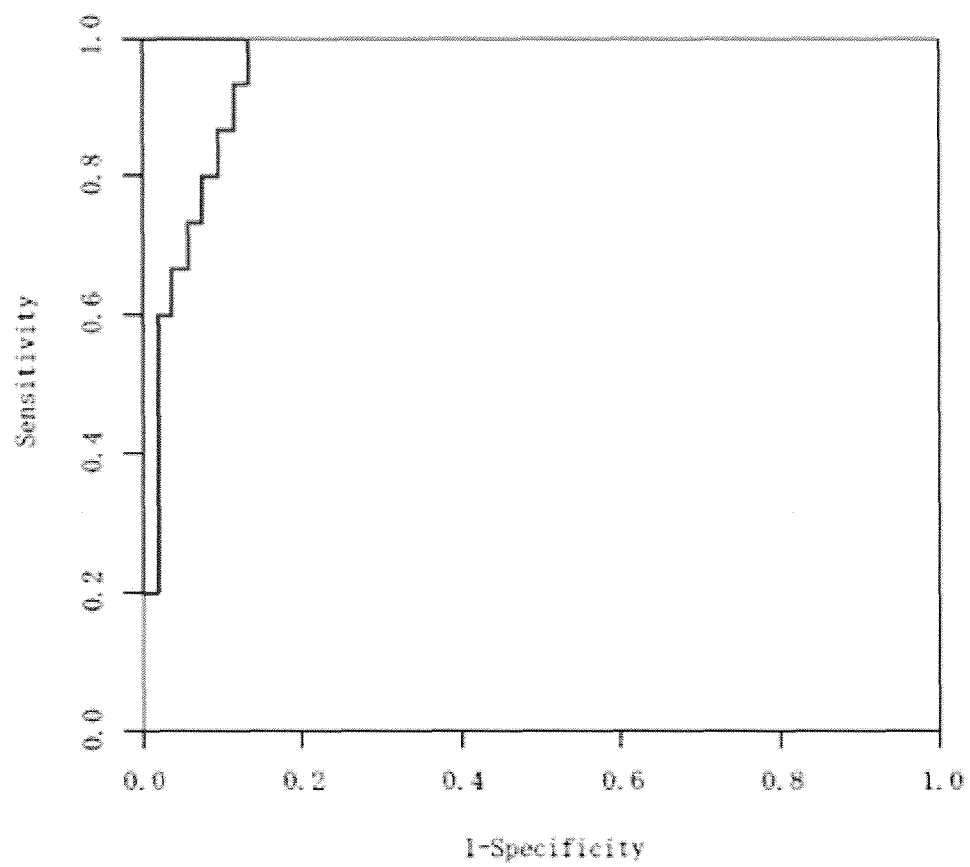
FIG. 46 is a graph showing area under the ROC curve of each amino acid explanatory variable in the 2-group discrimination between the prostatic cancer group and the prostatic cancer-free group.

To examine the prostatic cancer diagnostic ability using index formula 7, 2-group discrimination between the prostatic cancer group and the prostatic cancer-free group is evaluated by the area under the ROC curve (see FIG. 46). As a result, an AUC of 0.958±0.021 (in 95% confidence interval, 0.916 to 0.999) is obtained. In addition, the optimum cutoff value of 2-group discrimination between the prostatic cancer group and the prostatic cancer-free group using index formula 7 is calculated with the symptom prevalence of the prostatic cancer group of 37%. As a result, the cutoff value is 1.426, and 93.33% sensitivity, 88.46% specificity, 82.61% positive predictive value, 95.76% negative predictive value, and 90.26% correct diagnosis rate are obtained. From these results, it is found that index formula 7 is useful, with high diagnostic ability.

Example 11

The sample data used in Example 9 is used. Indices which maximize 2-group discriminative ability between the prostatic cancer group and the prostatic cancer-free group are searched for, by logistic analysis (explanatory variable coverage method according to the ROC maximum criterion). As a result, as index formula 8, a logistic regression equation having Tau, Thr, Ala, Trp, Orn, and Arg (the numeral coefficients of the amino acid explanatory variables Tau, Thr, Ala, Trp, Orn, and Arg, and the constant terms are 0.3610, −0.1862, 0.0604, −0.2344, 0.4838, −0.1130, and −25.0814 in order) is obtained. Other than this, a plurality of logistic regression equations having discriminative ability equivalent to index formula 8 are obtained. They are shown in FIGS. 47 and 48. The value of each coefficient in the equations shown in FIGS. 47 and 48 may be multiplied by a real number.

Figure 49:
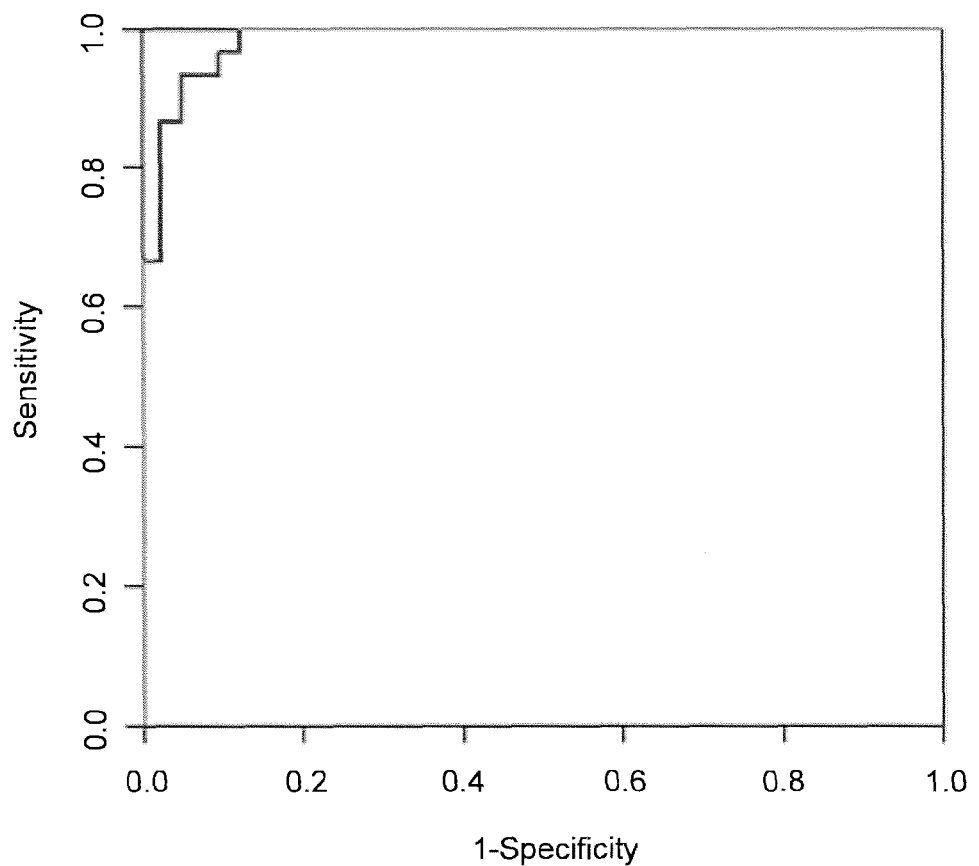
FIG. 49 is a graph showing area under the ROC curve of each amino acid explanatory variable in the 2-group discrimination between the prostatic cancer group and the prostatic cancer-free group.

To examine the prostatic cancer diagnostic ability using index formula 8, 2-group discrimination between the prostatic cancer group and the prostatic cancer-free group is evaluated by area under the ROC curve (see FIG. 49). As a result, an AUC of 0.985±0.014 (in 95% confidence interval, 0.957 to 1) is obtained. In addition, the optimum cutoff value of 2-group discrimination between the prostatic cancer group and the prostatic cancer-free group using index formula 8 is calculated with the symptom prevalence of the prostatic cancer group of 37%. As a result, the cutoff value is 0.355, and 96.67% sensitivity, 90.24% specificity, 85.34% positive predictive value, 97.88% negative predictive value, and 92.62% correct diagnosis rate are obtained. From these results, it is found that index formula 8 is useful, with high diagnostic ability.

Example 12

The sample data used in Example 9 is used. Indices which maximize 2-group discriminative ability between the prostatic cancer group and the prostatic cancer-free group are searched for, by linear discriminant analysis (explanatory variable coverage method). As a result, as index formula 9, a linear discriminant function having Tau, Thr, Ser, Ala, Orn, and Arg (the numeral coefficients of the amino acid explanatory variables Tau, Thr, Ser, Ala, Orn, and Arg are −6.459e−01, 1.829e−01, −1.391e−01, −7.718e−02, −6.794e−01, 2.498e−01, and 7.303e+01 in order) is obtained. Other than this, a plurality of linear discriminant functions having discriminative ability equivalent to index formula 9 are obtained. They are shown in FIGS. 50 and 51. The value of each coefficient in the functions shown in FIGS. 50 and 51 may be multiplied by a real number or by adding an arbitrary constant term thereto.

Figure 52:
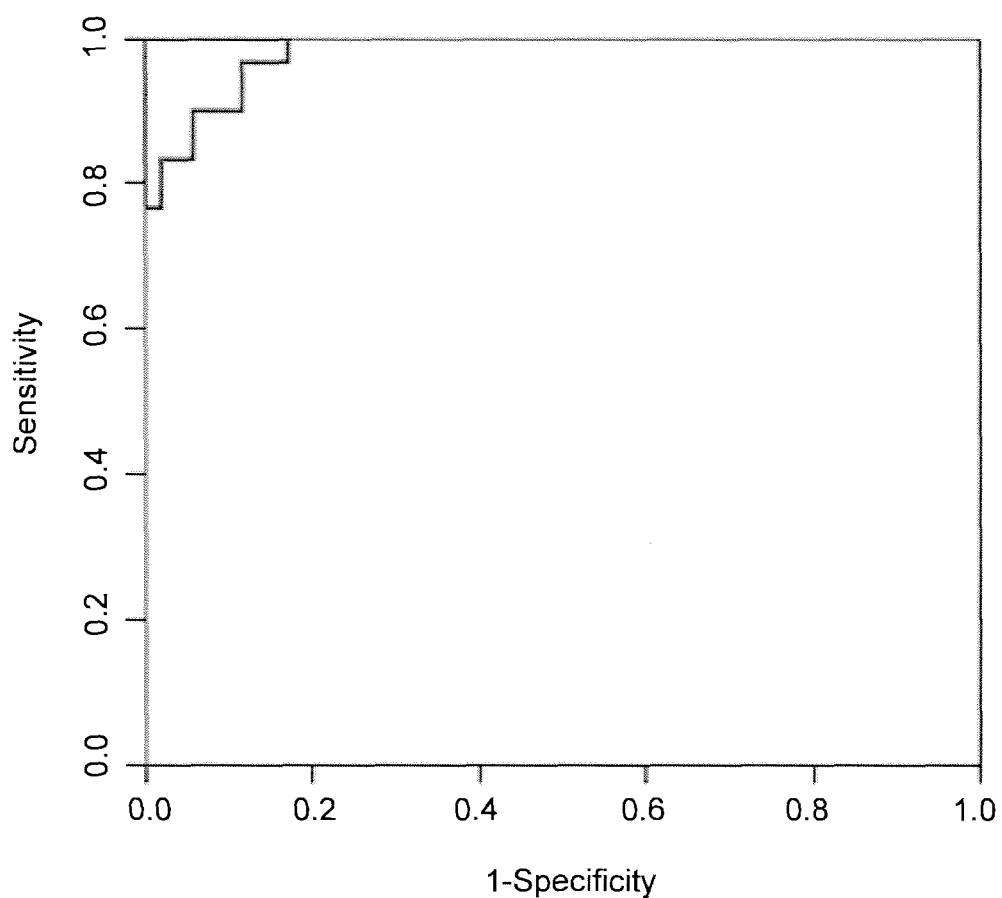
FIG. 52 is a graph showing area under the ROC curve of each amino acid explanatory variable in the 2-group discrimination between the prostatic cancer group and the prostatic cancer-free group.

To examine the prostatic cancer diagnostic ability using index formula 9, 2-group discrimination between the prostatic cancer group and the prostatic cancer-free group is evaluated by area under the ROC curve (see FIG. 52). As a result, an AUC of 0.981±0.014 (in 95% confidence interval, 0.954 to 1) is obtained. In addition, the optimum cutoff value of 2-group discrimination between the prostatic cancer group and the prostatic cancer-free group using index formula 9 is calculated with the symptom prevalence of the prostatic cancer group of 37%. As a result, the cutoff value is 2.32, and 96.67% sensitivity, 88.46% specificity, 83.12% positive predictive value, 97.83% negative predictive value, and 91.50% correct diagnosis rate are obtained. From these results, it is found that index formula 9 is useful, with high diagnostic ability.

Example 13

Figure 53:
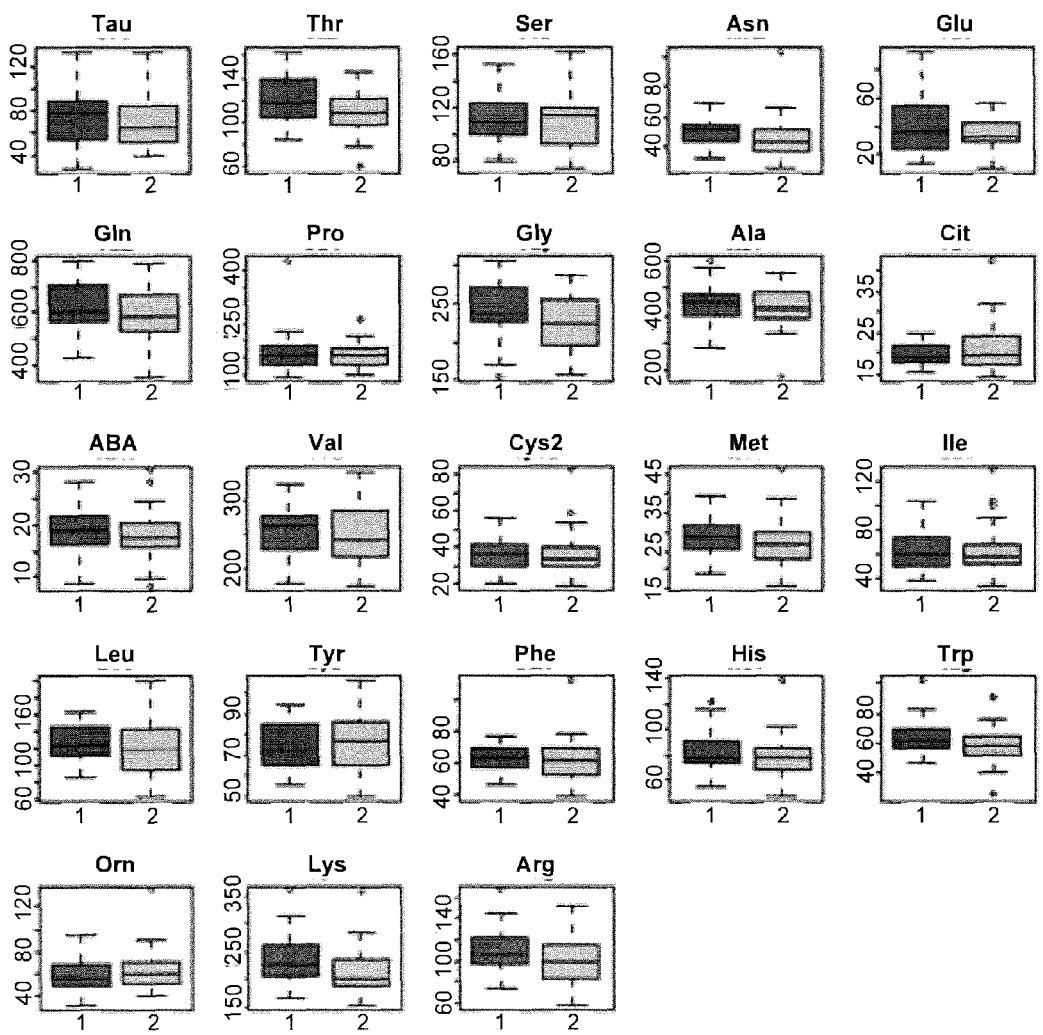
FIG. 53 is boxplots showing distributions of amino acid explanatory variables in a prostatic cancer group and a prostatic hypertrophy group.

Blood amino acid concentrations are measured from the blood samples of a prostatic cancer patient group subjected to prostatic cancer diagnosis by prostatic biopsy and the blood samples of a prostatic hypertrophy patient group by the amino acid analysis method. FIG. 53 is boxplots showing the distribution of the amino acid explanatory variables of the prostatic cancer group and the prostatic hypertrophy group (on the horizontal axis, the prostatic hypertrophy group: 1, and the prostatic cancer group: 2). The t-test between the two groups is conducted for the discrimination between the prostatic cancer group and the prostatic hypertrophy group.

Thr of the prostatic cancer group is decreased more significantly than that of the prostatic hypertrophy group. From this result, it is found that the amino acid explanatory variable Thr has 2-group discriminative ability between the prostatic cancer group and the prostatic hypertrophy group.

Example 14

The sample data used in Example 13 is used. Indices which maximize 2-group discriminative ability between the prostatic cancer group and the prostatic hypertrophy group are earnestly searched for, by using the method described in International publication WO 2004/052191 which is an international application by the present applicant. As a result, index formula 10 is obtained among a plurality of index formulae having equivalent ability. Other than this, a plurality of multivariate discriminants having discriminative ability equivalent to index formula 10 are obtained. They are shown in FIGS. 54 and 55. The value of each coefficient in the formulae shown in FIGS. 54 and 55 may be multiplied by a real number or by adding an arbitrary constant term thereto.

$$3.77(Ser)/(Gln)-0.31(Glu)/(Tau)+0.07(Ala)/(Asn)+0.26(Val)/(Thr)-0.16 \quad \text{Index formula 10}$$

Figure 56:
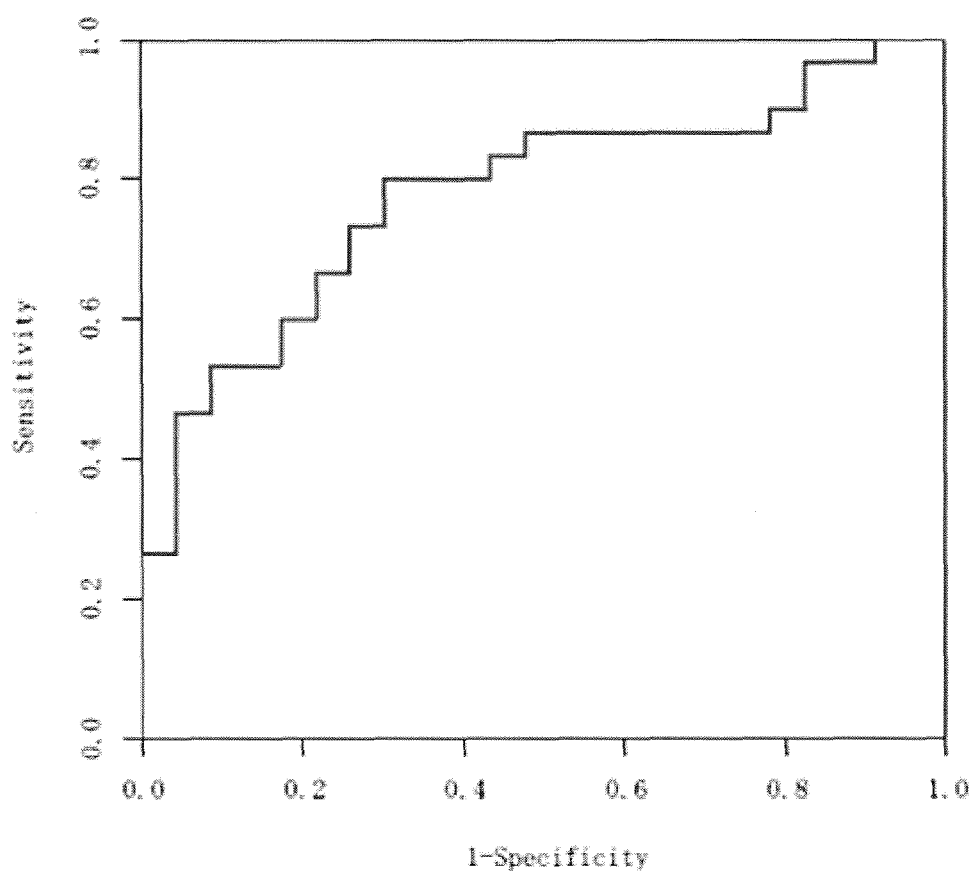
FIG. 56 is a graph showing area under the ROC curve of each amino acid explanatory variable in the 2-group discrimination between the prostatic cancer group and the prostatic hypertrophy group.

To examine the prostatic cancer diagnostic ability using index formula 10, 2-group discrimination between the prostatic cancer group and the prostatic hypertrophy group is evaluated by the area under the ROC curve (see FIG. 56). As a result, an AUC of 0.780±0.066 (in 95% confidence interval, 0.650 to 0.910) is obtained. In addition, the optimum cutoff value of 2-group discrimination between the prostatic cancer group and the prostatic hypertrophy group using index formula 10 is calculated with the symptom prevalence of the prostatic cancer group of 45%. As a result, the cutoff value is 1.587, and 73.33% sensitivity, 73.91% specificity, 69.70% positive predictive value, 77.21% negative predictive value, and 73.65% correct diagnosis rate are obtained. From these results, it is found that index formula 10 is useful, with high diagnostic ability.

Example 15

The sample data used in Example 13 is used. Indices which maximize 2-group discriminative ability between the prostatic cancer group and the prostatic hypertrophy group are searched for, by logistic analysis (explanatory variable coverage method according to the ROC maximum criterion). As a result, as index formula 11, a logistic regression equation having Thr, Ala, Val, Tyr, Trp, and Lys (the numeral coefficients of the amino acid explanatory variables Thr, Ala, Val, Tyr, Trp, and Lys, and the constant terms are −0.0634, 0.0101, 0.0169, 0.0569, −0.0934, −0.0224, and 5.3209 in order) is obtained. Other than this, a plurality of logistic regression equations having discriminative ability equivalent to index formula 11 are obtained. They are shown in FIGS. 57 and 58. The value of each coefficient in the equations shown in FIGS. 57 and 58 may be multiplied by a real number.

Figure 59:
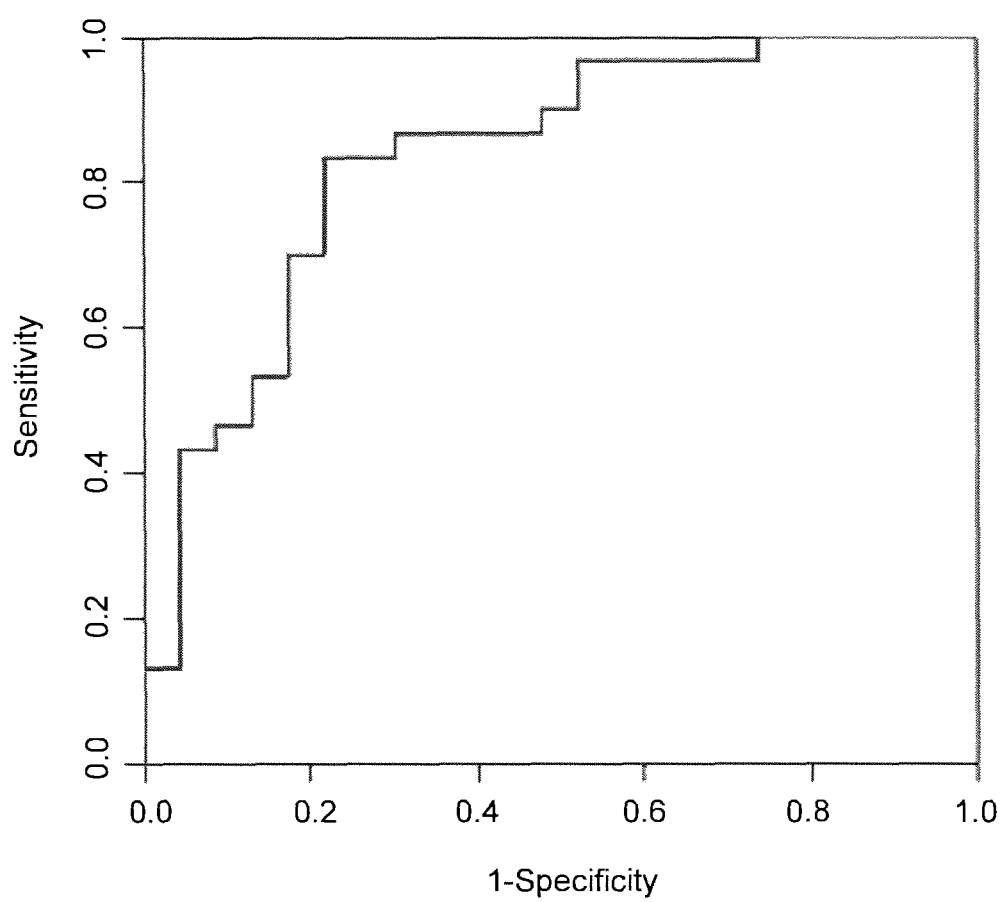
FIG. 59 is a graph showing area under the ROC curve of each amino acid explanatory variable in the 2-group discrimination between the prostatic cancer group and the prostatic hypertrophy group.

To examine the prostatic cancer diagnostic ability using index formula 11, 2-group discrimination between the prostatic cancer group and the prostatic hypertrophy group is evaluated by area under the ROC curve (see FIG. 59). As a result, an AUC of 0.832±0.059 (in 95% confidence interval, 0.716 to 0.948) is obtained. In addition, the optimum cutoff value of 2-group discrimination between the prostatic cancer group and the prostatic hypertrophy group using index formula 11 is calculated with the symptom prevalence of the prostatic cancer group of 37%. As a result, the cutoff value is 0.552, and 83.33% sensitivity, 78.26% specificity, 75.82% positive predictive value, 85.16% negative predictive value, and 80.54% correct diagnosis rate are obtained. From these results, it is found that index formula 11 is useful, with high diagnostic ability.

Example 16

The sample data used in Example 13 is used. Indices which maximize 2-group discriminative ability between the prostatic cancer group and the prostatic hypertrophy group are searched for, by linear discriminant analysis (explanatory variable coverage method). As a result, as index formula 12, a linear discriminant function having Thr, Ala, Val, Tyr, Trp, and Lys (the numeral coefficients of the amino acid explanatory variables Tau, Thr, Ser, Ala, Orn, and Arg are −5.143e−01, 8.710e−02, 1.289e−01, 4.425e−01, −6.921e−01, −1.912e−01, and 3.929e+01 in order) is obtained. Other than this, a plurality of linear discriminant functions having discriminative ability equivalent to index formula 12 are obtained. They are shown in FIGS. 60 and 61. The value of each coefficient in the functions shown in FIGS. 60 and 61 may be multiplied by a real number or by adding an arbitrary constant term thereto.

Figure 62:
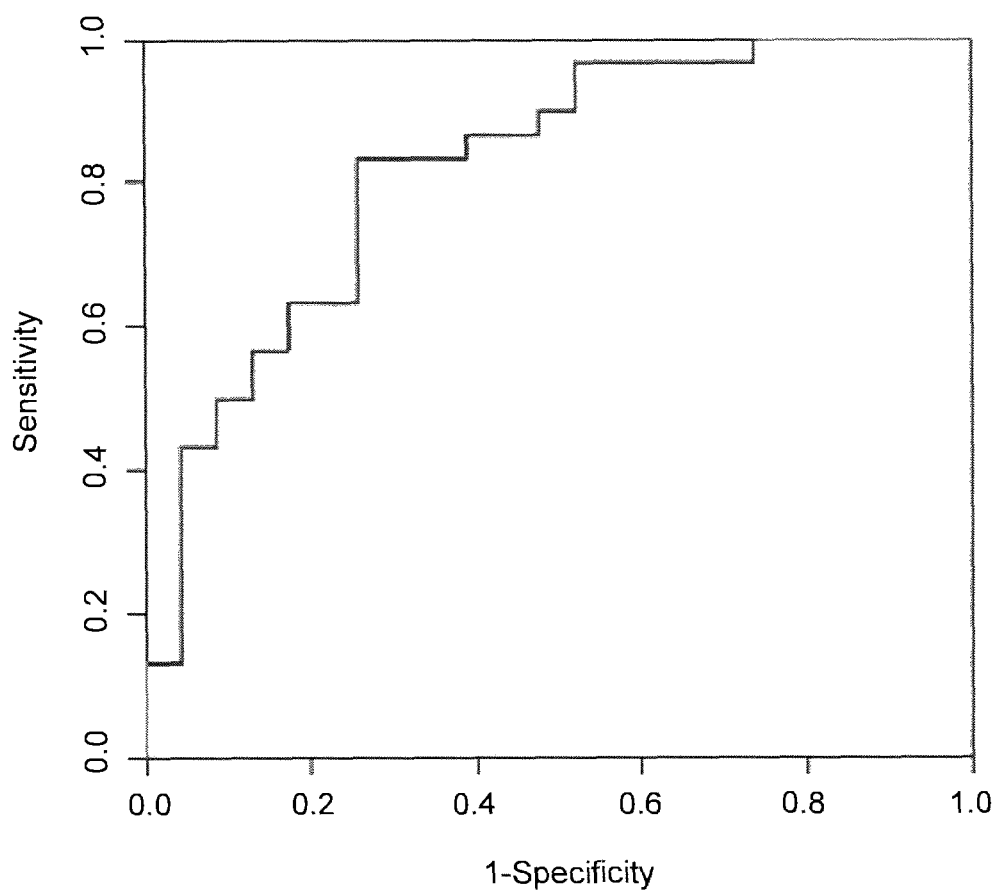
FIG. 62 is a graph showing area under the ROC curve of each amino acid explanatory variable in the 2-group discrimination between the prostatic cancer group and the prostatic hypertrophy group.

To examine the prostatic cancer diagnostic ability using index formula 12, 2-group discrimination between the prostatic cancer group and the prostatic hypertrophy group is evaluated by area under the ROC curve (see FIG. 62). As a result, an AUC of 0.820±0.061 (in 95% confidence interval, 0.700 to 0.940) is obtained. In addition, the optimum cutoff value of 2-group discrimination between the prostatic cancer group and the prostatic hypertrophy group using index formula 12 is calculated with the symptom prevalence of the prostatic cancer group of 45%. As a result, the cutoff value is −1.50, and 83.33% sensitivity, 73.91% specificity, 72.33% positive predictive value, 84.42% negative predictive value, and 78.15% correct diagnosis rate are obtained. From these results, it is found that index formula 12 is useful, with high diagnostic ability.

Example 17

Figure 63:
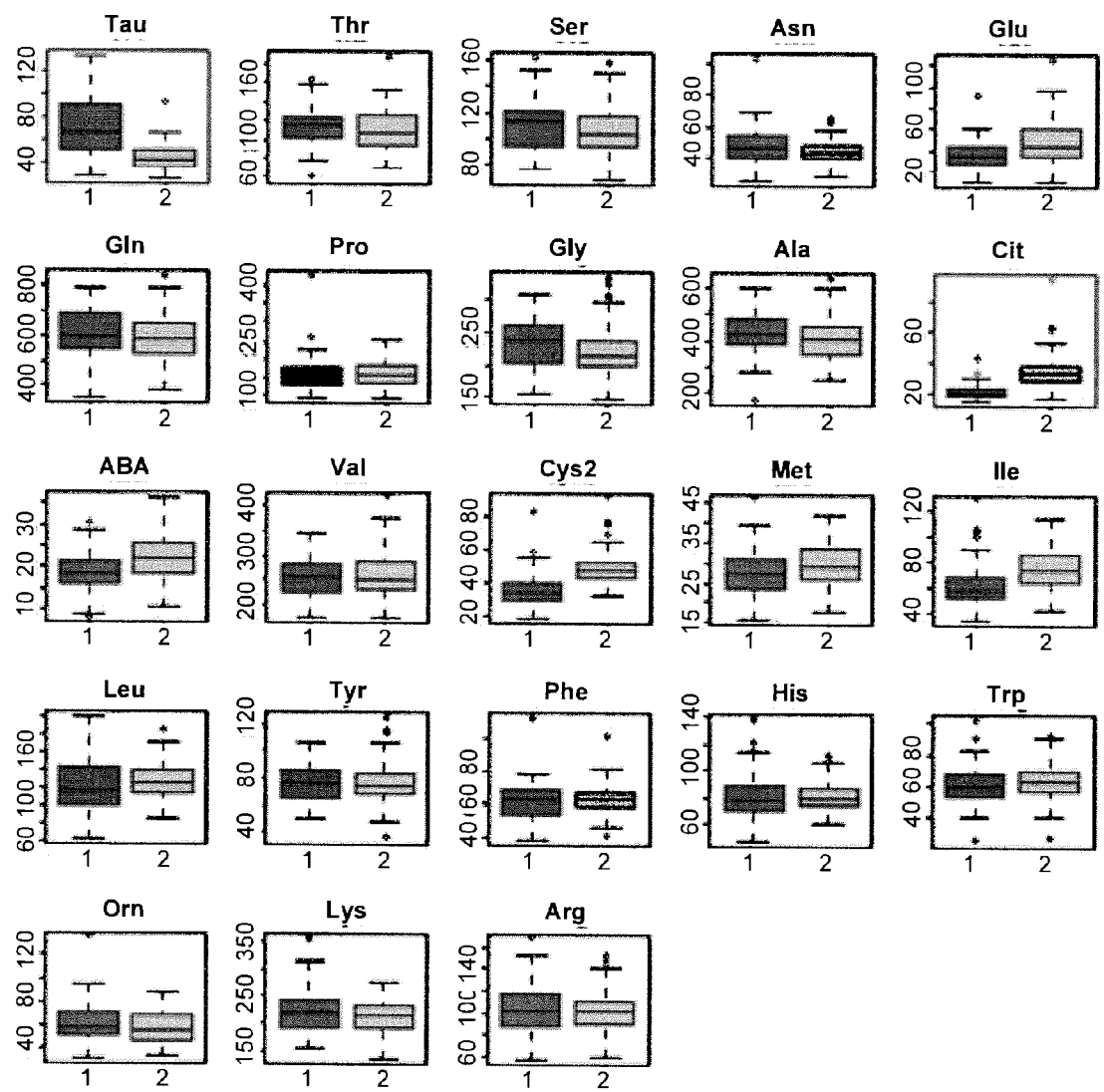
FIG. 63 is boxplots showing distributions of amino acid explanatory variables in a prostatic disease group and a prostatic disease-free group.

Blood amino acid concentrations are measured from the blood samples of a prostatic disease patient group such as prostatic cancer and prostatic hypertrophy subjected to prostatic cancer diagnosis by prostatic biopsy and the blood samples of a prostatic disease-free group by the amino acid analysis method. FIG. 63 is boxplots showing the distribution of the amino acid explanatory variables of the prostatic disease group and the prostatic disease-free group (on the horizontal axis, the prostatic disease-free group: 1, and the prostatic disease group: 2). The t-test between the two groups is conducted for the discrimination between the prostatic disease group and the prostatic disease-free group.

Tau, Asn, Gly, and Lys of the prostatic disease group are increased more significantly than those of the prostatic disease-free group, and Glu, Cit, ABA, Cys2, Met, and Ile are decreased more significantly than those of the prostatic disease-free group. From this result, it is found that the amino acid explanatory variables Tau, Asn, Gly, Lys, Glu, Cit, ABA, Cys2, Met, and Ile have 2-group discriminative ability between the prostatic disease group and the prostatic disease-free group.

Example 18

The sample data used in Example 17 is used. Indices which maximize 2-group discriminative ability between the prostatic disease group and the prostatic disease-free group are earnestly searched for, by using the method described in International publication WO 2004/052191 which is an international application by the present applicant. As a result, index formula 13 is obtained among a plurality of index formulae having equivalent ability. Other than this, a plurality of multivariate discriminants having discriminative ability equivalent to index formula 13 are obtained. They are shown in FIGS. 64 and 65. The value of each coefficient in the formulae shown in FIGS. 64 and 65 may be multiplied by a real number or by adding an arbitrary constant term thereto.

$$0.12(Tau)/(ABA)+0.14(Thr)/(Cit)-0.38(Glu)/(Ser)+0.01(Pro)/(Asn)+0.50 \quad \text{Index formula 13}$$

Figure 66:
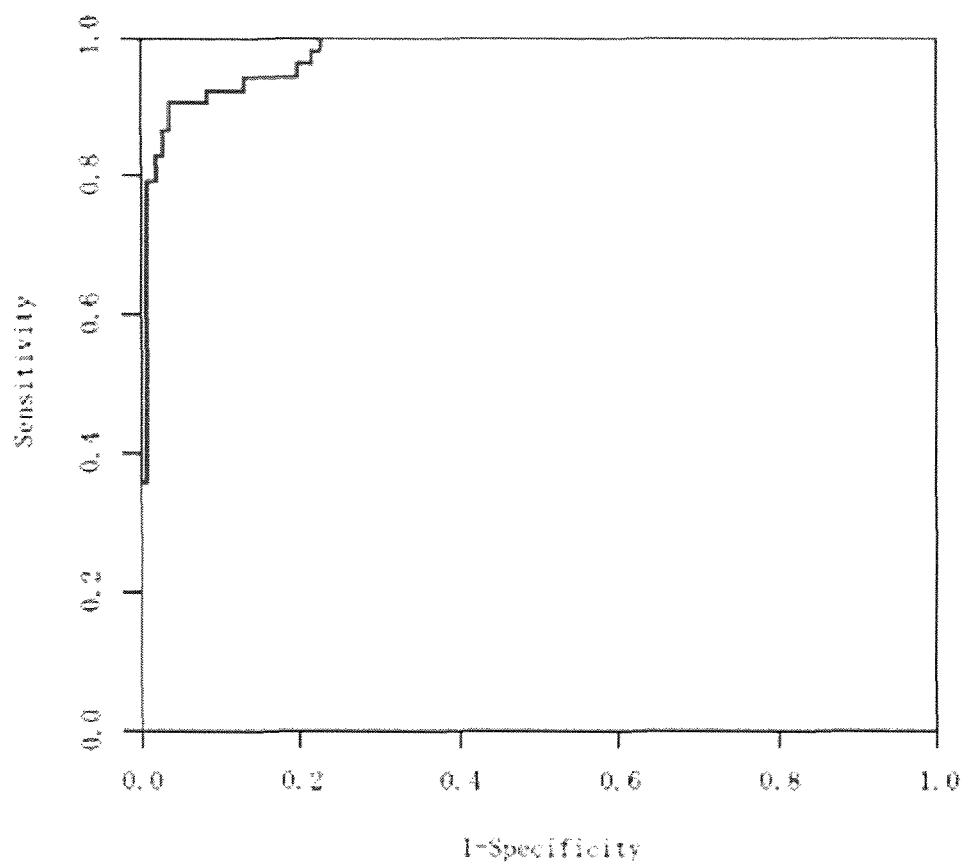
FIG. 66 is a graph showing area under the ROC curve of each amino acid explanatory variable in the 2-group discrimination between the prostatic disease group and the prostatic disease-free group.

To examine the prostatic disease diagnostic ability using index formula 13, 2-group discrimination between the prostatic disease group and the prostatic disease-free group is evaluated by the area under the ROC curve (see FIG. 66). As a result, an AUC of 0.977±0.011 (in 95% confidence interval, 0.955 to 0.998) is obtained. In addition, the optimum cutoff value of 2-group discrimination between the prostatic disease group and the prostatic disease-free group using index formula 13 is calculated with the symptom prevalence of the prostatic disease group of 33%. As a result, the cutoff value is 1.268, and 96.23% sensitivity, 80.19% specificity, 70.52% positive predictive value, 97.73% negative predictive value, and 85.48% correct diagnosis rate are obtained. From these results, it is found that index formula 13 is useful, with high diagnostic ability.

Example 19

The sample data used in Example 17 is used. Indices which maximize 2-group discriminative ability between the prostatic disease group and the prostatic disease-free group are searched for, by logistic analysis (explanatory variable coverage method according to the ROC maximum criterion). As a result, as index formula 14, a logistic regression equation having Tau, Glu, Pro, Ala, Cit, and ABA (the numeral coefficients of the amino acid explanatory variables Tau, Glu, Pro, Ala, Cit, and ABA, and the constant terms are 0.0778, −0.0705, −0.0074, 0.0209, −0.4891, −0.3098, and 9.2727 in order) is obtained. Other than this, a plurality of logistic regression equations having discriminative ability equivalent to index formula 14 are obtained. They are shown in FIGS. 67 and 68. The value of each coefficient in the equations shown in FIGS. 67 and 68 may be multiplied by a real number.

Figure 69:
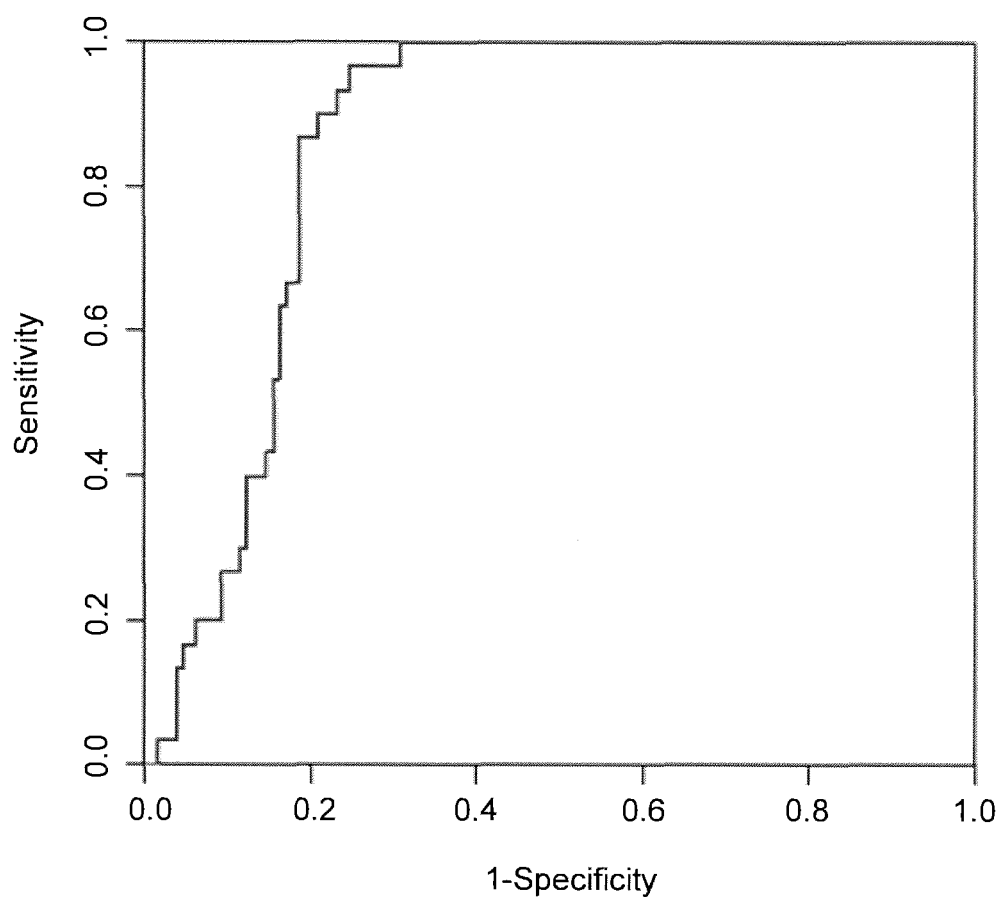
FIG. 69 is a graph showing area under the ROC curve of each amino acid explanatory variable in the 2-group discrimination between the prostatic disease group and the prostatic disease-free group.

To examine the prostatic disease diagnostic ability using index formula 14, 2-group discrimination between the prostatic disease group and the prostatic disease-free group is evaluated by area under the ROC curve (see FIG. 69). As a result, an AUC of 0.982±0.009 (in 95% confidence interval, 0.963 to 1.000) is obtained. In addition, the optimum cutoff value of 2-group discrimination between the prostatic disease group and the prostatic disease-free group using index formula 14 is calculated with the symptom prevalence of the prostatic disease group of 37%. As a result, the cutoff value is 0.450, and 90.57% sensitivity, 100.00% specificity, 100.00% positive predictive value, 95.56% negative predictive value, and 96.89% correct diagnosis rate are obtained. From these results, it is found that index formula 14 is useful, with high diagnostic ability.

Example 20

The sample data used in Example 17 is used. Indices which maximize 2-group discriminative ability between the prostatic disease group and the prostatic disease-free group are searched for, by linear discriminant analysis (explanatory variable coverage method). As a result, as index formula 15, a linear discriminant function having Tau, Glu, Gly, Cit, ABA, and Val (the numeral coefficients of the amino acid explanatory variables Tau, Glu, Gly, Cit, ABA, and Val are −3.158e−01, 1.439e−01, −5.537e−02, 6.746e−01, 6.473e−01, −4.858e−02, and 2.269e+00 in order) is obtained. Other than this, a plurality of linear discriminant functions having discriminative ability equivalent to index formula 15 are obtained. They are shown in FIGS. 70 and 71. The value of each coefficient in the functions shown in FIGS. 70 and 71 may be multiplied by a real number or by adding an arbitrary constant term thereto.

Figures 72, 73:
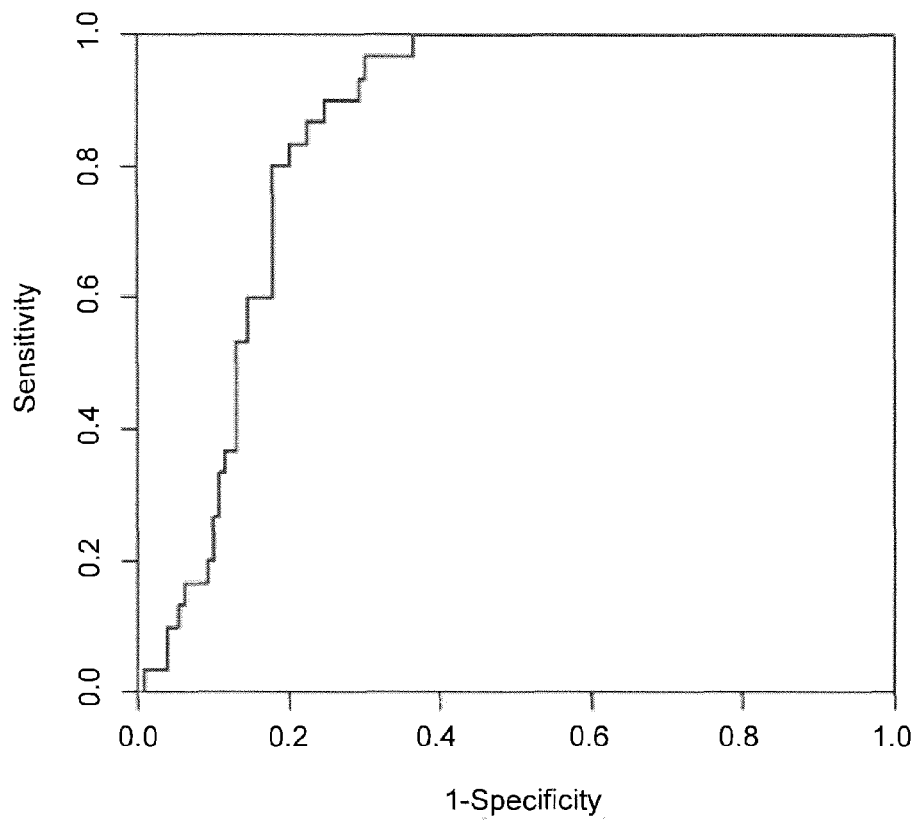
FIG. 72 is a graph showing area under the ROC curve of each amino acid explanatory variable in the 2-group discrimination between the prostatic disease group and the prostatic disease-free group.
FIG. 73 is a graph showing area under the ROC curve in each of the 2-group discriminations on each of the discriminants.

To examine the prostatic disease diagnostic ability using index formula 15, 2-group discrimination between the prostatic disease group and the prostatic disease-free group is evaluated by area under the ROC curve (see FIG. 72). As a result, an AUC of 0.850±0.032 (in 95% confidence interval, 0.788 to 0.913) is obtained. In addition, the optimum cutoff value of 2-group discrimination between the prostatic disease group and the prostatic disease-free group using index formula 15 is calculated with the symptom prevalence of the prostatic disease group of 33%. As a result, the cutoff value is −5.34, and 80.00% sensitivity, 80.62% specificity, 67.03% positive predictive value, 89.11% negative predictive value, and 80.41% correct diagnosis rate are obtained. From these results, it is found that index formula 15 is useful, with high diagnostic ability.

Example 21

The sample data used in Examples 1, 13, and 17 are used. As a comparative example with respect to Examples 2, 14, and 18, using index formulae 1, 10, 11, and 13 described in International publication WO 2008/016111 which is an international application by the present applicant, 2-group discriminative abilities between the prostatic cancer group and the healthy group, between the prostatic hypertrophy group and the prostatic cancer group, and between the prostatic disease group and the healthy group are examined. As a result, as shown in FIG. 73, even when any of the formulae is used for the respective 2-group discriminations, no ROC_AUC values above ROC_AUC obtained by Examples 2, 14, and 18 are obtained. From this, it is found that the multivariate discriminants in the present invention has higher discriminative ability with respect to these discriminations than the index formula group described in International publication WO 2008/016111 which is the international application by the present applicant.

Example 22

Figure 74:
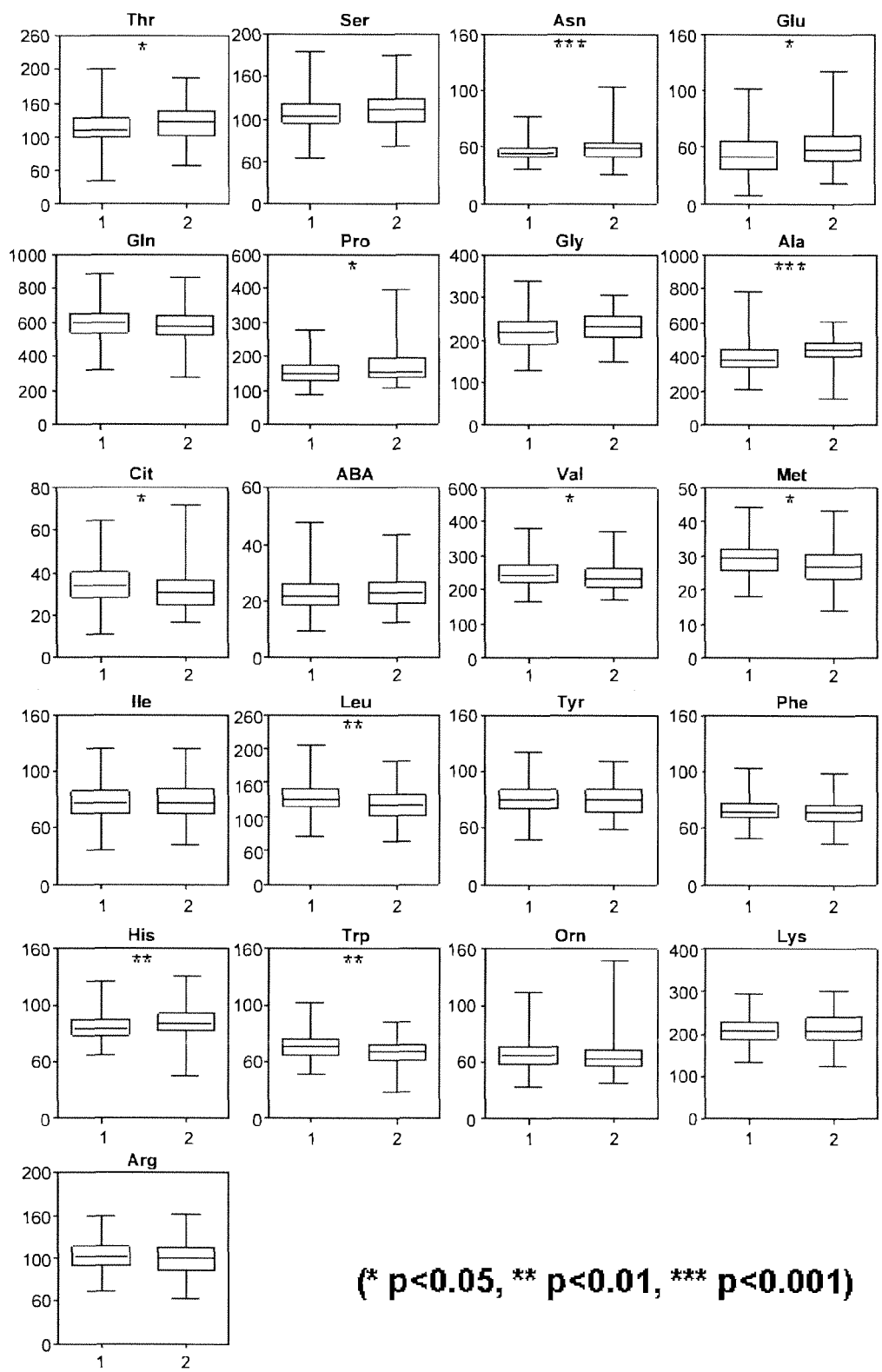
FIG. 74 is boxplots showing distributions of amino acid explanatory variables in a prostatic cancer group and a prostatic cancer-free group.

Blood amino acid concentrations are measured from the blood samples of a prostatic cancer patient group subjected to prostatic cancer diagnosis by prostatic biopsy and the blood samples of a prostatic cancer-free group by the amino acid analysis method. FIG. 74 is boxplots showing the distribution of the amino acid explanatory variables of the prostatic cancer group and the prostatic cancer-free group (on the horizontal axis, the prostatic cancer-free group: 1, and the prostatic cancer group: 2). The t-test between the two groups is conducted for the discrimination between the prostatic cancer group and the prostatic cancer-free group. Thr, Asn, Ala, and His of the prostatic cancer group are increased more significantly than those of the prostatic cancer-free group, and Val, Met, Leu, and Trp are decreased more significantly than those of the prostatic cancer-free group. From this result, it is found that the amino acid explanatory variables Thr, Asn, Ala, His, Val, Met, Leu, and Trp have 2-group discriminative ability between the prostatic cancer group and the prostatic cancer-free group.

Example 23

The sample data used in Example 22 is used. Indices which maximize 2-group discriminative ability between the prostatic cancer group and the prostatic cancer-free group are searched for, by logistic analysis (explanatory variable coverage method according to the ROC maximum criterion). As a result, as index formula 16, a logistic regression equation having Asn, Ala, Val, Met, Trp, and Arg (the numeral coefficients of the amino acid explanatory variables Asn, Ala, Val, Met, Trp, and Arg, and the constant terms are 0.08585, 0.01405, −0.01816, −0.11079, −0.08095, −0.02272, and 3.18118 in order) is obtained. Other than this, a plurality of logistic regression equations having discriminative ability equivalent to index formula 16 are obtained. They are shown in FIGS. 75, 76, 77, and 78. The value of each coefficient in the equations shown in FIGS. 75, 76, 77, and 78 may be multiplied by a real number.

Figure 79:
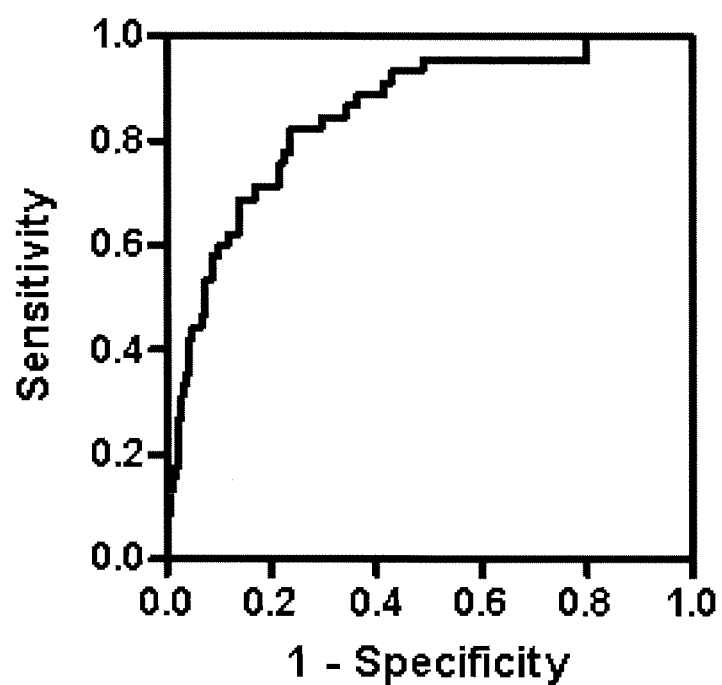
FIG. 79 is a graph showing the ROC curve of the index formula 16 in the 2-group discrimination between the prostatic cancer group and the prostatic cancer-free group.

To examine the prostatic cancer diagnostic ability using index formula 16, 2-group discrimination between the prostatic cancer group and the prostatic cancer-free group is evaluated by area under the ROC curve (see FIG. 79). As a result, an AUC of 0.850±0.031 (in 95% confidence interval, 0.789 to 0.911) is obtained. In addition, on the cutoff value of 2-group discrimination between the prostatic cancer group and the prostatic cancer-free group using index formula 16, the cutoff value which maximizes the average value of sensitivity and specificity is calculated. As a result, the cutoff value is −0.1574, and 82% sensitivity, and 76% specificity are obtained. From these results, it is found that index formula 16 is useful, with high diagnostic ability.

Example 24

The sample data used in Example 22 is used. Indices which maximize 2-group discriminative ability between the prostatic cancer group and the prostatic cancer-free group are searched for, by linear discriminant analysis (explanatory variable coverage method according to the ROC maximum criterion). As a result, as index formula 17, a linear discriminant function having Asn, Ala, Val, Met, Tyr, and Trp (the numeral coefficients of the amino acid explanatory variables Asn, Ala, Val, Met, Tyr, and Trp are 0.07557, 0.01311, −0.01544, −0.16644, 0.02693, −0.08447, and 2.48506 in order) is obtained. Other than this, a plurality of linear discriminant functions having discriminative ability equivalent to index formula 17 are obtained. They are shown in FIGS. 80, 81, 82, and 83. The value of each coefficient in the functions shown in FIGS. 80, 81, 82, and 83 may be multiplied by a real number or by adding an arbitrary constant term thereto.

Figures 84, 85:
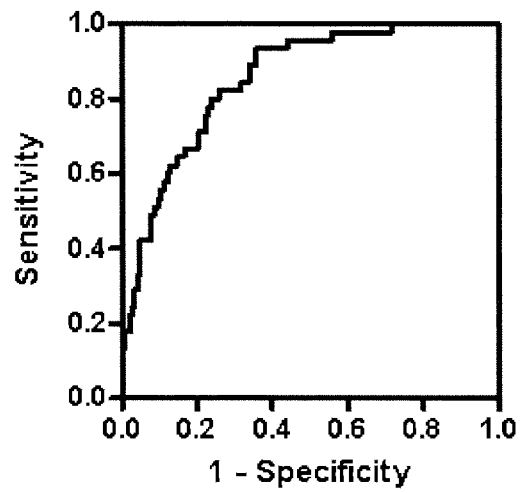
FIG. 84 is a graph showing the ROC curve of the index formula 17 in the 2-group discrimination between the prostatic cancer group and the prostatic cancer-free group.
FIG. 85 is a chart showing a list of amino acids extracted based on AUC of the ROC curve.

To examine the prostatic cancer diagnostic ability using index formula 17, 2-group discrimination between the prostatic cancer group and the prostatic cancer-free group is evaluated by area under the ROC curve (see FIG. 84). As a result, an AUC of 0.852±0.028 (in 95% confidence interval, 0.797 to 0.906) is obtained. In addition, on the cutoff value of 2-group discrimination between the prostatic cancer group and the prostatic cancer-free group using index formula 17, the cutoff value which maximizes the average value of sensitivity and specificity is calculated. As a result, the cutoff value is −0.4851, and 93% sensitivity, and 64% specificity are obtained. From these results, it is found that index formula 17 is useful, with high diagnostic ability.

Example 25

The sample data used in Example 22 is used. All the linear discriminants for performing 2-group discrimination between the prostatic cancer group and the prostatic cancer-free group are extracted by an explanatory variable coverage method. The areas under the ROC curve of all the discriminants satisfying the condition in which the maximum value of amino acid explanatory variables appearing in each of the discriminants is 6 are calculated. The frequencies with which the amino acids appear in the discriminants in which the areas under the ROC curve are above certain threshold values are measured. When the areas under the ROC curve of 0.7, 0.75, and 0.8 are threshold values, it is found that Ala, Trp, Val, Met, Leu, Asn, His, Thr, and Pro are in the top ten among the amino acids extracted at high frequency at all times. It is found that multivariate discriminants using these amino acids as explanatory variables have 2-group discriminative ability between the prostatic cancer group and the prostatic cancer-free group (see FIG. 85).

Example 26

Figure 86:
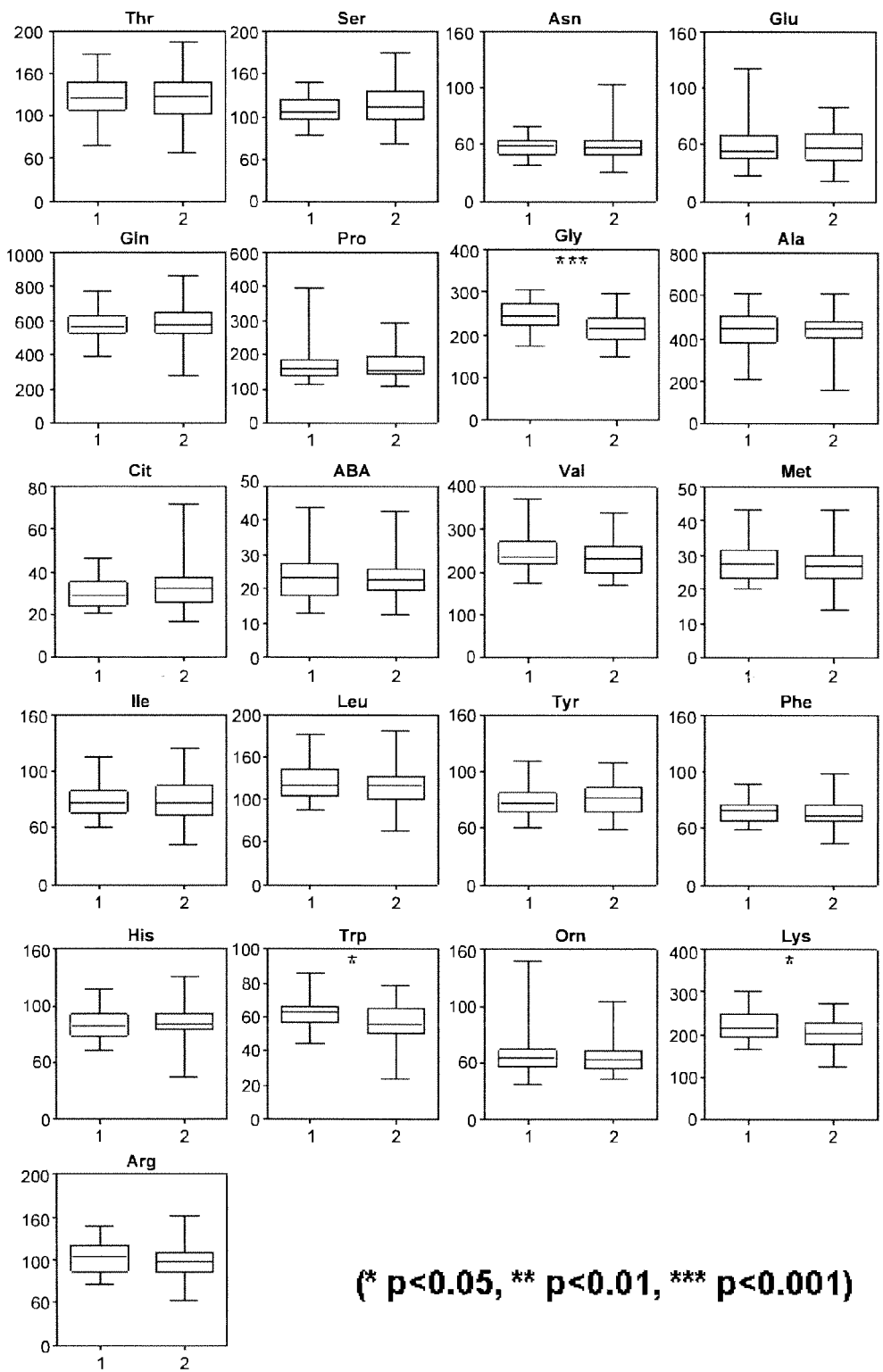
FIG. 86 is boxplots showing distributions of amino acid explanatory variables in a prostatic cancer group and a prostatic hypertrophy group.

Blood amino acid concentrations are measured from the blood samples of a prostatic cancer patient group subjected to prostatic cancer diagnosis by prostatic biopsy and the blood samples of a prostatic hypertrophy group by the amino acid analysis method. FIG. 86 is boxplots showing the distribution of the amino acid explanatory variables of the prostatic cancer group and the prostatic hypertrophy group (on the horizontal axis, the prostatic hypertrophy group: 1, and the prostatic cancer group: 2). The t-test between the two groups is conducted for the discrimination between the prostatic cancer group and the prostatic hypertrophy group. Gly, Trp, and Lys of the prostatic cancer group are decreased more significantly than those of the prostatic hypertrophy group (significant difference probability $p<0.05$). From this result, it is found that the amino acid explanatory variables Gly, Trp, and Lys have 2-group discriminative ability between the prostatic cancer group and the prostatic hypertrophy group.

Example 27

The sample data used in Example 26 is used. Indices which maximize 2-group discriminative ability between the prostatic cancer group and the prostatic hypertrophy group are searched for, by logistic analysis (explanatory variable coverage method according to the ROC maximum criterion). As a result, as index formula 18, a logistic regression equation having Ser, Gln, Gly, Cit, Val, and Trp (the numeral coefficients of the amino acid explanatory variables Ser, Gln, Gly, Cit, Val, and Trp, and the constant terms are 0.05102, 0.01259, −0.05243, 0.05778, −0.02344, −0.05969, and 6.78981 in order) is obtained. Other than this, a plurality of logistic regression equations having discriminative ability equivalent to index formula 18 are obtained. They are shown in FIGS. 87, 88, 89, and 90. The value of each coefficient in the equations shown in FIGS. 87, 88, 89, and 90 may be multiplied by a real number.

Figure 91:
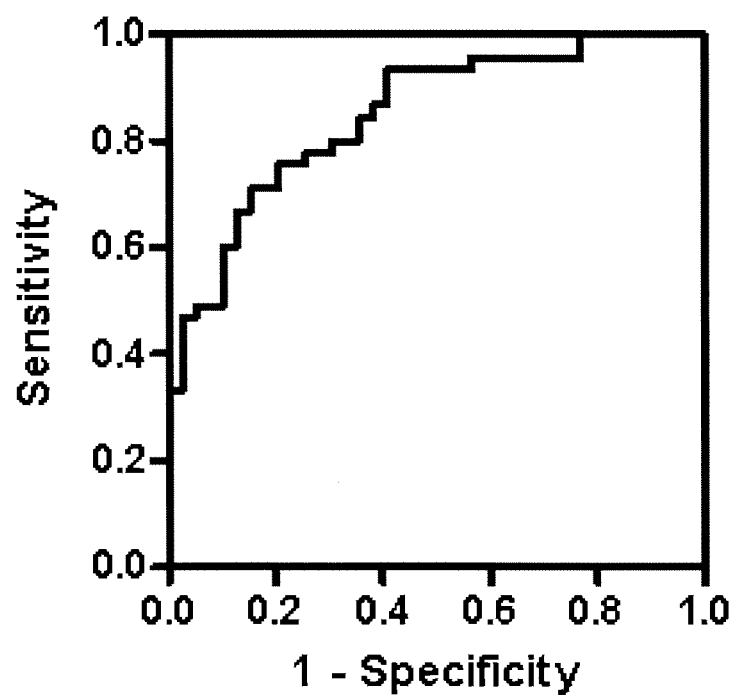
FIG. 91 is a graph showing the ROC curve of the index formula 18 in the 2-group discrimination between the prostatic cancer group and the prostatic hypertrophy group.

To examine the prostatic cancer diagnostic ability using index formula 18, 2-group discrimination between the prostatic cancer group and the prostatic hypertrophy group is evaluated by area under the ROC curve (see FIG. 91). As a result, an AUC of 0.848±0.041 (in 95% confidence interval, 0.768 to 0.929) is obtained. In addition, on the cutoff value of 2-group discrimination between the prostatic cancer group and the prostatic hypertrophy group using index formula 18, the cutoff value which maximizes the average value of sensitivity and specificity is calculated. As a result, the cutoff value is 0.3355, and 71% sensitivity, and 85% specificity are obtained. From these results, it is found that index formula 18 is useful, with high diagnostic ability.

Example 28

The sample data used in Example 26 is used. Indices which maximize 2-group discriminative ability between the prostatic cancer group and the prostatic hypertrophy group are searched for, by linear discriminant analysis (explanatory variable coverage method according to the ROC maximum criterion). As a result, as index formula 19, a linear discriminant function having Ser, Gln, Gly, Cit, Val, and Trp (the numeral coefficients of the amino acid explanatory variables Ser, Gln, Gly, Cit, Val, and Trp are 0.03070, 0.00620, −0.03718, 0.05108, −0.01641, −0.03504, and 5.98134 in order) is obtained. Other than this, a plurality of linear discriminant functions having discriminative ability equivalent to index formula 19 are obtained. They are shown in FIGS. 92, 93, 94, and 95. The value of each coefficient in the functions shown in FIGS. 92, 93, 94, and 95 may be multiplied by a real number or by adding an arbitrary constant term thereto.

Figures 96, 97:
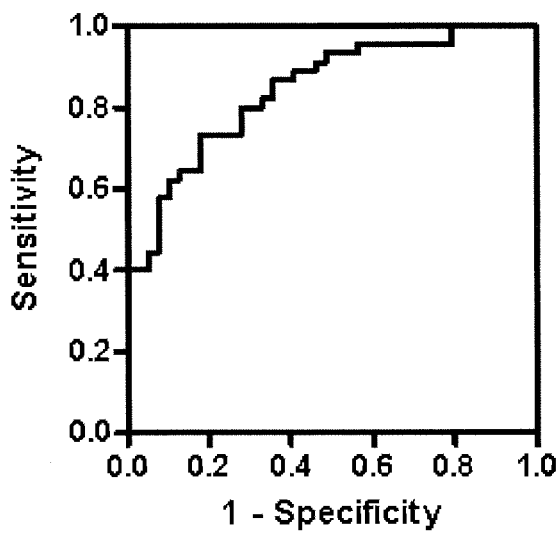
FIG. 96 is a graph showing the ROC curve of the index formula 19 in the 2-group discrimination between the prostatic cancer group and the prostatic hypertrophy group.
FIG. 97 is a chart showing a list of amino acids extracted based on AUC of the ROC curve.

To examine the prostatic cancer diagnostic ability using index formula 19, 2-group discrimination between the prostatic cancer group and the prostatic hypertrophy group is evaluated by area under the ROC curve (see FIG. 96). As a result, an AUC of 0.844±0.042 (in 95% confidence interval, 0.762 to 0.926) is obtained. In addition, on the cutoff value of 2-group discrimination between the prostatic cancer group and the prostatic hypertrophy group using index formula 19, the cutoff value which maximizes the average value of sensitivity and specificity is calculated. As a result, the cutoff value is −0.1540, and 73% sensitivity, and 82% specificity are obtained. From these results, it is found that index formula 19 is useful, with high diagnostic ability.

Example 29

The sample data used in Example 26 is used. All the linear discriminants for performing 2-group discrimination between the prostatic cancer group and the prostatic hypertrophy group are extracted by an explanatory variable coverage method. The areas under the ROC curve of all the discriminants satisfying the condition in which the maximum value of amino acid explanatory variables appearing in each of the discriminants is 6 are calculated. The frequencies with which the amino acids appear in the discriminants in which the areas under the ROC curve are above certain threshold values are measured. When the areas under the ROC curve of 0.7, 0.75, and 0.8 are threshold values, it is found that Gly, Val, Ser, Trp, Cit, Lys, and His are in the top ten among the amino acids extracted at high frequency at all times. It is found that multivariate discriminants using these amino acids as explanatory variables have 2-group discriminative ability between the prostatic cancer group and the prostatic hypertrophy group (see FIG. 97).

Example 30

Figure 98:
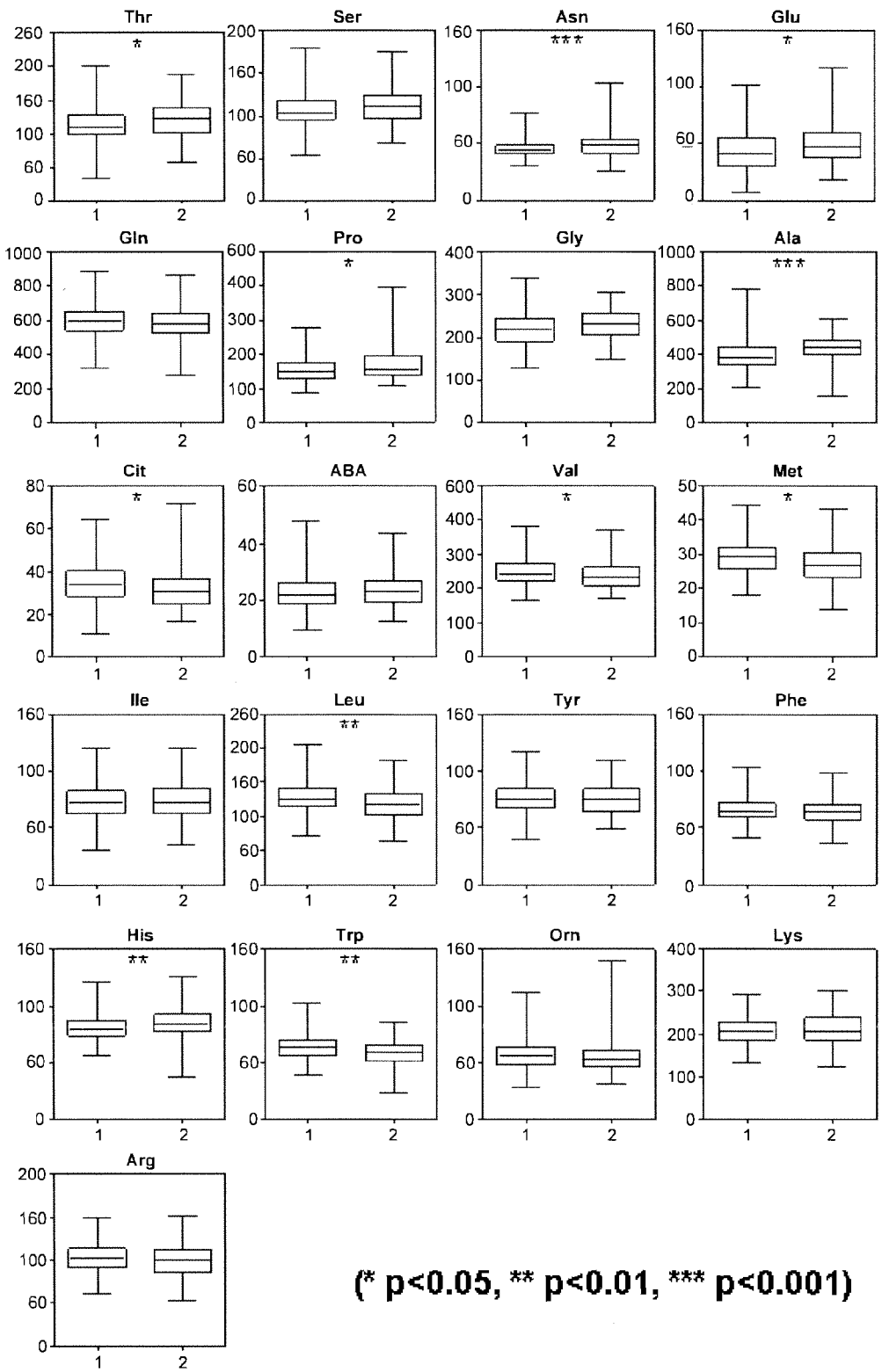
FIG. 98 is boxplots showing distributions of amino acid explanatory variables in a prostatic cancer group and a prostatic hypertrophy group.

Blood amino acid concentrations are measured from the blood samples of a prostatic disease patient group such as prostatic cancer and prostatic hypertrophy subjected to prostatic disease diagnosis by prostatic biopsy and the blood samples of a prostatic disease-free group by the amino acid analysis method. FIG. 98 is boxplots showing the distribution of the amino acid explanatory variables of the prostatic disease group and the prostatic disease-free group (on the horizontal axis, the prostatic disease-free group: 1, and the prostatic disease group: 2). The t-test between the two groups is conducted for the discrimination between the prostatic disease group and the prostatic disease-free group. Thr, Asn, Glu, Pro, Ala, and His of the prostatic disease group are increased more significantly than those of the prostatic disease-free group, and Cit, Val, Met, Leu, and Trp are decreased more significantly than those of the prostatic disease-free group. From this result, it is found that the amino acid explanatory variables Thr, Asn, Glu, Pro, Ala, His, Cit, Val, Met, Leu, and Trp have 2-group discriminative ability between the prostatic disease group and the prostatic disease-free group.

Example 31

The sample data used in Example 30 is used. Indices which maximize 2-group discriminative ability between the prostatic disease group and the prostatic disease-free group are searched for, by logistic analysis (explanatory variable coverage method according to the ROC maximum criterion). As a result, as index formula 20, a logistic regression equation having Asn, Glu, Ala, Val, Met, and Trp (the numeral coefficients of the amino acid explanatory variables Asn, Glu, Ala, Val, Met, and Trp, and the constant terms are 0.09273, 0.02241, 0.01196, −0.01415, −0.12983, −0.05678, and −0.7474 in order) is obtained. Other than this, a plurality of logistic regression equations having discriminative ability equivalent to index formula 20 are obtained. They are shown in FIGS. 99, 100, 101, and 102. The value of each coefficient in the equations shown in FIGS. 99, 100, 101, and 102 may be multiplied by a real number.

Figure 103:
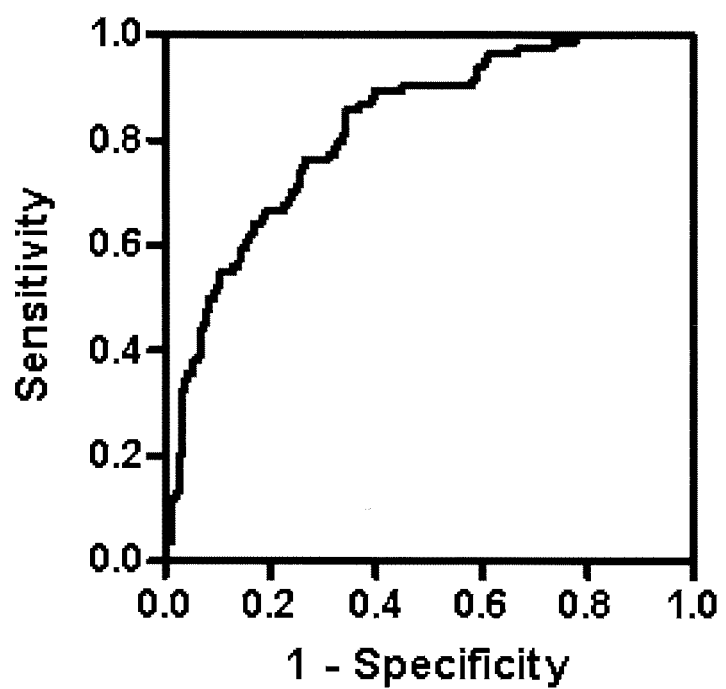
FIG. 103 is a graph showing the ROC curve of the index formula 20 in the 2-group discrimination between the prostatic disease group and the prostatic disease-free group.

To examine the prostatic disease diagnostic ability using index formula 20, 2-group discrimination between the prostatic disease group and the prostatic disease-free group is evaluated by area under the ROC curve (see FIG. 103). As a result, an AUC of 0.822±0.026 (in 95% confidence interval, 0.772 to 0.872) is obtained. In addition, on the cutoff value of 2-group discrimination between the prostatic disease group and the prostatic disease-free group using index formula 20, the cutoff value which maximizes the average value of sensitivity and specificity is calculated. As a result, the cutoff value is −1.239, and 86% sensitivity, and 66% specificity are obtained. From these results, it is found that index formula 20 is useful, with high diagnostic ability.

Example 32

The sample data used in Example 30 is used. Indices which maximize 2-group discriminative ability between the prostatic disease group and the prostatic disease-free group are searched for, by linear discriminant analysis (explanatory variable coverage method according to the ROC maximum criterion). As a result, as index formula 21, a linear discriminant function having Asn, Glu, Ala, Val, Met, and Trp (the numeral coefficients of the amino acid explanatory variables Asn, Glu, Ala, Val, Met, and Trp are 0.08591, 0.01994, 0.01194, −0.01250, −0.13483, −0.05252, and 0.15837 in order) is obtained. Other than this, a plurality of linear discriminant functions having discriminative ability equivalent to index formula 21 are obtained. They are shown in FIGS. 104, 105, 106, and 107. The value of each coefficient in the functions shown in FIGS. 104, 105, 106, and 107 may be multiplied by a real number or by adding an arbitrary constant term thereto.

Figures 108, 109:
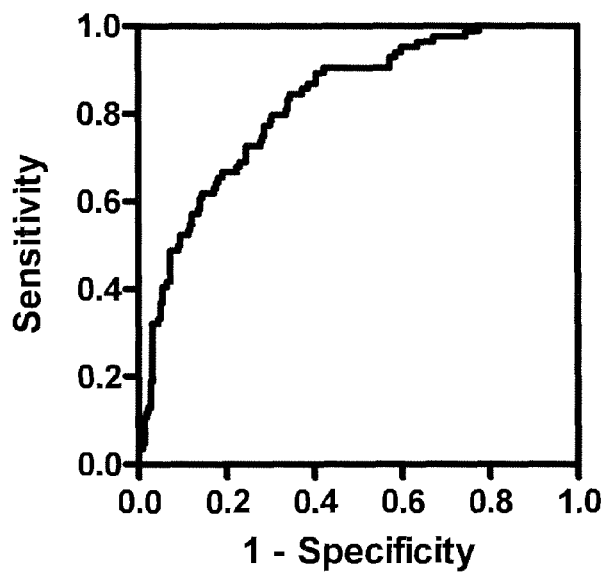
FIG. 108 is a graph showing the ROC curve of the index formula 21 in the 2-group discrimination between the prostatic disease group and the prostatic disease-free group.
FIG. 109 is a chart showing a list of amino acids extracted based on AUC of the ROC curve.

To examine the prostatic disease diagnostic ability using index formula 21, 2-group discrimination between the prostatic disease group and the prostatic disease-free group is evaluated by area under the ROC curve (see FIG. 108). As a result, an AUC of 0.822±0.026 (in 95% confidence interval, 0.772 to 0.872) is obtained. In addition, on the cutoff value of 2-group discrimination between the prostatic disease group and the prostatic disease-free group using index formula 21, the cutoff value which maximizes the average value of sensitivity and specificity is calculated. As a result, the cutoff value is −0.2271, and 85% sensitivity, and 65% specificity are obtained. From these results, it is found that index formula 21 is useful, with high diagnostic ability.

Example 33

The sample data used in Example 30 is used. All the linear discriminants for performing 2-group discrimination between the prostatic disease group and the prostatic disease-free group are extracted by an explanatory variable coverage method. The areas under the ROC curve of all the discriminants satisfying the condition in which the maximum value of amino acid explanatory variables appearing in each of the discriminants is 6 are calculated. The frequencies with which the amino acids appear in the discriminants in which the areas under the ROC curve are above certain threshold values are measured. When the areas under the ROC curve of 0.7, 0.75, and 0.8 are threshold values, it is found that Ala, Met, Asn, Trp, Leu, His, Val, Glu, and Cit are in the top ten among the amino acids extracted at high frequency at all times. It is found that multivariate discriminants using these amino acids as explanatory variables have 2-group discriminative ability between the prostatic disease group and the prostatic disease-free group (see FIG. 109).

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating prostatic disease, comprising:
obtaining concentration values of amino acids in blood of a subject to be evaluated;
evaluating, by a central processing unit (CPU) executing a prostatic disease-evaluating program stored on a computer-readable recording medium, a state of prostatic disease including at least one of prostatic cancer and prostatic hypertrophy in the subject, using at least concentration values of at least Trp and Ala contained in amino acid concentration data on the concentration values of the amino acids in blood of the subject,
wherein the concentration value criterion evaluating step further includes:
a discriminant value calculating step of calculating, by the CPU, a discriminant value that is a value of a multivariate discriminant, using at least both (i) the concentration values of at least Trp and Ala contained in the amino acid concentration data of the subject and (ii) the multivariate discriminant for evaluating the state of prostatic disease containing at least Trp and Ala as explanatory variables.

2. The method of evaluating prostatic disease according to claim 1, wherein the concentration value criterion evaluating step further includes a discriminant value criterion evaluating step of evaluating, by the CPU, the state of prostatic disease in the subject using at least the discriminant value;
wherein the discriminant value criterion evaluating step further includes a discriminant value criterion discriminating step of discriminating, by the CPU, between the prostatic disease and a prostatic disease-free, between the prostatic cancer and a prostatic cancer-free, or between the prostatic cancer and the prostatic hypertrophy in the subject, using at least the discriminant value.

3. The method of evaluating prostatic disease according to claim 2, wherein the multivariate discriminant is any one of a fractional expression, the sum of a plurality of the fractional expressions, a logistic regression equation, a linear discriminant, a multiple regression equation, a discriminant prepared by a support vector machine, a discriminant prepared by a Mahalanobis' generalized distance method, a discriminant prepared by canonical discriminant analysis, and a discriminant prepared by a decision tree.

4. The method of evaluating prostatic disease according to claim 3, wherein
(I) the discriminant value is calculated using at least both (i) the concentration values of at least Trp and Ala contained in the amino acid concentration data of the subject and (ii) the multivariate discriminant containing at least Trp and Ala as the explanatory variables, and
(II) at the discriminant value criterion discriminating step, the discrimination between the prostatic cancer and the prostatic cancer-free in the subject is conducted using at least the discriminant value.

5. The method of evaluating prostatic disease according to claim 4, wherein the multivariate discriminant is the logistic regression equation containing Tau, Ala, ABA, Trp, Orn, and Arg as the explanatory variables, the logistic regression equation containing Tau, Thr, Ala, Trp, Orn, and Arg as the explanatory variables, the logistic regression equation containing Asn, Ala, Val, Met, Trp, and Arg as the explanatory variables, the linear discriminant containing Tau, Ala, ABA, Trp, Orn, and Arg as the explanatory variables, or the linear discriminant containing Asn, Ala, Val, Met, Tyr, and Trp as the explanatory variables.

6. The method of evaluating prostatic disease according to claim 1, wherein the concentration value criterion evaluating step further includes a discriminant value criterion evaluating step of evaluating, by the CPU, the state of prostatic disease in the subject using at least the discriminant value.

7. The method of evaluating prostatic disease according to claim 1, wherein at the discriminant value calculating step, at least both (i) the concentration values of at least Trp, Ala, and Arg contained in the amino acid concentration data and (ii) the multivariate discriminant containing at least, Trp, Ala, and Arg as the explanatory variables are used.

8. The method of evaluating prostatic disease according to claim 1, wherein at the discriminant value calculating step, at least both (i) the concentration values of at least Trp, Ala, and Orn contained in the amino acid concentration data and (ii) the multivariate discriminant containing at least Trp, Ala, and Orn as the explanatory variables are used.

9. A prostatic disease-evaluating apparatus comprising a CPU executing a prostatic disease-evaluating program stored on a computer-readable recording medium, wherein the CPU is configured to calculate a discriminant value that is a value of a multivariate discriminant, using at least both (i) concentration values of at least Trp and Ala contained in amino acid concentration data on the concentration values of the amino acids in blood of a subject to be evaluated and (ii) the multivariate discriminant for evaluating a state of prostatic disease including at least one of prostatic cancer and prostatic hypertrophy,
wherein the multivariate discriminant contains at least Trp and Ala as explanatory variables.

10. The prostatic disease-evaluating apparatus according to claim 9, wherein the CPU is further configured to evaluate the state of prostatic disease in the subject using at least the discriminant value.

11. The prostatic disease-evaluating apparatus according to claim 9, wherein the CPU is configured to calculate the discriminant value using at least both (i) the concentration values of at least Trp, Ala, and Arg contained in the amino acid concentration data and (ii) the multivariate discriminant containing at least Trp, Ala, and Arg as the explanatory variables.

12. The prostatic disease-evaluating apparatus according to claim 9, wherein the CPU is configured to calculate the discriminant value using at least both (i) the concentration values of at least Trp, Ala and Orn contained in the amino acid concentration data and (ii) the multivariate discriminant containing at least Trp, Ala, and Orn as the explanatory variables.

13. A prostatic disease-evaluating method carried out with an information processing apparatus comprising a CPU executing a prostatic disease-evaluating program stored on a computer-readable recording medium, the CPU is configured to:
(I) calculate a discriminant value that is a value of a multivariate discriminant, using at least both (i) concentration values of at least Trp and Ala contained in amino acid concentration data on the concentration values of the amino acids in blood of a subject to be evaluated and (ii) the multivariate discriminant for evaluating a state of prostatic disease including at least one of prostatic cancer and prostatic hypertrophy,
wherein the multivariate discriminant contains at least Trp and Ala as explanatory variables.

14. The prostatic disease evaluating method according to claim 13, wherein the CPU is further configured to:
(II) evaluate the state of prostatic disease in the subject using at least the discriminant value.

15. A prostatic disease-evaluating system comprising (I) a prostatic disease-evaluating apparatus comprising a CPU executing a prostatic disease-evaluating program stored on a computer-readable recording medium, and (II) a terminal apparatus configured to provide amino acid concentration data on concentration values of amino acids in blood of a subject to be evaluated, wherein the apparatuses are connected to each other communicatively using a network,
wherein the terminal apparatus includes:
an amino acid concentration data-sending unit configured to transmit the amino acid concentration data of the subject to the prostatic disease-evaluating apparatus; and
a result-receiving unit configured to receive a discriminant value that is a value of a multivariate discriminant or an evaluation result of a state of prostatic disease including at least one of prostatic cancer and prostatic hypertrophy, transmitted from the prostatic disease-evaluating apparatus,
wherein the CPU is configured to:
receive the amino acid concentration data of the subject transmitted from the terminal apparatus;
calculate the discriminant value using at least both (i) the concentration values of at least Trp and Ala contained in the amino acid concentration data of the subject and (ii) the multivariate discriminant for evaluating a state of prostatic disease including at least one of prostatic cancer and prostatic hypertrophy or
calculate a discriminant value that is a value of a multivariate discriminant, using at least both (i) the concentration values of at least Trp and Ala contained in the amino acid concentration data of the subject and (ii) the multivariate discriminant for evaluating the state of prostatic disease, and evaluate the state of prostatic disease in the subject using at least the discriminant value; and
transmit the discriminant value or the evaluation result of the subject to the terminal apparatus,
wherein the multivariate discriminant contains at least Trp and Ala as explanatory variables.

16. A non-transitory computer-readable recording medium recorded therein a prostatic disease-evaluating program product, wherein the program product is executed by a CPU configured to:
(I) calculate a discriminant value that is a value of a multivariate discriminant, using at least both (i) concentration values of at least Trp and Ala contained in amino acid concentration data on the concentration values of the amino acids in blood of a subject to be evaluated and (ii) the multivariate discriminant for evaluating a state of prostatic disease including at least one of prostatic cancer and prostatic hypertrophy,
wherein the multivariate discriminant contains at least Trp and Ala as explanatory variables.

17. The non-transitory computer-readable recording medium according to claim 16, wherein the CPU is further configured to:
(II) evaluate the state of prostatic disease in the subject using at least the discriminant value.

18. A terminal apparatus comprising a CPU executing a computer program stored on a computer-readable recording medium,
wherein the CPU is configured to obtain a discriminant value that is a value of a multivariate discriminant or an evaluation result of a state of prostatic disease including at least one of prostatic cancer and prostatic hypertrophy,
wherein the discriminant value is calculated using at least both (i) concentration values of at least Trp and Ala contained in amino acid concentration data on the concentration values of the amino acids in blood of a subject to be evaluated and (ii) the multivariate discriminant for evaluating a state of prostatic disease including at least one of prostatic cancer and prostatic hypertrophy or
the evaluation result is the result of evaluating the state of prostatic disease in a subject to be evaluated using at least a discriminant value that is a value of a multivariate discriminant, wherein the discriminant value is calculated using at least both (i) concentration values of at least Trp and Ala contained in amino acid concentration data on the concentration values of the amino acids in blood of the subject and (ii) the multivariate discriminant for evaluating the state of prostatic disease,
wherein the multivariate discriminant contains at least Trp and Ala as explanatory variables.

19. The terminal apparatus according to claim 18, wherein the terminal apparatus is communicatively connected using a network to a prostatic disease-evaluating apparatus comprising a CPU executing a prostatic disease-evaluating program stored on a computer-readable recording medium to calculate the discriminant value or evaluate the state of prostatic disease,
wherein the CPU in the terminal apparatus is configured to receive the discriminant value or the evaluation result transmitted from the prostatic disease-evaluating apparatus.

20. A prostatic disease-evaluating apparatus comprising a CPU executing a prostatic disease-evaluating program stored on a computer-readable recording medium, wherein the apparatus is communicatively connected using a network to a terminal apparatus configured to provide amino acid concentration data on concentration values of amino acids in blood of a subject to be evaluated, wherein the CPU is configured to:
receive the amino acid concentration data of the subject transmitted from the terminal apparatus;
calculate a discriminant value that is a value of a multivariate discriminant, using a least both (i) the concentration values of at least Trp and Ala contained in the amino acid concentration data of the subject and (ii) the multivariate discriminant for evaluating a state of prostatic disease including at least one of prostatic cancer and prostatic hypertrophy or calculate a discriminant value that is a value of multivariate discriminant, using at least both (i) the concentration values of at least Trp and Ala contained in the amino acid concentration data of the subject and (ii) the multivariate discriminant for evaluating a state of prostatic disease including at least one of the prostatic cancer and prostatic hypertrophy, and evaluate the state of prostatic disease in the subject using at least the discriminant value; and
transmit the discriminant value or an evaluation result of the state of prostatic disease of the subject to the terminal apparatus,
wherein the multivariate discriminant contains at least Trp and Ala as explanatory variables.

21. A method of evaluating prostatic disease, comprising:
a discriminant value calculating step of calculating, by a CPU executing a prostatic disease-evaluating program stored on a computer-readable recording medium, a discriminant value that is a value of multivariate discriminant, using at least both (i) concentration values of at least Trp and Ala contained in amino acid concentration data on the concentration values of the amino acids in blood of a subject to be evaluated and (ii) the multivariate discriminant for evaluating a state of prostatic disease including at least one of prostatic cancer and prostatic hypertrophy,
wherein the multivariate discriminant contains at least Trp and Ala as explanatory variables.

22. The method of evaluating prostatic disease according to claim 21, wherein the method further includes a discriminant value criterion evaluating step of evaluating, by the CPU, the state of prostatic disease in the subject using at least the discriminant value calculated at the discriminant value calculating step.

23. A method of evaluating prostatic disease, comprising:
a discriminant value criterion evaluating step of evaluating, by a CPU executing a prostatic disease-evaluating program stored on a computer-readable recording medium, a state of prostatic disease including at least one of prostatic cancer and prostatic hypertrophy in a subject to be evaluated, using at least a discriminant value that is a value of multivariate discriminant,
wherein the discriminant value is calculated using at least both (i) concentration values of at least Trp and Ala contained in amino acid concentration data on the concentration values of the amino acids in blood of the subject (ii) the multivariate discriminant for evaluating the state of prostatic disease containing at least Trp and Ala as explanatory variables.

24. A prostatic disease-evaluating apparatus comprising a CPU executing a prostatic disease-evaluating program stored on a computer-readable recording medium, wherein the CPU is configured to:
evaluate a state of prostatic disease including at least one of prostatic cancer and prostatic hypertrophy in a subject to be evaluated, using at least a discriminant value that is a value of multivariate discriminant,
wherein the discriminant value is calculated using at least both (i) concentration values of at least Trp and Ala contained in amino acid concentration data on the concentration values of the amino acids in blood of the subject and (ii) the multivariate discriminant for evaluating the state of prostatic disease containing at least Trp and Ala as explanatory variables.

25. A prostatic disease-evaluating method carried out with an information processing apparatus comprising a CPU executing a prostatic disease-evaluating program stored on a computer-readable recording medium, wherein the CPU is configured to:
evaluate a state of prostatic disease including at least one of prostatic cancer and prostatic hypertrophy in a subject to be evaluated, using at least a discriminant value that is a value of a multivariate discriminant,
wherein the discriminant value is calculated using at least both (i) concentration values of at least Trp and Ala contained in amino acid concentration data on the concentration values of the amino acids in blood of the subject and (ii) the multivariate discriminant for evaluating the state of prostatic disease containing at least Trp and Ala as explanatory variables.

26. A non-transitory computer-readable recording medium recorded therein a prostatic disease-evaluating program product, wherein the program product is executed by a CPU configured to:
evaluate a state of prostatic disease including at least one of prostatic cancer and prostatic hypertrophy in a subject to be evaluated, using at least a discriminant value that is a value of a multivariate discriminant,
wherein the discriminant value is calculated using at least both (i) concentration values of at least Trp and Ala contained in amino acid concentration data on the concentration values of the amino acids in blood of the subject and (ii) the multivariate discriminant for evaluating the state of prostatic disease containing at least Trp and Ala as explanatory variables.

* * * * *